(12) United States Patent
Nemunaitis et al.

(10) Patent No.: US 11,400,170 B2
(45) Date of Patent: Aug. 2, 2022

(54) METHODS FOR TREATING CANCERS

(71) Applicant: GRADALIS, INC., Carrollton, TX (US)

(72) Inventors: John Nemunaitis, Carrollton, CA (US); Ernest Bognar, Carrollton, TX (US)

(73) Assignee: GRADALIS, INC., Carrollton, TX (US)

( * ) Notice: Subject to any disclaimer, the term of this patent is extended or adjusted under 35 U.S.C. 154(b) by 0 days.

(21) Appl. No.: 17/157,790

(22) Filed: Jan. 25, 2021

(65) Prior Publication Data

US 2021/0220488 A1  Jul. 22, 2021

Related U.S. Application Data

(63) Continuation of application No. PCT/US2021/013130, filed on Jan. 12, 2021.
(Continued)

(51) Int. Cl.
*A61K 35/13* (2015.01)
*A61K 39/00* (2006.01)
(Continued)

(52) U.S. Cl.
CPC .......... *A61K 48/0083* (2013.01); *A61K 35/13* (2013.01); *A61K 38/193* (2013.01);
(Continued)

(58) Field of Classification Search
CPC ...... A61K 35/13; A61K 38/193; A61K 39/00; A61K 39/0011; A61K 48/0066;
(Continued)

(56) References Cited

U.S. PATENT DOCUMENTS 8,252,526 B2  8/2012 Rao
8,333,988 B2  12/2012 Templeton
(Continued)

FOREIGN PATENT DOCUMENTS

WO  2011079070  6/2011
WO  2011079077  6/2011
WO  2015086473  6/2015

OTHER PUBLICATIONS

Lu et al, Oncology Reports 28: 21-26, 2012.*
(Continued)

*Primary Examiner* — Kevin K Hill
(74) *Attorney, Agent, or Firm* — Kilpatrick Townsend & Stockton LLP

(57) ABSTRACT

Compositions and methods for prevention of ovarian cancer recurrence and for the treatment of BRCA1/2-wild type ovarian cancer are disclosed herein. In some embodiments, the composition comprises an autologous tumor cell vaccine comprising cells genetically modified for furin knockdown and GM-CSF expression. In some embodiments, the method comprises administration of an autologous tumor cell vaccine prior to administration of a combination of the autologous tumor cell vaccine and atezolizumab. Also disclosed herein are methods for treating a cancer in an individual comprising a wild-type BRCA1 gene, a wild-type BRCA2 gene, or a combination thereof, and is identified as homologous recombination deficiency (HRD)-negative.

18 Claims, 58 Drawing Sheets

Specification includes a Sequence Listing.

Related U.S. Application Data

(60) Provisional application No. 62/960,583, filed on Jan. 13, 2020, provisional application No. 63/034,868, filed on Jun. 4, 2020, provisional application No. 63/061,634, filed on Aug. 5, 2020.

(51) Int. Cl.
  A61K 48/00 (2006.01)
  A61K 38/19 (2006.01)
  C12N 15/113 (2010.01)
  A61P 35/00 (2006.01)

(52) U.S. Cl.
  CPC ...... *A61K 39/0011* (2013.01); *A61K 48/0066* (2013.01); *A61P 35/00* (2018.01); *C12N 15/1137* (2013.01); *A61K 2039/5152* (2013.01); *C12N 2310/141* (2013.01); *C12N 2310/344* (2013.01); *C12N 2310/531* (2013.01); *C12N 2310/533* (2013.01)

(58) Field of Classification Search
  CPC ........ A61K 48/0083; A61K 2039/5152; A61P 35/00; A61P 37/00; C12N 15/1137; C12N 2310/141; C12N 2310/531; C12N 2310/533
  See application file for complete search history.

(56) References Cited

U.S. PATENT DOCUMENTS

| | | | |
|---|---|---|---|
| 8,361,983 | B2 | 1/2013 | Nemunaitis et al. |
| 8,758,998 | B2 | 6/2014 | Rao |
| 8,906,874 | B2 | 12/2014 | Rao et al. |
| 8,916,530 | B2 | 12/2014 | Shanahan et al. |
| 8,969,068 | B2 | 3/2015 | Templeton |
| 9,132,146 | B2 * | 9/2015 | Nemunaitis ............ C12N 15/85 |
| 9,157,084 | B2 | 10/2015 | Nemunaitis et al. |
| 9,290,763 | B2 | 3/2016 | Rao |
| 9,695,422 | B2 * | 7/2017 | Nemunaitis ............ C12N 15/85 |
| 9,790,518 | B2 * | 10/2017 | Nemunaitis ........ A61K 31/7088 |
| 2018/0073038 | A1 * | 3/2018 | Nemunaitis ............ A61P 17/00 |

OTHER PUBLICATIONS

Lim et al, Neoplasia 16(4): 343-353, 2014.*
Chu et al, Cancer Immunol. Immunother. 61: 629-641, 2012.*
Barve et al., Case Report: Vigil Therapy in Pathology Defined High-Risk Differentiated Thyroid Cancer Compounded by Post Ablation High-Risk Factors, Journal of Surgical Oncology and Clinical Research, Oct. 5, 2017, 3 pages.
Barve et al., Follow-up of bi-shRNAfurin /GM-CSF Engineered Autologous Tumor Cell (EATC) Immunotherapy Vigil in Patients with Advanced Melanoma, Biomedical Genetics and Genomics, vol. 1, No. 3, Jan. 2016, pp. 81-86.
Craig et al., Resident Memory T Cells and Their Effect on Cancer, Vaccines, vol. 8, No. 4, Oct. 1, 2020, 14 pages.
Creeden et al., The Role of TGβ in Clinical Cancer Response, Clinical Oncology and Research, Apr. 2020, pp. 1-8.
Ghisoli et al., Case Report: Immune-mediated Complete Response in a Patient with Recurrent Advanced Ewing Sarcoma (EWS) After Vigil Immunotherapy, Journal of Pediatric Hematology/Oncology, vol. 39, No. 4, May 2017, pp. e183-e186.
Ghisoli et al., Innovative Exploratory Clinical Approaches for Relapsed and/or Refractory Metastatic Ewing's Sarcoma, Clinics in Oncology, vol. 1, Article 1079, Sep. 8, 2016, 9 pages.
Ghisoli et al., Pilot Trial of FANG Immunotherapy in Ewing's Sarcoma, Molecular Therapy Family, vol. 23, No. 6, Jun. 2015, pp. 1103-1109.
Ghisoli et al., Three-year Follow up of GMCSF/bi-shRNAfurin DNA-transfected Autologous Tumor Immunotherapy (Vigil) in Metastatic Advanced Ewing's Sarcoma, Molecular Therapy, vol. 24, No. 8, Aug. 2016, pp. 1478-1483.
Gogineni, Current Ovarian Cancer Maintenance Strategies and Promising New Developments, Journal of Cancer, vol. 12, No. 1, Jan. 1, 2021, pp. 38-53.
Herron et al., Vigil: Personalized Immunotherapy Generating Systemic Cytotoxic T Cell Response, Cancer Science & Research, vol. 3, No. 1, Sep. 19, 2020, pp. 1-4.
Manning et al., Assessment of Low Dose Vigil® Engineered Autologous Tumor Cell (EATC) Immunotherapy in Patients with Advanced Solid Tumors, Clinics in Oncology, vol. 2, Article 1254, Apr. 3, 2017, 4 pages.
Manning et al., Harnessing the Immune Response to Target Tumors [version 1; peer review: 2 approved], F1000Research, vol. 6, May 18, 2017, 7 pages.
Maples et al., FANG Vaccine: Autologous Tumor Cell Vaccine Genetically Modified to Express GM-CSF and Block Production of Furin, BioProcessing Journal, vol. 8, No. 4, Mar. 2010, pp. 4-14.
Morand et al., BRCA1/2 Mutation Status Impact on Autophagy and Immune Response: Unheralded Target, JNCI Cancer Spectrum, vol. 4, No. 6, Aug. 24, 2020, 21 pages.
Nemunaitis et al., Severe Acute Respiratory Syndrome Coronavirus-2 (SARS-CoV-2) Infection: Let the Virus Be Its Own Demise, Future Virology, vol. 15, Apr. 2020, 16 pages.
Nemunaitis et al., Summary of bi-shRNA furin /GM-CSF Augmented Autologous Tumor Cell Immunotherapy (FANG TM) in Advanced Cancer of the Liver, Oncology, vol. 87, No. 1, 2014, pp. 21-29.
Nemunaitis et al., Tumor Vaccines and Cellular Immunotherapies, Annals of Translational Medicine, vol. 4, No. 1, Oct. 2016, 3 pages.
Oh et al., Long-term Follow-up of Phase 2A Trial Results Involving Advanced Ovarian Cancer Patients Treated with Vigil® in Frontline Maintenance, Gynecologic Oncology Reports, vol. 34, Sep. 17, 2020, 3 pages.
Oh et al., Phase II Study of Vigil® DNA Engineered Immunotherapy as Maintenance In Advanced Stage Ovarian Cancer, Gynecologic Oncology, vol. 143, 2016, pp. 504-510.
Rocconi et al., A Phase I Combination Study of Gemogenovatucel-T and Atezolizumab in Recurrent/Refractory Advanced Stage Ovarian Cancer: Efficacy Assessment in BRCA1/2-wt Patients, Journal of Clinical Oncology, vol. 38, No. 15, May 20, 2020, 31 pages.
Rocconi et al., Gemogenovatucel-T (Vigil) Immunotherapy as Maintenance in Frontline Stage III/IV Ovarian Cancer (Vital): a Randomised, Double-Blind, Placebo-Controlled, Phase 2b Trial, Supplementary Appendix, The Lancet Oncology, 2020, 111 pages.
Rocconi et al., Gemogenovatucel-T (Vigil) Immunotherapy as Maintenance In Frontline Stage III/IV Ovarian Cancer (Vital): A Randomised, Double-blind, Placebo-controlled, Phase 2b Trial, The Lancet Oncology, vol. 21, No. 12, Dec. 2020, pp. 1661-1672.
Rocconi et al., Randomized Double-blind Placebo Controlled Trial of Primary Maintenance Vigil Immunotherapy (Vital Study) in Stage III/IV Ovarian Cancer: Efficacy Assessment in BRCA1/2-wt Patients, LBA 7—Late Breaking Abstract Session, vol. 159, No. 1, May 29-31, 2020, 2 pages.
Senzer et al., Long Term Follow Up: Phase I Trial of "bi-shRNA furin/GMCSF DNA/ Autologous Tumor Cell Immunotherapy (FANG™) in Advanced Cancer", Journal of Vaccines and Vaccination, vol. 4, No. 8, Jan. 2013, pp. 1-8.
Senzer et al., Phase I Trial of "bi-shRNAifurin/GMCSF DNA/ Autologous Tumor Cell" Vaccine (FANG) in Advanced Cancer, Molecular Therapy, vol. 20, No. 3, Mar. 2012, pp. 679-686.
International Application No. PCT/US2021/013130, International Search Report and Written Opinion dated Apr. 22, 2021, 13 pages.
Rao et al., Enhanced Target Gene Knockdown by a Bifunctional shRNA: A Novel Approach of RNA Interference, Cancer Gene Therapy. vol. 17, No. 11, Nov. 2, 2010, pp. 780-791.
Tian et al., Evaluation of the BRCAness Phenotype and its Correlations with Clinicopathological Features in Triple-Negative Breast Cancers, Human Pathology, vol. 84, Oct. 16, 2018, pp. 231-238.

(56) References Cited

OTHER PUBLICATIONS

Zhang et al., A Genomic Instability Score in Discriminating Nonequivalent Outcomes of BRCA1/2 Mutations and in Predicting Outcomes of Ovarian Cancer Treated with Platinum-Based Chemotherapy, PLOS ONE. vol. 9, No. 12, Dec. 1, 2014, 16 pages.
Trial of Bi-shRNA-furin and Granulocyte Macrophage Colony Stimulating Factor (GMCSF) Augmented Autologous Tumor Cell Vaccine for Advanced Cancer (Fang); NCT01061840 Start date: Dec. 2009.
Trial of Adjuvant FANG™ Vaccine for High Risk Stage III/IV Ovarian Cancer; NCT01309230 Start Date: Feb. 2011.
Randomized Phase II Adjuvant Chemotherapy ± FANG™ in Colorectal Carcinoma With Liver Metastases; NCT01505166; Start Date: Mar. 2012.
Phase II Trial of Adjuvant Bi-shRNAfurin and GMCSF Augmented Autologous Tumor Cell Vaccine (FANG™) Integrated With Chemotherapy for Patients With Recurrent Cisplatinum Sensitive Ovarian Cancer Participating in Study; NCT01867086; Start Date: Jun. 2013.
Phase II Trial of Adjuvant Bi-shRNAfurin and GMCSF Augmented Autologous Tumor Cell Vaccine (FANG™) Integrated With Bevacizumab for Patients With Recurrent/Refractory Ovarian Cancer Participating in Study; NCT01551745; Start Date: Mar. 2012.
Phase II Fang™ in Advanced Melanoma; NCT01453361; Start Date: Oct. 2011.
A Randomized, Double-Blind, Placebo-Controlled Phase 2 Trial of Vigil Engineered Autologous Tumor Cell Immunotherapy in Subjects With Stage IIIb-IV Ovarian Cancer in Clinical Complete Response Following Surgery and Primary Chemotherapy; NCT02346747; Start Date: Feb. 2015.
A Two-part Phase IIb Trial of Vigil (Bi-shRNAfurin and GMCSF Augmented Autologous Tumor Cell Immunotherapy) in Ewing's Sarcoma; NCT02511132; May 27, 2017.
A Phase 2 Study of Vigil™ Augmented Autologous Tumor Cell Immunotherapy in Combination With Nivolumab PD-1 Inhibitor for Patients With Advanced Non-Small Cell Lung Cancer NCT02639234; Start Date: Mar. 2016.
A Pilot Study of Vigil™ Augmented Autologous Tumor Cell Immunotherapy in Combination With Pembrolizumab PD-1 Inhibitor for Patients With Advanced Melanoma; NCT02574533; Start Date: Oct. 2015.
Pilot Study of Durvalumab (MEDI4736) in Combination With Vigil in Advanced Women's Cancers; NCT02725489; Start Date: Jun. 2016.
A Randomized, Intra-patient Crossover, Safety, Biomarker and Anti-Tumor Activity Assessment of the Combination of Atezolizumab and Vigil in Patients With Advanced Gynecological Cancers; NCT03073525; Start Date May 25, 2016.
A Multi-Center Phase III, Randomized, Open-Label Trial of Vigil (Bi-shRNAfurin and GMCSF Augmented Autologous Tumor Cell Immunotherapy) in Combination With Irinotecan and Temozolomide as a Second-Line Regimen for Ewing's Sarcoma; NCT03495921; Start Date Aug. 2018.
An Expanded Access Trial of Vigil (Bi-shRNAfurin and GMCSF Augmented Autologous Tumor Cell Immunotherapy) in Advanced Solid Tumors; NCT03842865; First posted Feb. 15, 2019.
Rodney Paul Rocconi et al., A Phase I Combination Study of Gemogenovatucel-T and Atezolizumab in Recurrent/Refractory Advanced Stage Ovarian Cancer: Efficacy Assessment in BRCA1/2-wt Patients.OI: 10.1200/JCO.2020.38.15_suppl.3002 Journal of Clinical Oncology 38, No. 15_suppl (May 20, 2020) 3002-3002.; Published online May 25, 2020.
Rocconi, Rodney Paul et al., Randomized double-blind placebo-controlled trial of primary maintenance vigil immunotherapy (VITAL study) in stage III/IV ovarian cancer: Efficacy assessment in BRCA1/2-wt patients. Journal of Clinical Oncology 38, No. 15_suppl (May 20, 2020) 6017-6017. Published online May 25, 2020.
Rodney Paul Rocconi et al., Abstract 3002 presented in an "Oral Abstract Session" at the 2020 ASCO Virtual Meeting in May 2020. The ASCO Meeting was held May 29-31, 2020.
Rocconi RP, et al.;. Gemogenovatucel-T (Vigil) immunotherapy demonstrates clinical benefit in homologous recombination proficient (HRP) ovarian Cancer. Gynecologic Oncology. Jun. 2021; 161(3):676-680.
Rocconi RP, et al.; Long-Term Follow-Up of Gemogenovatucel-T (Vigil) Survival and Molecular Signals of Immune Response in Recurrent Ovarian Cancer; Vaccines. Aug. 2021 9(8):894, 16 pgs.
Rocconi RP, et al.; Proof of Principle Study of Sequential Combination Atezolizumab and Vigil in Relapsed Ovarian Cancer. Cancer Gene Therapy. Mar. 2021; 14 pgs.
Rodney Paul Rocconi et al., Abstract 6017 was presented in a "Poster Discussion Session" at the 2020 ASCO Virtual Scientific Program. The ASCO Meeting was held May 29-31, 2020. Poster 188. 3 pgs.

* cited by examiner

SEQ ID. NO. 12

```
GAUC       GUU      GA    GC                              GCCAC
    CUGCU     GA   CAGU  --- GGAGAAAGGAGUGAAACCUUA  GUGAA
    -----     --   ----  --- ||||||||||||||||||||
    GACGA     CU   GUCA  CG  CCUCUUUCCUCACUUUGGAAU  GUAGA
ACUC       AGG    CC    UC  UU
CUACAU

UACUC      GUU      GA    GC              AUA            GCCAC
    AGCU     GA   CAGU  ---  GGAGAAAG     UGAAACCUUA  GUGAA
    ----     --   ----  ---  ||||||||     ||||||||||
    UCGA     CU   GUCA  CG   CCUCUUUC     ACUUUGGAAU  GUAGA
GAAAUAAU   AGG    CC    UC  UU         CUC
```

SENSE (PASSENGER) STRAND
ANTISENSE (GUIDE) STRAND

FIG. 1

| Treatment Group | BRCA Mutational Status | HRD Status | N |
|---|---|---|---|
| Vigil | BRCAwt | Negative | 25 |
| | | Positive | 14 |
| | BRCAmut | Positive | 7 |
| Placebo | BRCAwt | Negative | 18 |
| | | Positive | 8 |
| | | Unknown* | 2* |
| | BRCAmut | Positive | 17 |

* In preparation

FIG. 13

| Treatment Group | BRCA Mutational Status | HRD Status | N |
|---|---|---|---|
| Vigil | BRCAwt | Negative | 25 |
| | | Positive | 14 |
| Placebo | BRCAwt | Negative | 18 |
| | | Positive | 8 |
| | | Unknown* | 2* |

\* In preparation

FIG. 16

*Stratified by randomization factors HR=0.356 with 90% CI [0.0.18 to 0.703] from procurement
Stratified by randomization factors HR=0.373 with 90% CI [0.189 to 0.736] from randomization.
Stratification factors: Surgical outcome (CR/microscopic vs. macroscopic) Frontline chemo (adjuvant vs. neoadjuvant)

* Stratified by randomization factors 0.362 with 90% CI [0.147 to 0.89] for BRCA-wt from time of surgery/procurement
Stratified by randomization factors HR=0362 with 90% CI [0.147 to 0.89] for BRCA1/2-wt from time of randomization
Stratification factors: Surgical outcome (CR/microscopic vs. macroscopic)
Frontline chemo (adjuvant vs. neoadjuvant)

| Agent | Sub-population BRCA-1 HRD Status | PFS / RFS | HR [PFS/RFS] (95% CI) | OS |
|---|---|---|---|---|
| BEV[1,2*] | N/A | 18.2 vs. 12.0 | 0.62 (0.52, 0.75) | HR=0.96 [0.85 – 1.09] |
| Olaparib / BEV[3] | BRCA-wt / HRP | 16.6 vs. 16.0[Δ] | 1.0 (0.75, 1.35) | Immature |
| Niraparib[4] | BRCA-wt / HRP | 8.1 vs. 5.4[Δ] | 0.68 (0.49, 0.94) | No Description |
| Vigil | BRCA-wt / HRP | Procurement 10 vs 12+y | 0.386 (0.18, 0.703) | HR=0.362 [0.147 – 0.89] |
| | BRCA-wt / HRP | Randomization 10.6 vs 5.6+y | 0.373 (0.189, 0.736) | HR=0.362 [0.147-0.89] |

°Consolidation plus maintenance
[Δ]Included PR and CR patients s/p consolidation
[+]Included only CR patients s/p consolidation

FIG. 27

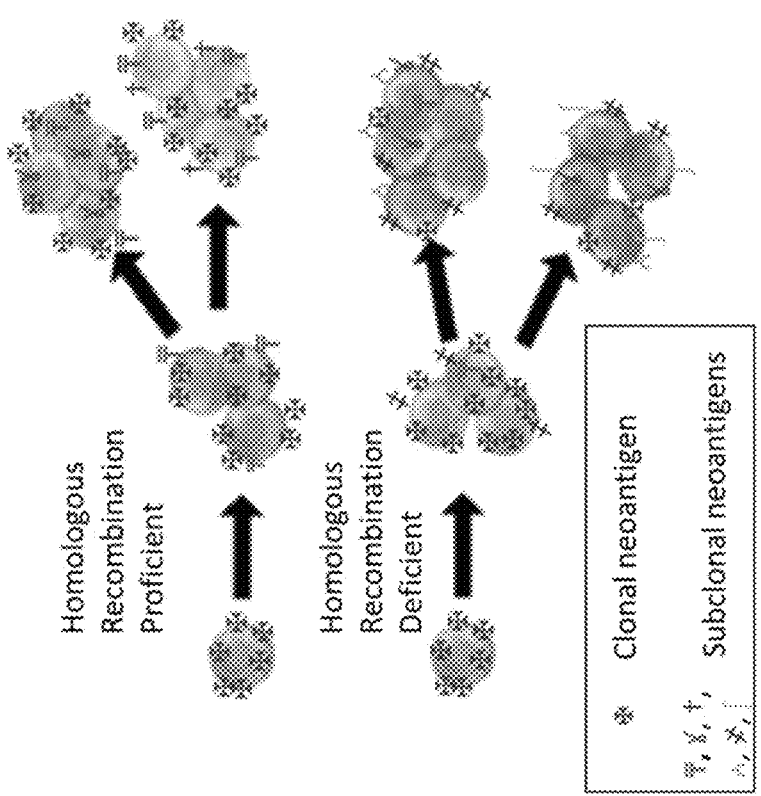

- Subclonal heterogeneity in HRD tumors dilutes clonal neoantigen visibility and cancer targeting T cells[1].
- High clonal neoantigen burden is associated with an inflamed (hot) microenvironment enriched with activated effector T cells[1].
- Diffuse variable subclonal neoantigens trigger immunoediting which removes limited clonal targeting T cells[2,3].
- Clinical efficacy of PD-L1 blockade correlates with high neoantigen clonal fraction and low subclonal fraction[1].
- Vigil benefit is enhanced in BRCA-wt / HRP population likely related to enhancement of clonal neoantigen expression BRCA-wt/HRP → ↑ DNA repair → ↓ subclonal neoantigens

FIG. 29

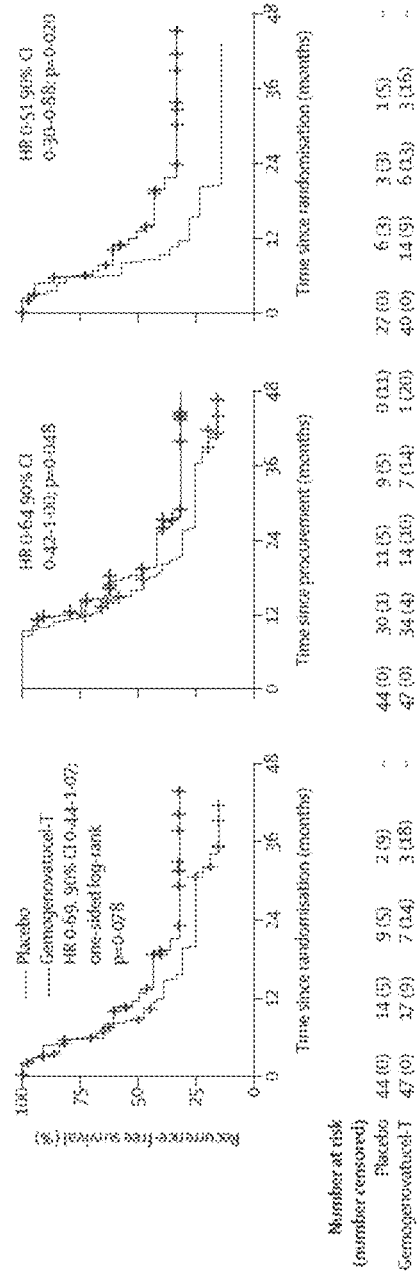
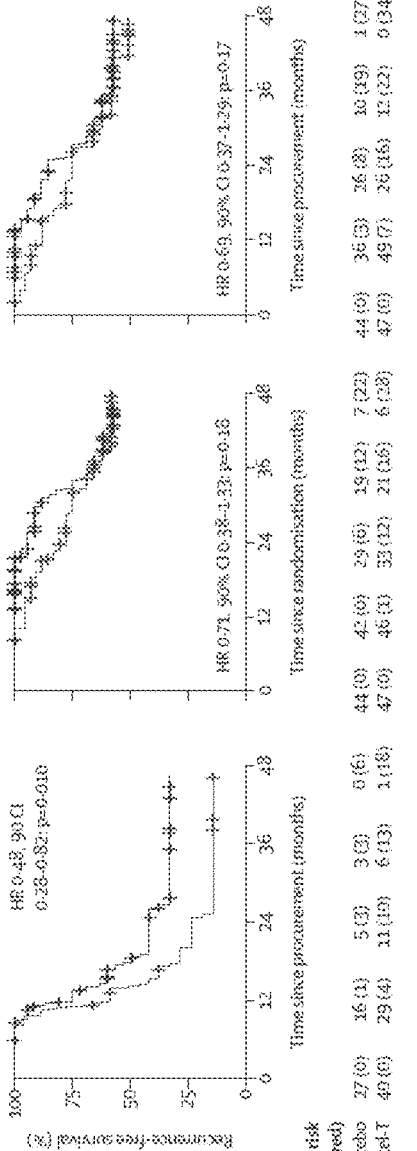
FIG. 35A  FIG. 35B  FIG. 35C
FIG. 35D  FIG. 35E  FIG. 35F

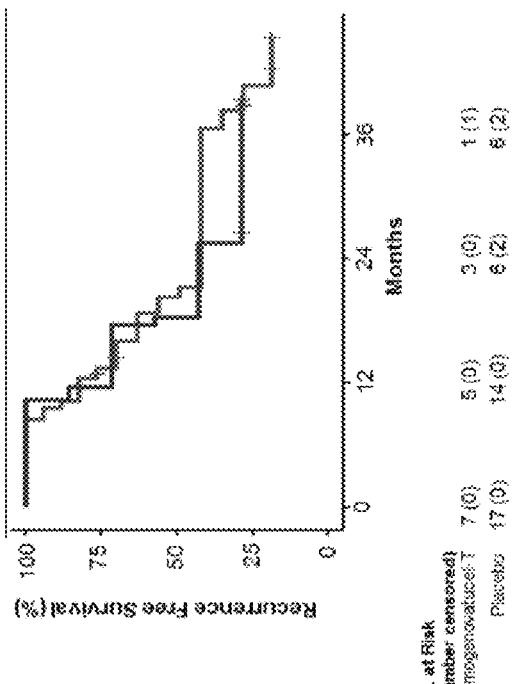
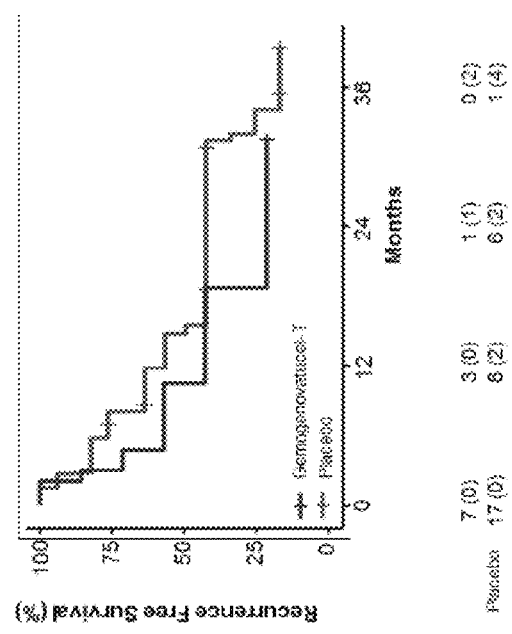
FIG. 41A
FIG. 41B

SEQUENCE LISTING

<160> NUMBER OF SEQ ID NOS: 12

<210> SEQ ID NO 1
<211> LENGTH: 4180
<212> TYPE: DNA
<213> ORGANISM: Unknown
<220> FEATURE:
<223> OTHER INFORMATION: Description of Unknown:
      mRNA transcript encoding furin sequence

<400> SEQUENCE: 1

| | | | | | |
|---|---|---|---|---|---|
| gcggggaagc | agcagcggcc | aggatgaatc | ccaggtgctc | tggagctgga | tggtgaaggt | 60 |
| cggcactctt | caccctcccg | agccctgccc | gtctcggccc | catgccccca | ccagtcagcc | 120 |
| ccgggccaca | ggcagtgagc | aggcacctgg | gagccgaggc | cctgtgacca | ggccaaggag | 180 |
| acgggcgctc | cagggtccca | gccacctgtc | cccccatgg | agctgaggcc | ctggttgcta | 240 |
| tgggtggtag | cagcaacagg | aaccttggtc | ctgctagcag | ctgatgctca | gggccagaag | 300 |
| gtcttcacca | acacgtgggc | tgtgcgcatc | cctggaggcc | cagcggtggc | aacagtgtg | 360 |
| gcacggaagc | atgggttcct | caacctgggc | cagatcttcg | gggactatta | ccacttctgg | 420 |
| catcgaggag | tgacgaagcg | gtccctgtcg | cctcaccgcc | cgcggcacag | ccggctgcag | 480 |
| agggagcctc | aagtacagtg | gctggaacag | caggtggcaa | agcgacggac | taaacgggac | 540 |
| gtgtaccagg | agcccacaga | ccccaagttt | cctcagcagt | ggtacctgtc | tggtgtcact | 600 |
| cagcgggacc | tgaatgtgaa | ggcggcctgg | gcgcagggct | acacagggca | ggcattgtg | 660 |
| gtctccattc | tggacgatgg | catcgagaag | aaccacccgg | acttggcagg | caattatgat | 720 |
| cctgggccca | gttttgatgt | caatgaccag | gaccctgacc | cccagcctcg | gtacacacag | 780 |
| atgaatgaca | acaggcacgg | cacacggtgt | gcggggaag | tggctgcggt | ggccaacaac | 840 |
| ggtgtctgtg | gtgtaggtgt | ggcctacaac | gcccgcattg | gagggtgcg | catgctggat | 900 |
| ggcgaggtga | cagatgcagt | ggaggcacgc | tcgctgggcc | tgaaccccaa | ccacatccac | 960 |
| atctacagtg | ccagctgggg | ccccgaggat | gacggcaaga | cagtggatgg | gccagcccgc | 1020 |
| ctcgccgagg | aggccttctt | ccgtgggtt | agccagggcc | gaggggggct | gggctccatc | 1080 |
| tttgtctggg | cctcggggaa | cggggccgg | gaacatgaca | gctgcaactg | cgacggctac | 1140 |
| accaacagta | tctacacgct | gtccatcagc | agcgccacgc | agtttggcaa | cgtgccgtgg | 1200 |
| tacagcgagg | cctgctcgtc | cacactggcc | acgacctaca | gcagtggcaa | ccagaatgag | 1260 |
| aagcagatcg | tgacgactga | cttgcggcag | aagtgcacgg | agtctcacac | gggcacctca | 1320 |
| gcctctgccc | ccttagcagc | cggcatcatt | gctctcaccc | tggaggccaa | taagaacctc | 1380 |
| acatggcggg | acatgcaaca | cctggtggta | cagaccctcga | agccagccca | cctcaatgcc | 1440 |
| aacgactggg | ccaccaatgg | tgtgggccgg | aaagtgagcc | actcatatgg | ctacgggctt | 1500 |
| ttggacgcag | cgccatggt | ggccctggcc | cagaattgga | ccacagtggc | ccccagcgg | 1560 |
| aagtgcatca | tcgacatcct | caccgagccc | aaagacatcg | ggaaacggct | cgaggtgcgg | 1620 |
| aagaccgtga | ccgcgtgcct | gggcgagccc | aaccacatca | ctcggctgga | gcacgctcag | 1680 |
| gcgcggctca | ccctgtccta | taatcgccgt | ggcgacctgg | ccatccacct | ggtcagcccc | 1740 |
| atgggcaccc | gctccaccct | gctggcagcc | aggccacatg | actactccgc | agatgggttt | 1800 |
| aatgactggg | ccttcatgac | aactcattcc | tgggatgagg | atccctctgg | cgagtgggtc | 1860 |
| ctagagattg | aaaacaccag | cgaagccaac | aactatggga | cgctgaccaa | gttcaccctc | 1920 |
| gtactctatg | gcaccgcccc | tgaggggctg | cccgtacctc | cagaaagcag | tggctgcaag | 1980 |

```
accctcacgt ccagtcaggc ctgtgtggtg tgcgaggaag gcttctccct gcaccagaag    2040
agctgtgtcc agcactgccc tccagggttc gcccccaag tcctcgatac gcactatagc    2100
accgagaatg acgtggagac catccgggcc agcgtctgcg cccctgcca cgcctcatgt    2160 gccacatgcc aggggccggc cctgacagac tgcctcagct gccccagcca cgcctccttg    2220
gaccctgtgg agcagacttg ctcccggcaa agccagagca gccgagagtc cccgccacag    2280
cagcagccac ctcggctgcc cccggaggtg gaggcgggc aacggctgcg ggcagggctg    2340
ctgccctcac acctgcctga ggtggtggcc ggcctcagct gcgccttcat cgtgctggtc    2400
ttcgtcactg tcttcctggt cctgcagctg cgctctggct ttagttttcg gggggtgaag    2460
gtgtacacca tggaccgtgg cctcatctcc tacaaggggc tgccccctga agcctggcag    2520
gaggagtgcc cgtctgactc agaagaggac gagggccggg gcgagaggac cgcctttatc    2580
aaagaccaga gcgccctctg atgagcccac tgcccacccc ctcaagccaa tcccctcctt    2640
gggcactttt taattcacca agtattttt ttatcttggg actgggtttg gaccccagct    2700
gggaggcaag aggggtggag actgcttccc atcctaccct cgggcccacc tggccacctg    2760
aggtgggccc aggaccagct ggggcgtggg gagggccgta ccccaccctc agcaccccTT    2820
ccatgtggag aaaggagtga aacctttagg gcagcttgcc ccggcccgg ccccagccag    2880 agttcctgcg gagtgaagag gggcagcccc tgcttgttgg gattcctgac ccaggccgca    2940
gctcttgccc ttccctgtcc ctctaaagca ataatggtcc catccaggca gtcgggggct    3000
ggcctaggag atatctgagg gaggaggcca cctctccaag ggcttctgca ccctccaccc    3060
tgtcccccag ctctggtgag tcttggcggc agcagccatc ataggaaggg accaaggcaa    3120
ggcaggtgcc tccaggtgtg cacgtggcat gtggcctgtg gcctgtgtcc catgacccac    3180
ccctgtgctc cgtgcctcca ccaccactgg ccaccaggct ggcgcagcca aggccgaagc    3240
tctggctgaa ccctgtgctg gtgtcctgac caccctcccc tctcttgcac ccgcctctcc    3300
cgtcagggcc caagtccctg ttttctgagc ccgggctgcc tgggctgttg gcactcacag    3360
acctggagcc cctgggtggg tggtggggag gggcgctggc ccagccggcc tctctggcct    3420
cccacccgat gctgctttcc cctgtgggga tctcagggc tgtttgagga tatatttca    3480 ctttgtgatt atttcacttt agatgctgat gatttgtttt tgtatttta atgggggtag    3540 cagctggact acccacgttc tcacacccac cgtccgccct gctcctccct ggctgccctg    3600
gccctgaggt gtggggctg cagcatgttg ctgaggagtg aggaatagtt gagccccaag    3660
tcctgaagag gcgggccagc caggcgggct caaggaaagg gggtcccagt gggagggca    3720 ggctgacatc tgtgtttcaa gtggggctcg ccatgccggg ggttcatagg tcactggctc    3780
tccaagtgcc agaggtgggc aggtggtggc actgagcccc cccaacactg tgccctggtg    3840
gagaaagcac tgacctgtca tgccccctc aaacctcctc ttctgacgtg cctttgcac    3900 ccctcccatt aggacaatca gtcccctccc atctgggagt cccttttct tttctaccct    3960 agccattcct ggtacccagc catctgccca ggggtgcccc ctcctctccc atcccctgc    4020 cctcgtggcc agcccggctg gttttgtaag atgctgggtt ggtgcacagt gattttttc    4080 ttgtaattta aacaggccca gcattgctgg ttctatttaa tggacatgag ataatgttag    4140
aggttttaaa gtgattaaac gtgcagacta tgcaaaccag                         4180

<210> SEQ ID NO 2
<211> LENGTH: 203
<212> TYPE: RNA
<213> ORGANISM: Artificial Sequence
```

<220> FEATURE:
<223> OTHER INFORMATION: Description of Artificial Sequence: Synthetic
      polynucleotide

<400> SEQUENCE: 2

| | | | | | |
|---|---|---|---|---|---|
| ggauccugcu | guugacagug | agcgcggaga | aaggagugaa | accuuaguga | agccacagau | 60 |
| guaagguuuc | acuccuuucu | ccuugccuac | ugccucggag | uccugcuguu | gacagugagc | 120 |
| gcggagaaag | auaugaaacc | uuagugaagc | cacagaugua | agguuucacu | ccuuucuccu | 180 |
| ugccuacugc | cucggaagcu | uug | | | | 203 |

<210> SEQ ID NO 3
<211> LENGTH: 5140
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

| | | | | | |
|---|---|---|---|---|---|
| ggccattgca | tacgttgtat | ccatatcata | atatgtacat | ttatattggc | tcatgtccaa | 60 |
| cattaccgcc | atgttgacat | tgattattga | ctagttatta | atagtaatca | attacggggt | 120 |
| cattagttca | tagcccatat | atggagttcc | gcgttacata | acttacggta | aatggcccgc | 180 |
| ctggctgacc | gcccaacgac | ccccgcccat | tgacgtcaat | aatgacgtat | gttcccatag | 240 |
| taacgccaat | agggactttc | cattgacgtc | aatgggtgga | gtatttacgg | taaactgccc | 300 |
| acttggcagt | acatcaagtg | tatcatatgc | caagtacgcc | ccctattgac | gtcaatgacg | 360 |
| gtaaatggcc | cgcctggcat | tatgcccagt | acatgacctt | atgggacttt | cctacttggc | 420 |
| agtacatcta | cgtattagtc | atcgctatta | ccatggtgat | gcggttttgg | cagtacatca | 480 |
| atgggcgtgg | atagcggttt | gactcacggg | gatttccaag | tctccacccc | attgacgtca | 540 |
| atgggagttt | gttttggcac | caaaatcaac | gggactttcc | aaaatgtcgt | aacaactccg | 600 |
| ccccattgac | gcaaatgggc | ggtaggcgtg | tacggtggga | ggtctatata | agcagagctc | 660 |
| gtttagtgaa | ccgtcagatc | gcctggagac | gccatccacg | ctgttttgac | ctccatagaa | 720 |
| gacaccggga | ccgatccagc | ctccgcggcc | gggaacggtg | cattggaacg | cggattcccc | 780 |
| gtgccaagag | tgacgtaagt | accgcctata | gactctatag | gcacacccct | ttggctctta | 840 |
| tgcatgctat | actgttttg | gctgggggcc | tatacacccc | cgcttcctta | tgctataggt | 900 |
| gatggtatag | cttagcctat | aggtgtgggt | tattgaccat | tattgaccac | tccaacggtg | 960 |
| gagggcagtg | tagtctgagc | agtactcgtt | gctgccgcgc | gcgccaccag | acataatagc | 1020 |
| tgacagacta | acagactgtt | cctttccatg | ggtcttttct | gcagtcaccg | tcgtcgacgg | 1080 |
| tatcgataag | cttgatatcg | aattccgctg | gaggatgtgg | ctgcagagcc | tgctgctctt | 1140 |
| gggcactgtg | gcctgcagca | tctctgcacc | cgcccgctcg | cccagcccca | gcacgcagcc | 1200 |
| ctgggagcat | gtgaatgcca | tccaggaggc | ccggcgtctc | ctgaacctga | gtagagacac | 1260 |
| tgctgctgag | atgaatgaaa | cagtagaagt | catctcagaa | atgtttgacc | tccaggagcc | 1320 |
| gacctgccta | cagacccgcc | tggagctgta | caagcagggc | ctgcggggca | gcctcaccaa | 1380 |
| gctcaagggc | cccttgacca | tgatggccag | ccactacaag | cagcactgcc | ctccaacccc | 1440 |
| ggaaacttcc | tgtgcaaccc | agactatcac | ctttgaaagt | ttcaaagaga | acctgaagga | 1500 |
| ctttctgctt | gtcatcccct | ttgactgctg | ggagccagtc | caggagtgag | accggccaga | 1560 |
| tgaggctggc | caagccgggg | agctgctctc | tcatgaaaca | agagctagaa | actcaggatg | 1620 |

-continued

```
gtcatcttgg agggaccaag gggtgggcca cagccatggt gggagtggcc tggacctgcc    1680
ctgggccaca ctgaccctga tacaggcatg cagaagaat gggaatattt tatactgaca    1740
gaaatcagta atatttatat atttatattt ttaaaatatt tatttattta tttatttaag   1800
ttcatattcc atatttattc aagatgtttt accgtaataa ttattattaa aaatatgctt   1860
ctaaaaaaaa aaaaaaaaa aaaaacggaa ttcacgtggg cccggtaccg tatactctag   1920
aagatctggc agcggagagg gcagaggaag tcttctaaca tgcggtgacg tggaggagaa   1980
tcccggccct aggatgtcta gagcggccgc ggatcctgct gttgacagtg agcgcggaga   2040
aaggagtgaa accttagtga agccacagat gtaaggtttc actcctttct ccttgcctac   2100
tgcctcggaa gcagctcact acattactca gctgttgaca gtgagcgcgg agaaagatat   2160
gaaaccttag tgaagccaca gatgtaaggt ttcactcctt tctccttgcc tactgcctcg   2220
gaagcttaat aaaggatctt ttattttcat tggatccaga tcttttttccc tctgccaaaa   2280
attatgggga catcatgaag ccccttgagc atctgacttc tggctaataa aggaaattta   2340
ttttcattgc aatagtgtgt tggaattttt tgtgtctctc actcggaagg acatatggga   2400
gggcaaatca tttaaaacat cagaatgagt atttggttta gagtttggca acatatgccc   2460
attcttccgc ttcctcgctc actgactcgc tgcgctcggt cgttcggctg cggcgagcgg   2520
tatcagctca ctcaaaggcg gtaatacggt tatccacaga atcaggggat aacgcaggaa   2580
agaacatgtg agcaaaaggc cagcaaaagg ccaggaaccg taaaaaggcc gcgttgctgg   2640
cgttttttcca taggctccgc ccccctgacg agcatcacaa aaatcgacgc tcaagtcaga   2700
ggtggcgaaa cccgacagga ctataaagat accaggcgtt tccccctgga agctccctcg   2760
tgcgctctcc tgttccgacc ctgccgctta ccggatacct gtccgccttt ctcccttcgg   2820
gaagcgtggc gctttctcat agctcacgct gtaggtatct cagttcggtg taggtcgttc   2880
gctccaagct gggctgtgtg cacgaacccc ccgttcagcc cgaccgctgc gccttatccg   2940
gtaactatcg tcttgagtcc aacccggtaa gacacgactt atcgccactg gcagcagcca   3000
ctggtaacag gattagcaga gcgaggtatg taggcggtgc tacagagttc ttgaagtggt   3060
ggcctaacta cggctacact agaagaacag tatttggtat ctgcgctctg ctgaagccag   3120
ttaccttcgg aaaaagagtt ggtagctctt gatccggcaa acaaaccacc gctggtagcg   3180
gtggtttttt tgtttgcaag cagcagatta cgcgcagaaa aaaaggatct caagaagatc   3240
ctttgatctt ttctacgggg tctgacgctc agtggaacga aaactcacgt taagggattt   3300
tggtcatgag attatcaaaa aggatcttca cctagatcct tttaaattaa aaatgaagtt   3360
ttaaatcaat ctaaagtata tatgagtaaa cttggtctga cagttaccaa tgcttaatca   3420
gtgaggcacc tatctcagcg atctgtctat ttcgttcatc catagttgcc tgactcgggg   3480
ggggggggcg ctgaggtctg cctcgtgaag aaggtgttgc tgactcatac caggcctgaa   3540
tcgccccatc atccagccag aaagtgaggg agccacggtt gatgagagct tgttgtagg    3600
tggaccagtt ggtgattttg aacttttgct ttgccacgga acggtctgcg ttgtcggaa    3660
gatgcgtgat ctgatccttc aactcagcaa aagttcgatt tattcaacaa agccgccgtc   3720
ccgtcaagtc agcgtaatgc tctgccagtg ttacaaccaa ttaaccaatt ctgattagaa   3780
aaactcatcg agcatcaaat gaaactgcaa tttattcata tcaggattat caataccata   3840
tttttgaaaa agccgtttct gtaatgaagg agaaaactca ccgaggcagt tccataggat   3900
ggcaagatcc tggtatcggt ctgcgattcc gactcgtcca acatcaatac aacctattaa   3960
tttcccctcg tcaaaaataa ggttatcaag tgagaaatca ccatgagtga cgactgaatc   4020
```

```
cggtgagaat ggcaaaagct tatgcatttc tttccagact tgttcaacag gccagccatt    4080
acgctcgtca tcaaaatcac tcgcatcaac caaaccgtta ttcattcgtg attgcgcctg    4140
agcgagacga aatacgcgat cgctgttaaa aggacaatta caaacaggaa tcgaatgcaa    4200
ccggcgcagg aacactgcca gcgcatcaac aatattttca cctgaatcag gatattcttc    4260
taatacctgg aatgctgttt tcccggggat cgcagtggtg agtaaccatg catcatcagg    4320
agtacggata aaatgcttga tggtcggaag aggcataaat tccgtcagcc agtttagtct    4380
gaccatctca tctgtaacat cattggcaac gctacctttg ccatgtttca gaaacaactc    4440
tggcgcatcg ggcttcccat acaatcgata gattgtcgca cctgattgcc cgacattatc    4500
gcgagcccat ttatacccat ataaatcagc atccatgttg gaatttaatc gcggcctcga    4560
gcaagacgtt tcccgttgaa tatggctcat acaccccctt gtattactgt ttatgtaagc    4620
agacagtttt attgttcatg atgatatatt tttatcttgt gcaatgtaac atcagagatt    4680
ttgagacaca acgtggcttt cccccccccc ccattattga agcatttatc agggttattg    4740
tctcatgagc ggatacatat ttgaatgtat ttagaaaaat aaacaaatag gggttccgcg    4800
cacatttccc cgaaaagtgc cacctgacgt ctaagaaacc attattatca tgacattaac    4860
ctataaaaat aggcgtatca cgaggccctt tcgtctcgcg cgtttcggtg atgacggtga    4920
aaacctctga cacatgcagc tcccggagac ggtcacagct tgtctgtaag cggatgccgg    4980
gagcagacaa gcccgtcagg gcgcgtcagc gggtgttggc gggtgtcggg gctggcttaa    5040
ctatgcggca tcagagcaga ttgtactgag agtgcaccat atgcggtgtg aaataccgca    5100
cagatgcgta aggagaaaat accgcatcag attggctatt                          5140

<210> SEQ ID NO 4
<211> LENGTH: 245
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 4
gauccugcug uugacaguga gcgcggagaa aggagugaaa ccuuagugaa gccacagaug     60
uaagguuuca cuccuuucuc cuugccuacu gccucggaag cagcucacua cauuacucag    120
cuguugacag ugagcgcgga gaagauaug aaaccuuagu gaagccacag auguaagguu    180
ucacuccuuu cuccuugccu acugccucgg aagcuuaaua aaggaucuuu uauuuucauu    240
ggauc                                                                245

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
ggagaaagga gugaaaccuu a                                               21

<210> SEQ ID NO 6
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 6
uaagguuuca cuccuuucuc c                                              21

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
ggagaaagau augaaaccuu a                                              21

<210> SEQ ID NO 8
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
gugaagccac agaug                                                     15

<210> SEQ ID NO 9
<211> LENGTH: 222
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 9
gauccugcug uugacaguga gcgcggagaa aggagugaaa ccuugugaag ccacagaugu     60
aagguuucac uccuuucucc uugccuacug ccucggaagc agcucacuac auuacucagc    120
uguugacagu gagcgcggag aaagauauga aaccuuagag aagccacaga uguaagguuu    180
cacuccuuuc uccuugccua cugccucgga agcuuaauaa ag                      222

<210> SEQ ID NO 10
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
atgtggctgc agagcctgct gctcttgggc actgtggcct gcagcatctc tgcacccgcc     60
cgctcgccca gccccagcac gcagccctgg gagcatgtga atgccatcca ggaggcccgg    120
cgtctcctga acctgagtag agacactgct gctgagatga atgaaacagt agaagtcatc    180
tcagaaatgt ttgacctcca ggagccgacc tgcctacaga cccgcctgga gctgtacaag    240
cagggcctgc ggggcagcct caccaagctc aagggcccct tgaccatgat ggccagccac    300
tacaagcagc actgccctcc aaccccggaa acttcctgtg caacccagac tatcaccttt    360
gaaagtttca agagaaccct gaaggacttt ctgcttgtca tccccttga ctgctgggag    420 ccagtccagg agtgagaccg gccagatgag gctggccaag ccggggagct gctctctcat    480
```

```
gaaacaagag ctagaaactc aggatggtca tcttggaggg accaaggggt gggccacagc    540
catggtggga gtggcctgga cctgccctgg gccacactga ccctgataca ggcatggcag    600
aagaatggga atattttata ctgacagaaa tcagtaatat ttatatattt atatttttaa    660
aatatttatt tatttattta tttaagttca tattccatat ttattcaaga tgttttaccg    720
taataattat tattaaaaat atgcttctaa                                     750
```

```
<210> SEQ ID NO 11
<211> LENGTH: 245
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
gatcctgctg ttgacagtga gcgcggagaa aggagtgaaa ccttagtgaa gccacagatg     60
taaggtttca ctcctttctc cttgcctact gcctcggaag cagctcacta cattactcag    120
ctgttgacag tgagcgcgga gaaagatatg aaaccttagt gaagccacag atgtaaggtt    180
tcactccttt ctccttgcct actgcctcgg aagcttaata aaggatcttt tattttcatt    240
ggatc                                                                245
```

```
<210> SEQ ID NO 12
<211> LENGTH: 223
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 12
gauccugcug uugacaguga gcgcggagaa aggagugaaa ccuuagugaa gccacagaug     60
uaagguuuca cuccuuucuc cuugccuacu gccucggaag cagcucacua cauuacucag    120
cuguugacag ugagcgcgga gaaagauaug aaaccuuagu gaagccacag auguaagguu    180
ucacuccuuu cuccuugccu acugccucgg aagcuuaaua aag                      223
```

METHODS FOR TREATING CANCERS

CROSS-REFERENCES TO RELATED APPLICATIONS

This application is a continuation of PCT/US2021/013130, filed Jan. 12, 2021, which claims priority to and the benefit of U.S. Provisional Application No. 62/960,583, filed Jan. 13, 2020; U.S. Provisional Application No. 63/034,868, filed on Jun. 4, 2020; and U.S. Provisional Application No. 63/061,634, filed on Aug. 5, 2020. All of the aforementioned applications are herein incorporated by reference for all purposes.

SEQUENCE LISTING

The instant application contains a Sequence Listing which has been submitted electronically in ASCII format and is hereby incorporated by reference in its entirety. Said ASCII copy, created on Jul. 30, 2021, is named 097999-1233545_SL.txt and is 17,451 bytes in size.

BACKGROUND

Ovarian cancer has a high lethality among female malignancies. The high lethality results from chemoresistance and frequent recurrence of ovarian carcinoma. Although agents have been developed to treat ovarian carcinoma, the mortality and rate of recurrence of ovarian carcinoma remain high. Typically, treatment for advanced ovarian carcinoma is based on the combination of surgery and chemotherapy. Surgery is followed by adjuvant platinum based chemotherapy. The two most important prognostic factors for patients with advanced ovarian carcinoma are the amount of residual disease left after surgery and the response to platinum based chemotherapy.

BRIEF SUMMARY

Disclosed herein are methods of treating a cancer in an individual in need thereof, the method comprising administering to the individual an expression vector comprising: a. a first insert comprising a nucleic acid sequence encoding a Granulocyte Macrophage Colony Stimulating Factor (GM-CSF) sequence; and b. a second insert comprising two stem-loop structures each with a miR-30a loop; the first stem-loop structure has complete complementary guiding strand and passenger strand, while the second stem-loop structure has three basepair (bp) mismatches at positions 9 to 11 of the passenger strand, wherein the individual is homologous recombination deficiency (HRD)-negative, and/or wherein the individual has a wild-type BRCA1 gene, a wild-type BRCA2 gene, or a combination thereof.

In some embodiments, the guiding strand in the first stem-loop structure comprises the sequence of SEQ ID NO:6 and the passenger strand in the first stem-loop structure has the sequence of SEQ ID NO:5.

In some embodiments, the guiding strand in the second stem-loop structure comprises the sequence of SEQ ID NO:6 and the passenger strand in the second stem-loop structure has the sequence of SEQ ID NO:7.

In some embodiments, the miR-30a loop comprises the sequence of SEQ ID NO:8.

Disclosed herein, in certain embodiments, are methods of treating a cancer in an individual in need thereof, the method comprising administering to the individual an autologous tumor cell transfected with an expression vector comprising: a. first insert comprising a nucleic acid sequence encoding a Granulocyte Macrophage Colony Stimulating Factor (GM-CSF) sequence; and b. a second insert comprising a sequence according to SEQ ID NO:2 or 4 (SEQ ID NO:4).

In some embodiments, the individual is homologous recombination deficiency (HRD)-negative. In some embodiments, the individual has been substantially eradicated of ovarian cancer and the method prevents or delays relapse or return of the substantially eradicated ovarian cancer. The term "relapse" is used interchangeably with "recurrence."

Disclosed herein, in certain embodiments, are methods of preventing recurrence or prophylactically treating recurrence of a substantially eradicated ovarian cancer in an individual in need thereof, the method comprising administering to the individual an autologous tumor cell transfected with an expression vector comprising: (a) a first insert comprising a nucleic acid sequence encoding a Granulocyte Macrophage Colony Stimulating Factor (GM-CSF) sequence; and (b) a second insert comprising a sequence according to SEQ ID: 2 or 4 (SEQ ID NO:4). In some embodiments, the substantially eradicated ovarian cancer is Stage III or Stage IV ovarian cancer. In some embodiments, the individual comprises a wild-type BRCA1 gene, a wild-type BRCA2 gene, or a combination thereof. In some embodiments, a recurrence free survival (RFS) of the individual is increased relative to an individual with substantially eradicated ovarian cancer who has not been administered the transfected tumor cell.

In some embodiments, the individual received an initial therapy. In some embodiments, the initial therapy comprises debulking surgery, chemotherapy, or the combination thereof. In some embodiments, the chemotherapy comprises administering a platinum-based drug and a taxane. In some embodiments, the platinum-based drug comprises carboplatin. In some embodiments, the taxane comprises paclitaxel.

In some embodiments, the GM-CSF is a human GM-CSF sequence. In some embodiments, the expression vector further comprises a promoter. In some embodiments, the promoter is a cytomegalovirus (CMV) mammalian promoter. In some embodiments, the expression vector further comprises a CMV enhancer sequence and a CMV intron sequence.

In some embodiments, the first insert and the second insert are operably linked to the promoter. In some embodiments, the expression vector further comprises a nucleic acid sequence encoding a picornaviral 2A ribosomal skip peptide between the first and the second nucleic acid inserts.

In some embodiments, the autologous tumor cell is administered to the individual as a dose of about $1\times10^6$ cells to about $5\times10^7$ cells. In some embodiments, the autologous tumor cells are administered to the individual once a month. In some embodiments, the autologous tumor cells are administered to the individual from 1 month's time to 12 months' time, such as 1, 2, 3, 4, 5, 6, 7, 8, 9, 10, 11 or 12 months. In some embodiments, the autologous tumor cell is administered to the individual by intradermal injection.

Disclosed herein, in certain embodiments, are methods of treating BRCA1/2 wild type ovarian cancer in an individual in need thereof, the method comprising administering to the individual an autologous tumor cell transfected with an expression vector comprising: (a) a first insert comprising a nucleic acid sequence encoding a Granulocyte Macrophage Colony Stimulating Factor (GM-CSF) sequence; and (b) a second insert comprising a sequence according to SEQ ID NO:2 or 4 (SEQ ID NO:4). In some embodiments, the ovarian cancer is Stage III or Stage IV ovarian cancer. In some embodiments, the ovarian cancer is recurrent ovarian cancer. In some embodiments, the ovarian cancer is refractory ovarian cancer. In some embodiments, the refractory ovarian cancer is refractory to a chemotherapy. In some embodiments, the chemotherapy comprises a platinum-based drug or a taxane. In some embodiments, the platinum-based drug comprises carboplatin. In some embodiments, the taxane comprises paclitaxel. In some embodiments, the ovarian cancer is recurrent/refractory (r/r) ovarian cancer. In some embodiments, recurrent or recurrent/refractory ovarian cancer is referred to as relapsed ovarian cancer.

In some embodiments, the method further comprises administering an additional therapeutic agent. In some embodiments, the additional therapeutic agent is selected from the group consisting of an angiogenesis inhibitor, a PARP inhibitor, and a checkpoint inhibitor to the individual. In some embodiments, the angiogenesis inhibitor is a vascular endothelial growth factor (VEGF) inhibitor. In some embodiments, the VEGF inhibitor is selected from the group consisting of: sorafenib, sunitinib, bevacizumab, pazopanib, axitinib, cabozantinib, and levatinib. In some embodiments, the VEGF inhibitor is bevacizumab. In some embodiments, the PARP inhibitor is selected from the group consisting of niraparib, olaparib, rucaparib, niraparib, talazoparib, veliparib, and pamiparib. In some embodiments, the PARP inhibitor is niraparib. In some embodiments, the checkpoint inhibitor is selected from the group consisting of a PD-1 inhibitor, a PD-L1 inhibitor, and a CTLA-4 inhibitor. In some embodiments, the checkpoint inhibitor is selected from the group consisting of pembrolizumab, nivolumab, cemiplimab, atezolizumab, avelumab, durvalumab, and ipilimumab.

In some embodiments, the GM-CSF is a human GM-CSF sequence. In some embodiments, the expression vector further comprises a promoter. In some embodiments, the promoter is a cytomegalovirus (CMV) mammalian promoter. In some embodiments, the expression vector further comprises a CMV enhancer sequence and a CMV intron sequence. In some embodiments, the first insert and the second insert are operably linked to the promoter. In some embodiments, the expression vector further comprises a nucleic acid sequence encoding a picornaviral 2A ribosomal skip peptide between the first and the second nucleic acid inserts.

In some embodiments, the autologous tumor cell is administered to the individual as a dose of about $1 \times 10^6$ cells to about $5 \times 10^7$ cells. In some embodiments, the autologous tumor cells are administered to the individual once a month. In some embodiments, the autologous tumor cells are administered to the individual from 1 to 12 months. In some embodiments, the autologous tumor cell is administered to the individual by intradermal injection.

Disclosed herein, in certain embodiments, are methods of preventing recurrence or prophylactically treating recurrence of a substantially eradicated ovarian cancer in an individual in need thereof, the method comprising administering to the individual: a. at least one first dose of an autologous tumor cell vaccine comprising autologous tumor cells transfected with an expression vector comprising: i. a first insert comprising a nucleic acid sequence encoding a Granulocyte Macrophage Colony Stimulating Factor (GM-CSF) sequence; and ii. a second insert comprising a sequence according to SEQ ID NO:2 or 4 (SEQ ID NO:4); and b. at least one second dose of the autologous tumor cell vaccine in combination with at least one dose of an additional therapeutic agent. In some embodiments, the substantially eradicated ovarian cancer is Stage III or Stage IV ovarian cancer. In some embodiments, the individual has a wild-type BRCA1 gene, a wild-type BRCA2 gene, or a combination thereof. In some embodiments, a recurrence free survival (RFS) of the individual is increased relative to an individual with substantially eradicated ovarian cancer who has not been administered the transfected tumor cell.

In some embodiments, the individual received an initial therapy. In some embodiments, the initial therapy comprises debulking surgery, chemotherapy, or the combination thereof. In some embodiments, the chemotherapy comprises administering a platinum-based drug and a taxane. In some embodiments, the platinum-based drug comprises carboplatin. In some embodiments, the taxane comprises paclitaxel. In some embodiments, the GM-CSF is a human GM-CSF sequence.

In some embodiments, the expression vector further comprises a promoter. In some embodiments, the promoter is a cytomegalovirus (CMV) mammalian promoter. In some embodiments, the expression vector further comprises a CMV enhancer sequence and a CMV intron sequence. In some embodiments, the first insert and the second insert are operably linked to the promoter. In some embodiments, the expression vector further comprises a nucleic acid sequence encoding a picornaviral 2A ribosomal skip peptide between the first and the second nucleic acid inserts.

In some embodiments, the additional therapeutic agent is selected from the group consisting of an angiogenesis inhibitor, a PARP inhibitor, and a checkpoint inhibitor to the individual. In some embodiments, the angiogenesis inhibitor is a vascular endothelial growth factor (VEGF) inhibitor. In some embodiments, the VEGF inhibitor is selected from the group consisting of: sorafenib, sunitinib, bevacizumab, pazopanib, axitinib, cabozantinib, and levatinib. In some embodiments, the VEGF inhibitor is bevacizumab. In some embodiments, the PARP inhibitor is selected from the group consisting of niraparib, olaparib, rucaparib, niraparib, talazoparib, veliparib, and pamiparib. In some embodiments, the PARP inhibitor is niraparib. In some embodiments, the checkpoint inhibitor is selected from the group consisting of a PD-1 inhibitor, a PD-L1 inhibitor, and a CTLA-4 inhibitor. In some embodiments, the checkpoint inhibitor is selected from the group consisting of pembrolizumab, nivolumab, cemiplimab, atezolizumab, avelumab, durvalumab, and ipilimumab. In some embodiments, the checkpoint inhibitor is atezolizumab.

In some embodiments, the at least one dose for administration of the additional therapeutic agent is from 1100 mg to 1300 mg. In some embodiments, the at least one first dose of the autologous tumor cell vaccine comprises from $1 \times 10^6$ cells to about $5 \times 10^7$ cells. In some embodiments, the at least one second dose of the autologous tumor cell vaccine comprises from $1 \times 10^6$ cells to about $5 \times 10^7$ cells. In some embodiments, the at least one first dose of the autologous tumor cell autologous tumor cell is administered to the individual by intradermal injection. In some embodiments, the at least one second dose of the autologous tumor cell autologous tumor cell is administered to the individual by intradermal injection. In some embodiments, the at least one dose of the additional therapeutic agent is administered via intravenous infusion.

In some embodiments, the at least one first dose of the autologous tumor cell vaccine comprises two doses, such as 2, 3, 4, or 5 doses or more. In some embodiments, each dose of the at least first dose of the autologous tumor cell vaccine is administered to the individual once a month. In some embodiments, each dose of the at least second dose of the autologous tumor cell vaccine is administered to the individual once a month. In some embodiments, each dose of the at least one dose of the additional therapeutic agent is administered to the individual at least once a month. In some embodiments, the at least first dose of the autologous tumor cell vaccine and at least second dose of the autologous tumor cell vaccine comprise a total of at least twelve doses.

Disclosed herein, in certain embodiments, are methods of treating BRCA1/2 wild type ovarian cancer in an individual in need thereof, the method comprising administering to the individual: a. at least one first does of an autologous tumor cell vaccine comprising autologous tumor cells transfected with an expression vector comprising: i. a first insert comprising a nucleic acid sequence encoding a Granulocyte Macrophage Colony Stimulating Factor (GM-CSF) sequence; and ii. a second insert comprising a sequence according to SEQ ID NO:2 or 4 (SEQ ID NO:4); and b. at least one second dose of the autologous tumor cell vaccine in combination with at least one dose of an additional therapeutic agent. In some embodiments, the ovarian cancer is Stage III or Stage IV ovarian cancer. In some embodiments, the ovarian cancer is refractory ovarian cancer. In some embodiments, the refractory ovarian cancer is refractory to a chemotherapy. In some embodiments, the chemotherapy comprises a platinum-based drug or a taxane. In some embodiments, the platinum-based drug comprises carboplatin. In some embodiments, the taxane comprises paclitaxel. In some embodiments, the GM-CSF is a human GM-CSF sequence.

In some embodiments, the expression vector further comprises a promoter. In some embodiments, the promoter is a cytomegalovirus (CMV) mammalian promoter. In some embodiments, the expression vector further comprises a CMV enhancer sequence and a CMV intron sequence. In some embodiments, the first insert and the second insert are operably linked to the promoter. In some embodiments, the expression vector further comprises a nucleic acid sequence encoding a picornaviral 2A ribosomal skip peptide between the first and the second nucleic acid inserts.

In some embodiments, the additional therapeutic agent is selected from the group consisting of an angiogenesis inhibitor, a PARP inhibitor, and a checkpoint inhibitor to the individual. In some embodiments, the angiogenesis inhibitor is a vascular endothelial growth factor (VEGF) inhibitor. In some embodiments, the VEGF inhibitor is selected from the group consisting of: sorafenib, sunitinib, bevacizumab, pazopanib, axitinib, cabozantinib, and levatinib. In some embodiments, the VEGF inhibitor is bevacizumab. In some embodiments, the PARP inhibitor is selected from the group consisting of niraparib, olaparib, rucaparib, niraparib, talazoparib, veliparib, and pamiparib. In some embodiments, the PARP inhibitor is niraparib. In some embodiments, the checkpoint inhibitor is selected from the group consisting of a PD-1 inhibitor, a PD-L1 inhibitor, and a CTLA-4 inhibitor. In some embodiments, the checkpoint inhibitor is selected from the group consisting of pembrolizumab, nivolumab, cemiplimab, atezolizumab, avelumab, durvalumab, and ipilimumab. In some embodiments, the checkpoint inhibitor is atezolizumab.

In some embodiments, the at least one dose of the additional therapeutic agent is from 1100 mg to 1300 mg. In some embodiments, the at least one first dose of the autologous tumor cell vaccine comprises from $1\times10^6$ cells to about $5\times10^7$ cells. In some embodiments, the at least one second dose of the autologous tumor cell vaccine comprises from $1\times10^6$ cells to about $5\times10^7$ cells. In some embodiments, the at least one first dose of the autologous tumor cell autologous tumor cell is administered to the individual by intradermal injection. In some embodiments, the at least one second dose of the autologous tumor cell autologous tumor cell is administered to the individual by intradermal injection. In some embodiments, the at least one dose of the additional therapeutic agent is administered via intravenous infusion.

In some embodiments, the at least one first dose of the autologous tumor cell vaccine comprises two doses. In some embodiments, each dose of the at least first dose of the autologous tumor cell vaccine is administered to the individual once a month. In some embodiments, each dose of the at least second dose of the autologous tumor cell vaccine is administered to the individual once a month. In some embodiments, each dose of the at least one dose of the additional therapeutic agent is administered to the individual at least once a month. In some embodiments, the at least first dose of the autologous tumor cell vaccine and at least second dose of the autologous tumor cell vaccine comprise a total of at least twelve doses.

In some embodiments, the disclosure features a method of treating a cancer in an individual in need thereof, the method comprising administering to the individual an expression vector comprising: a) a first insert comprising a nucleic acid sequence encoding a Granulocyte Macrophage Colony Stimulating Factor (GM-CSF) sequence: and b) a second insert comprising a sequence according to SEQ ID NO:2 or 4 (SEQ ID NO:4), wherein the individual has a wild-type BRCA1 gene, a wild-type BRCA2 gene, or a combination thereof, and is identified as homologous recombination deficiency (HRD)-negative.

In some embodiments, the GM-CSF is a human GM-CSF sequence.

In some embodiments, the expression vector further comprises a promoter. In some embodiments, the promoter is a cytomegalovirus (CMV) mammalian promoter. In some embodiments, the expression vector further comprises a CMV enhancer sequence and a CMV intron sequence. In some embodiments, the first insert and the second insert are operably linked to the promoter. In some embodiments, the expression vector further comprises a nucleic acid sequence encoding a picornaviral 2A ribosomal skip peptide between the first and the second nucleic acid inserts.

In some embodiments, the cancer is an HRD-negative, wild-type BRCA1/2 cancer. In some embodiments, the cancer is selected from the group consisting of a solid tumor cancer, ovarian cancer, adrenocortical carcinoma, bladder cancer, breast cancer, cervical cancer, cholangiocarcinoma, colorectal cancers, esophageal cancer, glioblastoma, glioma, hepatocellular carcinoma, head and neck cancer, kidney cancer, leukemia, lymphoma, lung cancer, melanoma, mesothelioma, multiple myeloma, pancreatic cancer, pheochromocytoma, plasmacytoma, neuroblastoma, prostate cancer, sarcoma, stomach cancer, uterine cancer, thyroid cancer, and a hematological cancer. In particular embodiments, the solid tumor cancer is selected from the group consisting of endometrial cancer, biliary cancer, bladder cancer, liver hepatocellular carcinoma, gastric/esophageal cancer, ovarian cancer, melanoma, breast cancer, pancreatic cancer, colorectal cancer, glioma, non-small-cell lung carcinoma, prostate cancer, cervical cancer, kidney cancer, thyroid cancer, a neuroendocrine cancer, small cell lung cancer, a sarcoma, head and neck cancer, brain cancer, clear cell renal cell carcinoma, skin cancer, endocrine tumor, thyroid cancer, tumor of unknown origin, and a gastrointestinal stromal tumor. In certain embodiments, the cancer is ovarian cancer.

In some embodiments, the method prevents or delays relapse of a substantially eradicated ovarian cancer. In particular embodiments, the substantially eradicated ovarian cancer is Stage III or Stage IV ovarian cancer. In some embodiments, the cancer is breast cancer. In some embodiments, the cancer is melanoma. In some embodiments, the cancer is lung cancer.

In some embodiments, the expression vector is within an autologous cancer cell that is transfected with the expression vector. In particular embodiments, the autologous cancer cell is administered to the individual as a dose of about $1 \times 10^6$ cells to about $5 \times 10^7$ cells. In some embodiments, the autologous cancer cells are administered to the individual once a month. In some embodiments, the autologous cancer cells are administered to the individual from 1 to 12 months. In some embodiments, the autologous cancer cell is administered to the individual by intradermal injection.

In some embodiments, the individual received an initial therapy. In particular embodiments, the initial therapy comprises debulking surgery, chemotherapy, or the combination thereof. In certain embodiments, the chemotherapy comprises administering a platinum-based drug and a taxane. In certain embodiments, the platinum-based drug comprises carboplatin. In some embodiments, the taxane comprises paclitaxel.

In some embodiments, the method further comprises administering an additional therapeutic agent. In certain embodiments, the additional therapeutic agent is a member selected from the group consisting of an angiogenesis inhibitor, a PARP inhibitor, and a checkpoint inhibitor to the individual.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1 is a schematic showing the bi-shRNAfurin comprising two stemloop structures each with a miR-30a loop; the first stem-loop structure has complete complementary guiding strand and passenger strand, while the second stem-loop structure has three basepair (bp) mismatches at positions 9 to 11 of the passenger strand. FIG. 1 discloses SEQ ID NO: 12.

FIG. 2A illustrates RFS of BRCA1/2 wild type(wt) population from surgery/procurement. FIG. 2B illustrates RFS of BRCA1/2 wild type(wt) population from randomization of Vigil® vs. placebo. FIG. 2C illustrates RFS from surgery/procurement irrespective of BRCA1/2 status. FIG. 2D illustrates RFS from randomization of Vigil® vs. placebo irrespective of BRCA1/2 status. Number at risk refers to the number of patients, in the survival curve, who are still recurrence-free and/or alive and whose follow-up extends at least that far into the curve.

FIG. 3A illustrates the fraction of all recurrent disease between Vigil® (n=24) and placebo (n=24) BRCA1/2-wt patients. FIG. 3B illustrates the fraction of all recurrent disease between Vigil® (n=46) and placebo (n=45) of all n=91 per-protocol patients.

FIG. 6A illustrates RFS of all patients from randomization. FIG. 6B illustrates RFS of all patients from surgery/procurement. FIG. 6C illustrates RFS of BRCA1/2 wild type(wt) population from randomization. FIG. 6D illustrates RFS of BRCA1/2 wild type(wt) population from surgery/procurement. FIG. 6E illustrates OS of BRCA1/2 wild type(wt) population from randomization. FIG. 6F illustrates OS of BRCA1/2 wild type (wt) population from surgery/procurement. Number at risk refers to the number of patients, in the survival curve, who are still recurrence-free and/or alive and whose follow-up extends at least that far into the curve.

FIG. 7A illustrates a forest plot for key subgroups of PP with RFS calculated from time of randomization until the first date of documented recurrence or death. FIG. 7B illustrates a forest plot for key subgroups of the BRCA-wt population with RFS calculated from time of randomization until the first date of documented recurrence or death.

FIG. 9A illustrates Overall Survival (OS) of all study subjects in Vigil®-1$^{st}$ (n=11) and Atezo-1$^{st}$ (n=10), median OS (mOS) NR vs 10.8 months, Hazard Ratio (HR) 0.33 (95% CI [0.064-1.7], p=0.097). FIG. 9B illustrates OS of BRCA1/2-wt comparing Vigil®-1$^{st}$ (n=6) and Atezo-1 (n=7), median OS NR vs 5.2 months, HR 0.16 (95% CI [0.026-1.03], p=0.027). FIG. 9C illustrates progression free survival (PFS) of all study subjects in Vigil®-1$^{st}$ (n=11) and Atezo-1$^{st}$ (n=10) investigator-assessed by RECIST1.1, median PFS (mPFS) 3.4 months vs 2.8 months, HR 0.76 (95% CI [0.28-2.0], p=0.29). FIG. 9D illustrates PFS of BRCA1/2-wt comparing Vigil®-1$^{st}$ (n=6) and Atezo-1$^{st}$ (n=7), median PFS 3.5 months vs 2.8 months, HR 0.60 (95% CI [0.16-2.2], p=0.22).

FIG. 10A illustrates RFS of BRCA1/2 wild type(wt) population from surgery/procurement. FIG. 10B illustrates RFS of BRCA1/2 wild type(wt) population from randomization of Vigil® vs. placebo. FIG. 10C illustrates RFS from surgery/procurement irrespective of BRCA1/2 status. FIG. 10D illustrates RFS from randomization of Vigil® vs. placebo irrespective of BRCA1/2 status. Number at risk refers to the number of patients, in the survival curve, who are still recurrence-free and/or alive and whose follow-up extends at least that far into the curve.

FIG. 11A illustrates the fraction of all recurrent disease between Vigil® (n=24) and placebo (n=24) BRCA1/2-wt patients. FIG. 11B illustrates the fraction of all recurrent disease between Vigil® (n=46) and placebo (n=45) of all n=91 per-protocol patients.

FIG. 13 shows the BRCA mutational status and HRD status of individuals receiving placebo and individuals receiving Vigil®.

FIG. 16 shows the BRCA mutational status and HRD status of individuals receiving placebo and individuals receiving Vigil®.

FIG. 27 shows BRCA status, HRD status, and OS of patients receiving Vigil® and other agents.

FIG. 29 shows the relationships among BRCA status, HRD status, and expressions of other proteins.

FIGS. 35A-35F show recurrence-free survival of all patients from randomization (35A) and tissue procurement (35B). Recurrence-free survival of patients with BRCA wild type disease from randomization (35C) and tissue procurement (35D). Overall survival of all patients from randomization (35E) and tissue procurement (35F). HR=hazard ratio.

FIGS. 41A and 41B show relapse free survival of BRCA mutant patients from time of randomization (FIG. 41A) and tissue procurement (FIG. 41B).

DETAILED DESCRIPTION

Figure 2A:
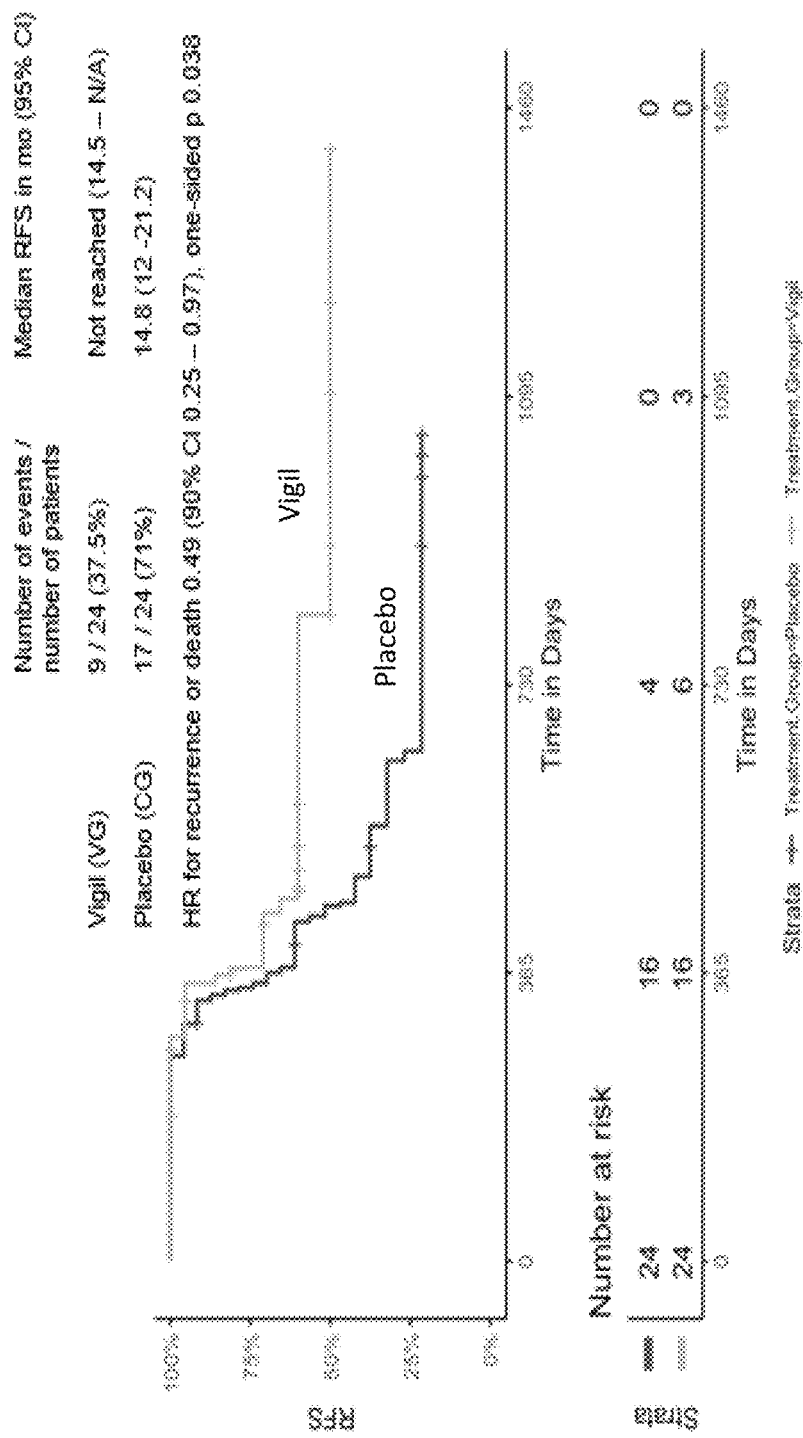
FIGS. 2A-2D illustrate relapse-free survival (RFS) of patients from surgery/procurement or randomization of Vigil® vs. placebo.

The majority of women diagnosed with cancer of the ovary present in an advanced stage. Optimal standard of care will achieve 5-year survival rates that vary by stage from 41% (Stage IIIa) to 20% (Stage IV). Standard of care for newly diagnosed ovarian cancer (Stage III/IV) involves optimal debulking surgery and frontline chemotherapy with paclitaxel and carboplatin. Most patients achieve complete remission, but approximately 75% will relapse, including 70% of those achieving pathologic complete response, within approximately 12 months. A number of studies have attempted to improve outcome in first treated ovarian cancer by administering maintenance therapy after patients achieve complete response following consolidation with paclitaxel and carboplatin, but none have demonstrated significant advantage in relapse free (RFS) or overall survival (OS).

Disclosed herein, in certain embodiments, are methods of treating a cancer in an individual in need thereof, the method comprising administering to the individual an expression vector comprising: a. a first insert comprising a nucleic acid sequence encoding a Granulocyte Macrophage Colony Stimulating Factor (GM-CSF) sequence; and b. a second insert comprising two stem-loop structures each with a miR-30a loop; the first stem-loop structure has complete complementary guiding strand and passenger strand, while the second stem-loop structure has three basepair (bp) mismatches at positions 9 to 11 of the passenger strand, wherein the individual is homologous recombination deficiency (HRD)-negative, and/or wherein the individual has a wild-type BRCA1 gene, a wild-type BRCA2 gene, or a combination thereof. Descriptions of the miR-30a loop and its sequence are known in the art, see, e.g., Rao et al., *Cancer Gene Ther.* 17(11):780-91, 2010; Jay et al., *Cancer Gene Ther.* 20(12):683-9, 2013; Rao et al., *Mol Ther.* 24(8):1412-22, 2016; Phadke et al., *DNA Cell Biol.* 30(9):715-26, 2011; Barve et al., *Mol Ther.* 23(6):1123-1130, 2015; Rao et al., *Methods Mol Biol.* 942:259-78, 2013; and Senzer et al., *Mol Ther.* 20(3):679-86, 2012. In some embodiments, the miR-30a loop comprises the sequence of GUGAAGC-CACAGAUG (SEQ ID NO:8). In some embodiments, the guiding strand in the first stem-loop structure comprises the sequence of SEQ ID NO:6 and the passenger strand in the first stem-loop structure has the sequence of SEQ ID NO:5. In some embodiments, the guiding strand in the second stem-loop structure comprises the sequence of SEQ ID NO:6 and the passenger strand in the second stem-loop structure has the sequence of SEQ ID NO:7.

Disclosed herein, in certain embodiments, are methods of preventing relapse of a substantially eradicated ovarian cancer in an individual in need thereof, the method comprising administering to the individual an autologous tumor cell transfected with an expression vector comprising: a) first insert comprising a nucleic acid sequence encoding a Granulocyte Macrophage Colony Stimulating Factor (GM-CSF) sequence; and b) a second insert comprising a sequence according to SEQ ID NO:2 or 4 (SEQ ID NO:4). Further disclosed herein, in certain embodiments, are methods of treating BRCA1/2 wildtype ovarian cancer in an individual in need thereof, the method comprising administering to the individual an autologous tumor cell transfected with an expression vector comprising: a) first insert comprising a nucleic acid sequence encoding a Granulocyte Macrophage Colony Stimulating Factor (GM-CSF) sequence; and b) a second insert comprising a sequence according to SEQ ID NO:2 or 4 (SEQ ID NO:4).

The majority of women diagnosed with ovarian cancer present in an advanced stage. Optimal standard of care will achieve 5-year survival rates that vary by stage from 41% (Stage IIIa) to 20% (Stage IV). Standard of care for newly diagnosed ovarian cancer (Stage III/IV) involves primary debulking surgery followed by adjuvant chemotherapy with paclitaxel and carboplatin or neoadjuvant chemotherapy with interval debulking surgery. Most patients achieve complete remission, but approximately 75% will relapse within 2 years. A number of studies have attempted to improve outcome in frontline treated ovarian cancer by administering maintenance therapy after patients achieve complete response, but despite benefit in progression free survival (PFS) none have demonstrated significant advantage in RFS or OS and toxicity limits dosing. Poly (ADP-ribose) polymerase (PARP) inhibitors have offered clinical a novel platform for frontline maintenance but activity is predominant to BRCA-m patients. PARP inhibitors are also approved in recurrent platinum-sensitive maintenance regardless of BRCA status; however, the magnitude of benefit is greatest in those patients who are BRCA-m or exhibit homologous recombination deficiency (HRD).

Disclosed herein, in certain embodiments, are methods of preventing recurrence or prophylactically treating recurrence of a substantially eradicated ovarian cancer in an individual in need thereof, the method comprising administering to the individual an autologous tumor cell transfected with an expression vector comprising: a) first insert comprising a nucleic acid sequence encoding a Granulocyte Macrophage Colony Stimulating Factor (GM-CSF) sequence; and b) a second insert comprising a sequence according to SEQ ID NO:2 or 4 (SEQ ID NO:4). Further disclosed herein, in certain embodiments, are methods of treating BRCA1/2 wild type ovarian cancer in an individual in need thereof, the method comprising administering to the individual an autologous tumor cell transfected with an expression vector comprising: a) first insert comprising a nucleic acid sequence encoding a Granulocyte Macrophage Colony Stimulating Factor (GM-CSF) sequence; and b) a second insert comprising a sequence according to SEQ ID NO:2 or 4 (SEQ ID NO:4). In some embodiments, the BRCA1/2 wild type ovarian cancer does not have a germline mutation in a BRCA gene. In some embodiments, the BRCA1/2 wild type ovarian cancer does not have a somatic mutation in a BRCA gene. In some embodiments, the BRCA gene is a BRCA1 gene, a BRCA2 gene, or the BRCA1 and BRCA2 genes.

Disclosed herein, in certain embodiments, are methods of treating a cancer in an individual in need thereof by administering to the individual an expression vector comprising: a) a first insert comprising a nucleic acid sequence encoding a Granulocyte Macrophage Colony Stimulating Factor (GM-CSF) sequence; and b) a second insert comprising a sequence according to SEQ ID NO:2 or 4 (SEQ ID NO:4), in which the individual has a wild-type BRCA1 gene, a wild-type BRCA2 gene, or a combination thereof, and is identified as homologous recombination deficiency (HRD)-negative.

Definitions

Unless defined otherwise, all technical and scientific terms used herein have the same meaning as is commonly understood by one of skill in the art to which the claimed subject matter belongs.

As used herein, ranges and amounts can be expressed as "about" a particular value or range. About also includes the exact amount. Hence "about 5 μg" means "about 5 μg" and also "5 μg." Generally, the term "about" includes an amount that would be expected to be within experimental error. In some embodiments, "about" refers to the number or value recited. "+" or "−" 20%, 10%, or 5% of the number or value.

The terms "effective amount" or "therapeutically effective amount," as used herein, refer to a sufficient amount of an agent or a compound being administered which will relieve to some extent one or more of the symptoms of the disease or condition being treated or prevent the onset or recurrence of the one or more symptoms of the disease or condition being treated. In some embodiments, the result is reduction and/or alleviation of the signs, symptoms, or causes of a disease, or any other desired alteration of a biological system. For example, an "effective amount" for therapeutic uses is the amount of the autologous tumor cell vaccine required to provide a clinically significant decrease in disease symptoms without undue adverse side effects. In another example, an "effective amount" for therapeutic uses is the amount of the autologous tumor cell vaccine as disclosed herein required to prevent a recurrence of disease symptoms without undue adverse side effects. An appropriate "effective amount" in any individual case may be determined using techniques, such as a dose escalation study. The term "therapeutically effective amount" includes, for example, a prophylactically effective amount. An "effective amount" of a compound disclosed herein, is an amount effective to achieve a desired effect or therapeutic improvement without undue adverse side effects. It is understood that, in some embodiments, "an effective amount" or "a therapeutically effective amount" varies from subject to subject, due to variation in metabolism of the autologous tumor cell vaccine, age, weight, general condition of the subject, the condition being treated, the severity of the condition being treated, and the judgment of the prescribing physician.

As used herein, the terms "subject," "individual," and "patient" are used interchangeably. None of the terms are to be interpreted as requiring the supervision of a medical professional (e.g., a doctor, nurse, physician's assistant, orderly, hospice worker). As used herein, the subject is any animal, including mammals (e.g., a human or non-human animal) and non-mammals. In one embodiment of the methods and autologous tumor cell vaccines provided herein, the mammal is a human.

As used herein, the terms "treat," "treating," or "treatment," and other grammatical equivalents, including, but not limited to, alleviating, abating, or ameliorating one or more symptoms of a disease or condition, ameliorating, preventing or reducing the appearance, severity, or frequency of one or more additional symptoms of a disease or condition, ameliorating or preventing the underlying metabolic causes of one or more symptoms of a disease or condition, inhibiting the disease or condition, such as, for example, arresting the development of the disease or condition, relieving the disease or condition, causing regression of the disease or condition, relieving a condition caused by the disease or condition, preventing recurrence or prophylactically treating recurrence of the disease or condition, or inhibiting the symptoms of the disease or condition either prophylactically and/or therapeutically. In a non-limiting example, for prophylactic benefit, an autologous tumor cell vaccine composition disclosed herein is administered to an individual at risk of developing a particular disease or condition, predisposed to developing a particular disease or condition, or to an individual previously suffering from and treated for the disease or condition. In some embodiments, the disease or condition is ovarian cancer.

As used herein, the term "prevention" means a prophylactic treatment performed before the subject suffers from a disease or the disease previously diagnosed is deteriorated, thereby enabling the subject to avoid, prevent or reduce the likelihood of the symptoms or related diseases of the disease. The subject may be a subject with an increased risk of developing a disease or a disease previously diagnosed to be deteriorated.

As used herein, the term "intradermal injection" is superficial injection of a substance into the dermis, which is located between the epidermis and the hypodermis.

As used herein, the term "transfection" refers to the introduction of foreign DNA into eukaryotic cells. In some embodiments, transfection is accomplished by any suitable means, such as for example, calcium phosphate-DNA co-precipitation, DEAE-dextran-mediated transfection, polybrene-mediated transfection, electroporation, microinjection, liposome fusion, lipofection, protoplast fusion, retroviral infection, or biolistics.

As used herein the term "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. In some embodiments, nucleic acid molecules are composed of monomers that are naturally-occurring nucleotides (such as DNA and RNA), or analogs of naturally-occurring nucleotides (e.g., α-enantiomeric forms of naturally-occurring nucleotides), or a combination of both. In some embodiments, modified nucleotides have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, in some embodiments, the entire sugar moiety is replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. In some embodiments, nucleic acid monomers are linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. In some embodiments, the term "nucleic acid" or "nucleic acid molecule" also includes so-called "peptide nucleic acids," which comprise naturally-occurring or modified nucleic acid bases attached to a polyamide backbone. In some embodiments, nucleic acids are single stranded or double stranded.

As used herein, the term "expression vector" refers to nucleic acid molecules encoding a gene that is expressed in a host cell. In some embodiments, an expression vector comprises a transcription promoter, a gene, and a transcription terminator. In some embodiments, gene expression is placed under the control of a promoter, and such a gene is said to be "operably linked to" the promoter. In some embodiments, a regulatory element and a core promoter are operably linked if the regulatory element modulates the activity of the core promoter. As used herein, the term "promoter" refers to any DNA sequence which, when associated with a structural gene in a host yeast cell, increases, for that structural gene, one or more of 1) transcription, 2) translation or 3) mRNA stability, compared to transcription, translation or mRNA stability (longer half-life of mRNA) in the absence of the promoter sequence, under appropriate growth conditions.

As used herein the term "bi-functional" refers to a shRNA having two mechanistic pathways of action, that of the siRNA and that of the miRNA. The term "traditional" shRNA refers to a DNA transcription derived RNA acting by the siRNA mechanism of action. The term "doublet" shRNA refers to two shRNAs, each acting against the expression of two different genes but in the "traditional" siRNA mode.

The additional therapeutic agent can be from 1100 mg to 1300 mg such as 1100, 1125, 1150, 1175, 1200, 1225, 1250, 1275, or 1300 mg.

The autologous tumor cell vaccine comprises from $1\times10^6$ cells to about $5\times10^7$ cells such as $1\times10^6$ cells, $2\times10^6$ cells, $3\times10^6$ cells, $4\times10^6$ cells, $5\times10^6$ cells, $6\times10^6$ cells, $7\times10^6$ cells, $8\times10^6$ cells $9\times10^6$ cells, $1\times10^7$ cells, $2\times10^7$ cells, $3\times10^7$ cells, $4\times10^7$ cells, or $5\times10^7$ Stage III ovarian cancer means that the cancer is found in one or both ovaries and has spread outside the pelvis to other parts of the abdomen and/or nearby lymph nodes. It is also considered Stage III ovarian cancer when it has spread to the surface of the liver. In Stage IV ovarian cancer, the cancer has spread beyond the abdomen to other parts of the body, such as the lungs or tissue inside the liver. Cancer cells in the fluid around the lungs is also considered Stage IV ovarian cancer.

Methods of Treating Ovarian Cancer

Disclosed herein, in certain embodiments, are methods of preventing recurrence or prophylactically treating recurrence of a substantially eradicated ovarian cancer in an individual in need thereof, the method comprising administering to the individual an autologous tumor cell vaccine comprising autologous tumor cells transfected with an expression vector comprising a first nucleic acid encoding Granulocyte Macrophage Colony Stimulating Factor (GM-CSF) and a second nucleic acid encoding at least one short hairpin RNA (shRNA) capable of hybridizing to a region of an mRNA transcript encoding furin, thereby inhibiting furin expression via RNA interference. Further disclosed herein, in certain embodiments, are methods of treating BRCA1/2 wild type ovarian cancer in an individual in need thereof, the method comprising administering to the individual an autologous tumor cell vaccine comprising autologous tumor cells transfected with an expression vector comprising a first nucleic acid encoding Granulocyte Macrophage Colony Stimulating Factor (GM-CSF) and a second nucleic acid encoding at least one short hairpin RNA (shRNA) capable of hybridizing to a region of an mRNA transcript encoding furin, thereby inhibiting furin expression via RNA interference. In some embodiments, the second nucleic acid comprises a sequence according to SEQ ID NO:2 or 4 (SEQ ID NO:4). In some embodiments, the expression vector is a bishRNA$^{furin}$/GMCSF expression vector. In some embodiments, inhibition of furin expression inhibits the expression of transforming growth factor beta (TGFβ). In some embodiments, TGFβ comprises TGF-β isoforms: TGFβ1 and TGFβ2.

Further disclosed herein, in certain embodiments, are methods of preventing recurrence or prophylactically treating recurrence of a substantially eradicated ovarian cancer in an individual in need thereof, the method comprising administering to the individual: (a) at least one first dose of an autologous tumor cell vaccine comprising autologous tumor cells transfected with an expression vector comprising (i) a first nucleic acid encoding Granulocyte Macrophage Colony Stimulating Factor (GM-CSF) and (ii) a second nucleic acid encoding at least one short hairpin RNA (shRNA) capable of hybridizing to a region of an mRNA transcript encoding furin, thereby inhibiting furin expression via RNA interference; and (b) at least one second dose of the autologous tumor cell vaccine in combination with at least one dose of an additional therapeutic agent. Further disclosed herein, in certain embodiments, are methods of treating BRCA1/2 wild type ovarian cancer in an individual in need thereof, the method comprising administering to the individual: (a) at least one first dose of an autologous tumor cell vaccine comprising autologous tumor cells transfected with an expression vector comprising (i) a first nucleic acid encoding Granulocyte Macrophage Colony Stimulating Factor (GM-CSF) and (i) a second nucleic acid encoding at least one short hairpin RNA (shRNA) capable of hybridizing to a region of an mRNA transcript encoding furin, thereby inhibiting furin expression via RNA interference; and (b) at least one second dose of the autologous tumor cell vaccine in combination with at least one dose of an additional therapeutic agent.

In some embodiments, the second nucleic acid comprises a sequence according to SEQ ID NO:2 or 4 (SEQ ID NO:4). In some embodiments, the expression vector is a bishRNA-$^{furin}$/GMCSF expression vector. In some embodiments, inhibition of furin expression inhibits the expression of transforming growth factor beta (TGFβ). In some embodiments, TGFβ comprises TGF-β isoforms: TGFβ1 and TGFβ2.

Disclosed herein, in certain embodiments, are methods of treating a cancer in an individual in need thereof by administering to the individual an expression vector comprising: a) a first insert comprising a nucleic acid sequence encoding a Granulocyte Macrophage Colony Stimulating Factor (GM-CSF) sequence; and b) a second insert comprising a sequence according to SEQ ID NO:2 or 4 (SEQ ID NO:4), in which the individual has a wild-type BRCA1 gene, a wild-type BRCA2 gene, or a combination thereof, and is identified as homologous recombination deficiency (HRD)-negative.

Homologous recombination (HR) is a mechanism cells employs to repair double-stranded DNA breaks using a homologous template. HR deficiency may affect DNA repair. However, when only HR is deficient, the activities of other DNA repair mechanisms can prohibit the accumulation of excessive DNA damage and apoptosis. As used herein, the term "homologous recombination deficiency-positive," "HRD-positive," and "HRD" are used interchangeably and they refer to the status that HR is deficient. Conversely, the term "homologous recombination deficiency negative," "HRD-negative," "homologous recombination proficient," and "HRP" are used interchangeably, and they refer to the status that HR is not deficient.

In some embodiments, the HRD can be evaluated by screening germline or somatic mutations of genes related to HR repair. For example, DNA from blood or other tissues can be analyzed by next generation sequencing.

In some embodiments, to characterize whether an individual is HRD-positive or HRD-negative, an HRD score can be determined. In some embodiments, an HRD score can be calculated based on scores for the loss of heterozygosity (LOH), telomeric allelic imbalance (TAI), and large-scale state transitions (LSTs). In some embodiments, the LOH is indicated by the presence of a single allele. In some embodiments, the LOH is defined as the number of chromosomal loss of heterozygosity regions longer than 15 Mb. In some embodiments, the TAI is indicated by a discrepancy in the 1 to 1 allele ratio at the end of the chromosome. In some embodiments, the LSTs are indicated by transition points between regions of abnormal and normal DNA or between two different regions of abnormality. In some embodiments, the LSTs are defined as the number of break points between regions longer than 10 Mb after filtering out regions shorter than 3 Mb. In certain embodiments, the HRD score is calculated as the sum of the LOH, TAI, and LST scores. Methods of determining an HRD score is available in the art, e.g., as described in Takaya et al., *Sci Rep.* 10(1):2757, 2020, Telli et al., *Clin Cancer Res* 22(15):3764-73, 2016, and Marchetti and McNeish, *Cancer Breaking News* 5(1):15-20, 2017. Further, commercial services for HRD score determination are also available, for example, services provided by Ambry Genetics, Caris Life Sciences, Counsylgenetic, Foundation Medicine, GeneDX, Integrated Genetics, Invitae, Myriad Genetics, and Neogenomics.

In methods described herein, an individual has a wild-type BRCA1 gene, a wild-type BRCA2 gene, or a combination thereof. In some embodiments, an individual having a wild-type BRCA1 gene, a wild-type BRCA2 gene, or a combination thereof can be HRD-negative or HRD-positive. In other embodiments, a mutation in the BRCA1/2 gene can lead to HRD. In other words, a mutation in the BRCA1/2 gene can lead to an individual having a HRD-positive status. In particular embodiments, an individual identified as having an HRD-positive status has an HRD score of 42 or greater (e.g., 42, 43, 44, 45, 46, 47, 48, 49, 50, 51, 52, 53, 54, 55, 56, 57, 58, 59, 60, or greater). Other mechanisms, such as germline and somatic mutations in other homologous recombination genes and epigenetic modifications, may also be implicated in homologous recombination.

Expression Vector

In some embodiments, the at least one shRNA is at least one bifunctional shRNA (bi-shRNA). In some embodiments, the bi-shRNA comprises a first stem-loop structure that comprises an siRNA component and a second stem-loop structure that comprises a miRNA component. In some embodiments, the bi-functional shRNA has two mechanistic pathways of action, that of the siRNA and that of the miRNA. Thus, in some embodiments, the bi-functional shRNA described herein is different from a traditional shRNA, i.e., a DNA transcription derived RNA acting by the siRNA mechanism of action or from a "doublet shRNA" that refers to two shRNAs, each acting against the expression of two different genes but in the traditional siRNA mode. In some embodiments, the bi-shRNA incorporates siRNA (cleavage dependent) and miRNA (cleavage-independent) motifs.

In some embodiments, the GM-CSF in the expression vector is a human GM-CSF sequence. In some embodiments, the expression vector further comprises a promoter, e.g., the promoter is a cytomegalovirus (CMV) mammalian promoter. In some embodiments, the mammalian CMV promoter comprises a CMV immediate early (IE) 5' UTR enhancer sequence and a CMV IE Intron A. In further embodiments, the expression vector further comprises a CMV enhancer sequence and a CMV intron sequence.

The first insert and the second insert in the expression vector can be operably linked to the promoter. In particular embodiments, the expression vector further comprises a nucleic acid sequence encoding a picornaviral 2A ribosomal skip peptide between the first and the second nucleic acid inserts.

In some embodiments, the expression vector comprises at least one bifunctional shRNA (bi-shRNA). In some embodiments, the bi-shRNA comprises a first stem-loop structure that comprises an siRNA component and a second stem-loop structure that comprises a miRNA component. In some embodiments, the bi-functional shRNA has two mechanistic pathways of action, that of the siRNA and that of the miRNA. Thus, in some embodiments, the bi-functional shRNA described herein is different from a traditional shRNA, i.e., a DNA transcription derived RNA acting by the siRNA mechanism of action or from a "doublet shRNA" that refers to two shRNAs, each acting against the expression of two different genes but in the traditional siRNA mode. In some embodiments, the bi-shRNA incorporates siRNA (cleavage dependent) and miRNA (cleavage-independent) motifs.

In some embodiments, the at least one bi-shRNA is capable of hybridizing to one of more regions of an mRNA transcript encoding furin. In some embodiments, the mRNA transcript encoding furin is a nucleic acid sequence of SEQ ID NO:1. In some embodiments, the one or more regions of the mRNA transcript encoding furin is selected from base sequences 300-318.731-740, 1967-1991, 2425-2444, 2827-2851 and 2834-2852 of SEQ ID NO:1. In some embodiments, the expression vector targets the coding region of the furin mRNA transcript, the 3' UTR region sequence of the furin mRNA transcript, or both the coding sequence and the 3' UTR sequence of the furin mRNA transcript simultaneously. In some embodiments, the bi-shRNA comprises SEQ ID NO:2 or 4 (SEQ ID NO:4). In some embodiments, a bi-shRNA capable of hybridizing to one or more regions of an mRNA transcript encoding furin is referred to herein as bi-shRNA$^{furin}$. In some embodiments, the bi-shRNA$^{furin}$ comprises or consists of two stem-loop structures each with a miR-30a loop. In some embodiments, a first stem-loop structure of the two stem-loop structures comprises complementary guiding strand and passenger strand (FIG. 1). In some embodiments, the second stem-loop structure of the two stem-loop structures comprises three mismatches in the passenger strand. In some embodiments, the three mismatches are at positions 9 to 11 in the passenger strand.

TABLE 1

Sequences

| SEQ ID NO: | Description | Sequence |
|---|---|---|
| 1 | mRNA transcript encoding furin | GCGGGGAAGCAGCAGCGGCCAGGATGAATCCCAGGTGCTC<br>TGGAGCTGGATGGTGAAGGTCGGCACTCTTCACCCTCCCGA<br>GCCCTGCCCGTCTCGGCCCCATGCCCCCACCAGTCAGCCCC<br>GGGCCACAGGCAGTGAGCAGGCACCTGGGAGCCGAGGCCC<br>TGTGACCAGGCCAAGGAGACGGGCGCTCCAGGGTCCCAGC<br>CACCTGTCCCCCCCATGGAGCTGAGGCCCTGGTTGCTATGG<br>GTGGTAGCAGCAACAGGAACCTTGGTCCTGCTAGCAGCTGA<br>TGCTCAGGGCCAGAAGGTCTTCACCAACACGTGGGCTGTGC<br>GCATCCCTGGAGGCCCAGCGGTGGCCAACAGTGTGGCACG<br>GAAGCATGGGTTCCTCAACCTGGGCCAGATCTTCGGGGACT<br>ATTACCACTTCTGGCATCGAGGAGTGACGAAGCGGTCCCTG<br>TCGCCTCACCGCCCGCGGCACAGCCGGCTGCAGAGGGAGC<br>CTCAAGTACAGTGGCTGGAACAGCAGGTGGCAAAGCGACG<br>GACTAAACGGGACGTGTACCAGGAGCCCACAGACCCCAAG<br>TTTCCTCAGCAGTGGTACCTGTCTGGTGTCACTCAGCGGGA<br>CCTGAATGTGAAGGCGGCCTGGGCGCAGGGCTACACAGGG<br>CACGGCATTGTGGTCTCCATTCTGGACGATGGCATCGAGAA<br>GAACCACCCGGACTTGGCAGGCAATTATGATCCTGGGGCCA<br>GTTTTGATGTCAATGACCAGGACCCTGACCCCCAGCCTCGG<br>TACACACAGATGAATGACAACAGGCACGGCACACGGTGTG<br>CGGGGGAAGTGGCTGCGGTGGCCAACAACGGTGTCTGTGG<br>TGTAGGTGTGGCCTACAACGCCCGCATTGGAGGGGTGCGCA<br>TGCTGGATGGCGAGGTGACAGATGCAGTGGAGGCACGCTC<br>GCTGGGCCTGAACCCCAACCACATCCACATCTACAGTGCCA<br>GCTGGGGCCCCGAGGATGACGGCAAGACAGTGGATGGGCC<br>AGCCCGCCTCGCCGAGGAGGCCTTCTTCCGTGGGGTTAGCC<br>AGGGCCGAGGGGGGCTGGGCTCCATCTTTGTCTGGGCCTCG<br>GGGAACGGGGGCCGGGAACATGACAGCTGCAACTGCGACG<br>GCTACACCAACAGTATCTACACGCTGTCCATCAGCAGCGCC<br>ACGCAGTTTGGCAACGTGCCGTGGTACAGCGAGGCCTGCTC<br>GTCCACACTGGCCACGACCTACAGCAGTGGCAACCAGAAT<br>GAGAAGCAGATCGTGACGACTGACTTGCGGCAGAAGTGCA<br>CGGAGTCTCACACGGGCACCTCAGCCTCTGCCCCCTTAGCA<br>GCCGGCATCATTGCTCTCACCCTGGAGGCCAATAAGAACCT<br>CACATGGCGGGACATGCAACACCTGGTGGTACAGACCTCG<br>AAGCCAGCCCACCTCAATGCCAACGACTGGGCCACCAATG<br>GTGTGGGCCGGAAAGTGAGCCACTCATATGGCTACGGGCTT<br>TTGGACGCAGGCGCCATGGTGGCCCTGGCCCAGAATTGGAC<br>CACAGTGGCCCCCCAGCGGAAGTGCATCATCGACATCCTCA<br>CCGAGCCCAAAGACATCGGGAAACGGCTCGAGGTGCGGAA<br>GACCGTGACCGCGTGCCTGGGCGAGCCCAACCACATCACTC<br>GGCTGGAGCACGCTCAGGCGCGGCTCACCCTGTCCTATAAT<br>CGCCGTGGCGACCTGGCCATCCACCTGGTCAGCCCCATGGG<br>CACCCGCTCCACCCTGCTGGCAGCCAGGCCACATGACTACT<br>CCGCAGATGGGTTTAATGACTGGGCCTTCATGACAACTCAT<br>TCCTGGGATGAGGATCCCTCTGGCGAGTGGGTCCTAGAGAT<br>TGAAAACACCAGCGAAGCCAACAACTATGGGACGCTGACC<br>AAGTTCACCCTCGTACTCTATGGCACCGCCCCTGAGGGGCT<br>GCCCGTACCTCCAGAAAGCAGTGGCTGCAAGACCCCTCACGT<br>CCAGTCAGGCCTGTGTGGTGTGCGAGGAAGGCTTCTCCCTG |

TABLE 1-continued

Sequences

| SEQ ID NO: | Description | Sequence |
|---|---|---|
| | | CACCAGAAGAGCTGTGTCCAGCACTGCCCTCCAGGGTTCGC<br>CCCCCAAGTCCTCGATACGCACTATAGCACCGAGAATGACG<br>TGGAGACCATCCGGGCCAGCGTCTGCGCCCCCTGCCACGCC<br>TCATGTGCCACATGCCAGGGGCCGGCCCTGACAGACTGCCT<br>CAGCTGCCCCAGCCACGCCTCCTTGGACCCTGTGGAGCAGA<br>CTTGCTCCCGGCAAAGCCAGAGCAGCCGAGAGTCCCCGCC<br>ACAGCAGCAGCCACCTCGGCTGCCCCCGGAGGTGGAGGCG<br>GGGCAACGGCTGCGGGCAGGGCTGCTGCCCTCACACCTGC<br>CTGAGGTGGTGGCCGGCCTCAGCTGCGCCTTCATCGTGCTG<br>GTCTTCGTCACTGTCTTCCTGGTCCTGCAGCTGCGCTCTGGC<br>TTTAGTTTTCGGGGGGTGAAGGTGTACACCATGGACCGTGG<br>CCTCATCTCCTACAAGGGGCTGCCCCCTGAAGCCTGGCAGG<br>AGGAGTGCCCGTCTGACTCAGAAGAGGACGAGGGCCGGGG<br>CGAGAGGACCGCCTTTATCAAAGACCAGAGCGCCCTCTGAT<br>GAGCCCACTGCCCACCCCCTCAAGCCAATCCCCTCCTTGGG<br>CACTTTTTAATTCACCAAAGTATTTTTTTATCTTGGGACTGG<br>GTTTGGACCCCAGCTGGGAGGCAAGAGGGGTGGAGACTGC<br>TTCCCATCCTACCCTCGGGCCCACCTGGCCACCTGAGGTGG<br>GCCCAGGACCAGCTGGGGCGTGGGGAGGGCCGTACCCCAC<br>CCTCAGCACCCCTTCCATGTGGAGAAAGGAGTGAAACCTTT<br>AGGGCAGCTTGCCCCGGCCCCGGCCCCAGCCAGAGTTCCTG<br>CGGAGTGAAGAGGGCAGCCCTTGCTTGTTGGGATTCCTGA<br>CCCAGGCCGCAGCTCTTGCCCTTCCCTGTCCCTCTAAAGCA<br>ATAATGGTCCCATCCAGGCAGTCGGGGGCTGGCCTAGGAG<br>ATATCTGAGGGAGGAGGCCACCTCTCCAAGGGCTTCTGCAC<br>CCTCCACCCTGTCCCCAGCTCTGGTGAGTCTTGGCGGCAG<br>CAGCCATCATAGGAAGGGACCAAGGCAAGGCAGGTGCCTC<br>CAGGTGTGCACGTGGCATGTGGCCTGTGGCCTGTGTCCCAT<br>GACCCACCCCTGTGCTCCGTGCCTCCACCACCACTGGCCAC<br>CAGGCTGGCGCAGCCAAGGCCGAAGCTCTGGCTGAACCCT<br>GTGCTGGTGTCCTGACCACCCTCCCCTCTCTTGCACCCGCCT<br>CTCCCGTCAGGGCCCAAGTCCCTGTTTTCTGAGCCCCGGGCT<br>GCCTGGGCTGTTGGCACTCACAGACCTGGAGCCCCTGGGTG<br>GGTGGTGGGGAGGGGCGCTGGCCCAGCCGGCCTCTCTGGC<br>CTCCCACCCGATGCTGCTTTCCCCTGTGGGGATCTCAGGGG<br>CTGTTTGAGGATATATTTTCACTTTGTGATTATTTCACTTTA<br>GATGCTGATGATTTGTTTTTGTATTTTTAATGGGGGTAGCAG<br>CTGGACTACCCACGTTCTCACACCCACCGTCCGCCCTGCTC<br>CTCCCTGGCTGCCCTGGCCCTGAGGTGTGGGGGCTGCAGCA<br>TGTTGCTGAGGAGTGAGGAATAGTTGAGCCCCAAGTCCTGA<br>AGAGGCGGGCCAGCCAGGCGGGCTCAAGGAAAGGGGTCC<br>CAGTGGGAGGGGCAGGCTGACATCTGTGTTTCAAGTGGGG<br>CTCGCCATGCCGGGGGTTCATAGGTCACTGGCTCTCCAAGT<br>GCCAGAGGTGGGCAGGTGGTGGCACTGAGCCCCCCCAACA<br>CTGTGCCCTGGTGGAGAAAGCACTGACCTGTCATGCCCCCC<br>TCAAACCTCCTCTTCTGACGTGCCTTTTGCACCCCTCCCATT<br>AGGACAATCAGTCCCCTCCCATCTGGGAGTCCCCTTTTCTTT<br>TCTACCCTAGCCATTCCTGGTACCCAGCCATCTGCCCAGGG<br>GTGCCCCCTCCTCTCCCATCCCCCTGCCCTCGTGGCCAGCCC<br>GGCTGGTTTTGTAAGATGCTGGGTTGGTGCACAGTGATTTT<br>TTTCTTGTAATTTAAACAGGCCCAGCATTGCTGGTTCTATTT<br>AATGGACATGAGATAATGTTAGAGGTTTTAAAGTGATTAAA<br>CGTGCAGACTATGCAAACCAG |
| 2 | bi-shRNA<sup>*furin*</sup> | GGAUCCUGCUGUUGACAGUGAGCGCGGAGAAAGGAGUGA<br>AACCUUAGUGAAGCCACAGAUGUAAGGUUUCACUCCUUU<br>CUCCUUGCCUACUGCCUCGGAGUCCUGCUGUUGACAGUG<br>AGCGCGGAGAAAGAUAUGAAACCUUAGUGAAGCCACAGA<br>UGUAAGGUUUCACUCCUUUCUCCUUGCCUACUGCCUCGG<br>AAGCUUUG |
| 4 | bi-shRNA<sup>*furin*</sup> | GAUCCUGCUGUUGACAGUGAGCGCGGAGAAAGGAGUGAA<br>ACCUUAGUGAAGCCACAGAUGUAAGGUUUCACUCCUUUC<br>UCCUUGCCUACUGCCUCGGAAGCAGCUCACUACAUUACUC<br>AGCUGUUGACAGUGAGCGCGGAGAAAGAUAUGAAACCUU<br>AGUGAAGCCACAGAUGUAAGGUUUCACUCCUUUCUCCUU<br>GCCUACUGCCUCGGAAGCUUAAUAAAGGAUCUUUUAUUU<br>UCAUUGGAUC |
| 5 | Passenger strand in first stem-loop structure in bi-shRNA<sup>*furin*</sup> | GGAGAAAGGAGUGAAACCUUA |

TABLE 1-continued

Sequences

| SEQ ID NO: | Description | Sequence |
|---|---|---|
| 6 | Guide strand in both first and second stem-loop structures in bi-shRNA$^{furin}$ | UAAGGUUUCACUCCUUUCUCC |
| 7 | Passenger strand in second stem-loop structure in bi-shRNA$^{furin}$ | GGAGAAAGAUAUGAAACCUUA |
| 8 | miR-30a loop | GUGAAGCCACAGAUG |

An expression vector comprising a first nucleic acid encoding GM-CSF and a second nucleic acid encoding at least one bifunctional short hairpin RNA (bi-shRNA) capable of hybridizing to a region of an mRNA transcript encoding furin is referred to as a bishRNA$^{furin}$/GMCSF expression vector.

In some embodiments, the first nucleic acid and the second nucleic acid are operably linked to a promoter. In some embodiments, the promoter is a cytomegalovirus (CMV) promoter. In some embodiments, the CMV promoter is a mammalian CMV promoter. In some embodiments, the mammalian CMV promoter comprises a CMV immediate early (IE) 5' UTR enhancer sequence and a CMV IE Intron A.

In some embodiments, the GM-CSF is human GM-CSF. In some embodiments, a nucleotide sequence encoding a picornaviral 2A ribosomal skip peptide sequence is intercalated between the first and the second nucleic acid inserts.

In some embodiments, the expression vector plasmid can have a sequence that is at least 90% (e.g., 90%, 91%, 92%, 93%, 94%, 95%, 96%, 97%, 98%, 99%, or 100%) identical to the sequence of SEQ ID NO:3. The vector plasmid can comprise a first nucleic acid insert operably linked to a promoter, wherein the first insert encodes the GM-CSF cDNA, a second nucleic acid insert operably linked to the promoter, wherein the second insert encodes one or more short hairpin RNAs (shRNA) capable of hybridizing to a region of a mRNA transcript encoding furin, thereby inhibiting furin expression via RNA interference.

SEQ ID NO: 3

GGCCATTGCATACGTTGTATCCATATCATAATATGTACATTTATATTGG

CTCATGTCCAACATTACCGCCATGTTGACATTGATTATTGACTAGTTAT

TAATAGTAATCAATTACGGGGTCATTAGTTCATAGCCCATATATGGAGT

TCCGCGTTACATAACTTACGGTAAATGGCCCGCCTGGCTGACCGCCCAA

CGACCCCCGCCCATTGACGTCAATAATGACGTATGTTCCCATAGTAACG

CCAATAGGGACTTTCCATTGACGTCAATGGGTGGAGTATTTACGGTAAA

CTGCCCACTTGGCAGTACATCAAGTGTATCATATGCCAAGTACGCCCCC

TATTGACGTCAATGACGGTAAATGGCCCGCCTGGCATTATGCCCAGTAC

ATGACCTTATGGGACTTTCCTACTTGGCAGTACATCTACGTATTAGTCA

-continued

TCGCTATTACCATGGTGATGCGGTTTTGGCAGTACATCAATGGGCGTGG

ATAGCGGTTTGACTCACGGGGATTTCCAAGTCTCCACCCCATTGACGTC

AATGGGAGTTTGTTTTGGCACCAAAATCAACGGGACTTTCCAAAATGTC

GTAACAACTCCGCCCCATTGACGCAAATGGGCGGTAGGCGTGTACGGTG

GGAGGTCTATATAAGCAGAGCTCGTTTAGTGAACCGTCAGATCGCCTGG

AGACGCCATCCACGCTGTTTTGACCTCCATAGAAGACACCGGGACCGAT

CCAGCCTCCGCGGCCGGGAACGGTGCATTGGAACGCGGATTCCCCGTGC

CAAGAGTGACGTAAGTACCGCCTATAGACTCTATAGGCACACCCCTTTG

GCTCTTATGCATGCTATACTGTTTTTGGCTTGGGGCCTATACACCCCCG

CTTCCTTATGCTATAGGTGATGGTATAGCTTAGCCTATAGGTGTGGGTT

ATTGACCATTATTGACCACTCCAACGGTGGAGGGCAGTGTAGTCTGAGC

AGTACTCGTTGCTGCCGCGCGCCACCAGACATAATAGCTGACAGACT

AACAGACTGTTCCTTTCCATGGGTCTTTTCTGCAGTCACCGTCGTCGAC

GGTATCGATAAGCTTGATATCGAATTCCGCTGGAGGATGTGGCTGCAGA

GCCTGCTGCTCTTGGGCACTGTGGCCTGCAGCATCTCTGCACCCGCCCG

CTCGCCCAGCCCCAGCACGCAGCCCTGGGAGCATGTGAATGCCATCCAG

GAGGCCCGGCGTCTCCTGAACCTGAGTAGAGACACTGCTGCTGAGATGA

ATGAAACAGTAGAAGTCATCTCAGAAATGTTTGACCTCCAGGAGCCGAC

CTGCCTACAGACCCGCCTGGAGCTGTACAAGCAGGGCCTGCGGGGCAGC

CTCACCAAGCTCAAGGGCCCCTTGACCATGATGGCCAGCCACTACAAGC

AGCACTGCCCTCCAACCCCGGAAACTTCCTGTGCAACCCAGACTATCAC

CTTTGAAAGTTTCAAAGAGAACCTGAAGGACTTTCTGCTTGTCATCCCC

TTTGACTGCTGGGAGCCAGTCCAGGAGTGAGACCGGCCAGATGAGGCTG

GCCAAGCCGGGGAGCTGCTCTCTCATGAAACAAGAGCTAGAAACTCAGG

ATGGTCATCTTGGAGGGACCAAGGGGTGGGCCACAGCCATGGTGGGAGT

GGCCTGGACCTGCCCTGGGCCACACTGACCCTGATACAGGCATGGCAGA

AGAATGGGAATATTTTATACTGACAGAAATCAGTAATATTTATATATTT

ATATTTTTAAAATATTTATTTATTTATTTATTTAAGTTCATATTCCATA

```
TTTATTCAAGATGTTTTACCGTAATAATTATTATTAAAAATATGCTTCT
AAAAAAAAAAAAAAAAAAAAAAACGGAATTCACGTGGGCCCGGTACCGT
ATACTCTAGAAGATCTGGCAGCGGAGAGGGCAGAGGAAGTCTTCTAACA
TGCGGTGACGTGGAGGAGAATCCCGGCCCTAGGATGTCTAGAGCGGCCG
CGGATCCTGCTGTTGACAGTGAGCGCGGAGAAAGGAGTGAAACCTTAGT
GAAGCCACAGATGTAAGGTTTCACTCCTTTCTCCTTGCCTACTGCCTCG
GAAGCAGCTCACTACATTACTCAGCTGTTGACAGTGAGCGCGGAGAAAG
ATATGAAACCTTAGTGAAGCCACAGATGTAAGGTTTCACTCCTTTCTCC
TTGCCTACTGCCTCGGAAGCTTAATAAAGGATCTTTTATTTTCATTGGA
TCCAGATCTTTTTCCCTCTGCCAAAAATTATGGGGACATCATGAAGCCC
CTTGAGCATCTGACTTCTGGCTAATAAAGGAAATTTATTTTCATTGCAA
TAGTGTGTTGGAATTTTTTGTGTCTCTCACTCGGAAGGACATATGGGAG
GGCAAATCATTTAAAACATCAGAATGAGTATTTGGTTTAGAGTTTGGCA
ACATATGCCCATTCTTCCGCTTCCTCGCTCACTGACTCGCTGCGCTCGG
TCGTTCGGCTGCGGCGAGCGGTATCAGCTCACTCAAAGGCGGTAATACG
GTTATCCACAGAATCAGGGGATAACGCAGGAAAGAACATGTGAGCAAAA
GGCCAGCAAAAGGCCAGGAACCGTAAAAAGGCCGCGTTGCTGGCGTTTT
TCCATAGGCTCCGCCCCCCTGACGAGCATCACAAAAATCGACGCTCAAG
TCAGAGGTGGCGAAACCCGACAGGACTATAAAGATACCAGGCGTTTCCC
CCTGGAAGCTCCCTCGTGCGCTCTCCTGTTCCGACCCTGCCGCTTACCG
GATACCTGTCCGCCTTTCTCCCTTCGGGAAGCGTGGCGCTTTCTCATAG
CTCACGCTGTAGGTATCTCAGTTCGGTGTAGGTCGTTCGCTCCAAGCTG
GGCTGTGTGCACGAACCCCCCGTTCAGCCCGACCGCTGCGCCTTATCCG
GTAACTATCGTCTTGAGTCCAACCCGGTAAGACACGACTTATCGCCACT
GGCAGCAGCCACTGGTAACAGGATTAGCAGAGCGAGGTATGTAGGCGGT
GCTACAGAGTTCTTGAAGTGGTGGCCTAACTACGGCTACACTAGAAGAA
CAGTATTTGGTATCTGCGCTCTGCTGAAGCCAGTTACCTTCGGAAAAAG
AGTTGGTAGCTCTTGATCCGGCAAACAAACCACCGCTGGTAGCGGTGGT
TTTTTTGTTTGCAAGCAGCAGATTACGCGCAGAAAAAAAGGATCTCAAG
AAGATCCTTTGATCTTTTCTACGGGGTCTGACGCTCAGTGGAACGAAAA
CTCACGTTAAGGGATTTTGGTCATGAGATTATCAAAAAGGATCTTCACC
TAGATCCTTTTAAATTAAAAATGAAGTTTTAAATCAATCTAAAGTATAT
ATGAGTAAACTTGGTCTGACAGTTACCAATGCTTAATCAGTGAGGCACC
TATCTCAGCGATCTGTCTATTTCGTTCATCCATAGTTGCCTGACTCGGG
GGGGGGGGCGCTGAGGTCTGCCTCGTGAAAGGTGTTGCTGACTCATAC
CAGGCCTGAATCGCCCCATCATCCAGCCAGAAAGTGAGGGAGCCACGGT
TGATGAGAGCTTTGTTGTAGGTGGACCAGTTGGTGATTTTGAACTTTTG
CTTTGCCACGGAACGGTCTGCGTTGTCGGGAAGATGCGTGATCTGATCC
TTCAACTCAGCAAAAGTTCGATTTATTCAACAAAGCCGCCGTCCCGTCA
AGTCAGCGTAATGCTCTGCCAGTGTTACAACCAATTAACCAATTCTGAT
TAGAAAAACTCATCGAGCATCAAATGAAACTGCAATTTATTCATATCAG
GATTATCAATACCATATTTTTGAAAAAGCCGTTTCTGTAATGAAGGAGA
AAACTCACCGAGGCAGTTCCATAGGATGGCAAGATCCTGGTATCGGTCT
GCGATTCCGACTCGTCCAACATCAATACAACCTATTAATTTCCCCTCGT
CAAAAATAAGGTTATCAAGTGAGAAATCACCATGAGTGACGACTGAATC
CGGTGAGAATGGCAAAAGCTTATGCATTTCTTTCCAGACTTGTTCAACA
GGCCAGCCATTACGCTCGTCATCAAAATCACTCGCATCAACCAAACCGT
TATTCATTCGTGATTGCGCCTGAGCGAGACGAAATACGCGATCGCTGTT
AAAAGGACAATTACAAACAGGAATCGAATGCAACCGGCGCAGGAACACT
GCCAGCGCATCAACAATATTTTCACCTGAATCAGGATATTCTTCTAATA
CCTGGAATGCTGTTTTCCCGGGGATCGCAGTGGTGAGTAACCATGCATC
ATCAGGAGTACGGATAAAATGCTTGATGGTCGGAAGAGGCATAAATTCC
GTCAGCCAGTTTAGTCTGACCATCTCATCTGTAACATCATTGGCAACGC
TACCTTTGCCATGTTTCAGAAACAACTCTGGCGCATCGGGCTTCCCATA
CAATCGATAGATTGTCGCACCTGATTGCCCGACATTATCGCGAGCCCAT
TTATACCCATATTCAGCATCCATGTTGGAATTTAATCGCGGCCTCGAGC
AAGACGTTTCCCGTTGAATATGGCTCATAACACCCCTTGTATTACTGTT
TATGTAAGCAGACAGTTTTATTGTTCATGATGATATATTTTTATCTTGT
GCAATGTAACATCAGAGATTTTGAGACACAACGTGGCTTTCCCCCCCCC
CCCATTATTGAAGCATTTATCAGGGTTATTGTCTCATGAGCGGATACAT
ATTTGAATGTATTTAGAAAAATAAACAAATAGGGGTTCCGCGCACATTT
CCCCGAAAAGTGCCACCTGACGTCTAAGAAACCATTATTATCATGACAT
TAACCTATAAAAATAGGCGTATCACGAGGCCCTTTCGTCTCGCGCGTTT
CGGTGATGACGGTGAAAACCTCTGACACATGCAGCTCCCGGAGACGGTC
ACAGCTTGTCTGTAAGCGGATGCCGGGAGCAGACAAGCCCGTCAGGGCG
CGTCAGCGGGTGTTGGCGGGTGTCGGGGCTGGCTTAACTATGCGGCATC
AGAGCAGATTGTACTGAGAGTGCACCATATGCGGTGTGAAATACCGCAC
AGATGCGTAAGGAGAAAATACCGCATCAGATTGGCTATT
```

An expression vector comprising a first nucleic acid encoding GM-CSF and a second nucleic acid encoding at least one bifunctional short hairpin RNA (bi-shRNA) capable of hybridizing to a region of an mRNA transcript encoding furin is referred to as a bishRNA$^{furin}$/GMCSF expression vector.

Tumor Cells

In some embodiments, the cells are autologous tumor cells, xenograft expanded autologous tumor cells, allogeneic tumor cells, xenograft expanded allogeneic tumor cells, or combinations thereof. In some embodiments, the cells are autologous tumor cells. In some embodiments, the allogenic tumor cells are established cell lines. In some embodiments, autologous tumor cells are obtained from the individual in need thereof. In some embodiments, when the cells are autologous tumor cells, the composition is referred to as an autologous tumor cell vaccine.

In some embodiments, the cells are harvested from an individual. In some embodiments, the cells are harvested from a tissue of the individual. In some embodiments, the tissue is a tumor tissue. In some embodiments, the tumor tissue is ovarian tumor tissue. In some embodiments, the tumor tissue is harvested during a biopsy or a cytoreduction surgery on the individual. In some embodiments, the tumor tissue or cells from the tumor tissue are placed in an antibiotic solution in a sterile container. In some embodiments, the antibiotic solution comprises gentamicin, sodium chloride, or a combination thereof.

Methods of Use

In some embodiments, the ovarian cancer is Stage III or Stage IV ovarian cancer. In some embodiments, the Stage III ovarian cancer is Stage IIIb or worse. In some embodiments, the ovarian cancer is a high-grade serous ovarian carcinoma, a clear cell ovarian carcinoma, endometroid ovarian carcinoma, mucinous ovarian carcinoma, or a low-grade serous ovarian carcinoma.

In some embodiments, the individual has a wild-type BRCA) gene, a wild-type BRCA2 gene, or a both a wild-type BRCA1 gene and wild-type BRCA2 gene. In some embodiments, the wild-type BRCA1 gene does not comprise a mutation in the germline BRCA1 gene. In some embodiments, the wild-type BRCA2 gene does not comprise a mutation in the germline BRCA2 gene. In some embodiments, the ovarian cancer of an individual having a wild-type BRCA1 gene and a wild-type BRCA2 gene is referred to herein as BRCA1/2-wt ovarian cancer, BRCA-wt ovarian cancer, or BRCA1/2 wild type ovarian cancer. In contrast, in some embodiments, the ovarian cancer of an individual comprising a mutant BRCA1 gene, a mutant BRCA2 gene, or both a mutant BRCA1 gene and mutant BRCA2 gene is referred to herein as BRCA1/2-m ovarian cancer or BRCA-m ovarian cancer ovarian cancer. In some embodiments, the mutant BRCA1 gene or mutant BRCA2 gene comprises a germline mutation. In some embodiments, the mutant BRCA1 gene or mutant BRCA2 gene comprises a somatic mutation. In some embodiments, a recurrence free survival (RFS) of the individual is increased relative to an individual with substantially eradicated ovarian cancer who has not been administered the autologous tumor cell vaccine.

In some embodiments, the cancer is an HRD-negative, wild-type BRCA1/2 cancer. In some embodiments, the cancer is selected from the group consisting of a solid tumor cancer, ovarian cancer, adrenocortical carcinoma, bladder cancer, breast cancer, cervical cancer, cholangiocarcinoma, colorectal cancers, esophageal cancer, glioblastoma, glioma, hepatocellular carcinoma, head and neck cancer, kidney cancer, leukemia, lymphoma, lung cancer, melanoma, mesothelioma, multiple myeloma, pancreatic cancer, pheochromocytoma, plasmacytoma, neuroblastoma, prostate cancer, sarcoma, stomach cancer, uterine cancer, thyroid cancer, and a hematological cancer. Examples of solid tumor cancers include, but are not limited to, endometrial cancer, biliary cancer, bladder cancer, liver hepatocellular carcinoma, gastric/esophageal cancer, ovarian cancer, melanoma, breast cancer, pancreatic cancer, colorectal cancer, glioma, non-small-cell lung carcinoma, prostate cancer, cervical cancer, kidney cancer, thyroid cancer, a neuroendocrine cancer, small cell lung cancer, a sarcoma, head and neck cancer, brain cancer, clear cell renal cell carcinoma, skin cancer, endocrine tumor, thyroid cancer, tumor of unknown origin, and a gastrointestinal stromal tumor.

As used herein, the term "recurrence free survival," is used interchangeably with the term "relapse free survival," and refers to the time after administration of an initial therapy to treat a cancer that the cancer remains undetectable (i.e., until the cancer recurrence). In some embodiments, recurrence free survival of an individual receiving the autologous tumor cell vaccine is from 5 months to 11 months longer than recurrence free survival of an individual not receiving the autologous tumor cell vaccine. In some embodiments, recurrence free survival of an individual receiving the autologous tumor cell vaccine is at least 5 months, 6 months, 7 months 8 months, 9 months, 10 months, or 11 months longer than recurrence free survival of an individual not receiving the autologous tumor cell vaccine.

As used herein, the term "substantially eradicated" refers to an ovarian cancer which is not detectable (e.g., below a detectable level or below the limit of detection (LOD)) in an individual following an initial therapy to treat the ovarian cancer. In some embodiments, detection of ovarian cancer, or lack thereof, is by a chest x-ray, computed tomography (CT) scan, magnetic resonance imaging (MRI), detection of a cancer antigen 125 (CA-125) level, physical examination or presence of symptoms suggestive of active cancer, or any combination thereof. In some embodiments, a detection of cancer antigen 125 (CA-125) levels of S 35 units/ml indicates no ovarian cancer is present in the individual. In some embodiments, an ovarian cancer which has been substantially eradicated is referred to as having achieved a clinical complete response (cCR). In some embodiments, an ovarian cancer which is detected in subject after a prior substantial eradication of ovarian cancer in the subject is referred to as recurrent or relapsed ovarian cancer.

In some embodiments, recurrence free survival of an individual receiving the autologous tumor cell vaccine is at least 5 months longer than recurrence free survival of an individual not receiving the autologous tumor cell vaccine, regardless of the status (i.e. mutant or not mutant) of BRCA1, BRCA2, or the combination thereof. In some embodiments, recurrence free survival of a BRCA-wt individual receiving the autologous tumor cell vaccine is greater than 15 months from time of surgical debulking, wherein a recurrence free survival of an individual not receiving the autologous tumor cell vaccine is less than 15 months from time of surgical debulking. In some embodiments, recurrence free survival of a BRCA-wt individual receiving the autologous tumor cell vaccine is at least 11 months longer than recurrence free survival of an individual not receiving the autologous tumor cell vaccine.

In some embodiments, the individual received an initial therapy. In some embodiments, administration of an initial therapy results in a clinical completely response of the cancer to the therapy. In some embodiments, the initial therapy comprises debulking, administration of a chemotherapy, administration of a therapeutic agent, or the combination thereof. In some embodiments, the chemotherapy comprises a platinum-based drug, a taxane, or a combination thereof. In some embodiments, the platinum-based drug comprises cisplatin, carboplatin, oxaliplatin, nedaplatin, triplatin tetranitrate, phenanthriplatin, picoplatin, satraplatin, or a combination thereof. In some embodiments, the platinum-based drug comprises carboplatin. In some embodiments, the taxane comprises paclitaxel, docetaxel, cabazitaxel, or a combination thereof. In some embodiments, the taxane comprises paclitaxel. In some embodiments, the therapeutic agent comprises an angiogenesis inhibitor, a PARP inhibitor, a checkpoint inhibitor, or a combination thereof. In some embodiments, the angiogenesis inhibitor comprises a vascular endothelial growth factor (VEGF) inhibitor. In some embodiments, the VEGF inhibitor comprises sorafenib, sunitinib, bevacizumab, pazopanib, axitinib, cabozantinib, levatinib, or a combination thereof. In some embodiments, the VEGF inhibitor is bevacizumab. In some embodiments, the PARP inhibitor comprises niraparib, olaparib, rucaparib, niraparib, talazoparib, veliparib, pamiparib, or a combination thereof. In some embodiments, the PARP inhibitor is niraparib. In some embodiments, the checkpoint inhibitor comprises a PD-1 inhibitor, a PD-L1 inhibitor, a CTLA-4 inhibitor, or a combination thereof. In some embodiments, the checkpoint inhibitor comprises pembrolizumab, nivolumab, cemiplimab, atezolizumab, avelumab, durvalumab, ipilimumab, or a combination thereof. In some embodiments, the ovarian cancer is resistant or refractory to the chemotherapy or the therapeutic agent.

In some embodiments, the method further comprises determining a status (i.e. wild type or mutant) of the BRCA1 gene, a BRCA2 gene, or the combination thereof in the individual. In some embodiments, the determining comprises sequencing of the BRCA1 gene, BRCA2 gene, or a combination thereof. In some embodiments, the sequencing comprises Sanger sequencing or next generation sequencing. In some embodiments, the next generation sequencing comprises massively parallel sequencing. In some embodiments, the determining comprises hybridization of nucleic acid extracted from the individual to an array. In some embodiments, the array is a microarray. In some embodiments, the determining comprises array comparative genomic hybridization of nucleic acid extracted from the individual.

Administration, Formulations and Dosing

In some embodiments, the autologous tumor cell vaccine comprises about $1\times10^6$ or about $1\times10^7$ autologous tumor cells transfected as described herein. In some embodiments, the autologous tumor cell vaccine comprises at least $1\times10^6$ or at least $1\times10^7$ autologous tumor cells transfected as described herein. In some embodiments, the autologous tumor cell vaccine comprises from about $1\times10^6$ cells to about $1\times10^7$ autologous tumor cells transfected as described herein. In some embodiments, the autologous tumor cell vaccine comprises from about $1\times10^6$ cells to about $2.5\times10^7$ autologous tumor cells transfected as described herein. In some embodiments, the autologous tumor cell vaccine comprises from about $1\times10^6$ cells to about $5\times10^7$ autologous tumor cells transfected as described herein.

In some embodiments, the autologous tumor cell vaccine further comprises one or more vaccine adjuvants.

In some embodiments, the autologous tumor cell vaccine is in a unit dosage form. The term "unit dosage form," as used herein, describes a physically discrete unit containing a predetermined quantity of the autologous tumor cell vaccine described herein, in association with other ingredients (e.g., vaccine adjuvants). In some embodiments, the predetermined quantity is a number of cells.

In some embodiments, an individual is administered one dose of the autologous tumor cell vaccine per month. In some embodiments, a dose of the autologous tumor cell vaccine is administered to the individual once a month for from 1 months to 12 months. In some embodiments, the individual is administered at least one dose of the autologous tumor cell vaccine. In some embodiments, the individual is administered no more than twelve doses of the autologous tumor cell vaccine. In some embodiments, the individual is administered 1, 2, 3, 4, 5, 6, 7, 8, 9, 10, 11, or 12 doses of the autologous tumor cell vaccine. In some embodiments, the dose is a unit dosage form of the autologous tumor cell vaccine. In some embodiments, a dose of the autologous tumor cell vaccine is administered to the individual every three months, every two months, once a month, twice a month, or three times a month. In some embodiments, the autologous tumor cell vaccine is administered to the individual for up to 1 month, 2 months, 3 months, 4 months, 5 months, 6 months, 12 months, 18 months, 24 months, or 36 months. In some embodiments, the autologous tumor cell vaccine is administered to the individual by injection. In some embodiments, the injection is an intradermal injection. In some embodiments, a first dose of the autologous tumor cell vaccine is administered to the individual following confirmation of the individual achieving a clinical complete response (cCR). In some embodiments, a first dose of the autologous tumor cell vaccine is administered to the individual no earlier than the same day as the final treatment of the initial therapy. In some embodiments, a first dose of the autologous tumor cell vaccine is administered to the individual no later than 8 weeks following the final treatment of the initial therapy.

Combinations

In some embodiments, the autologous tumor cell vaccine is administered to an individual with an additional therapeutic agent. In some embodiments, at least one first dose of the autologous tumor cell vaccine is administered to the individual in the absence of the additional therapeutic agent and at least one second dose of the autologous tumor cell vaccine is administered to the individual in combination with at least one dose of the additional therapeutic agent. In some embodiments, as used herein, "in combination with" refers to administration of a dose of the additional therapeutic agent within 1 day, 2 days, 3 days, 4 days, 5 days, 6 days, week, 2 weeks, 3 weeks, or 4 weeks of the dose of an autologous tumor cell vaccine or on the same day as the dose of the autologous tumor cell vaccine. The additional therapeutic agent can be administered before, concurrently or after the autologous tumor cell vaccine.

In one illustrative example, an individual receives two doses of the autologous tumor cell vaccine spaced one month apart via intradermal injection, and starting from the third month receives both: (i) an additional 10 doses of the tumor cell vaccine each spaced one month apart, and (ii) 12 doses of atezolizumb each spaced 3 weeks apart via intravenous infusion.

In another illustrative example, an individual receives two doses of the autologous tumor cell vaccine spaced one month apart via intradermal injection, and starting from the third month receives both: (i) an additional 10 doses of the tumor cell vaccine each spaced one month apart, and (ii) 10 doses of atezolizumb administered via intravenous infusion on the same day as the additional 10 doses of the tumor cell vaccine.

In some embodiments, administration of the autologous tumor cell vaccine to the individual first followed by administration of a combination of the autologous tumor cell vaccine and additional therapeutic agent results in a reduced toxicity relative to administration of the additional therapeutic agent alone. In some embodiments, administration of the autologous tumor cell vaccine to the individual first followed by administration of a combination of the autologous tumor cell vaccine and a checkpoint inhibitor results in a reduced toxicity relative to administration of the checkpoint alone.

In some embodiments, at least 1, 2, 3, 4, 5, 6, 7, 8, 9, 10, 11, or 12 doses of the autologous tumor cell vaccine is administered to the individual prior to administration of the autologous tumor cell vaccine in combination with the additional therapeutic agent. In some embodiments, at least two doses of the autologous tumor cell vaccine are administered to the individual prior to administration of the combination of the autologous tumor cell vaccine and additional therapeutic agent.

In some embodiments, the additional therapeutic agent comprises an angiogenesis inhibitor, a PARP inhibitor, a checkpoint inhibitor, or a combination thereof. In some embodiments, the angiogenesis inhibitor comprises a vascular endothelial growth factor (VEGF) inhibitor. In some embodiments, the VEGF inhibitor comprises sorafenib, sunitinib, bevacizumab, pazopanib, axitinib, cabozantinib, levatinib, or a combination thereof. In some embodiments, the VEGF inhibitor is bevacizumab. In some embodiments, the PARP inhibitor comprises niraparib, olaparib, rucaparib, niraparib, talazoparib, veliparib, pamiparib, or a combination thereof. In some embodiments, the PARP inhibitor is niraparib. In some embodiments, the checkpoint inhibitor comprises a PD-1 inhibitor, a PD-L1 inhibitor, a CTLA-4 inhibitor, or a combination thereof. In some embodiments, the checkpoint inhibitor comprises pembrolizumab, nivolumab, cemiplimab, atezolizumab, avelumab, durvalumab, ipilimumab, or a combination thereof. In some embodiments, the additional therapeutic agent is a checkpoint inhibitor. In some embodiments, the checkpoint inhibitor is atezolizumab. In some embodiments, the additional therapeutic agent is a VEGF inhibitor. In some embodiments, the VEGF inhibitor is bevacizumab. In some embodiments, the additional therapeutic agent is a PARP inhibitor. In some embodiments, the additional therapeutic agent is administered by intravenous infusion.

In some embodiments, the additional therapeutic agent comprises a therapeutically effective dose of atezolizumab. In some embodiments, the therapeutically effective dose of atezolizumab is from about 900 mg to about 1500 mg or from about 1100 mg to 1300 mg. In some embodiments, the therapeutically effective dose of atezolizumab is about 900 mg, 1000 mg, 1100 mg, 1200 mg, 1300 mg, 1400 mg, or 1500 mg. In some embodiments, the therapeutically effective dose of atezolizumab is about 1200 mg. In some embodiments, the atezolizumab is administered by intravenous infusion.

In some embodiments, the additional therapeutic agent comprises a therapeutically effective dose of γIFN (gamma interferon). In some embodiments, the therapeutically effective dose of γIFN is from about 50 $\mu g/m^2$ to about 100 $\mu g/m^2$. In some embodiments, the therapeutically effective dose of γIFN is about 50 $\mu g/m^2$, about 60 $\mu g/m^2$, about 70 $\mu g/m^2$, about 80 $\mu g/m^2$, about 90 $\mu g/m^2$, or about 100 $\mu g/m^2$.

In some embodiments, the expression vector or the autologous cancer cell vaccine is administered with an additional therapeutic agent. In some embodiments, the additional therapeutic agent comprises a therapeutically effective dose of γIFN (gamma interferon). In some embodiments, the therapeutically effective dose of γIFN is from about 50 $\mu g/m^2$ to about 100 $\mu g/m^2$. In some embodiments, the therapeutically effective dose of γIFN is about 50 $\mu g/m^2$, about 60 $\mu g/m^2$, about 70 $\mu g/m^2$, about 80 $\mu g/m^2$, about 90 $\mu g/m^2$, or about 100 $\mu g/m^2$. In some embodiments, the additional therapeutic agent comprises an angiogenesis inhibitor, a PARP inhibitor, a checkpoint inhibitor, or a combination thereof. In some embodiments, the angiogenesis inhibitor comprises a vascular endothelial growth factor (VEGF) inhibitor. In some embodiments, the VEGF inhibitor comprises sorafenib, sunitinib, bevacizumab, pazopanib, axitinib, cabozantinib, levatinib, or a combination thereof. In some embodiments, the VEGF inhibitor is bevacizumab. In some embodiments, the PARP inhibitor comprises olaparib, rucaparib, niraparib, talazoparib, veliparib, pamiparib, or a combination thereof. In some embodiments, the checkpoint inhibitor comprises a PD-1 inhibitor, a PD-L1 inhibitor, a CTLA-4 inhibitor, or a combination thereof. In some embodiments, the checkpoint inhibitor comprises pembrolizumab, nivolumab, cemiplimab, atezolizumab, avelumab, durvalumab, ipilimumab, or a combination thereof.

Manufacture

In some embodiments, a method of making the autologous tumor cell vaccine described herein comprises the steps of: (i) harvesting one or more cancer cells from an individual aseptically, (ii) placing the harvested cells in an antibiotic solution in a sterile container, (iii) forming a cell suspension from the harvested solution, wherein the formation of the cell, (iv) suspension is achieved by enzymatic dissection, mechanical disaggregation or both, (v) modifying the cells genetically by electroporating the cell suspension to make the vaccine with a bishRNA$^{furin}$/GMCSF expression vector plasmid, wherein the vector plasmid comprises a first nucleic acid insert operably linked to a promoter, wherein the first insert encodes the GM-CSF cDNA, a second nucleic acid insert operably linked to the promoter, wherein the second insert encodes one or more short hairpin RNAs (shRNA) capable of hybridizing to a region of a mRNA transcript encoding furin, thereby inhibiting furin expression via RNA interference, (vi) harvesting the vaccine, (vii) irradiating the vaccine and (viii) freezing the vaccine. In some embodiments, the antibiotic solution comprises gentamicin. In some embodiments, the one or more cancer cells are harvested from a patient suffering from ovarian cancer. In some embodiments, the genetically modified cells have been rendered proliferation-incompetent by irradiation. In some embodiments, the genetically modified cells are autologous, allogenic, or xenograft expanded cells. In some embodiments, the method further comprises the step of incubating the genetically modified cells with γIFN after transfection. In some embodiments, the dose of γIFN applied to the genetically modified cells after transfection is approximately 250 U/ml (500 U/ml over 24 hours to 100 U/ml over 48 hours). In some embodiments, the autologous tumor cell vaccine is placed in a media prior to freezing. In some embodiments, the media the autologous tumor cell vaccine is placed in prior to freezing comprises DMSO, human serum albumin (HSA), or a combination hereof. In some embodiments, the autologous tumor cell vaccine, optionally including DMSO and HSA, is frozen at a final fill volume of from 1.1 to 1.3 mL, or about 1.2 mL. In some embodiments, the autologous tumor cell vaccine is frozen at about −80° C.

EXEMPLARY EMBODIMENTS

The following are the non-limiting embodiments of the invention.

Embodiment 1. A method of preventing relapse of a substantially eradicated ovarian cancer in an individual in need thereof, the method comprising administering to the individual an autologous tumor cell transfected with an expression vector comprising:
   a. a first insert comprising a nucleic acid sequence encoding a Granulocyte Macrophage Colony Stimulating Factor (GM-CSF) sequence; and
   b. a second insert comprising a sequence according to SEQ ID NO:2 or 4 (SEQ ID NO:4).

Embodiment 2. The method of embodiment 1, wherein the substantially eradicated ovarian cancer is Stage III or Stage IV ovarian cancer.

Embodiment 3. The method of embodiment 1 or embodiment 2, wherein the individual comprises a wild-type BRCA1 gene, a wild-type BRCA2 gene, or a combination thereof.

Embodiment 4. The method of any one of embodiments 1-3, wherein a recurrence free survival (RFS) of the individual is increased relative to an individual with substantially eradicated ovarian cancer who has not been administered the transfected tumor cell.

Embodiment 5. The method of any one of embodiments 1-4, wherein the individual received an initial therapy.

Embodiment 6. The method of embodiment 5, wherein the initial therapy comprises debulking surgery, chemotherapy, or the combination thereof.

Embodiment 7. The method of embodiment 6, wherein the chemotherapy comprises administering a platinum-based drug and a taxane.

Embodiment 8. The method of embodiment 7, wherein the platinum-based drug comprises carboplatin.

Embodiment 9. The method of embodiment 7, wherein the taxane comprises paclitaxel.

Embodiment 10. The method of any one of embodiments 1-9, wherein the GM-CSF is a human GM-CSF sequence.

Embodiment 11. The method of any one of embodiments 1-10, wherein the expression vector further comprises a promoter.

Embodiment 12. The method of embodiment 11, wherein the promoter is a cytomegalovirus (CMV) mammalian promoter.

Embodiment 13. The method of embodiment 12, wherein the expression vector further comprises a CMV enhancer sequence and a CMV intron sequence.

Embodiment 14. The method of any one of embodiments 11-13, wherein the first insert and the second insert are operably linked to the promoter.

Embodiment 15. The method of any one of embodiments 1-14, wherein the expression vector further comprises a nucleic acid sequence encoding a picornaviral 2A ribosomal skip peptide between the first and the second nucleic acid inserts.

Embodiment 16. The method of any one of embodiments 1-15, wherein the autologous tumor cell is administered to the individual as a dose of about $1 \times 10^6$ cells to about $5 \times 10^7$ cells.

Embodiment 17. The method of embodiment 16, wherein the autologous tumor cells are administered to the individual once a month.

Embodiment 18. The method of embodiment 17, wherein the autologous tumor cells are administered to the individual from 1 to 12 months.

Embodiment 19. The method of any one of embodiments 1-18, wherein the autologous tumor cell is administered to the individual by intradermal injection.

Embodiment 20. A method of treating BRCA1/2 wild type ovarian cancer in an individual in need thereof, the method comprising administering to the individual an autologous tumor cell transfected with an expression vector comprising:
  a. a first insert comprising a nucleic acid sequence encoding a Granulocyte Macrophage Colony Stimulating Factor (GM-CSF) sequence; and
  b. a second insert comprising a sequence according to SEQ ID NO:2 or 4 (SEQ ID NO:4).

Embodiment 21. The method of embodiment 20, wherein the ovarian cancer is Stage III or Stage IV ovarian cancer.

Embodiment 22. The method of embodiment 20 or embodiment 21, wherein the ovarian cancer is refractory ovarian cancer.

Embodiment 23. The method of embodiment 22, wherein the refractory ovarian cancer is refractory to a chemotherapy.

Embodiment 24. The method of embodiment 23, wherein the chemotherapy comprises a platinum-based drug or a taxane.

Embodiment 25. The method of embodiment 24, wherein the platinum-based drug comprises carboplatin.

Embodiment 26. The method of embodiment 24, wherein the taxane comprises paclitaxel.

Embodiment 27. The method of any one of embodiments 20-26, further comprising administering an additional therapeutic agent.

Embodiment 28. The method of embodiment 27, wherein the additional therapeutic agent is selected from the group consisting of an angiogenesis inhibitor, a PARP inhibitor, and a checkpoint inhibitor to the individual.

Embodiment 29. The method of embodiment 28, wherein the angiogenesis inhibitor is a vascular endothelial growth factor (VEGF) inhibitor.

Embodiment 30. The method of embodiment 29, wherein the VEGF inhibitor is selected from the group consisting of: sorafenib, sunitinib, bevacizumab, pazopanib, axitinib, cabozantinib, and levatinib.

Embodiment 31. The method of embodiment 29, wherein the VEGF inhibitor is bevacizumab.

Embodiment 32. The method of embodiment 28, wherein the PARP inhibitor is selected from the group consisting of niraparib, olaparib, rucaparib, niraparib, talazoparib, veliparib, and pamiparib.

Embodiment 33. The method of embodiment 28, wherein the PARP inhibitor is niraparib.

Embodiment 34. The method of embodiment 28, wherein the checkpoint inhibitor is selected from the group consisting of a PD-1 inhibitor, a PD-L1 inhibitor, and a CTLA-4 inhibitor.

Embodiment 35. The method of embodiment 28, wherein the checkpoint inhibitor is selected from the group consisting of pembrolizumab, nivolumab, cemiplimab, atezolizumab, avelumab, durvalumab, and ipilimumab administered via intravenous infusion.

Embodiment 36. The method of any one of embodiments 20-35, wherein the GM-CSF is a human GM-CSF sequence.

Embodiment 37. The method of any one of embodiments 20-36, wherein the expression vector further comprises a promoter.

Embodiment 38. The method of embodiment 37, wherein the promoter is a cytomegalovirus (CMV) mammalian promoter.

Embodiment 39. The method of embodiment 38, wherein the expression vector further comprises a CMV enhancer sequence and a CMV intron sequence.

Embodiment 40. The method of any one of embodiments 37-39, wherein the first insert and the second insert are operably linked to the promoter.

Embodiment 41. The method of any one of embodiments 20-40, wherein the expression vector further comprises a nucleic acid sequence encoding a picornaviral 2A ribosomal skip peptide between the first and the second nucleic acid inserts.

Embodiment 42. The method of any one of embodiments 20-41, wherein the autologous tumor cell is administered to the individual as a dose of about $1 \times 10^6$ cells to about $5 \times 10^7$ cells.

Embodiment 43. The method of embodiment 42, wherein the autologous tumor cells are administered to the individual once a month.

Embodiment 44. The method of embodiment 43, wherein the autologous tumor cells are administered to the individual from 1 to 12 months.

Embodiment 45. The method of any one of embodiments 20-44, wherein the autologous tumor cell is administered to the individual by intradermal injection.

Embodiment 46. A method of preventing recurrence or prophylactically treating recurrence of a substantially eradicated ovarian cancer in an individual in need thereof, the method comprising administering to the individual:
   a. at least one first dose of an autologous tumor cell vaccine comprising autologous tumor cells transfected with an expression vector comprising:
      i. a first insert comprising a nucleic acid sequence encoding a Granulocyte Macrophage Colony Stimulating Factor (GM-CSF) sequence; and
      ii. a second insert comprising a sequence according to SEQ ID NO:2 or 4 (SEQ ID NO:4); and
   b. at least one second dose of the autologous tumor cell vaccine in combination with at least one dose of an additional therapeutic agent.

Embodiment 47. The method of embodiment 46, wherein the substantially eradicated ovarian cancer is Stage III or Stage IV ovarian cancer.

Embodiment 48. The method of embodiment 46 or embodiment 47, wherein the individual comprises a wild-type BRCA1 gene, a wild-type BRCA2 gene, or a combination thereof.

Embodiment 49. The method of any one of embodiments 46-48, wherein a recurrence free survival (RFS) of the individual is increased relative to an individual with substantially eradicated ovarian cancer who has not been administered the transfected tumor cell.

Embodiment 50. The method of any one of embodiments 46-49, wherein the individual received an initial therapy.

Embodiment 51. The method of embodiment 50, wherein the initial therapy comprises debulking surgery, chemotherapy, or the combination thereof.

Embodiment 52. The method of embodiment 51, wherein the chemotherapy comprises administering a platinum-based drug and a taxane.

Embodiment 53. The method of embodiment 52, wherein the platinum-based drug comprises carboplatin.

Embodiment 54. The method of embodiment 52, wherein the taxane comprises paclitaxel.

Embodiment 55. The method of any one of embodiments 46-54, wherein the GM-CSF is a human GM-CSF sequence.

Embodiment 56. The method of any one of embodiments 46-55, wherein the expression vector further comprises a promoter.

Embodiment 57. The method of embodiment 56, wherein the promoter is a cytomegalovirus (CMV) mammalian promoter.

Embodiment 58. The method of embodiment 57, wherein the expression vector further comprises a CMV enhancer sequence and a CMV intron sequence.

Embodiment 59. The method of any one of embodiments 56-58, wherein the first insert and the second insert are operably linked to the promoter.

Embodiment 60. The method of any one of embodiments 46-59, wherein the expression vector further comprises a nucleic acid sequence encoding a picornaviral 2A ribosomal skip peptide between the first and the second nucleic acid inserts.

Embodiment 61. The method of any one of embodiments 46-60, wherein the additional therapeutic agent is selected from the group consisting of an angiogenesis inhibitor, a PARP inhibitor, and a checkpoint inhibitor to the individual.

Embodiment 62. The method of embodiment 61, wherein the angiogenesis inhibitor is a vascular endothelial growth factor (VEGF) inhibitor.

Embodiment 63. The method of embodiment 62, wherein the VEGF inhibitor is selected from the group consisting of: sorafenib, sunitinib, bevacizumab, pazopanib, axitinib, cabozantinib, and levatinib.

Embodiment 64. The method of embodiment 62, wherein the VEGF inhibitor is bevacizumab.

Embodiment 65. The method of embodiment 61, wherein the PARP inhibitor is selected from the group consisting of niraparib, olaparib, rucaparib, niraparib, talazoparib, veliparib, and pamiparib.

Embodiment 66. The method of embodiment 61, wherein the PARP inhibitor is niraparib.

Embodiment 67. The method of embodiment 61, wherein the checkpoint inhibitor is selected from the group consisting of a PD-1 inhibitor, a PD-L1 inhibitor, and a CTLA-4 inhibitor.

Embodiment 68. The method of embodiment 61, wherein the checkpoint inhibitor is selected from the group consisting of pembrolizumab, nivolumab, cemiplimab, atezolizumab, avelumab, durvalumab, and ipilimumab.

Embodiment 69. The method of embodiment 61, wherein the checkpoint inhibitor is atezolizumab.

Embodiment 70. The method of any one of embodiments 46-69, wherein the at least one dose of the additional therapeutic agent is from 1100 mg to 1300 mg.

Embodiment 71. The method of any one of embodiments 46-70, wherein the at least one first dose of the autologous tumor cell vaccine comprises from $1\times10^6$ cells to about $5\times10^7$ cells.

Embodiment 72. The method of any one of embodiments 46-71, wherein the at least one second dose of the autologous tumor cell vaccine comprises from $1\times10^6$ cells to about $5\times10^7$ cells.

Embodiment 73. The method of any one of embodiments 46-72, wherein the at least one first dose of the autologous tumor cell autologous tumor cell is administered to the individual by intradermal injection.

Embodiment 74. The method of any one of embodiments 46-73, wherein the at least one second dose of the autologous tumor cell autologous tumor cell is administered to the individual by intradermal injection.

Embodiment 75. The method of any one of embodiments 46-74, wherein the at least one dose of the additional therapeutic agent is administered via intravenous infusion.

Embodiment 76. The method of any one of embodiments 46-75, wherein the at least one first dose of the autologous tumor cell vaccine comprises two doses.

Embodiment 77. The method of any one of embodiments 46-76, wherein each dose of the at least first dose of the autologous tumor cell vaccine is administered to the individual once a month.

Embodiment 78. The method of any one of embodiments 46-77, wherein each dose of the at least second dose of the autologous tumor cell vaccine is administered to the individual once a month.

Embodiment 79. The method of any one of embodiments 46-78, wherein each dose of the at least one dose of the additional therapeutic agent is administered to the individual at least once a month.

Embodiment 80. The method of any one of embodiments 46-79, wherein the at least first dose of the autologous tumor cell vaccine and at least second dose of the autologous tumor cell vaccine comprise a total of at least twelve doses.

Embodiment 81. A method of treating BRCA1/2 wild type ovarian cancer in an individual in need thereof, the method comprising administering to the individual:
   a. at least one first does of an autologous tumor cell vaccine comprising autologous tumor cells transfected with an expression vector comprising:
      i. a first insert comprising a nucleic acid sequence encoding a Granulocyte Macrophage Colony Stimulating Factor (GM-CSF) sequence; and
      ii. a second insert comprising a sequence according to SEQ ID NO:2 or 4 (SEQ ID NO:4); and
   b. at least one second dose of the autologous tumor cell vaccine in combination with at least one dose of an additional therapeutic agent.

Embodiment 82. The method of embodiment 81, wherein the ovarian cancer is Stage III or Stage IV ovarian cancer.

Embodiment 83. The method of embodiment 81 or embodiment 82, wherein the ovarian cancer is refractory ovarian cancer.

Embodiment 84. The method of embodiment 83, wherein the refractory ovarian cancer is refractory to a chemotherapy.

Embodiment 85. The method of embodiment 84, wherein the chemotherapy comprises a platinum-based drug or a taxane.

Embodiment 86. The method of embodiment 85, wherein the platinum-based drug comprises carboplatin.

Embodiment 87. The method of embodiment 85, wherein the taxane comprises paclitaxel.

Embodiment 88. The method of any one of embodiments 81-87, wherein the GM-CSF is a human GM-CSF sequence.

Embodiment 89. The method of any one of embodiments 81-88, wherein the expression vector further comprises a promoter.

Embodiment 90. The method of embodiment 89, wherein the promoter is a cytomegalovirus (CMV) mammalian promoter.

Embodiment 91. The method of embodiment 90, wherein the expression vector further comprises a CMV enhancer sequence and a CMV intron sequence.

Embodiment 92. The method of any one of embodiments 89-91, wherein the first insert and the second insert are operably linked to the promoter.

Embodiment 93. The method of any one of embodiments 81-92, wherein the expression vector further comprises a nucleic acid sequence encoding a picornaviral 2A ribosomal skip peptide between the first and the second nucleic acid inserts.

Embodiment 94. The method of any one of embodiments 81-93, wherein the additional therapeutic agent is selected from the group consisting of an angiogenesis inhibitor, a PARP inhibitor, and a checkpoint inhibitor to the individual.

Embodiment 95. The method of embodiment 94, wherein the angiogenesis inhibitor is a vascular endothelial growth factor (VEGF) inhibitor.

Embodiment 96. The method of embodiment 95, wherein the VEGF inhibitor is selected from the group consisting of: sorafenib, sunitinib, bevacizumab, pazopanib, axitinib, cabozantinib, and levatinib.

Embodiment 97. The method of embodiment 95, wherein the VEGF inhibitor is bevacizumab.

Embodiment 98. The method of embodiment 94, wherein the PARP inhibitor is selected from the group consisting of niraparib, olaparib, rucaparib, niraparib, talazoparib, veliparib, and pamiparib.

Embodiment 99. The method of embodiment 94, wherein the PARP inhibitor is niraparib.

Embodiment 100. The method of embodiment 94, wherein the checkpoint inhibitor is selected from the group consisting of a PD-1 inhibitor, a PD-L1 inhibitor, and a CTLA-4 inhibitor.

Embodiment 101. The method of embodiment 94, wherein the checkpoint inhibitor is selected from the group consisting of pembrolizumab, nivolumab, cemiplimab, atezolizumab, avelumab, durvalumab, and ipilimumab.

Embodiment 102. The method of embodiment 94, wherein the checkpoint inhibitor is atezolizumab.

Embodiment 103. The method of any one of embodiments 81-102, wherein the at least one dose of the additional therapeutic agent is from 1100 mg to 1300 mg.

Embodiment 104. The method of any one of embodiments 81-103, wherein the at least one first dose of the autologous tumor cell vaccine comprises from $1 \times 10^6$ cells to about $5 \times 10^7$ cells.

Embodiment 105. The method of any one of embodiments 81-104, wherein the at least one second dose of the autologous tumor cell vaccine comprises from $1 \times 10^6$ cells to about $5 \times 10^7$ cells.

Embodiment 106. The method of any one of embodiments 81-105, wherein the at least one first dose of the autologous tumor cell autologous tumor cell is administered to the individual by intradermal injection.

Embodiment 107. The method of any one of embodiments 81-106, wherein the at least one second dose of the autologous tumor cell autologous tumor cell is administered to the individual by intradermal injection.

Embodiment 108. The method of any one of embodiments 81-107, wherein the at least one dose of the additional therapeutic agent is administered via intravenous infusion.

Embodiment 109. The method of any one of embodiments 81-108, wherein the at least one first dose of the autologous tumor cell vaccine comprises two doses.

Embodiment 110. The method of any one of embodiments 81-109, wherein each dose of the at least first dose of the autologous tumor cell vaccine is administered to the individual once a month.

Embodiment 111. The method of anyone of embodiments 81-110, wherein each dose of the at least second dose of the autologous tumor cell vaccine is administered to the individual once a month.

Embodiment 112. The method of anyone of embodiments 81-111, wherein each dose of the at least one dose of the additional therapeutic agent is administered to the individual at least once a month.

Embodiment 113. The method of anyone of embodiments 81-112, wherein the at least first dose of the autologous tumor cell vaccine and at least second dose of the autologous tumor cell vaccine comprise a total of at least twelve doses.

Embodiment 114. A method of treating a cancer in an individual in need thereof, the method comprising administering to the individual an expression vector comprising:
   a) a first insert comprising a nucleic acid sequence encoding a Granulocyte Macrophage Colony Stimulating Factor (GM-CSF) sequence; and
   b) a second insert comprising a sequence according to SEQ ID NO:2 or 4 (SEQ ID NO:4).
wherein the individual comprises a wild-type BRCA1 gene, a wild-type BRCA2 gene, or a combination thereof, and is identified as homologous recombination deficiency (HRD)-negative.

Embodiment 115. The method of embodiment 114, wherein the GM-CSF is a human GM-CSF sequence.

Embodiment 116. The method of embodiment 114, wherein the expression vector further comprises a promoter.

Embodiment 117. The method of embodiment 116, wherein the promoter is a cytomegalovirus (CMV) mammalian promoter.

Embodiment 118. The method of embodiment 114, wherein the expression vector further comprises a CMV enhancer sequence and a CMV intron sequence.

Embodiment 119. The method of embodiment 114, wherein the first insert and the second insert are operably linked to the promoter.

Embodiment 120. The method of embodiment 114, wherein the expression vector further comprises a nucleic acid sequence encoding a picornaviral 2A ribosomal skip peptide between the first and the second nucleic acid inserts.

Embodiment 121. The method of embodiment 114, wherein the cancer is an HRD-negative, wild-type BRCA1/2 cancer.

Embodiment 122. The method of embodiment 114, wherein the cancer is selected from the group consisting of a solid tumor cancer, ovarian cancer, adrenocortical carcinoma, bladder cancer, breast cancer, cervical cancer, cholangiocarcinoma, colorectal cancers, esophageal cancer, glioblastoma, glioma, hepatocellular carcinoma, head and neck cancer, kidney cancer, leukemia, lymphoma, lung cancer, melanoma, mesothelioma, multiple myeloma, pancreatic cancer, pheochromocytoma, plasmacytoma, neuroblastoma, prostate cancer, sarcoma, stomach cancer, uterine cancer, thyroid cancer, and a hematological cancer.

Embodiment 123. The method of embodiment 122, wherein the solid tumor cancer is selected from the group consisting of endometrial cancer, biliary cancer, bladder cancer, liver hepatocellular carcinoma, gastric/esophageal cancer, ovarian cancer, melanoma, breast cancer, pancreatic cancer, colorectal cancer, glioma, non-small-cell lung carcinoma, prostate cancer, cervical cancer, kidney cancer, thyroid cancer, a neuroendocrine cancer, small cell lung cancer, a sarcoma, head and neck cancer, brain cancer, clear cell renal cell carcinoma, skin cancer, endocrine tumor, thyroid cancer, tumor of unknown origin, and a gastrointestinal stromal tumor.

Embodiment 124. The method of embodiment 122, wherein the cancer is ovarian cancer.

Embodiment 125. The method of embodiment 124, wherein the method prevents or delays relapse of a substantially eradicated ovarian cancer.

Embodiment 126. The method of embodiment 125, wherein the substantially eradicated ovarian cancer is Stage III or Stage IV ovarian cancer.

Embodiment 127. The method of embodiment 122, wherein the cancer is breast cancer.

Embodiment 128. The method of embodiment 122, wherein the cancer is melanoma.

Embodiment 129. The method of embodiment 122, wherein the cancer is lung cancer.

Embodiment 130. The method of embodiment 114, wherein the expression vector is within an autologous cancer cell that is transfected with the expression vector.

Embodiment 131. The method of embodiment 130, wherein the autologous cancer cell is administered to the individual as a dose of about $1\times10^6$ cells to about $5\times10^7$ cells.

Embodiment 132. The method of embodiment 131, wherein the autologous cancer cells are administered to the individual once a month.

Embodiment 133. The method of embodiment 131, wherein the autologous cancer cells are administered to the individual from 1 to 12 months.

Embodiment 134. The method of embodiment 114, wherein the autologous cancer cell is administered to the individual by intradermal injection.

Embodiment 135. The method of embodiment 114, wherein the individual received an initial therapy.

Embodiment 136. The method of embodiment 135, wherein the initial therapy comprises debulking surgery, chemotherapy, or the combination thereof.

Embodiment 137. The method of embodiment 135, wherein the chemotherapy comprises administering a platinum-based drug and a taxane.

Embodiment 138. The method of embodiment 137, wherein the platinum-based drug comprises carboplatin.

Embodiment 139. The method of embodiment 137, wherein the taxane comprises paclitaxel.

Embodiment 140. The method of anyone of embodiments 1-139, further comprising administering an additional therapeutic agent.

Embodiment 141. The method of embodiment 140, wherein the additional therapeutic agent is a member selected from the group consisting of an angiogenesis inhibitor, a PARP inhibitor, and a checkpoint inhibitor to the individual.

EXAMPLES

Example 1—BRCA1/2 Wild Type Frontline Stage III/IV Ovarian Cancer Recurrence Free and Overall Survival Advantage Using Vigil®

Given the limitations of frontline treatment for advanced ovarian cancer, relationship of high TGFβ expression to immune inhibition in ovarian cancer, and limited treatment options in BRCA1/2-wt patients, a study was initiated to examine the use of Vigil® as frontline maintenance therapy in patients with ovarian cancer.

Materials and Methods

Trial Design and Treatments

This Phase 2b, double-blind trial of Vigil® vs. placebo involved 25 sites. Patients with Stage III/IV high-grade serous ovarian cancer in clinical complete response (cCR) following combination of surgery and chemotherapy involving carboplatin and paclitaxel were included. Patients enrolled could have either primary debulking surgery followed by adjuvant chemotherapy or neoadjuvant chemotherapy followed by interval debulking surgery and adjuvant chemotherapy. Germline and/or somatic BRCA1/2 molecular profiling of tissue/blood was collected and analyzed (Ocean Ridge Biosciences, Deerfield Beach, Fla.). Patients received either 1×10e7 cells/intradermal injection of Vigil® or placebo once a month (within 8 weeks after last chemotherapy) for up to 12 doses. Treatment was continued until disease recurrence or exhaustion of treatment supply. Toxicity was assessed using CTCAE v 4.03.

Patients

Women who had histologically confirmed Stage III or IV high-grade serous ovarian cancer (HGSC) that obtained a cCR after combination of surgery and chemotherapy were included in the trial.

Tumor Procurement Relationship to Manufacturing

Gradalis, Inc. (Carrollton, Tex.) manufactured Vigil® from harvested tumor tissue. Equal doses of placebo (freeze media) based on the number of vials of Vigil® were manufactured. Ten to thirty grams of tissue was required for vaccine manufacturing. Lesions extending into bowel lumen were excluded (risk of bacterial contamination).

Investigational Product and Placebo Manufacturing

Surgically excised tumor tissue was procured and cut into 1/4 inch sections before being placed in specimen containers supplemented with gentamicin (Fresenius Kabi) and packaged in wet ice for overnight transport. On Day 1, transport medium and tumor specimen were tested for sterility (BacT/Alert 3D Microbial Identification System, BioMerieux). The tumor tissue was trimmed and dissociated by scalpel followed by enzymatic dissociation (Type I collagenase solution) and incubated at 37° C. to form a single cell suspension. The suspension was adjusted to a concentration to 40 million cells/mL and electroporated using a Gene Pulser XL (BioRad) to facilitate plasmid insertion.

On Day 2, the overnight culture was harvested and resuspended in fresh X-VIVO media. QC samples and a minimum of 4 doses per patient were required before proceeding. The cells were washed with PlasmaLyte (Baxter) supplemented with 1% Human Serum Albumin (HSA) (Octapharma) and QC samples were removed. The cells were placed into freeze media consisting of 10% DMSO (dimethyl sulfoxide; Cryoserv USP; Mylan), 1% HSA (Octapharma) in Plasma-Lyte A at pH 7.4 (Baxter) and aseptically aliquoted at 1×10e7 cells/mL into sterile 2.0 mL borosilicate glass vials (Algroup Wheaton Pharmaceutical and Cosmetics Packaging); closed with a butyl rubber stopper coated with Flurotec® barrier file (West Pharmaceutical Services) with a final fill volume of 1.2 mL. The final product vials were frozen at a controlled rate using CoolCell® freezing containers (Biocision) placed into −80° C. freezers (Sanyo).

Placebo was made up of freeze media consisting of 10% DMSO (Cryoserv USP; Mylan), 1% HSA (Octapharma) in Plasma-Lyte A at pH 7.4 (Baxter). After slow freezing the media to −80° C. the vials were stored in the vapor phase of liquid nitrogen pending sterility and endotoxin release testing. Placebo vial production was matched to the available product doses manufactured for the subject.

Disease Evaluation

Subjects remained on treatment until disease recurrence or exhaustion of the subject's Vigil® or placebo supply. Disease recurrence was evaluated by WorldCare Clinical (WCC) (Boston, Mass.) using the Response Evaluation Criteria in Solid Tumors Version 1.1 (RECIST 1.1).

End Points and Statistical Assessment

The primary endpoint was recurrence-free survival (RFS) from randomization comparing Vigil® vs. placebo. All statistical analyses planned prior to unblinding were independently performed (Stat Beyond Consulting, Irvin, Calif. Secondary endpoints in order of priority included RFS of BRCA-wt from time of procurement, RFS of BRCA-wt from time of randomization, RFS of all patients from time of procurement, OS of all patients from time of randomization, and OS of all patients from time of procurement. OS of BRCA-wt from time of randomization and procurement was a preplanned sub analysis. All patients (who received at least one dose of Vigil® or placebo) were included in the safety analyses. Per protocol, a one-sided p value of 0.05 or less (stratified log-rank test) was considered to indicate statistical significance in analyses. Based on sample size calculations, a total of 54 events were needed for this analysis. Hazard ratios of RFS were estimated via a Cox proportional hazards model stratified by the randomization stratification factors [residual disease (macroscopic/microscopic), frontline chemotherapy (neoadjuvant, adjuvant)]. Distribution of RFS was estimated using the Kaplan-Meier method. Planned subgroup analysis was assessed by forest plot for all patients and BRCA-wt patients. Subgroups included number of injections, age, ECOG, BRCA-wt/m, race, stage, and manufacturing release criteria (TGFβ1, GMCSF, viability). P values to check the balance of baseline demographics variables are calculated using 2-sided Fisher's exact test for categorical data and 2-sided t-test for continuous data without multiplicity adjustment. Grambsch and Therneau's test was done to check the proportional hazards assumption for the Cox model with stratification.

Results

Patients

From February 2015 to March 2017, 310 patients were consented at 22 sites. One hundred twenty-eight patients were deemed ineligible due to histology or screen failure parameters. Of the remaining 181 that underwent manufacturing, 92 subjects (56%) were successfully manufactured and randomized, although one withdrew after randomization prior to treatment for personal reasons in good health. Seventeen did not sign consent for randomization and 72 failed product release criteria (65 for insufficient cells). Ninety-one subjects received Vigil® (n=46) or placebo (n=45) and were analyzed for safety and efficacy. Sixty-seven subjects were BRCA-wt (Vigil®: 39 BRCA-wt, placebo: 28BRCA-wt) and 24 BRCA-m. Fifty-five recurrence events were observed in the trial by independent third-party radiological evaluation (WCC) by August 2019. Demographics are shown in Table 2. No significant differences were detected between cohorts except 45.7% Vigil® patients had ECOG 1 performance compared to 20% placebo.

TABLE 2

Demographics of per protocol population (PP)

| | Treatment Group, No. (%) | | | |
| --- | --- | --- | --- | --- |
| | All Patients | | BRCA1/2-wt | |
| Characteristic | Vigil ® | Placebo | Vigil ® | Placebo |
| No. of patients | 46 | 45 | 39 | 28 |
| Age, years | | | | |
| Median | 62.5 | 63.0 | 63 | 64 |
| Range | 42-84 | 38-79 | 42-84 | 38-79 |
| <65 | 25 (54.3) | 28 (62.2) | 21 (53.8) | 15 (53.6) |
| >=65 | 21 (45.7) | 17 (37.8) | 18 (46.2) | 13 (46.4) |
| Race | | | | |
| Asian | 0 (0) | 2 (4.4) | 0 (0) | 1 (3.6) |
| Black or African American | 1 (2.2) | 4 (8.9) | 0 (0) | 2 (7.1) |
| White | 45 (97.8) | 38 (84.4) | 39 (100) | 24 (85.7) |
| Not Reported | 0 (0) | 1 (2.2) | 0 (0) | 0 (0) |

TABLE 2-continued

Demographics of per protocol population (PP)

| | Treatment Group, No. (%) | | | |
| | All Patients | | BRCA1/2-wt | |
| Characteristic | Vigil ® | Placebo | Vigil ® | Placebo |
| --- | --- | --- | --- | --- |
| Ethnicity | | | | |
| Hispanic or Latino | 1 (2.2) | 0 (0) | 1 (2.6) | 0 (0) |
| Non Hispanic or Latino | 45 (97.8) | 44 (97.8) | 38 (97.4) | 27 (96.4) |
| Not Reported | 0 (0) | 1 (2.2) | 0 (0) | 1 (2.2) |
| ECOG | | | | |
| 0 | 25 (54.3) | 36 (80.0) | 21 (53.8) | 22 (78.6) |
| 1 | 21 (45.7) | 9 (20.0) | 18 (46.2) | 6 (21.4) |
| FIGO Stage | | | | |
| III | 37 (80.4) | 40 (88.9) | 31 (79.5) | 25 (89.3) |
| IV | 9 (19.6) | 5 (11.1) | 8 (20.5) | 3 (10.7) |
| Frontline Chemotherapy | | | | |
| Neoadjuvant | 38 (82.6) | 38 (84.4) | 34 (87.2) | 26 (92.9) |
| Adjuvant | 8 (17.4) | 7 (15.6) | 5 (12.8) | 2 (7.1) |
| Frontline surgery residual disease status | | | | |
| Macroscopic | 15 (32.6) | 12 (26.7) | 13 (33.3) | 9 (32.1) |
| Microscopic/NED | 31 (67.4) | 33 (73.3) | 26 (67.7) | 19 (67.9) |
| Histology | | | | |
| Endometrioid carcinoma | 1 (2.2) | 0 (0) | 1 (2.6) | 0 (0) |
| Mixed serous/clear cell | 0 (0) | 1 (2.2) | 0 (0) | 1 (2.2) |
| High grade serous carcinoma | 45 (97.8) | 44 (97.8) | 38 (97.4) | 27 (96.4) |
| BRCA mutational status | | | | |
| BRCA-wt | 39 (84.8) | 28 (62.2) | 39 (100) | 28 (100) |
| BRCA-m | 7 (15.2) | 17 (37.8) | 0 (0) | 0 (0) |
| Time from last chemo given to first dose of Vigil ®/ placebo | | | | |
| Mean | 49.5 (1.6 mo.) | 47.2 (1.5 mo.) | 49.6 (1.6 mo.) | 47.9 (1.6 mo.) |
| Median (range) | 49 (22-121) (1.6 mo. (0.7 mo.-4.0 mo.) | 47 (16-110) (1.5 mo. (0.5 mo.-3.6 mo.) | 49 (22-121) (1.6 mo. (0.7 mo.-4.0 mo.) | 46 (23-110) (1.5 mo. (0.8 mo.-3.6 mo.) |
| Solid Tumor Weight (g) | | | | |
| Mean (SD) | 54 (28) | 56 (30) | 55 (27) | 59 (27) |
| Median (range) | 51.8 (9.6-136.5) | 51.6 (7.8-137.5) | 54 (10-136) | 53 (11-114) |
| Cells harvested per gram of tumor tissue (×10e6) | | | | |
| Mean (SD) | 6 (4) | 7 (7) | 5 (3) | 6 (5) |
| Median (range) | 4.8 (0.7-17.0) | 4.7 (1.6-33.6) | 5 (1-13) | 5 (2-29) |
| Time from surgery to randomization range | | | | |
| Mean | 214.1 (7.1 mo.) | 200.3 (6.7 mo.) | 205.7 (6.8 mo.) | 201.8 (6.6 mo.) |
| Median | 208.5 (161-471) (7.0 mo. (5.3 mo.-15.5 mo.) | 200 (156-315) (6.7 mo. (5.1 mo.-10.4 mo.) | 204 (161-286) (6.7 mo. (5.3 mo.-9.4 mo.) | 198.5 (156-315) (6.5 mo. (5.1 mo.-10.4 mo.) |

Efficacy

Figure 6A:
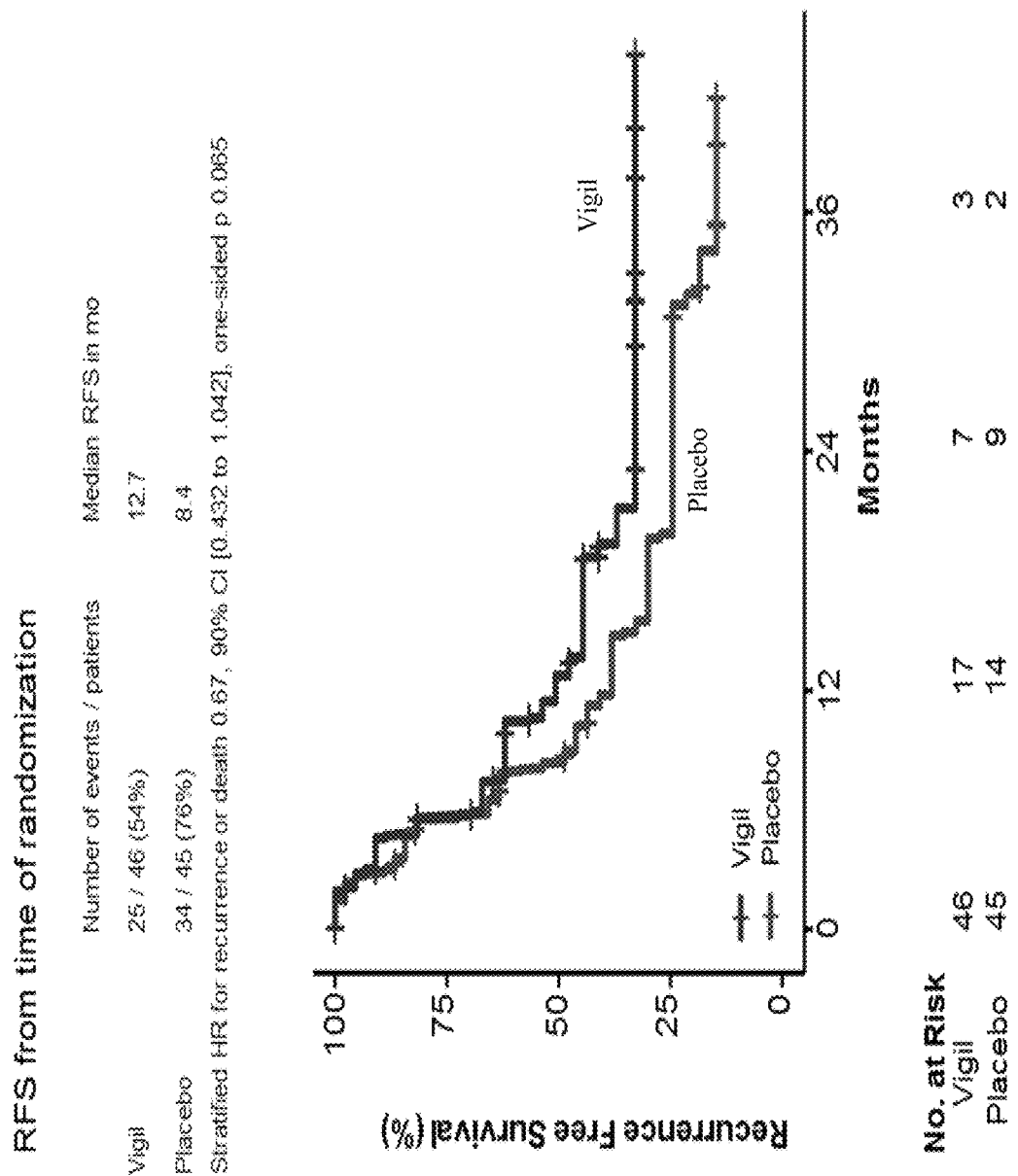
FIGS. 6A-6F illustrate recurrence-free survival (RFS) or overall survival (OS) of patients from surgery/procurement or randomization of Vigil® vs. placebo.
Figure 6B:
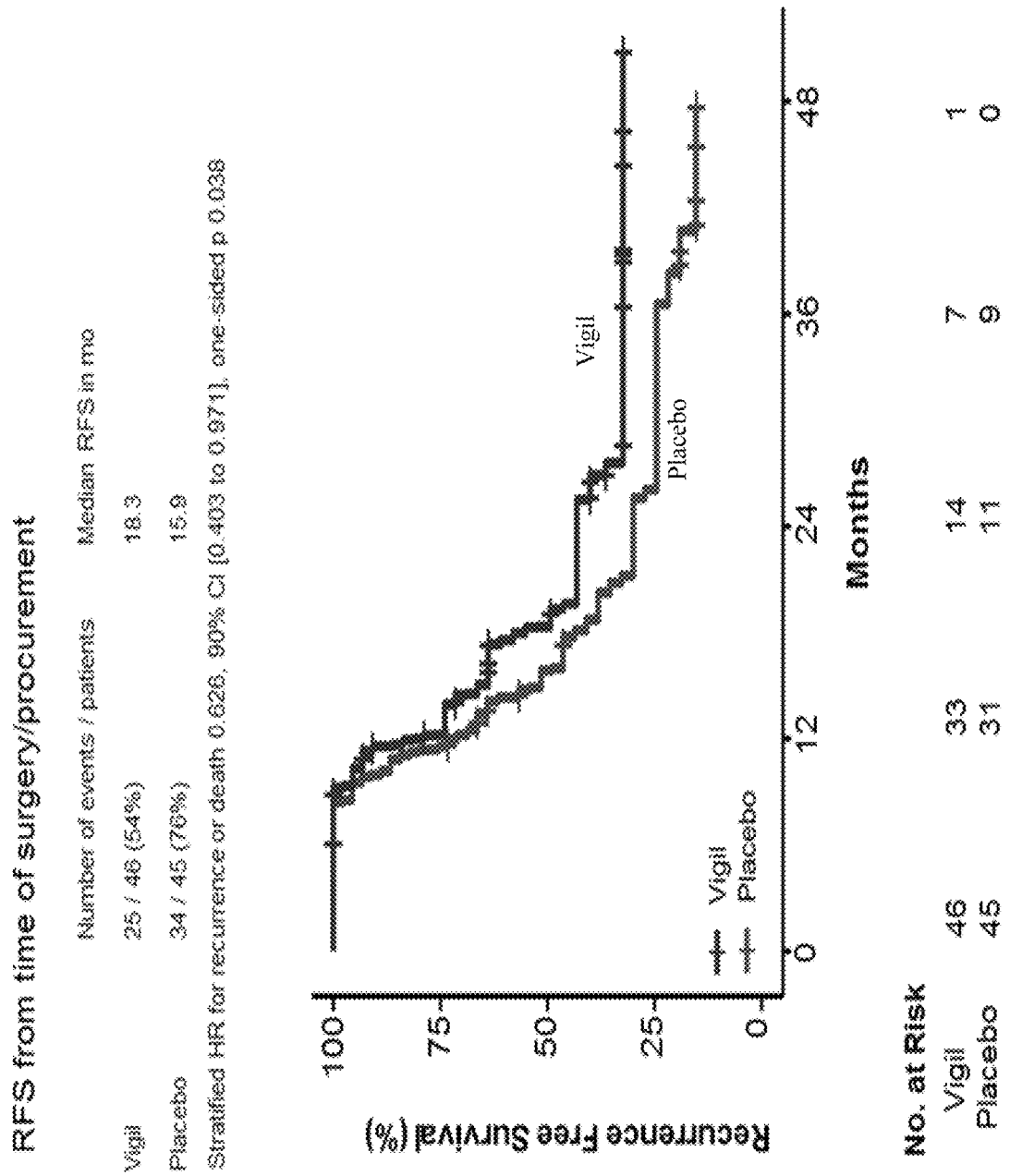

Primary endpoint of median RFS calculated from time of randomization of all patients comparing Vigil® vs. placebo was 12.7 to 8.4 months (HR 0.67, 90% CI of [0.432 to 1.042], one-sided p=0.065). RFS from time of surgery/procurement was 18.3 to 15.9 months (Vigil® vs. placebo) HR of 0.63 (90% CI [0.403 to 0.97], one-sided p=0.038) (FIGS. 6A-6B). Recurrence between Vigil® and placebo was 54% to 76% (Fisher's exact p=0.048). Moreover, the 1-year RFS rate was 51% for Vigil® versus 38% for placebo (p 0.13, one-sided Z test), and the 2-year RFS rate was 33% for Vigil® versus 25% for placebo (p 0.22, one-sided Z test) from time of randomization. Median follow up from first dose of gemogenovatucel-T was 38.5 months and placebo was 38.6 months. Both PP and ITT analysis revealed same results. Median time from surgery to randomization was 7.0 and 6.7 months and median duration from the end of chemotherapy to the start of treatment was 1.6 and 1.5 months (gemogenovatucel-T, placebo, respectively).

Figure 6C:
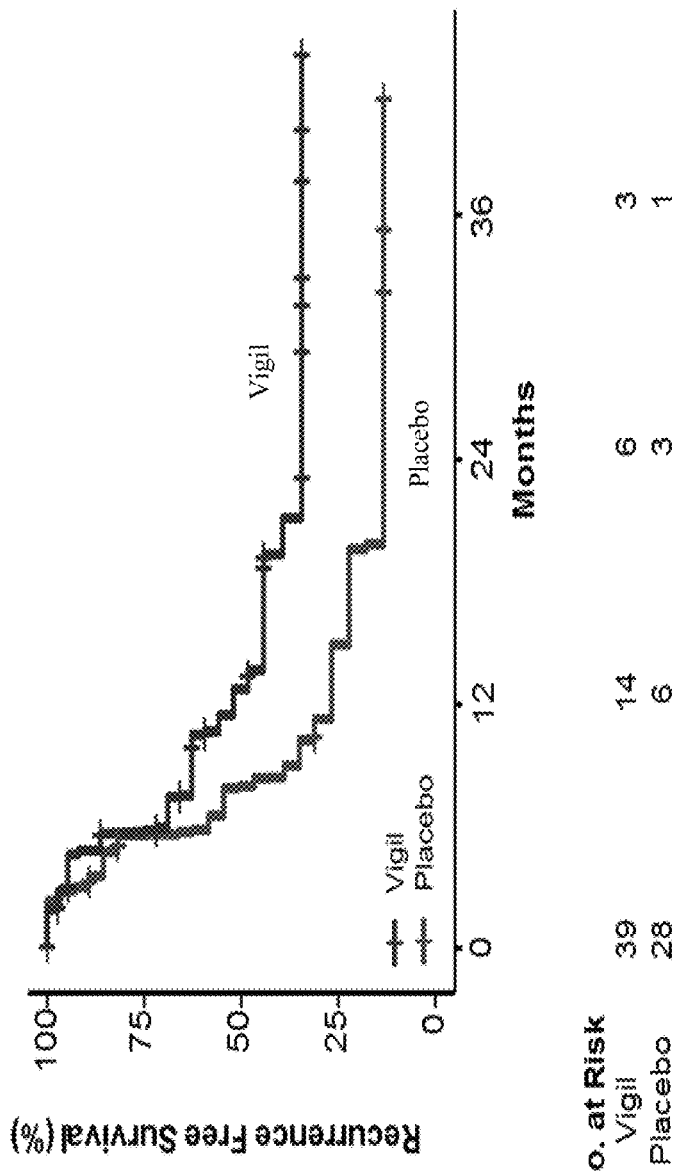
Figure 6D:
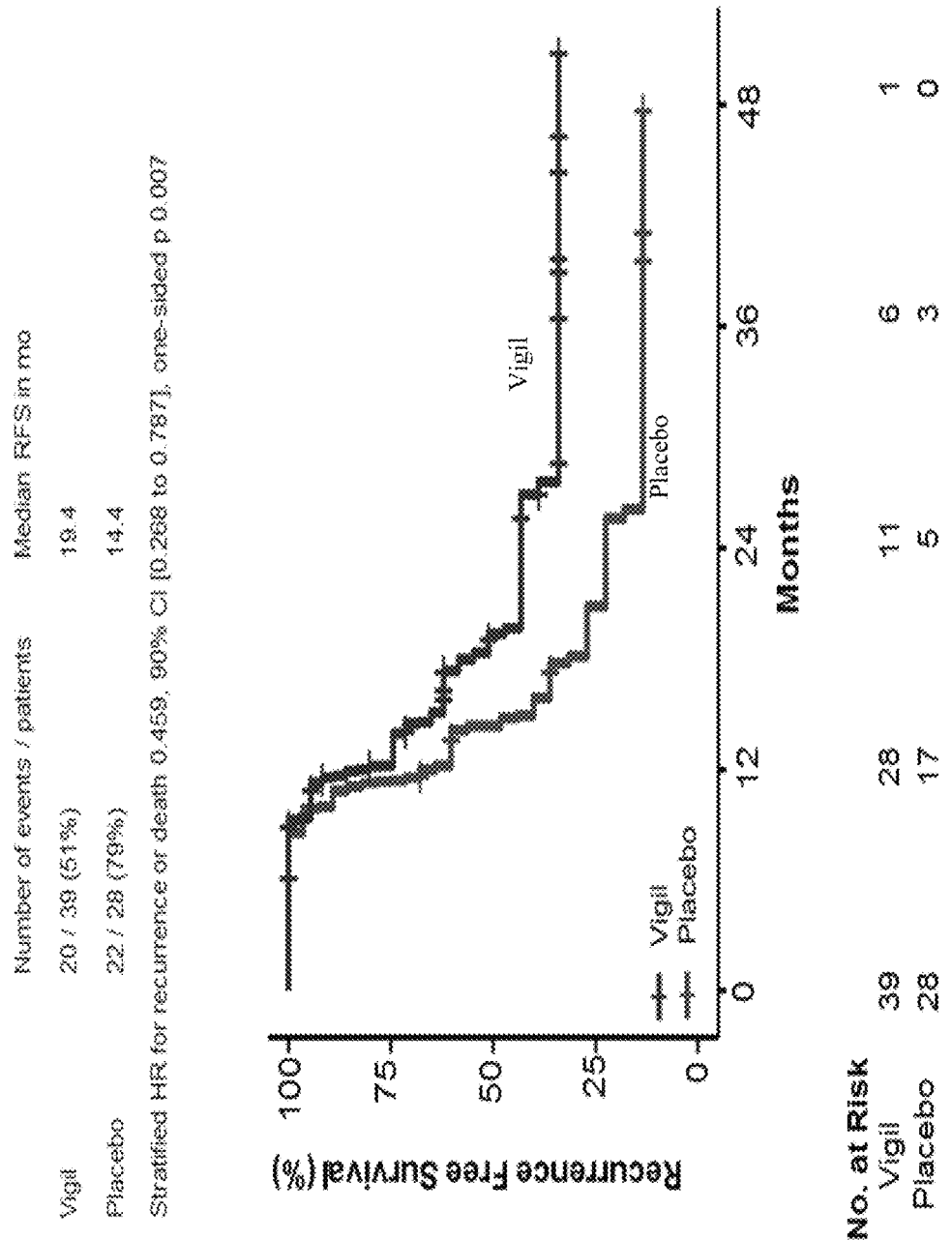
Figure 6E:
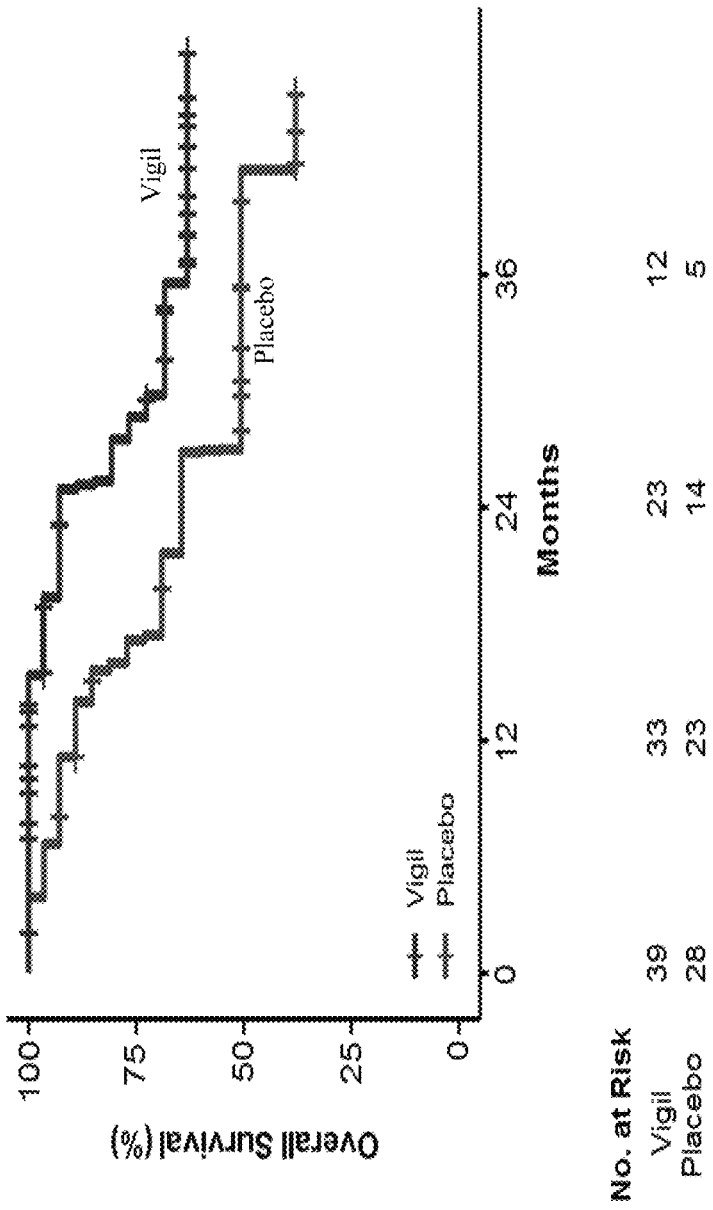
Figure 6F:
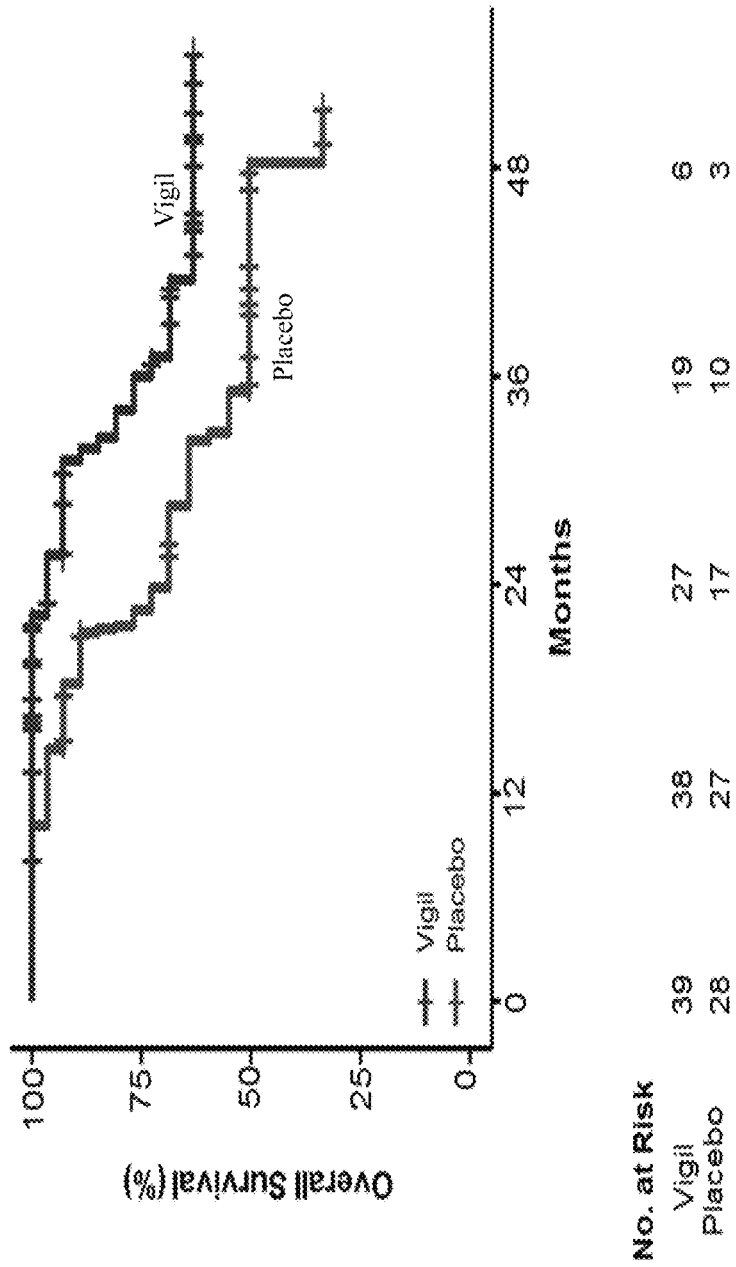

Stratification by BRCA status demonstrated improvement of Vigil® BRCA-wt patients. Median RFS (FIG. 6C) in Vigil® BRCA-wt from randomization was 12.7 months compared to 8.0 months in placebo (HR 0.493, 90% CI [0.287 to 0.846], one-sided p=0.014) and from time of surgery/procurement was 19.4 months in Vigil® and 14.4 months in placebo (HR 0.459, 90% CI [0.268 to 0.787], one-sided p=0.007) (FIG. 6D). Fifty-one percent of Vigil® BRCA1/2-wt patients demonstrated relapsed disease compared to 79% of placebo BRCA1/2-wt patients (Fisher's exact p=0.039). Overall survival advantage was observed in planned sub analysis of Vigil® BRCA-wt patients from randomization and time of surgery/procurement (FIGS. 6E-6F) in comparison to placebo. Intent to treat analysis of RFS as well as survival calculated from time of randomization and surgery/procurement revealed similar results.

Figure 7A:
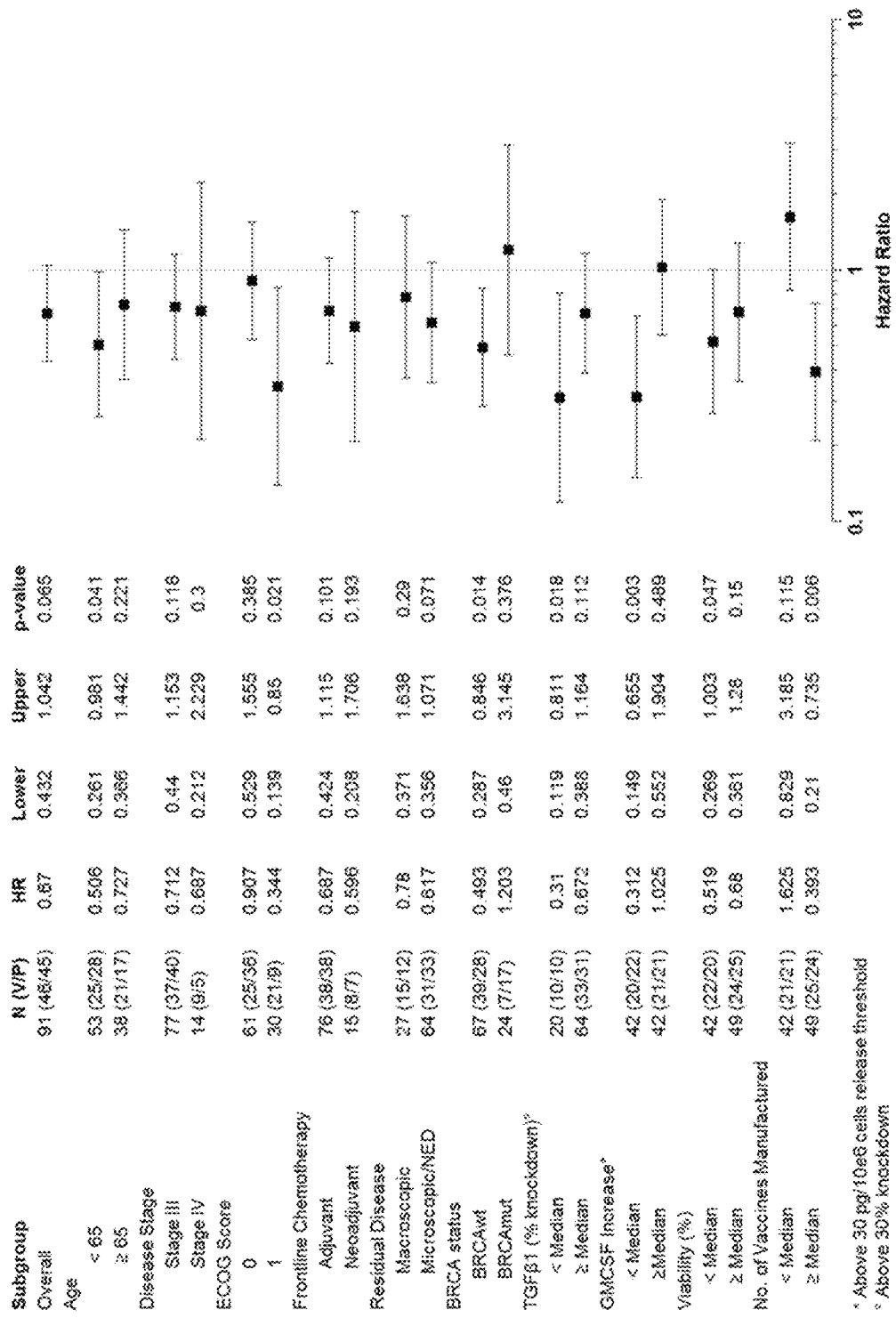
FIGS. 7A-7B illustrate forest plots.
Figure 7B:
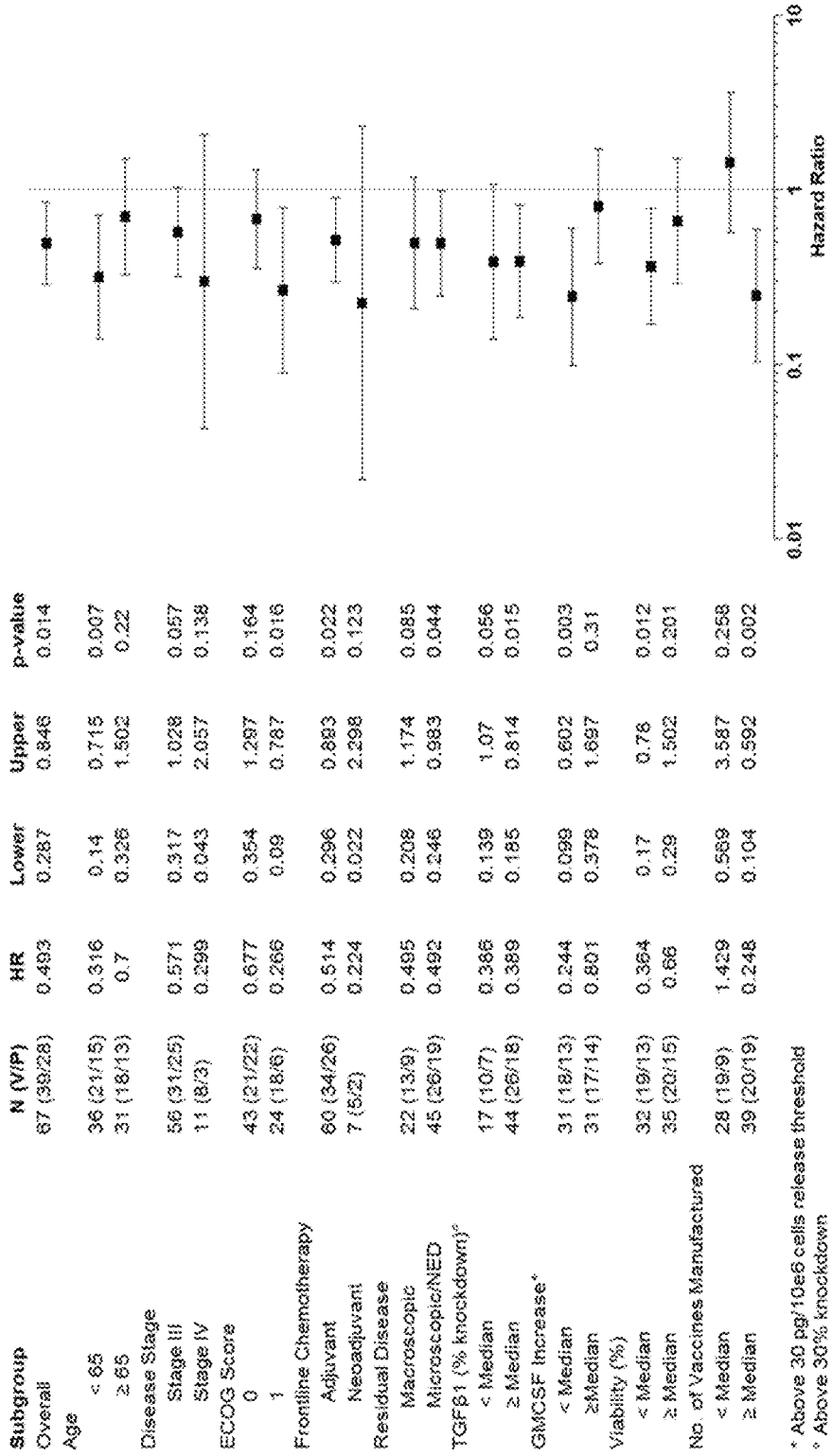

Median RFS from randomization of BRCA-m patients was 10.5 months for Vigil® and 13.3 months for placebo. Pre-study demographics related to disease effect (planned sub analysis) including pre identified stratification (residual disease, chemotherapy schedule) and product release criteria are shown for impact of BRCA-wt and all patients to RFS from time of randomization in FIGS. 7A-7B.

The secondary endpoint of median RFS calculated from time of surgery/procurement of BRCA-wt patients comparing Vigil® vs. placebo was 19.4 months in gemogenovatucel-T and 14.4 months in placebo (HR 0.459, 90% CI [0.268 to 0.787], one-sided p 0.007) (FIG. 6D). At the time of efficacy assessment, 51% of Vigil® BRCA1/2-wt patients demonstrated relapsed disease compared to 79% of placebo BRCA-wt patients (p 0.0195, one-sided Fisher's exact t test). The 1-year RFS rate was 80% for Vigil® BRCA-wt patients versus 64% for placebo BRCA-wt patients (p 0.075, one-sided Z test), and the 2-year RFS rate was 43% for Vigil® versus 23% for placebo (p 0.05, one-sided Z test) from time of surgery/procurement. Median RFS of Vigil® BRCA-wt patients from randomization was 12.7 months compared to 8.0 months in placebo (HR 0.493, 90% CI [0.287 to 0.846], one-sided p 0.014) (FIG. 6C). For BRCA-wt patients, the 1-year RFS rate was 52% for Vigil® versus 27% for placebo (p 0.02, one-sided Z test), and the 2-year RFS rate was 34% for Vigil® versus 13% for placebo (p 0.035, one-sided Z test) from time of randomization. Intent to treat analysis of RFS calculated from time of randomization and surgery/procurement revealed similar results (FIG. 5A-D). Median RFS from time of surgery/procurement in all patients was 18.3 to 15.9 months (Vigil® vs. placebo) HR of 0.63 (90% CI [0.403 to 0.971], one-sided p 0.038) (FIG. 6B).

Sensitivity analysis based on the RMST for the BRCA-wt patients was performed to compare Vigil® with placebo and the results were consistent with those based on the stratified log-rank test. RMST difference between Vigil® and placebo was 7.8 months (p 0.021) for RFS from randomization and was 7.1 months (p 0.020) for OS from randomization for the BRCA-wt patients. A truncation point equal to the minimum of the longest follow-up time of either arm was used in the RMST analysis.

Safety

A median of 6 Vigil® (range 1 to 12) or 6 placebo (range 3 to 12) injections were administered per patient. One treatment delay of a placebo patient due to a pelvic infection that was recorded as possibly related to study drug. Two placebo patients experienced Grade 3 related toxicity; no Vigil® Grade 3 treatment-related adverse events were observed, 9% of reported AEs were grade Grade 2, 3 adverse events in Vigil® vs. 2.9% placebo. Seven (4 placebo; 3 Vigil®) patients had 11 serious adverse events (SAE) reported. All but one were unlikely related or not related to study treatment.

Product Release Results

Eighty-four (92%) subjects met all product release criteria. The median tumor mass harvested was 52 gm (range 8-137 gm). Median viability of the product release was 88% (72-98%, n=91). Seven (8%, 5 Vigil®, RFS randomization 7.4 months/2 placebo) of the 91 did not show sufficient increase in GMCSF expression following plasmid transfer. However, six of these seven (6 of 7) patients demonstrated adequate TGFβ1 knockdown. Additional product release results are shown in Table 3. Evaluable median GMCSF production (pg/10e6 cells) was 860 (36-37669, n=84) and evaluable median TGFβ1 knockdown was 100% (66-100%, n=84). TGFβ1 knockdown results were also undetermined in 7 patients (six with adequate GMCSF expression release, 3 Vigil®, RFS randomization 5.6 months/4 placebo), however 78 (86%) patients had ≥90% TGFβ1 knockdown demonstrating robust activity related to furin bi-shRNAi knockdown although RFS was not significantly different. Baseline TGFβ1 production prior to plasmid transfection with detectable levels in all patients revealed a median TGFβ1 expression of 164 pg/10e6 cells (mean 241, range 52-882). BRCA1/2-wt TGFβ1 expression revealed a median of 181 (mean 249, range 60-662) pg/10e6 cells for both groups and BRCA1/2-m TGFβ1 expression revealed median 146 (mean 219, range 52-882) pg/10e6 cells. (Table 4)

TABLE 3

Summary of numerical release

|  | Viability (%) | GMCSF Production (pg/10^6 cells) | TGF-β1 Knockdown (%) | Gel-clot Endotoxin (Vaccine <EU/mL) |
|---|---|---|---|---|
| Count | 91 | 91 | 84 | 91 |
| Average | 86% | 1806 | 96% | 0.4 |
| StDev | 5% | 2433 | 8% | 0.4 |
| Median | 86% | 826 | 100% | 0.4 |
| Min | 72% | −1339 | 66% | 0.2 |
| Max | 98% | 10151 | 100% | 3.2 |
| Range | 0 | 11491 | 34% | 3.0 |

Cell dose 1 × 10^7 for all patients; USP<71> sterility negative all patients; mycoplasma DNA negative all patients Table 4

BRCA ½ mutation status correlation with TGFβ1

|  | Vigils ® | | | Placebo | | | Overall | | |
|---|---|---|---|---|---|---|---|---|---|
|  | ½ wt | ½ mut | all | ½ wt | ½ mut | all | ½ wt | ½ mut | all |
| Subjects | 24 | 4 | 46 | 24 | 10 | 45 | 48 | 14 | 91 |
| TGFβ1 Pre |  |  |  |  |  |  |  |  |  |
| Count | 24 | 4 | 43 | 22 | 9 | 41 | 46 | 13 | 84 |
| Mean (pg/10^6) | 263 | 131 | 224 | 247 | 275 | 259 | 255 | 231 | 241 |
| SD (pg/10^6) | 161 | 98 | 148 | 150 | 267 | 175 | 154 | 234 | 162 |
| Median (pg/10^6) | 262 | 93 | 164 | 166 | 146 | 168 | 212 | 122 | 166 |
| Min (pg/10^6) | 71 | 65 | 60 | 86 | 52 | 52 | 71 | 52 | 52 |
| Max (pg/10^6) | 662 | 273 | 662 | 561 | 882 | 882 | 662 | 882 | 882 |

Efficacy

Figure 2B:
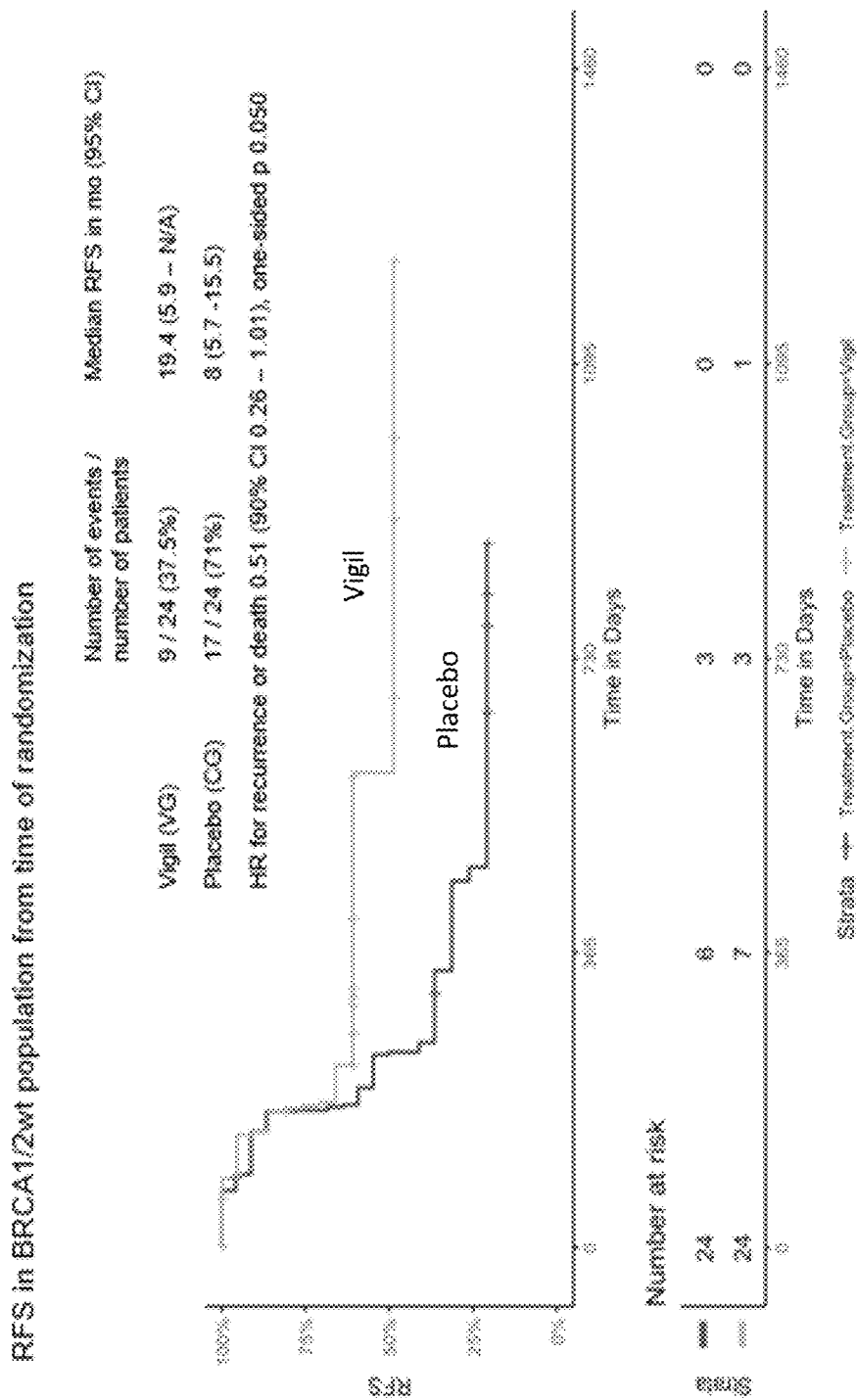
Figures 3A, 3B:
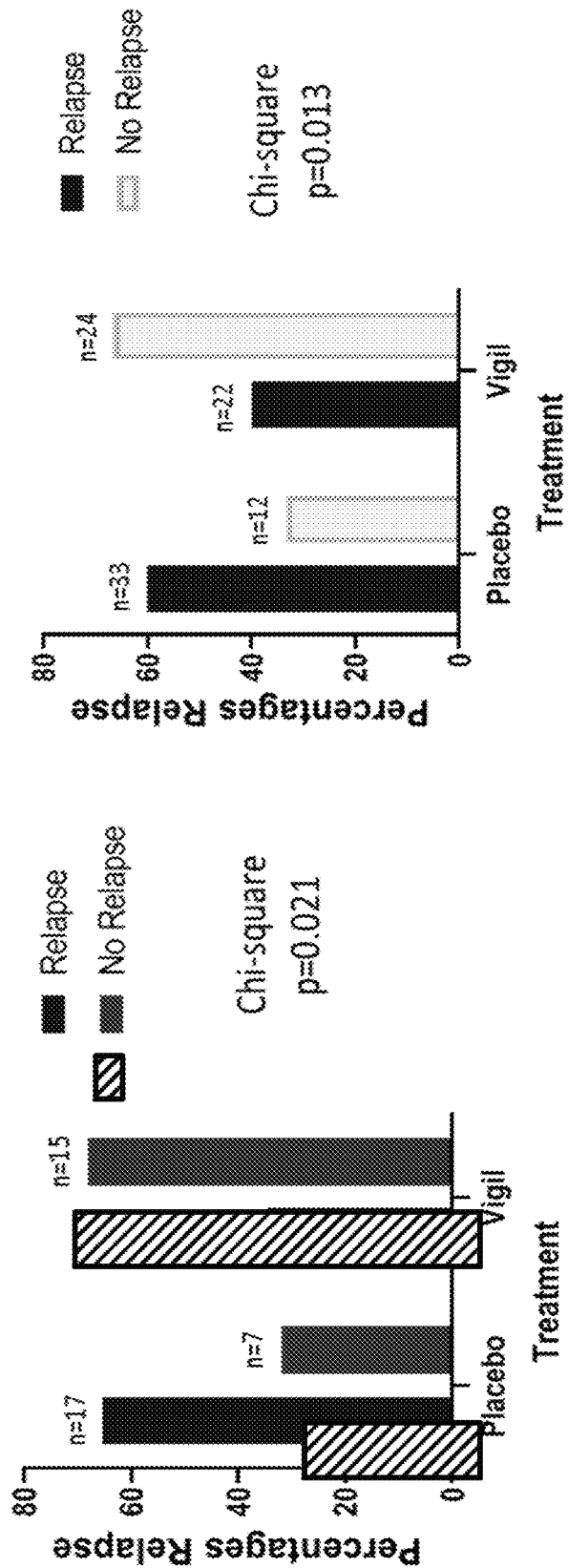
FIGS. 3A-3B illustrate the fraction of all recurrent disease between Vigil® and placebo.

Out of the 91 evaluable patients, there were 62 patients that had BRCA)/2 molecular profile at local site analysis. The subgroup of BRCA1/2-wt patients showed RFS benefit in the Vigil® cohort compared with the Placebo cohort. Results are shown in FIGS. 2A-2B. Median RFS calculated from time of surgery/procurement was not reached in BRCA-wt ovarian patients in the Vigil® cohort vs. 14.8 months in placebo cohort (HR=0.49, 90% CI, 0.25-0.97, one-sided p=0.038). Similarly, when RFS was calculated from time of randomization, median RFS in the BRCA-wt subgroup was 19.4 months in the Vigil® compared to 8.0 months in the placebo arm (HR=0.51, 90% CI, 0.26-1.01, one-sided p=0.050). Thirty-eight percent of Vigil® treated patients who were BRCA/2-wt demonstrated relapsed disease compared to 71% of placebo BRCA1/2-wt patients (chi-square 0=0.021) (FIG. 3A). Sixty-two percent of Vigil® patients, who were BRCA-wt, continue recurrence relapse free to date (Oct. 31, 2019).

Figure 2C:
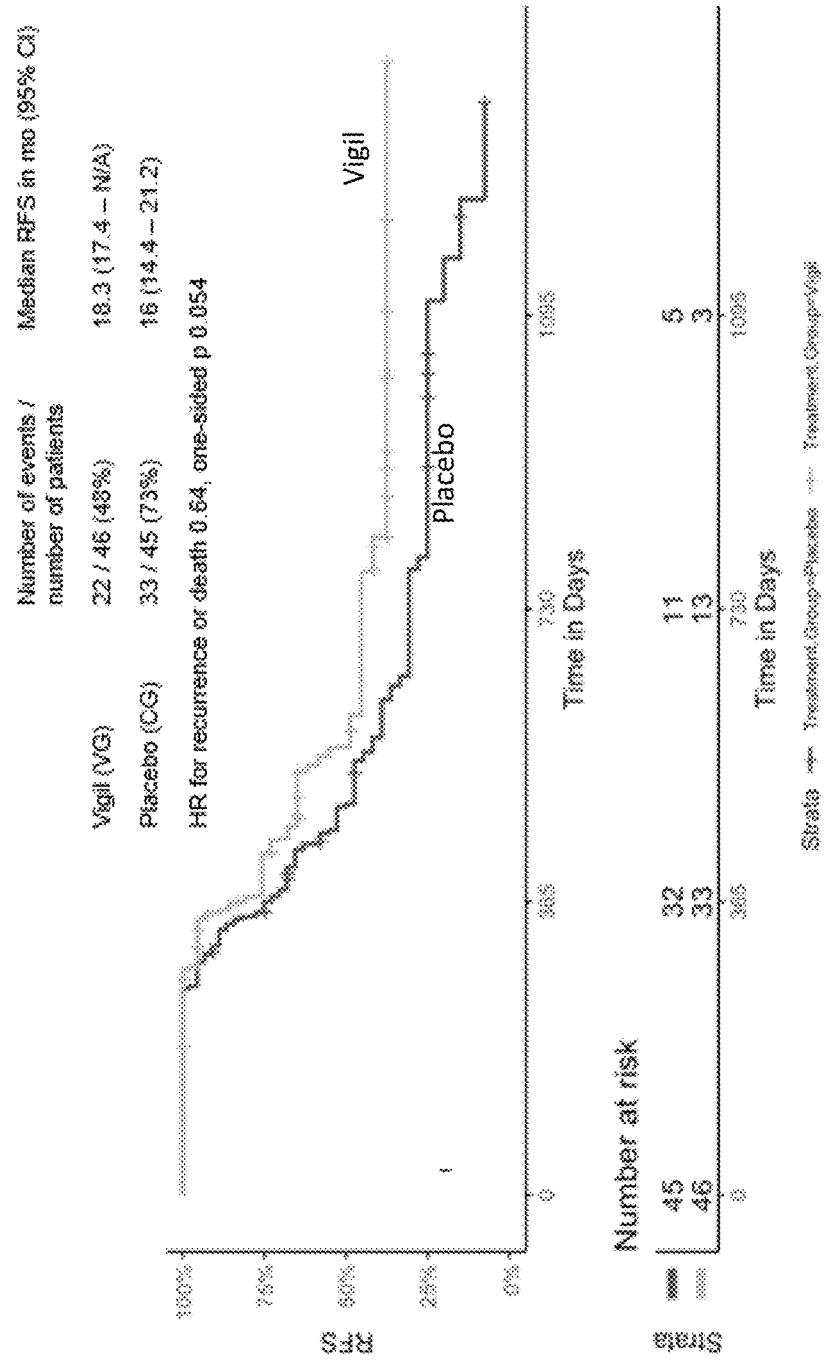
Figure 2D:
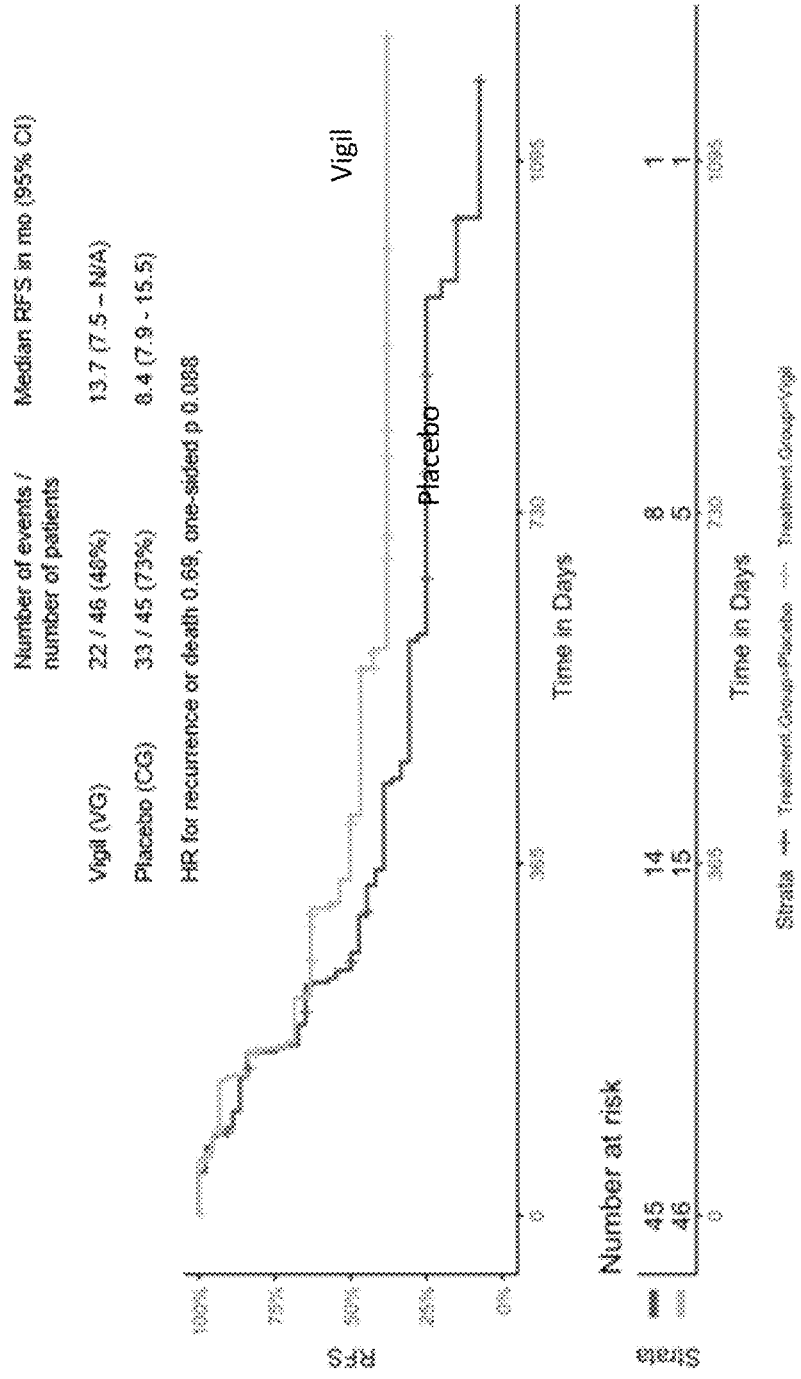
Figure 4:
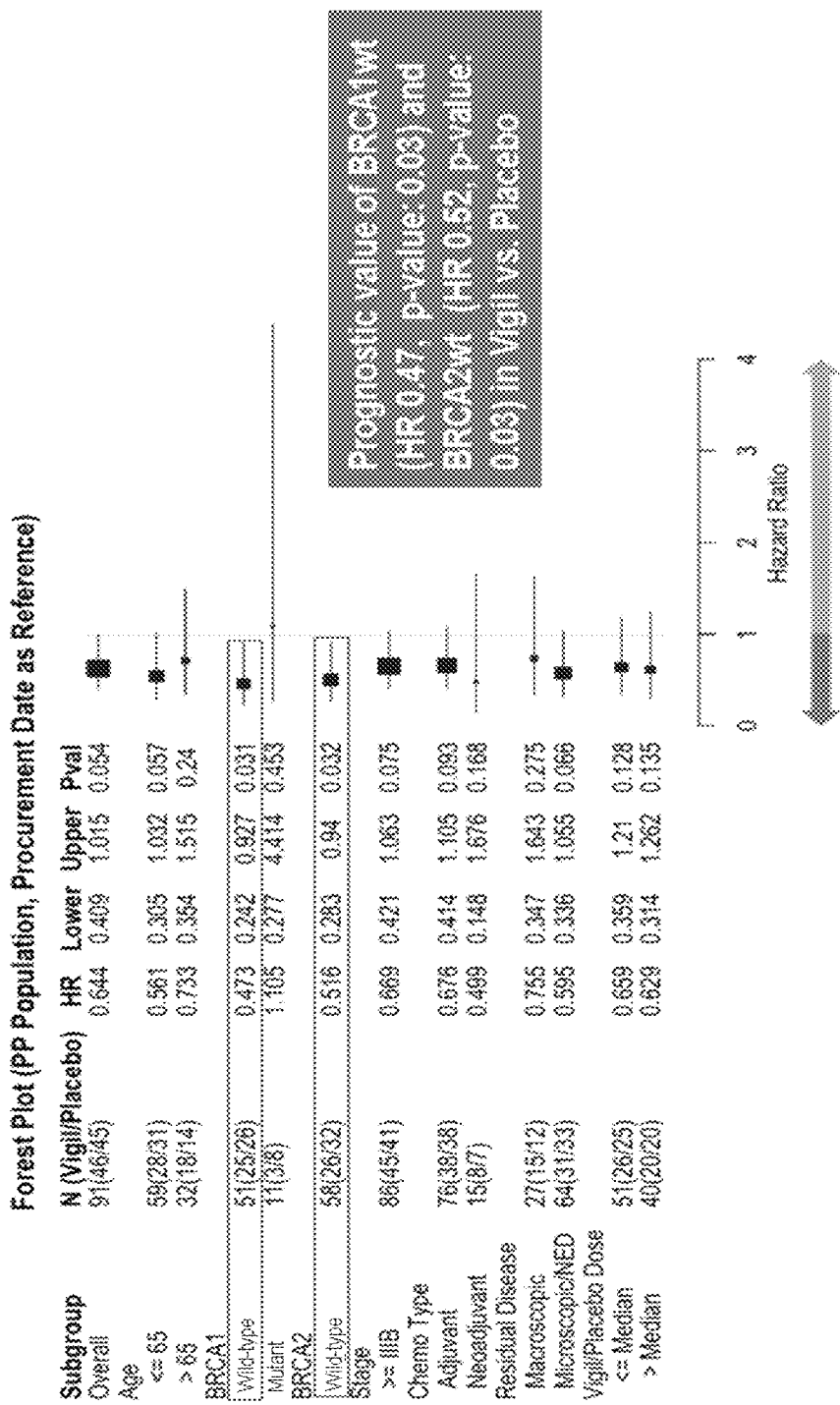
FIG. 4 illustrates forest plot key demographics between Vigil®/placebo patients.
Figure 5:
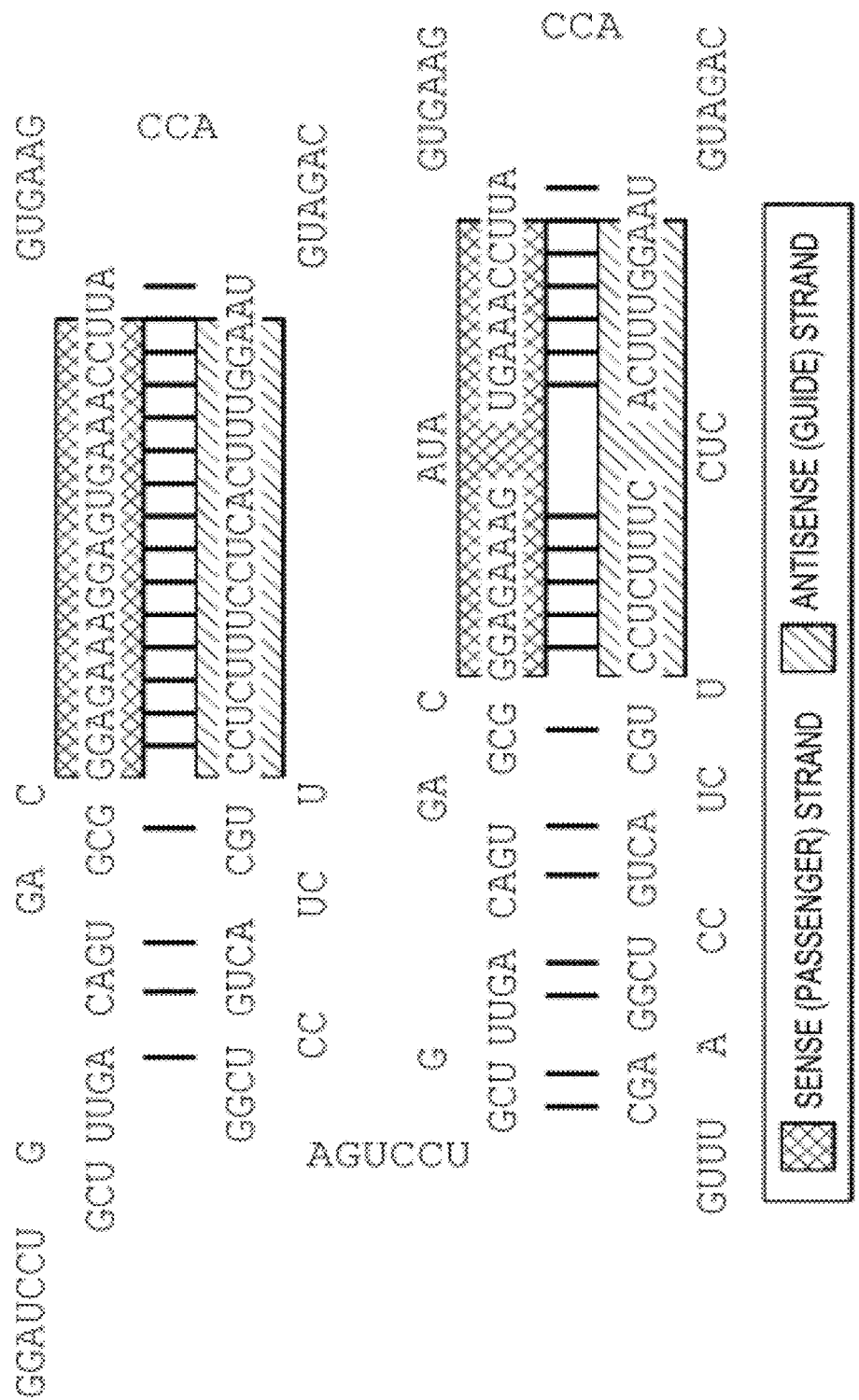
FIG. 5 shows a schematic showing the bi-shRNA$^{furin}$ (SEQ ID NO:2) comprising two stem-loop structures each with a miR-30a loop: the first stem-loop structure has complete complementary guiding strand and passenger strand, while the second stem-loop structure has three basepair (bp) mismatches at positions 9 to 11 of the passenger strand.

RFS calculated from time of debulking surgery and from time of randomization regardless of BRCA1/2 status are shown in FIGS. 2C-2D. The median RFS calculated from time of randomization in the Vigil® cohort was 13.67 months (416 days) compared to 8.38 months (255 days) in the placebo cohort (HR=0.69, one-sided log rank p=−0.054). RFS calculated from time of debulking surgery was improved with a HR of 0.64 (one-sided p=0.054). Relapse was reported in 48% of Vigil® treated patients compared to 73% of placebo patients (chi-square p=0.013) (FIG. 3B). Other factors associated with trend advantage to Vigil® response was younger age S 65 (p 0.057), late stage IIIb-IV (p 0.075), and microscopic residual disease (<10 mm)/no evidence of disease (p=0.066) (FIG. 4).

Discussion

BRCA1/2-wt patients demonstrated significant RFS (calculated from time of debulking surgery) advantage to Vigil® over placebo (not reached vs. 14.8 months; HR=0.49, one-sided p=0.038) and occurrence of lower relapse post treatment (38% vs. 71%, p=0.021). These results supported consideration of Vigil® as maintenance in BRCA1/2-wt ovarian cancer patients following complete debulking surgery and adjuvant or neoadjuvant chemotherapy. Safety analysis demonstrated no evidence of toxic effect to Vigil® over placebo.

Increasing evidence suggests that GMCSF is involved in the augmentation of tumor antigen presentation by dendritic cells (DCs). It has been shown to induce a subset of DCs that are superior for the phagocytosis of apoptotic tumor cells. It evokes higher levels of co-stimulatory molecules, which is characteristic of greater functional maturation and more efficient T cell stimulation, thereby broadening the arsenal of induced lymphocyte effector mechanisms. GMCSF also promotes the presentation of lipid antigens by dendritic cells which in turn leads to activation of Natural Killer T cells (NKT cells) a population of lymphocytes that may be pivotal in both endogenous and therapeutic responses to tumors. Dendritic cells prime antigen-specific immune responses and express diverse receptors that allow for the recognition and capture of antigens in peripheral tissues like the dermis. They process this material efficiently into the MHC Class I and II presentation pathways, upregulate costimulatory molecules upon maturation, and migrate to secondary lymphoid tissues where they present antigens to T cells. Vigil® GMCSF protein was upregulated at a robust mean/median of 1806/826 pg/10e6 cells. In 84 of the 91 (91%) patients manufactured, this was exclusively related to GMCSF plasmid transfer.

It had also previously been shown that ovarian malignant cell expression of TGFβ is much higher in malignant over non-malignant ovarian tissue. A gene expression meta-analysis conducted in over 1500 OvC patients identified high- and low-risk groups based on the expression of several genes and validated the results by IHC or qRT-PCR. Pathway analysis of the gene signature showed an enrichment of TGFβ signaling in poor-prognosis patients. TGFβ signal is mediated through binding to serine/threonine kinase receptors TGFβRI and II which leads to phosphorylation and activation of the intracellular effectors Smad2 and Smad3. Smad2/3 forms a transcriptional complex with Smad4, translocates to the nucleus, and regulates gene expression of TGFβ-regulated genes. TGFβ is involved in the progression from non-invasive serous ovarian tumors to invasive serous ovarian carcinoma. It can be activated by Smad-dependent and Smad-independent pathways and is thought to promote tumor metastasis in ovarian cancer. TGFβ overexpression and correlation with tumor cell proliferation and metastasis has also been described in prostate, colon and renal cell carcinoma.

Secreted TGFβ from ovarian cancer cells generate immunosuppressive Treg cell (CD4+CD25+) expansion in the tumor microenvironment. This has been shown to be associated with poor outcome in patients with high-grade serous ovarian carcinoma treated with frontline debulking surgery/chemotherapy. TGFβ inhibits GMCSF induced maturation of bone marrow derived dendritic cells (DCs) as well as expression of MHC Class II and co-stimulatory molecules. TGFβ also inhibits activated macrophages including their antigen presenting function, as well as, ovarian cancer and tumor associated myeloid cell PD-L1 ligand expression, which has also been further linked to poor overall survival in ovarian cancer. Evidence reveals that modulation of related antitumor immunity can repair immune surveillance related to TGFβ.

TGFβ1 has also been shown to downregulate the miR181/BRCA1 axis thereby orchestrating DNA-repair deficiency and inducing "BRCAness" in breast cancers carrying wild-type BRCA genes. The term "BRCAness" has been used to identify sporadic tumors that have clinicopathological and molecular characteristics akin to those associated with BRCA1/2 germline mutations (DNA repair suppression). Additionally, it has been demonstrated that elevated TGFβ signaling in HRD-low tumors that can induce NF-kB activation and elicit antitumor immune responses in lymphocytes. Thus it appears that in addition to the BRCA molecular signal, the homologous recombination deficiency (HRD) scores may also be relevant to predict outcomes and responses to TGFβ modulating immunotherapies.

Results of improved RFS in the BRCA-wt population in this trial would further support a relationship of TGFβ suppression and immune responsiveness thereby supporting use of Vigil® in BRCA-wt patients as well as possibly other cancer subpopulations of other histologic types, such as prostate cancer, renal cell carcinoma, and colorectal cancer, with high TGFβ expression. High levels of furin mRNA and protein are also widely expressed in ovarian cancer and in many other human tumors where the gene is differentially expressed between malignant (high) and non-malignant (low) cell populations. The expression of furin which is a TGFβ1, TGFβ2 convening enzyme appears to be inversely correlated with survival and likely contributes significantly to the maintenance of tumor directed, TGFβ-mediated peripheral immune tolerance. Down regulation of furin using bi-shRNAi method, as verified in this trial, induced marked TGFβ1 expression reduction. Remarkably 73% of the Vigil® vaccines constructed had TGFβ1 knockdown of ≥90% compared to non-transfected same patient tumor cells.

BRCA-wt and HRD low ovarian cancers also demonstrate elevated tumor infiltrating lymphocyte (TIL) fraction in cancer microenvironment, high PD-L1 expression, high type 1 IFN gamma signal activity in mononuclear cells and high Perforin 1 expression, which generally would suggest improved immune responsiveness. However, several attempts to enhance both frontline and recurrent/refractory ovarian response to checkpoint inhibitor therapy have failed. This hypothetically could also be related to high TGFβ suppressive effect within local tumor microenvironment as previously described.

PARP inhibitors bind to and trap PARP proteins on DNA in addition to blocking their catalytic action. This leads to multiple double-strand DNA breaks and ultimately cell death. Lynparza® (olaparib) was one of the first PARP inhibitors approved for patients with high-grade serous ovarian cancer with germline BRCA mutations. Previous studies have shown increased progression-free survival in BRCA1/2-mu ovarian cancer (HR 0.3, p<0.0001). A recent long-term follow-up of olaparib (Study 19) in platinum-sensitive, recurrent ovarian cancer patients shows favorable OS results with HR 0.73 (p=0.0138) for all patients enrolled although activity appears to be limited to the BRCA-mu population HR 0.62 (p=0.02140) as opposed to the BRCA-wt population which did not show benefit HR 0.84 (p=0.34) in BRCA-wt (82). However, some BRCA-wt patients with recurrent or refractory disease who have high homologous recombination deficiency (HRD) may benefit from PARP inhibitors. Recent reports show that some HRD high tumors were associated with better response to niraparib. Moreover, recent studies showed that BRCA-wt and HRD-low tumors have elevated immunogenic signals including increased abundance of TILs demonstrating high IFN gamma 1 signaling. This is consistent with what was observed with Vigil® benefit in RFS most significantly demonstrated in the BRCA-wt population. Consideration of further clinical testing of Vigil® with PARP inhibition in BRCA-wt ovarian cancer is justified.

Bevacizumab is indicated maintenance therapy of frontline treated ovarian cancer although no evidence of recurrence free or overall survival advantage involving bevacizumab alone as maintenance has been observed. Vascular endothelial growth factor (VEGF) inhibitors (i.e. bevacizumab) target the pleiomorphic growth factor VEGF which is not only a key regulator of tumor angiogenesis but also suppresses the immune system. The hypoxic tumor microenvironment stimulates the secretion of the pro-angiogenic factor VEGF-A (known as VEGF) which binds to receptor tyrosine kinase VEGF receptors (VEGFRs)-1 (FLT1) and -2 (FLK1/KDR) and VEGFR co-receptors neuropilins (NRPs) 1 and 2. This pro-angiogenic switch in the tumor microenvironment not only favors tumor angiogenesis, tumor maturation, and metastatic dissemination, but also exerts immunosuppressive effects such as inhibition of dendritic cell (DC) maturation, promotion of regulatory T cell function and expands tumor-associated macrophage development, and accumulation of myeloid-derived suppressor cells. PD-1 expression on CD8+ T cells is also increased. In ovarian cancer, VEGF-A and its receptors VEGFR1, VEGFR2, and NRP1 are commonly upregulated.

Clinical effectiveness of bevacizumab in ovarian cancer however remains challenging not only as related to the limited clinical response and moderate toxicity profile but also from the relatively rapid activation of anticancer resistance following initiation of angiogenesis inhibition. However, a potential direction being explored in use of anti-angiogenesis inhibitors is intensification of the immunotherapeutic activity. There is evidence that combination of bevacizumab with therapeutic vaccines may induce infiltrating T lymphocyte response and will shift the immunosuppression balance from T regulatory suppression to CD8 T cells activation and will create a T cell inflamed tumor microenvironment ("hot tumor") that is more immunologically responsive to immunotherapy.

Results demonstrating advantage in BRCA1/2-wt population may relate to clonal neoantigen exposure, which may be diluted in comparison to subclonal neoantigen exposure in the BRCA1/2-m patients in relationship to increased repair deficiency. BRCA-wt ovarian cancers demonstrate an elevated tumor infiltrating lymphocyte (TIL) fraction in the cancer microenvironment, high PD-L1 expression, high type 1 IFN gamma signal activity in mononuclear cells and high Perforin 1 expression compared to BRCA deficient ovarian cancers, which is also consistent with higher clonal neoantigen fraction. BRCA1-wt expression also significantly impacts autophagy and association with MHC expression of tumor antigens. As such BRCA1-m is disruptive of this process which may limit neoantigen visibility and Vigil® activity.

GMCSF is involved in the augmentation of tumor antigen presentation by dendritic cells (DCs) and evokes higher levels of co-stimulatory molecules, which induce more efficient T cell stimulation. GMCSF also promotes the presentation of lipid antigens by dendritic cells which in turn leads to activation of Natural Killer T cells (NKT cells).

Additionally, TGFβ is higher in malignant over non-malignant ovarian tissue. A gene expression meta-analysis in over 1500 ovarian cancer patients identified high- and low-risk groups based on the expression of several genes and validated the results by IHC or qRT-PCR. Pathway analysis of the gene signature showed an enrichment of TGFβ signaling in poor-prognosis patients. TGFβ is involved in the progression from non-invasive serous ovarian tumors to invasive serous ovarian carcinoma. Moreover, TGFβ overexpression correlates with tumor cell proliferation and metastasis.

Secreted TGFβ from ovarian cancer cells generate immunosuppressive regulatory T cell (Treg) (CD4+CD25+) expansion in the tumor microenvironment. This has been shown to be associated with poor outcome in frontline treated patients with high-grade serous ovarian carcinoma. TGFβ inhibits GMCSF induced maturation of bone marrow derived DCs as well as expression of MHC Class II and co-stimulatory molecules. TGFβ also inhibits activated macrophages including their antigen presenting function, as well as, ovarian cancer and tumor associated myeloid cell PD-L1 ligand expression, which has also been further linked to poor overall survival in ovarian cancer. Knockdown of TGFβ1, as demonstrated in this trial, may contribute to suppression of TGFβ effect which may be more relevant in BRCA-wt patients.

Considering that Vigil® is well tolerated, easily administered and demonstrates promising efficacy which makes it an ideal maintenance therapy for ovarian cancer patients. Strengths of the results presented include safety and clinical validation of RFS and OS advantage in BRCA-wt patients. However, the BRCA-wt subset was a secondary endpoint and use of autologous tumor harvest as a component of product manufacturing provides limits to product application. Further evaluation with combination bevacizumab and/or niraparib is reasonable.

In conclusion. Vigil® demonstrated convincing RFS advantage and low toxic effect as single-agent maintenance therapy in frontline ovarian (Stage III/IV) cancer patients with BRCA1/2-wt molecular profile. Further studies as single agent and with combination angiogenesis inhibitors, PARP inhibitors and checkpoint inhibitors are also justified.

Example 2—Proof of Principle Study of Sequential Combination Atezolizumab and Vigil® in Relapsed Ovarian Cancer Despite impressive evidence of immune modulatory advantage to checkpoint inhibitor (CI) therapy in many cancer types, little advantage has been shown in OC. Theories point to this inefficiency being likely due to lack of specificity of CI combined with significant heterogenicity and genetic instability in OC. Recent reports detail how ovarian cancer (OC) cells can acquire potential escape mechanisms to evade host immunity via several immunosuppressive factors, including a loss of MHC expression and the upregulation of immunosuppressive factors including TGF-beta (TGFβ), indoleamine 2,3-dioxygenase (IDO) and cyclooxygenase (COX-1 and COX-2).

Vigil® is an autologous tumor cell vaccine in which tumor cells are harvested from patients at the time of debulking surgery and transfected via electroporation extracorporeally with a plasmid encoding for the GMCSF gene, an immune-stimulatory cytokine, and a bifunctional, short hairpin RNA (bi-shRNA) which specifically knocks down the expression of furni, the critical convertase responsible for activation of two TGFβ isoforms TGFβ-1 and TGFβ-2 (cancer immune effector suppressors). By downregulating TGFβ expression, cancer cells have a reduced ability to evade host immune responses. Vigil® is a personalized "neoantigen educating" immunotherapy which has been administered safely at doses up to 2.5×10e7 cells/injection and has shown evidence of benefit in Phase 2 testing of cancer patients including OC. Improved expression of clonal tumor neoantigen and reduced tumor suppressor effect of TGFβ is hypothesized to synergistically enhance activity of checkpoint inhibitor treatment. Moreover, preclinical evidence supports that prior administration of neoantigen educating therapy prior to cycle 1 (C1) will enhance immunotherapeutic anticancer activity of C1. The first clinical combination of Vigil® and atezolizumab together and in sequence using single agent prior clinically validated safe dose levels was explored, comparing Vigil® first (Vigil®-$1^{st}$) vs. atezolizumab first (Atezo-$1^{st}$) in order to assess safety and preliminary evidence of benefit.

Methods

Trial Design and Treatments

This Phase 1, 2-part, open-label trial was conducted at 6 centers across the United States. Part 1 explored safety of the combination of Vigil® and atezolizumab. Part 2 was a randomized study of Vigil® first vs atezolizumab first, followed by the combination of Vigil® plus atezolizumab. Patients entering a Vigil® vaccine construction protocol involving ovarian cancer were eligible for this trial. Tissue and peripheral blood mononuclear cell samples were collected and analyzed for BRCA1/2 molecular profiling using a call quality of 40 and a minimum allele depth of 5 (Ocean Ridge Biosciences, Deerfield Beach, Fla.). Patients received Vigil® (1×10e6-10e7 cells/dose intradermally) and atezolizumab (1200 mg/dose intravenous infusion) once every 3 weeks for up to 12 doses. Informed consent was obtained prior to procurement and prior to main study registration/randomization. Written documentation of full IRB approval of the protocol and consent documents were required before a patient could be registered at any site.

Patients

Women who had relapsed OC, stable medical conditions and failed at least one prior line of systemic therapy in the recurrent setting or platinum resistant disease were eligible for the trial. Subjects were required to have at least 4 vials of Vigil® manufactured, ECOG performance status (PS)≤1, and normal organ and marrow function were required and defined per protocol (Absolute neutrophil count—≥1,500/mm$^3$; Platelets—≥100,000/mm$^3$; Hemoglobin—≥5.59 mmol/L; serum bilirubin—≤1.5× institutional upper limit of normal; AST/ALT—≤2.5× institutional upper limit of normal; Creatinine—>50 mL/min; TSH within institutional limits). Patients were excluded for prior immunotherapy and active autoimmune disease.

Tumor Procurement and Manufacturing

Gradalis, Inc. (Carrollton, Tex.) manufactured Vigil® from the harvested tumor tissue. Manufacturing was a 2-day process. The equivalent of a "golf ball size" mass (10-30 g tissue, cumulative) was required for vaccine manufacturing (3 cm by radiological scan). Lesions extending into bowel lumen were excluded due to the risk of bacterial contamination.

Investigational Product and Placebo Manufacturing

Surgically excised tumor tissue was procured during the debulking procedure and cut into 1/4-1/2 inch sections before being placed in up to four specimen containers containing sterile 0.9% sodium chloride (Baxter) supplemented with gentamicin (Fresenius Kabi) and packaged on wet ice for overnight transport to the manufacturing facility. On Day 1, the transport medium and tumor specimen in each container were tested for sterility (BacT/Alert 3D Microbial Identification System, BioMerieux). The tumor tissue was trimmed to remove fat, connective/necrotic tissue, sutures/staples and mechanically dissociated by scalpel followed by enzymatic dissociation (Type I collagenase solution) and incubated at 37° C. for up to 45 minutes to form a single cell suspension. The cell suspension was filtered across a sterile 100 um strainer (Corning) to separate the cells from the debris, and the liberated cells were washed with PlasmaLyte (Baxter) supplemented with 1% Human Serum Albumin (Octapharma) and manually counted via hemocytometer (InCyto). Quality control (QC) samples were removed for retain, immune monitoring, and a pre-transfection culture initiated to obtain baseline cytokine levels by ELISA for GMCSF (R&D Systems) and TGFβ1 (R&D Systems). The cell suspension was adjusted to a concentration of 40 million cells/mL and electroporated using a Gene Pulser XL (Bio-Rad) to insert the plasmid DNA into cells. The transfected cells were plated into sterile T-225 cm$^2$ flasks (Corning) at 1×10e6 cells/mL in X-VIVO 10 media (Lonza) supplemented with gentamicin (Fresenius Kabi) and incubated overnight (14 to 22 hrs) at 37° C. with 5% CO$_2$ overlay (Sanyo) to allow for incorporation of bi-shRNA furin and GMCSF mRNA into the tumor cells.

On Day 2, the overnight culture was harvested by scraping cells from each flask, collecting media containing free-floating cells and resuspending in fresh X-VIVO media. The cells were manually counted to determine that a minimum of 80 million cells were available for QC samples and a minimum of 4 doses before proceeding. Two 1-mL mycoplasma samples containing cells were taken and frozen at −80° C. The cells were irradiated 4×25Gy cycles using gamma-ray irradiator to arrest replication/growth. The cells were washed with PlasmaLyte (Baxter) supplemented with 1% human serum albumin (Octapharma) and QC samples were removed for retain, immune monitoring, and a post-transfection culture initiated to obtain transfected cytokine levels for GMCSF and TGFβ1 by ELISA (or ELLA machine for one patient). The cells were placed into freeze media consisting of 10% DMSO (dimethyl sulfoxide; Cryoserv USP; Mylan), 1% Human Serum Albumin (Octapharma) in Plasma-Lyte A at pH 7.4 (Baxter) and aseptically aliquoted at 1×10e6 cells/mL or 1×10e7 cells/mL into sterile 2.0 mL borosilicate glass vials (Algroup Wheaton Pharmaceutical and Cosmetics Packaging); closed with a butyl rubber stopper coated with Flurotec® barrier file (West Pharmaceutical Services) with a final fill volume of 1.2 mL. The final product vials were frozen at a controlled rate using CoolCell® freezing containers (Biocision) placed into −80° C. freezers (Sanyo). After freezing, the cells were stored in the vapor phase of liquid nitrogen tanks pending release testing. Frozen product vials were used for sterility (USP <71>) and endotoxin testing by gel-clot (Limulus Amoebocyte Lysate, Lonza).

Atezolizumab was provided by Roche/Genentech and distributed by Gradalis, Inc. Atezolizumab was formulated as 60 mg/mL atezolizumab in 20 mM histidine acetate, 120 mM sucrose, 0.04% polysorbate 20, pH 5.8 (Phase III formulation). Atezolizumab was preservative-free and provided for single-use only. Atezolizumab in formulation F03 (1200 mg per vial) was administered in 250 mL 0.9% NaCl IV infusion bags and prepared and diluted under aseptic conditions.

Disease Evaluation

Subjects remained on treatment until disease progression or death or product toxic effect. Disease progression was determined radiographically by local investigators using the Response Evaluation Criteria in Solid Tumors Version 1.1 (RECIST 1.1). In Part 1, disease progression was accessed at baseline and every third cycle thereafter. In Part 2, disease was assessed at baseline, at the end of cycle 2 of single agent therapy, and every third cycle thereafter.

End Points and Statistical Assessment

The data cut-off date for the primary analysis was arbitrary at Dec. 20, 2019. Primary endpoint was safety. Efficacy assessments and endpoints included progression-free survival (PFS) and overall survival (OS) between Vigil®-$1^{st}$ group and Atezo-$1^{st}$ group. The time to progression was calculated from date of randomization until the first date of documented progression or death. PFS and OS was sequentially analyzed in the BRCA1/2-wt subgroup and compared between Vigil®-$1^{st}$ and Atezo-$1^{st}$. Median follow-up time was calculated from data cut-off date subtracted from time of treatment start. A one-sided p value of 0.05 or less (log-rank) was considered to indicate statistical significance in analyses. The hazard ratios (HRs) of PFS and OS were estimated via a Mantel-Haenszel hazards model. Distribution of PFS and OS were estimated using the Kaplan-Meier method. Toxicity was assessed using NCI CTCAE v 4.03.

Results

Patients

From Jun. 2, 2017 through Feb. 13, 2019, three patients were entered into Part 1 of the study and 21 were randomized to Part 2 of the study (n=1 Vigil®-$1^{st}$: n=10 Atezo-$1^{st}$). All patients failed at least one prior systemic therapy (Part 1/Vigil®-$1^{st}$/Atezo-$1^{st}$: 0/5/2 received one regimen, 1/4/3 received two regimens, 1/2/4 received three regimens and 1/0/1 received four regiments), Individual (Part 2 only) and all patients summarized demographics are shown in Table 5. Germline and somatic BRCA (g/sBRCA) status was determined for all 24 patients. Median follow-up time for Part 1 was 29.3 months, and for Part 2 was 21.3 months.

TABLE 5

Demographics of patients

| Study Part | Part 1 | Part 2 | | Part 2 | |
|---|---|---|---|---|---|
| Characteristic | ITT | ITT | | BRCA$^{wt}$ | |
| Treatment Arm | Vigil ® + Atezo | Atezo-$1^{st}$ | Vigil ®-$1^{st}$ | Atezo-$1^{st}$ | Vigil ®-$1^{st}$ |
| Patients | 3 | 10 | 11 | 7 | 6 |
| Age-Years | | | | | |
|   Median | 61 | 59.5 | 67 | 63 | 65 |
|   Mean | 65 | 59.7 | 63.9 | 62.3 | 63.5 |
|   Range | 59-75 | 44-77 | 50-75 | 50-77 | 50-75 |
| Race - no. (%) | | | | | |
|   White | 3 (100) | 8 (80.0) | 9 (81.8) | 5 (71.4) | 6 (100) |
|   Asian | 0 (0) | 1 (10.0) | 0 (0) | 1 (14.3) | 0 (0) |
|   Black or African American | 0 (0) | 1 (10.0) | 2 (18.2) | 1 (14.3) | 0 (0) |
| Staging - no. (%) † | | | | | |
|   III | 1 (33.3) | 9 (90.0) | 8 (72.7) | 6 (85.7) | 4 (66.7) |
|   IV | 2 (66.7) | 1 (10.0) | 3 (27.3) | 1 (14.3) | 2 (33.3) |
| ECOG-performance status-score - no. (%) ‡ | | | | | |
|   0 | 2 (66.7) | 2 (20.0) | 7 (63.6) | 0 (0) | 5 (83.3) |
|   1 | 1 (33.3) | 8 (80.0) | 4 (36.4) | 7 (100) | 1 (16.7) |
| No. of Prior Lines - no. (%) | | | | | |
|   Median | 3 | 2.5 | 2 | 3 | 2 |
|   Mean | 3 | 2.4 | 1.73 | 2.6 | 2 |
|   Range | 2-4 | 1-4 | 1-3 | 1-4 | 1-3 |
| Receipt of Frontline Chemo - no. (%) | | | | | |
|   Neoadjuvant | 2 (66.7) | 4 (40.0) | 3 (27.3) | 4 (57.1) | 2 (33.3) |
|   Adjuvant | 1 (33.3) | 6 (60.0) | 8 (72.7) | 3 (42.9) | 4 (66.7) |
| BRCA status - no. (%) § | | | | | |
|   BRCA$^{wt}$ | 3 (100) | 7 (70.0) | 6 (54.5) | 7 (100) | 6 (100) |
|   g/sBRCA$^{mut}$ | 0 (0) | 3 (30.0) | 5 (45.5) | 0 (0) | 0 (0) |
| Vaccine Dose (cells/dose) | | | | | |
|   1 × 10e6 | 0 | 0 | 1 | 0 | 1 (16.7) |
|   1 × 10e7 | 3 | 10 | 10 | 7 | 5 (83.3) |

* Percentages may not total 100 because of rounding.
† Staging based on the International Federation of Gynecology and Obstetrics (FIGO) guidelines.
‡ Eastern Cooperative Oncology Group (ECOG) performance-status scores are assessed on a 5-point scale, with higher scores indicating greater disability.
§ Deleterious BRCA mutations summarizing germline (blood) BRCA1 and BRCA2 mutations and somatic mutations.

Safety

No Grade 3 or 4 treatment related toxicities were observed in Part 1. Therefore, accrual was opened to Part 2. There were 30 treatment related adverse events in the Atezo-1$^{st}$ group and 83 events in the Vigil®-1$^{st}$ group. Twenty-five of the 30 (83.3%) Atezo-1$^{st}$ events were Grade 1, 2 with a majority attributed to atezolizumab treatment (24/25). Eighty-one out of 83 (97.6%) events in the Vigil®-1$^{st}$ treatment group were Grade 1, 2 events with 61.7% (50/81) attributed to atezolizumab treatment and 38.3% (31/81) related to Vigil® treatment.

Figure 8:
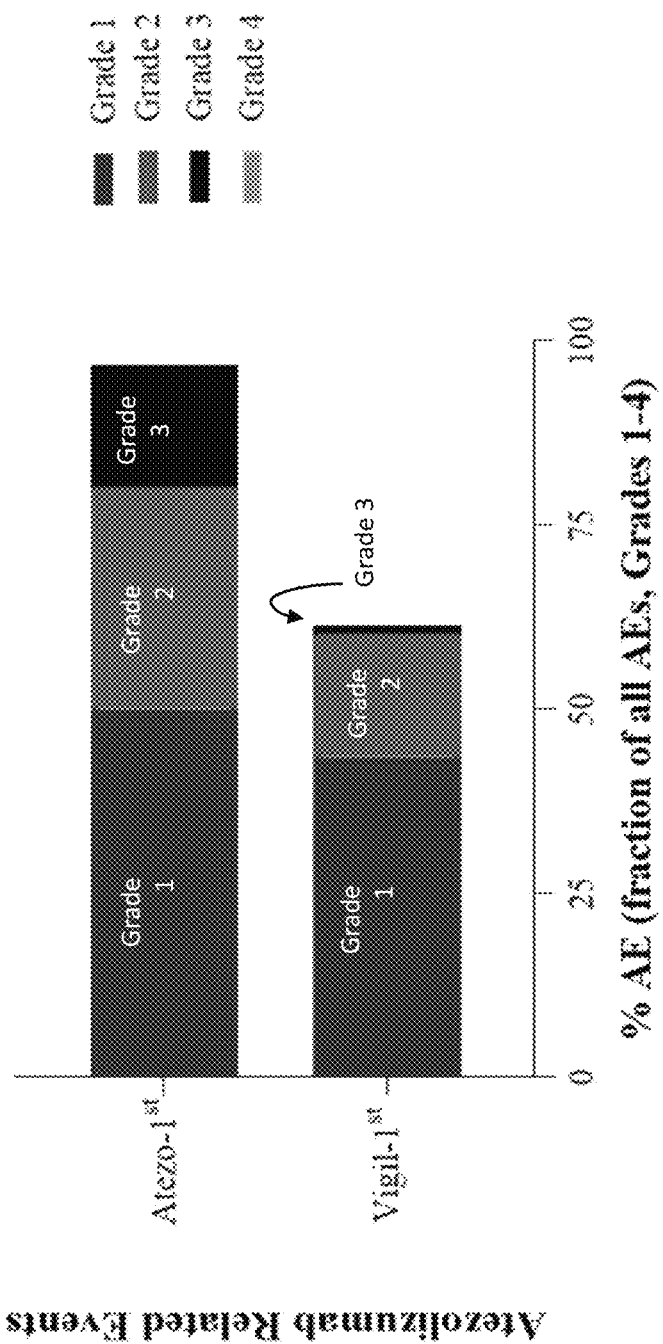
FIG. 8 illustrates all atezolizumab-related adverse events (AE) in Vigil®-1$^{st}$ vs. Atezo-1$^{st}$ in study part 2. There were 24 Grade 1, 2 atezolizumab-related AEs in the Atezo-1$^{st}$ group and 50 in the Vigil®-1$^{st}$ group. There was 1 Grade 1, 2 Vigil®-related AE in the Atezo-1$^{st}$ group and 31 in the Vigil®-1$^{st}$ group. There were 5 Grade 3, 4 atezolizumab-related AEs in the Atezo-1$^{st}$ group and 1 in the Vigil®-1$^{st}$ group. There were 0 Grade 3, 4 Vigil®-related AEs in the Atezo-1$^{st}$ group and 1 in the Vigil®-1$^{st}$ group.

A comparison of all and Grade 3, 4 atezolizumab-related events between Vigil®-1$^{st}$ and Atezo-1$^{st}$ groups is shown in FIG. 8. Grade 3, 4 treatment-related events were higher in the Atezo-1$^{st}$ arm (17.2%) vs. Vigil®-1$^{st}$ (5.1%). Grade 3 atezolizumab related events in the Atezo-1$^{st}$ group included blood and lymphatic disorders (6.9%), general disorders (3.5%), injury (3.5%), respiratory, thoracic, and mediastinal disorders (3.5%). No Vigil®, related Grade 3 events were observed in the Atezo-1$^{st}$ group. In the Vigil®-1$^{st}$ group, two Grade 3 events were urinary disorders (1 related to atezolizumab and 1 related to Vigil®). Moreover, atezolizumab-related adverse events (any Grade) were much higher in the Atezo-1$^{st}$ group (96.7%) compared to the Vigil®-1$^{st}$ group (61.3%).

Product Release Results

Vigil® vaccine from twenty subjects (83.3%) met all product release criteria. The median tumor mass harvested was 51.65 g (range 11.52 g-114.23 g). Four subjects (16.7%) did not demonstrate sufficient increase in GMCSF expression following plasmid transfer but were provided exception onto the study (n=1 Part 1, n=3 Part 2). Key product release results are shown in Table 6. Significant TGFβ1 knockdown was detectable in 23/24 (95.8%) patients. Fifteen (62.5%) patients had ≥90% TGFβ1 knockdown demonstrating robust activity related to furin bi-shRNAi knockdown. Baseline TGFβ1 production prior to plasmid transfection of all patients with detectable levels revealed a median TGFβ1 expression of 158 μg/10e6 cells (mean 206, range 93-445). BRCA1/2-wt TGFβ1 expression (n=13 Part 2) revealed a median of 139 μg/10e6 cells (mean 188, range 93-361) for Atezo-1$^{st}$ and Vigil®-1$^{st}$ groups, and BRCA1/2-m TGFβ1 expression (n=8 Part 2) revealed a median of 223 μg/10e6 cells (mean 215, range 111-307).

TABLE 6

Summary of Product Release

| Parameter | TGFβ1 Knockdown (%) | GMCSF Production (pg/10e6 cells) | Viability (%) | Gel-clot Endotoxin (Vaccine <EU/mL) |
|---|---|---|---|---|
| Study Arm | | Part 1 (N = 3) | | |
| Count* | 3 | 2^ | 3 | 3 |
| Average | 84% | 479 | 91% | 0.29 |
| StDev | 11% | 291 | 1% | 0.08 |
| Median | 79% | 479 | 91% | 0.24 |
| Min | 74% | 188 | 90% | 0.24 |
| Max | 100% | 769 | 93% | 0.40 |
| Range | 74%-100% | 188-769 | 90%-93% | 0.24-0.4 |
| Study Arm | | Part 2 (N = 21) | | |
| Count* | 20° | 18^ | 21 | 21 |
| Average | 94% | 1382 | 86% | 0.34 |
| StDev | 8% | 1480 | 6% | 0.10 |
| Median | 100% | 550 | 87% | 0.40 |
| Min | 74% | 114 | 72% | 0.20 |
| Max | 100% | 4593 | 96% | 0.50 |
| Range | 74%-100% | 114-4593 | 72%-96% | 0.2-0.5 |

Figure 9A:
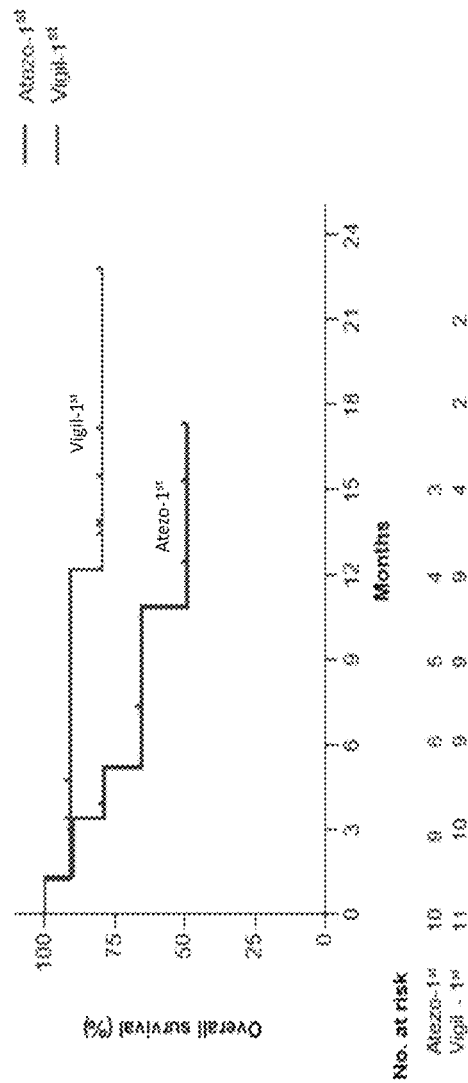
FIGS. 9A-9D illustrate efficacy analysis from time of study randomization.
Figure 9B:
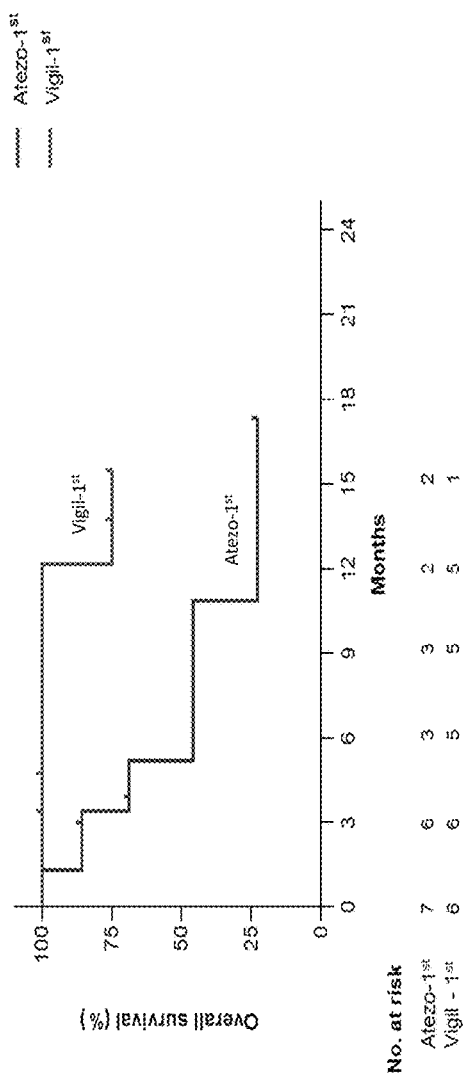
Figure 9C:
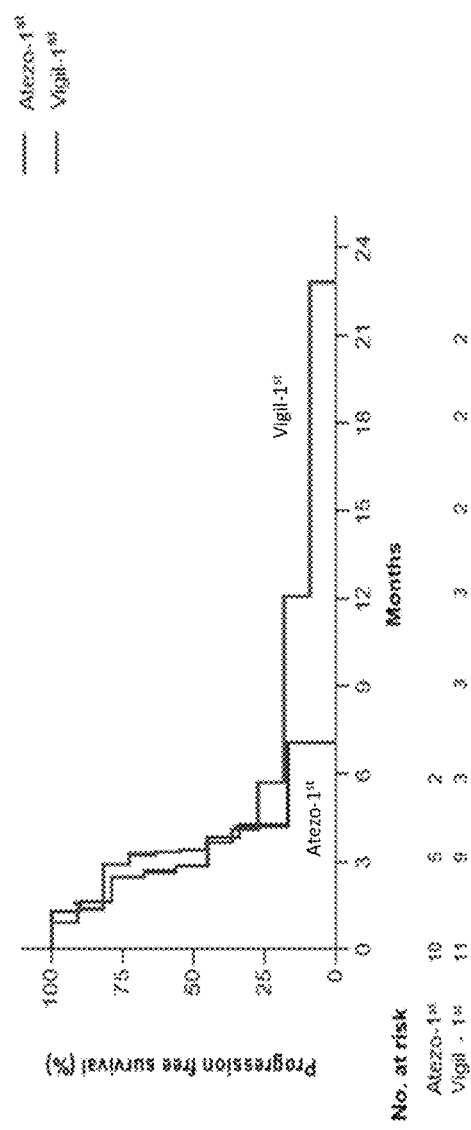
Figure 9D:
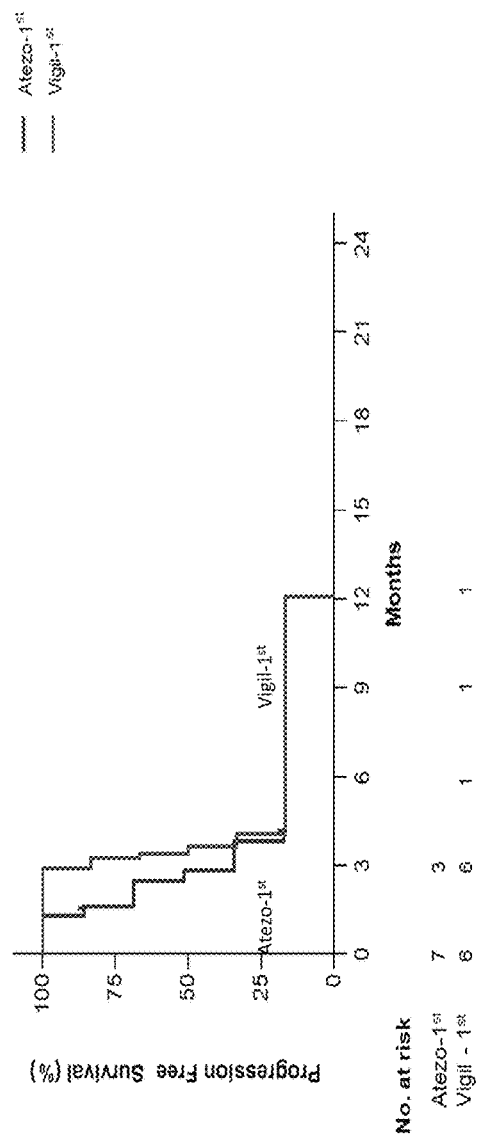

Cell dose 1 × 10e6 or 1 × 10e7; USP<71> sterility negative for all patients; mycoplasma DNA negative for all patients
*Count represents no. of patients that met product release criteria specifications. TGFβ1 (% KD)
Spec: ≥ 30%; GMCSF production (pg/10^6 cells) Spec: ≥ 30; Viability Spec: ≥ 70%
°1 patient did not meet TGFβ1 release
^4 patients did not meet GMCSF release Efficacy The median OS in the Vigil®-1$^{st}$ cohort was not reached and was 10.8 months in the Atezo-1$^{st}$ cohort (HR 0.33; 95% confidence interval (CI) [0.064-1.7]; p=0.097) (FIG. 9A). Median duration of follow-up was 21.3 months for Part 2. Subset analysis by BRCA status demonstrated improvement of ovarian cancer in BRCA1/2-wt patients in Vigil®-1$^{st}$ compared to Atezo-1$^{st}$ (HR 0.16, 95% CI [0.026-1.03]; p=0.027, FIG. 9B). There was no benefit in OS in the BRCA-m cohort between Vigil®-1$^{st}$ and Atezo-1$^{st}$ cohorts. No significant benefit was observed in PFS (FIGS. 9C-9D).

Discussion

Despite the fact that most ovarian cancer patients achieve a complete clinical response with primary surgery and combination chemotherapy, the overwhelming majority (75%) of these patients will unfortunately relapse within 16-24 months and ultimately succumb to their disease. Treatment for those patients who recur is largely based upon the recurrence free interval. Women who recur 6 months or more after completing platinum based chemotherapy have traditionally been considered to be platinum-sensitive, and are usually retreated with a platinum doublet and often maintenance therapy with bevacizumab or a PARP inhibitor.

Patients who relapse within 6 months of completing platinum based therapy (platinum-resistant) are usually managed with non-platinum based therapy with or without bevacizumab. PARP inhibitors have shown improvement in progression-free survival (PFS) as maintenance therapy following initial chemotherapy and following platinum sensitive recurrent OC therapy. Bevacizumab has been found to improve PFS when combined with initial chemotherapy or with chemotherapy following relapse and is commonly used in combination regimens in relapsed OC.

Results demonstrated here justify continued combination of Vigil® and atezolizumab testing in recurrent ovarian cancer and suggested sequential Vigil® prior to the combination therapy of Vigil®/atezolizumab has clinical advantage over Atezo-$1^{st}$. The more favorable toxicity profile with encouraging clinical benefit suggested a superior therapeutic index with Vigil®-$1^{st}$ delivery particularly in the BRCA-wildtype patients. This is particularly encouraging given limited benefit to single agent checkpoint inhibitor therapy involving ovarian cancer.

Given increased expression of TGFβ in ovarian cancer tissue compared to many other cancers particularly involving recurrent disease and direct activity of Vigil® acting to knockdown TGFβ1 and TGFβ2 via furin inhibition, Vigil® may be directly addressing a mechanism of resistance in ovarian cancer that is mediated through TGFβ1 expression. Based on these results, Vigil® may be a viable mechanism of improving neoantigen exposure and T cell activation thereby enabling optimal function for checkpoint inhibitor therapy despite TGFβ expression. Secreted TGFβ from ovarian cancer cells generate immunosuppressive Treg cells (CD4+CD25+) from peripheral CD4+CD25– cells within the tumor microenvironment. Treg tumor infiltration is associated with poor outcome in patients with high-grade serous ovarian carcinoma treated with neoadjuvant chemotherapy. Accordingly, the CD8/Treg ratio is also a prognostic indicator. It was hypothesized at initiation of this study that Vigil®-$1^{st}$ treatment before Vigil®+atezolizumab combination would focus immune effector cell visualization of relevant tumor neoantigen before checkpoint functional activity, thereby limiting off target toxicity and potentially maximizing immune effector cell availability and response. These observed results support this hypothesis and work by others in preclinical models, including evidence of selective TGFβ knockdown in overcoming resistance to checkpoint blockade.

To mount an effective anti-tumor immune response, T cells need to be educated to the neoantigen repertoire of the tumor. T cells further differentiate into memory T cells, thus providing long-term immunologic memory and presumably a durable disease control. It has been reported that tumors with low neoantigen heterogeneity respond better to checkpoint inhibition with pembrolizumab. The same report also showed that T cells were unable to recognize subclonal neoantigens, indicating that the abundance of neoantigens visible for recognition is important and may dilute visibility of clonal neoantigens. T cell recognition of tumor specific clonal neoantigens to the same patient disease is more likely when utilizing autologous tumor tissue (personalized) as opposed to allogeneic tumor tissue.

Over 1,400 doses of Vigil® have been administered in clinical trials. The most frequently reported adverse reactions attributed to Vigil® engineered cell administration are injection site reactions which are mild to moderate in intensity, consist primarily of redness and swelling at the injection site, which is thought to be related to immune activation at the injection site. There have been no severe or life threatening (CTC Grade 3 or 4) adverse events attributed to Vigil® treatment. No new or unexpected toxic effects were observed with Vigil® in combination with atezolizumab.

In conclusion, the combination of a personalized autologous ovarian cancer vaccine, followed by a checkpoint inhibitor (atezolizumab) demonstrated encouraging efficacy, with low toxicity.

Example 3—BRCA1/2 Wild Type Frontline Stage III/IV Ovarian Cancer Relapse Free Survival Advantage Using Vigil®

Given limits of frontline treatment options for advanced ovarian cancer, particularly in high TGFβ expressive ovarian cancer and involving the BRCA1/2-wt population (85% of ovarian cancer patients), a double-blind, placebo-controlled study of Vigil® as frontline maintenance therapy in ovarian cancer patients with Stage III/IV disease following debulking surgery and combination paclitaxel and carboplatin was carried out.

1. Materials and Methods

Trial Design and Treatments

This Phase Iib, double-blind trial was conducted at 25 sites. This was a placebo-controlled trial of Vigil® in patients with Stage IIIa-c or IV high-grade serous, clear cell, or endometrioid ovarian cancer in clinical complete response (cCR) following surgery and consolidation chemotherapy (5-8 cycles) involving carboplatin and paclitaxel, as classified level 1 category, NCCN guidelines (Version 3.2015). Tumor tissue was harvested at the time of surgical debulking. Tissue was used for vaccine construction and histologic confirmation of disease by local pathology department. When available, germline and/or somatic BRCA1/2 molecular profiling was collected. Peripheral blood mononuclear cell samples were analyzed for germline testing of BRCA1/2, molecular profile (Ocean Ridge Biosciences, Deerfield Beach, Fla.). Patients achieving cCR following primary surgical debulking and platinum/taxane adjuvant chemotherapy were randomized 1:1 to the Vigil® (Vigil® group, VG) or Placebo (control group, CG) cohort. Randomization was stratified by i) extent of surgical cytoreduction (complete/microscopic NED vs. macroscopic residual disease) and ii) neoadjuvant vs. adjuvant chemotherapy. Patients received either 1×10e7 cells/intradermal injection of Vigil® or placebo once a month (within 8 weeks after last chemotherapy) for up to 12 doses. Treatment was continued until disease recurrence or exhaustion of the patient's vaccine or placebo supply. Drug Safety Monitoring Board was put in place prior to study initiation to maintain safety of all study patients. No unacceptable toxic effect was determined. Informed consent was obtained prior to procurement. Written documentation of full IRB approval of the protocol and consent documents were required before a patient could be registered at any site.

Patients

Women who had histologically confirmed Stage IIIa-c or IV high-grade papillary serous, clear cell, or endometrioid ovarian cancer were included in the trial. A cCR defined as no evidence of malignancy on chest x-ray (CT scan was acceptable) and CT scan or MRI of the abdomen and pelvis, CA-125 antigen level ≤35 units/ml, and no findings on physical examination or symptoms suggestive of active cancer, following completion of surgical debulking and chemotherapy was required at time of randomization. Acceptable chemotherapy regimens included 5-8 cycles of standard platinum/taxane divided into neoadjuvant and adjuvant therapy. Subjects must have initiated adjuvant chemotherapy no more than 8 weeks following primary debulking surgery. ECOG performance status (PS) 0-1 and normal organ and marrow function were required and defined per protocol (Absolute granulocyte count—≥1,500/mm3; Absolute lymphocyte count—≥500/mm3; Platelets—≥75,000/mm3; Total bilirubin—≤2 mg/dL; AST(SGOT)/ALT (SGPT)—≤2× institutional upper limit of normal; Creatinine—<1.5 mg/dL). All patients were required to have the ability to understand and the willingness to sign a written informed protocol specific consent.

Tumor Procurement and Manufacturing

Gradalis, Inc. manufactured Vigil® from the harvested tumor tissue. Equal doses of Placebo (Freeze media) based on the number of vials of Vigil® were manufactured. Manufacturing was a 2-day process. The equivalent of a "golf ball size" mass (10-30 g tissue, cumulative) was required for vaccine manufacturing (3 cm by radiological scan). Lesions extending into bowel lumen were excluded due to the risk of bacterial contamination.

Investigational Product and Placebo Manufacturing

Surgically excised tumor tissue (mean=55 g) was procured at the debulking procedure and cut into 1/4 inch sections before being placed in up to four specimen containers containing sterile 0.9% sodium chloride (Baxter) supplemented with gentamicin (Fresenius Kabi) and packaged on wet ice for overnight transport to the manufacturing facility. On Day 1, the transport medium and tumor specimen in each container were tested for sterility (BacT/Alert 3D Microbial Identification System, BioMerieux). The tumor tissue was trimmed to remove fat, connective/necrotic tissue, sutures/staples and mechanically dissociated by scalpel followed by enzymatic dissociation (Type I collagenase solution) and incubated at 37° C. up to 45 minutes to form a single cell suspension. The cell suspension was filtered across a sterile 100 um strainer (Corning) to separate the cells from the debris, and the liberated cells were washed with PlasmaLyte (Baxter) supplemented with 1% Human Serum Albumin (Octapharma) and manually counted using a disposable hemocytometer (InCyto). Quality control (QC) samples were removed for retain, immune monitoring, and a pre-transfection culture initiated to obtain baseline cytokine levels by ELISA for GMCSF (R&D Systems), TGFβ1 (R&D Systems) and TGFβ2 (R&D Systems). The cell suspension was adjusted to a concentration of 40 million cells/mL and electroporated using a Gene Pulser XL (Bio-Rad) to insert the plasmid DNA into cells. The transfected cells were plated into sterile T-225cm2 flasks (Corning) at 1×10e6 cells/mL in X-VIVO 10 media (Lonza) supplemented with gentamicin (Fresenius Kabi) and incubated overnight (14 to 22 hrs) at 37° C. with 5% C02 overlay (Sanyo) to allow for incorporation of bi-shRNA furin and GMCSF mRNA into the tumor cells.

On Day 2, the overnight culture was harvested by scraping cells from flask, collecting media containing free-floating cells and resuspending in fresh X-VIVO media. The cells were manually counted to determine that a minimum of 80 million cells were available for QC samples and a minimum of 4 doses before proceeding. Two 1 mL mycoplasma samples containing cells were taken and frozen at −80° C. The cells were irradiated 4×25Gy cycles using RS-3400 X-ray (RadSource) to arrest replication/growth. The cells were washed with PlasmaLyte (Baxter) supplemented with 1% human serum albumin (Octapharma) and QC samples were removed for retain, immune monitoring, and a post-transfection culture initiated to obtain transfected cytokine levels for GMCSF, TGFβ1 and TGFβ2. The cells were placed into freeze media consisting of 10% DMSO (dimethylsulfoxide; Cryoserv USP; Mylan), 1% Human Serum Albumin (Octapharma) in Plasma-Lyte A at pH 7.4 (Baxter) and aseptically aliquoted at 1×10e7 cells/mL into sterile 2.0 mL borosilicate glass vials (Algroup Wheaton Pharmaceutical and Cosmetics Packaging); closed with a butyl rubber stopper coated with Flurotec® barrier file (West Pharmaceutical Services) with a final fill volume of 1.2 mL. The final product vials were slow frozen using CoolCell® freezing containers (Biocision) placed into −80° C. freezer (Sanyo). After freezing the cells were stored in the vapor phase of liquid nitrogen tanks pending release testing. Frozen product vials were used for sterility (USP <71>) and endotoxin testing by gel-clot (Limulus Amoebobyte Lysate, Lonza). Assay validation for (GMCSF, TGFβ1, TGFβ2) was completed after the study and data shown are calculated with appropriate validated parameters.

Placebo was made up of freeze media consisting of 10% DMSO (dimethylsulfoxide; Cryoserv USP; Mylan), 1% Human Serum Albumin (Octapharma) in Plasma-Lyte A at pH 7.4 (Baxter). After slow freezing the media to −80° C. the vials were stored in the vapor phase of liquid nitrogen pending sterility and endotoxin only release testing. Placebo vial production was matched to the available product doses manufactured for the subject. Study drug (Vigil® or Placebo) was distributed to the site monthly via portable liquid nitrogen container. After withdrawing the product site pharmacy staff were instructed to adhere blinding tape on the barrel of the syringe to maintain the blind, concealing any potential visual differences between Vigil® and Placebo.

Disease Evaluation

Subjects remained on treatment until disease recurrence or exhaustion of the subject's Vigil® or Placebo supply. Disease relapse was evaluated by World Care Clinical (Boston, Mass.) using the Response Evaluation Criteria in Solid Tumors Version 1.1 (RECIST 1.1). Two reviewers were assigned to each case with adjudication assigned, when necessary. Data was forwarded to third party statistician for analysis. Treatment group assignments were discussed between QA department and statisticians, keeping other departments blinded. Disease recurrence was defined per RECIST 1.1, as the appearance of any measurable or evaluable lesion or as asymptomatic CA-125 levels >35 U/ml at two consecutive measurements, at least one month apart.

End Points and Statistical Assessment

The primary endpoint was recurrence-free survival (RFS) in the Vigil® group compared to the Placebo group. Tumor assessments were evaluated by World Care Clinical (Boston, Mass.) according RECIST 1.1 at time of randomization (baseline) and at protocol-defined intervals until disease recurrence or death. The time to recurrence was calculated from 1) date of randomization and 2) date of debulking surgery/procurement until the first date of documented relapse or death. RFS was sequentially analyzed in the BRCA-wt subgroup and compared between Vigil® and Placebo. All patients who received at least one dose of Vigil® or placebo were included in the safety analyses. A one-sided p value of 0.05 or less (log-rank) was considered to indicate statistical significance in analyses. The hazard ratios of recurrence-free survival were estimated via a Cox proportional hazards model without covariates. Distribution of RFS were estimated using the Kaplan-Meier method. The chi-square goodness of fit test was used to evaluate whether the number of patients who relapsed in the placebo group was different from the number of patients who relapsed in the Vigil® group. Patients in the BRCA-wt subgroup were evaluated whether there was a significant difference between the number of patients who relapsed in the placebo group compared with the number of patients who relapsed in the Vigil® group.

2. Results

Patients

From February 2015 to March 2017, 310 ovarian cancer patients were consented at 22 sites and tissue was harvested for manufacturing Vigil®. One hundred twenty-eight patients were deemed to be ineligible due to pathology or screen failure parameters (i.e. staging). Of the remaining 181 that completed underwent manufacturing 92 subjects (56%) were successfully manufactured and randomized, 17 elected other treatment options and 72 failed product release criteria (65 for insufficient cells). One patient withdrew after randomization but prior to treatment date for personal reasons in good health. This patient was not included in analysis. Ninety-one subjects were analyzed for safety and response with 46 patients randomized to Vigil® and 45 patients randomized to Placebo. Fifty-five relapse events were observed by independent third-party radiological evaluation (WCC) by August 2019. Demographics are shown in Table 7. No significant differences were detected between cohorts except 21/46, 45.7% Vigil® patients had lower performance (ECOG 1) compared to placebo (9/45, 20.0%; p=0.0093).

TABLE 7

Demographics of evaluable patients

| Characteristic | Treatment Group, No. (%) | |
|---|---|---|
| | Vigil ® | Placebo |
| No. of patients | 46 | 45 |
| Age, years | | |
| Median | 62.5 | 63.0 |
| Range | 42-84 | 38-79 |
| RACE | | |
| Asian | 0 (0%) | 2 (4.4%) |
| Black or African American | 1 (2.2%) | 4 (8.9%) |
| White | 45 (97.8%) | 38 (84.4%) |
| Not Reported | 0 (0%) | 1 (2.2%) |
| Ethnicity | | |
| Hispanic or Latino | 1 (2.2%) | 0 (0%) |
| Non Hispanic or Latino | 45 (97.8%) | 44 (97.8%) |
| Not Reported | 0 (0%) | 1 (2.2%) |
| ECOG | | |
| 0 | 25 (54.3%) | 36 (80.0%) |
| 1 | 21 (45.7%) | 9 (20.0%) |
| Staging | | |
| III | 1 (2.2%) | 0 |
| IIIA1 | 0 (0%) | 3 (6.7%) |
| IIIB | 5 (10.9%) | 5 (11.1%) |
| IIIC | 31 (67.4%) | 32 (71.1%) |
| IV | 9 (19.6%) | 5 (11.1%) |
| Chemotherapy | | |
| Neoadjuvant | 8 | 7 |
| Adjuvant | 38 | 38 |
| Residual disease post-surgery | | |
| Macroscopic | 15 (32.6%) | 12 (26.7%) |
| Microscopic/NED | 31 (67.4%) | 33 (73.3%) |
| Histology | | |
| Endometrioid carcinoma | 1 (2.2%) | 0 (0%) |
| Mixed serous/clear cell | 0 (0%) | 1 (2.2%) |
| High grade serous carcinoma | 45 (97.8%) | 44 (97.8%) |

TABLE 7-continued

Demographics of evaluable patients

| Characteristic | Treatment Group, No. (%) | |
|---|---|---|
| | Vigil ® | Placebo |
| BRCA1/2 | | |
| Mutant (Positive) | 4 | 10 |
| Wildtype (Negative) | 24 | 24 |
| Missing | 18 | 11 |
| CA-125 prior to randomization | | |
| <=35 | 46 (100%) | 44 (97.8%) |
| >35 | 0 (0) | 1 (2.2%) |
| Time from last chemo given to first dose of Vigil ®/ placebo | | |
| Mean | 50.2 | 46.8 |
| Median (range) | 49 (29-107) | 48 (16-102) |
| Solid Tumor Weight (g) | | |
| Mean (SD) | 54 (28) | 56 (30) |
| Median (range) | 51.8 (9.6-136.5) | 51.6 (7.8-137.5) |
| Cells harvested per gram of tumor tissue (×10e6) | | |
| Mean (SD) | 6 (4) | 7 (7) |
| Median (range) | 4.8 (0.7-17.0) | 4.7 (1.6-33.6) |

A median of 6 Vigil® (range 1 to 12) or 6 placebo (range 3 to 12) injections were administered per patient. No treatment delays or withdrawals due to treatment-related toxic effect were reported. One patient in the Vigil® arm experienced a Grade 3 drug related toxic effect (nausea and vomiting), and two patients in the placebo arm experienced Grade 3 related toxicity (1 with bone pain, generalized muscle weakness, dyspnea and syncope and arthralgia in the other). More Grade 2, 3 adverse events were observed in the placebo arm vs. Vigil® (18% vs. 8%). Seven (4 placebo, 3 Vigil®) patients had 14 serious adverse events (SAE) reported. In two, the SAE's were possibly related (1 placebo/1 Vigil®). Otherwise, SAE events were unlikely related or not related to study treatment.

Product Release Results

Eighty-four (92%) subjects met all product release criteria. The median tumor mass harvested was 52 gm (range 8-137 gm). Seven (8%) of the 91 did not show sufficient increase in GMCSF expression following plasmid transfer. However, six of these 7 patients demonstrated robust TGFβ1 knockdown. Additional product release results are shown in Table 8. TGFβ1 knockdown results were also undetermined in 7 patients (6 with adequate GMCSF expression release), however 66 (73%) patients had ≥90% TGFβ1 knockdown demonstrating robust activity related to furin bi-shRNAi knockdown. Baseline TGFβ1 production prior to plasmid transfection of all patients with detectable levels revealed a median TGFβ1 expression of 166 pg/10e6 cells (mean 241, range 52-882). BRCA1/2-wt TGFβ1 expression revealed a median of 212 (mean 255, range 71-662) pg/10e6 cells for both groups and BRCA1/2-mu TGFβ1 expression revealed median 122 (mean 231, range 52-882) pg/10e6 cells (Table 9).

TABLE 8

Summary of numerical release

| | Viability (%) | GMCSF Production (pg/10^6 cells) | TGF-β1 Knockdown (%) | Gel-clot Endotoxin (Vaccine<EU/mL) |
|---|---|---|---|---|
| Count | 91 | 91 | 84 | 91 |
| Average | 86% | 1806 | 96% | 0.4 |
| StDev | 5% | 2433 | 8% | 0.4 |

TABLE 8-continued

Summary of numerical release

| | Viability (%) | GMCSF Production (pg/10^6 cells) | TGF-β1 Knockdown (%) | Gel-clot Endotoxin (Vaccine<EU/mL) |
|---|---|---|---|---|
| Median | 86% | 826 | 100% | 0.4 |
| Min | 72% | −1339 | 66% | 0.2 |
| Max | 98% | 10151 | 100% | 3.7 |
| Range | 0 | 11491 | 34% | 3.0 |

Cell dose 1 × 10$^7$ for all patients; USP<71> sterility negative all patients; mycoplasma DNA negative all patients

TABLE 9

BRCA ½ mutation status correlation with TGFβ1

| | Vigil ® | | | Placebo | | | Overall | | |
|---|---|---|---|---|---|---|---|---|---|
| | ½ wt | ½ mut | all | ½ wt | ½ mut | all | ½ wt | ½ mut | all |
| Subjects | 24 | 4 | 46 | 24 | 10 | 45 | 48 | 14 | 91 |
| TGFβ1 Pre | | | | | | | | | |
| Count | 24 | 4 | 43 | 22 | 9 | 41 | 46 | 13 | 84 |
| Mean (pg/10$^6$) | 263 | 131 | 224 | 247 | 275 | 259 | 255 | 231 | 241 |
| SD (pg/10$^6$) | 161 | 98 | 148 | 150 | 267 | 175 | 154 | 234 | 162 |
| Median (pg/10$^6$) | 262 | 93 | 164 | 166 | 146 | 168 | 212 | 122 | 166 |
| Min (pg/10$^6$) | 71 | 65 | 60 | 86 | 52 | 52 | 71 | 52 | 52 |
| Max (pg/10$^6$) | 662 | 273 | 662 | 561 | 882 | 882 | 662 | 882 | 882 |

Efficacy

Figure 10A:
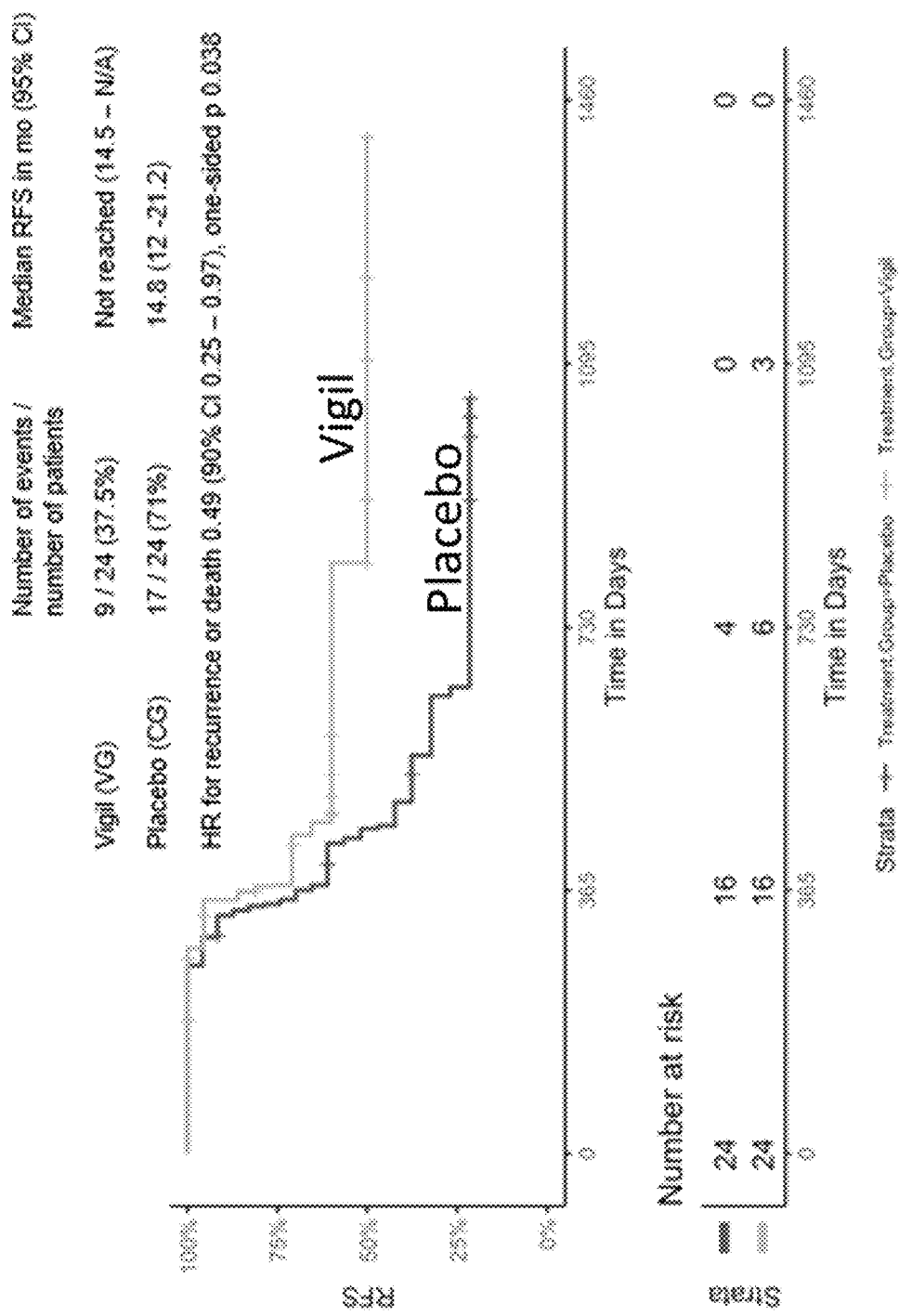
FIGS. 10A-10D illustrate relapse-free survival (RFS) of patients from surgery/procurement or randomization of Vigil® vs. placebo.
Figure 10B:
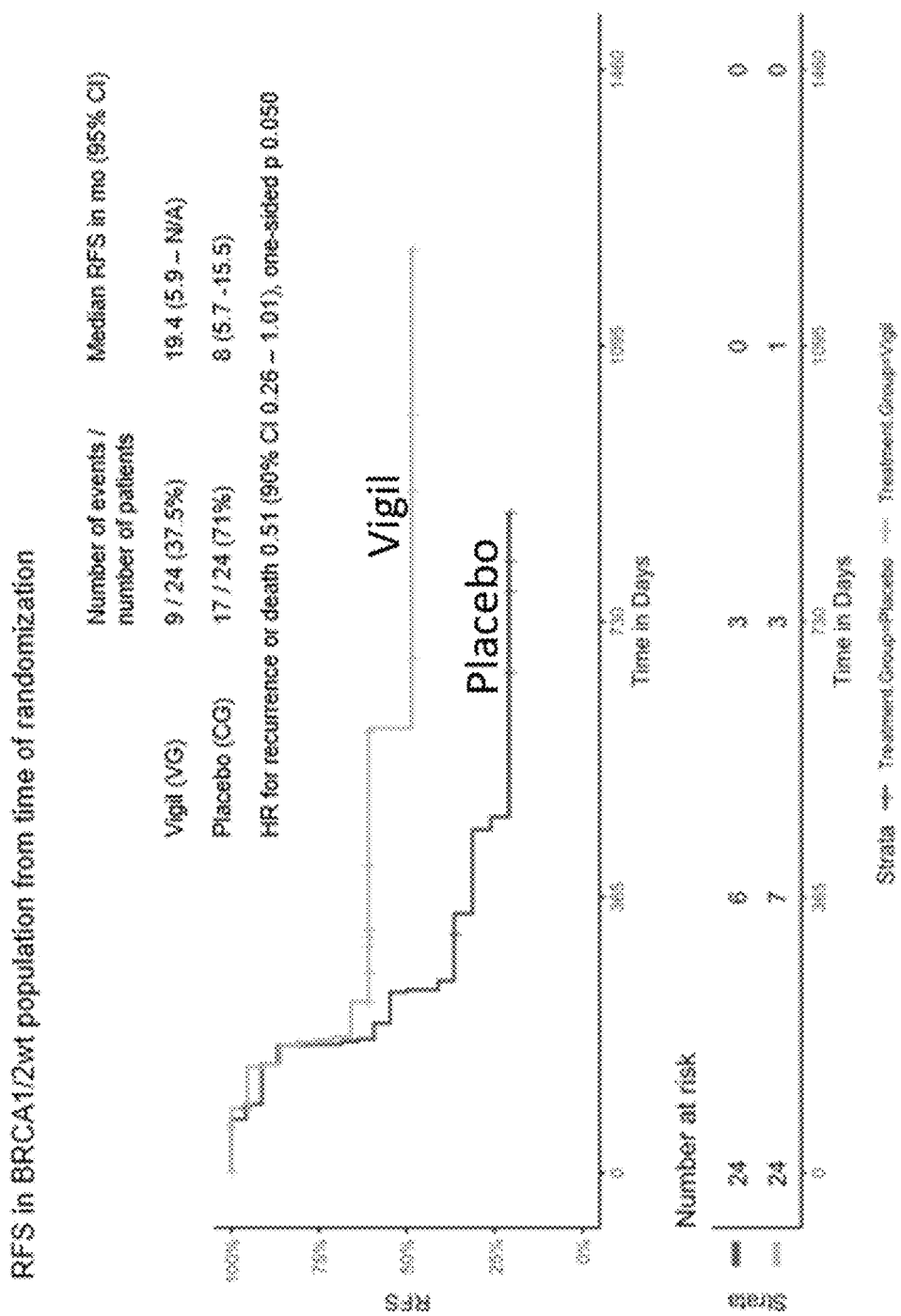

Out of the 91 evaluable patients, there were 62 patients that had BRCA1/2 molecular profile at local site analysis. The subgroup of BRCA1/2-wt patients showed RFS benefit in the Vigil® cohort compared with the Placebo cohort. Results are shown in FIGS. 10A-10B. Median RFS calculated from time of surgery/procurement was not reached in BRCA-wt ovarian patients in the Vigil® cohort vs. 14.8 months in placebo cohort (HR=0.49, 90% CI, 0.25-0.97, one-sided p=0.038). Similarly, when RFS was calculated from time of randomization, median RFS in the BRCA-wt subgroup was 19.4 months in the Vigil® compared to 8.0 months in the placebo arm (HR=0.51, 90% CI, 0.26-1.01, one-sided p=0.050). Thirty-eight percent of Vigil® treated patients who were BRCA1/2-wt demonstrated relapsed disease compared to 71% of placebo BRCA1/2-wt patients (chi-square 0=0.021) (FIG. 1A). Sixty-two percent of Vigil® patients, who were BRCA-wt, continue recurrence relapse free to date (Oct. 31, 2019).

Figure 10C:
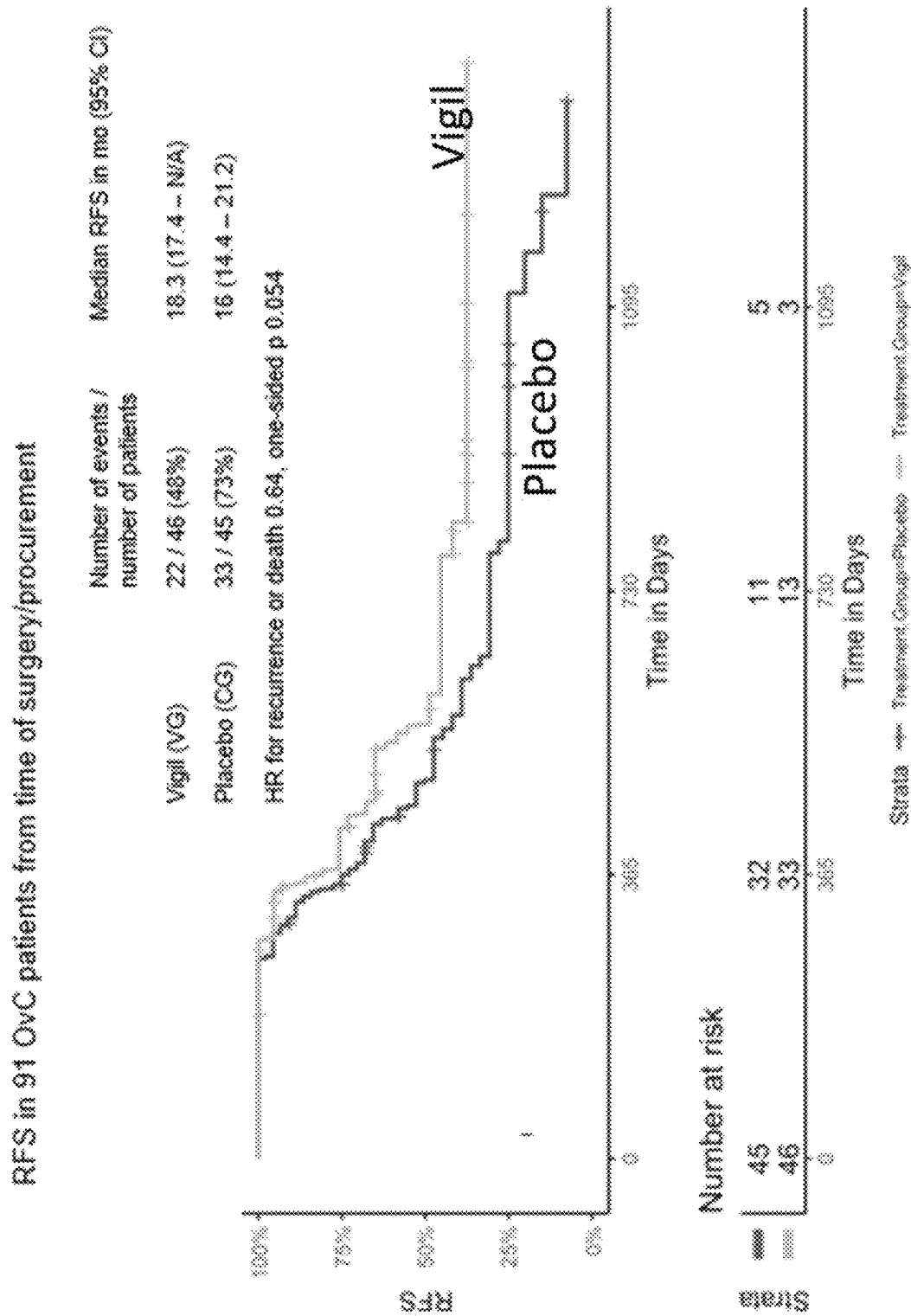
Figure 10D:
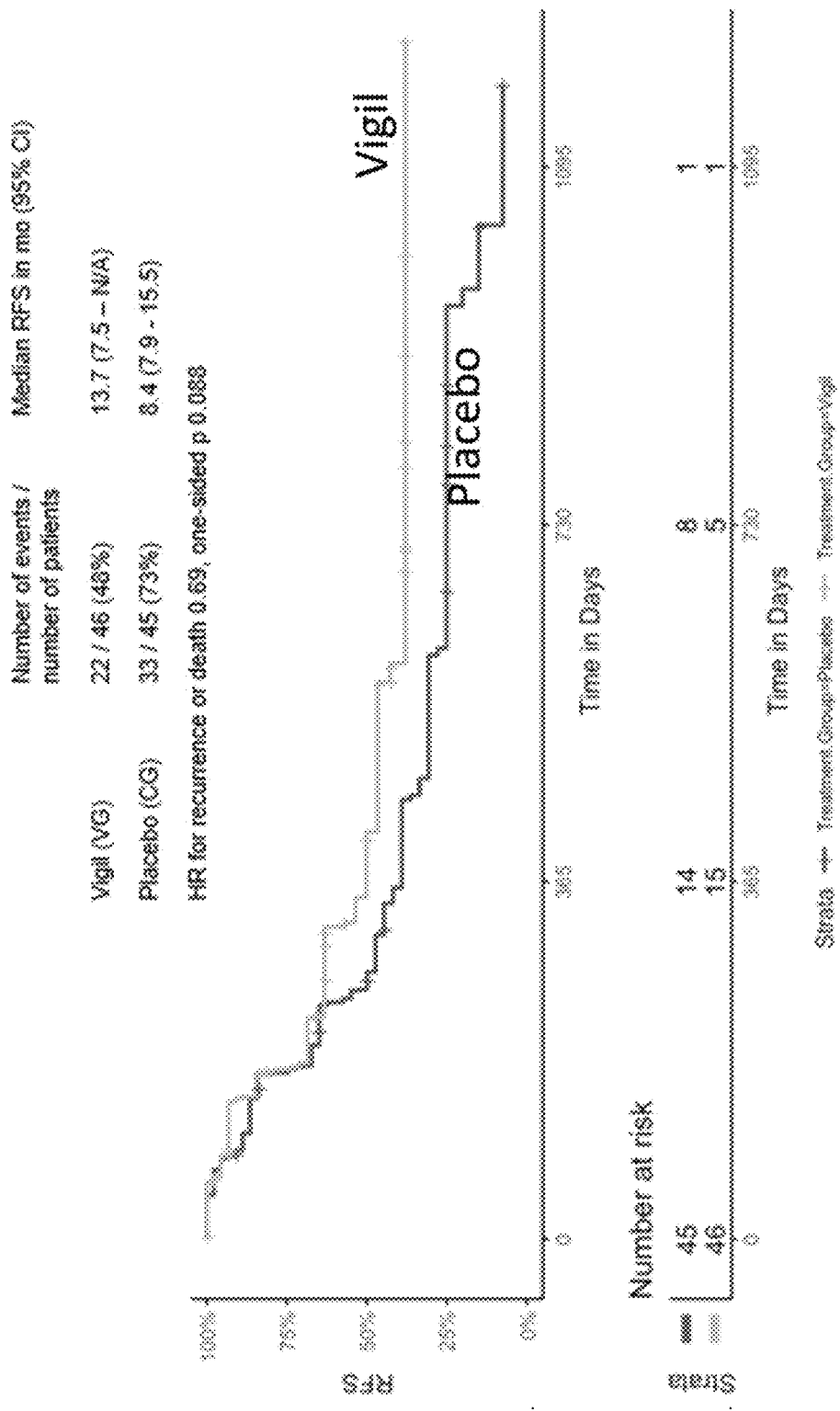
Figure 11A:
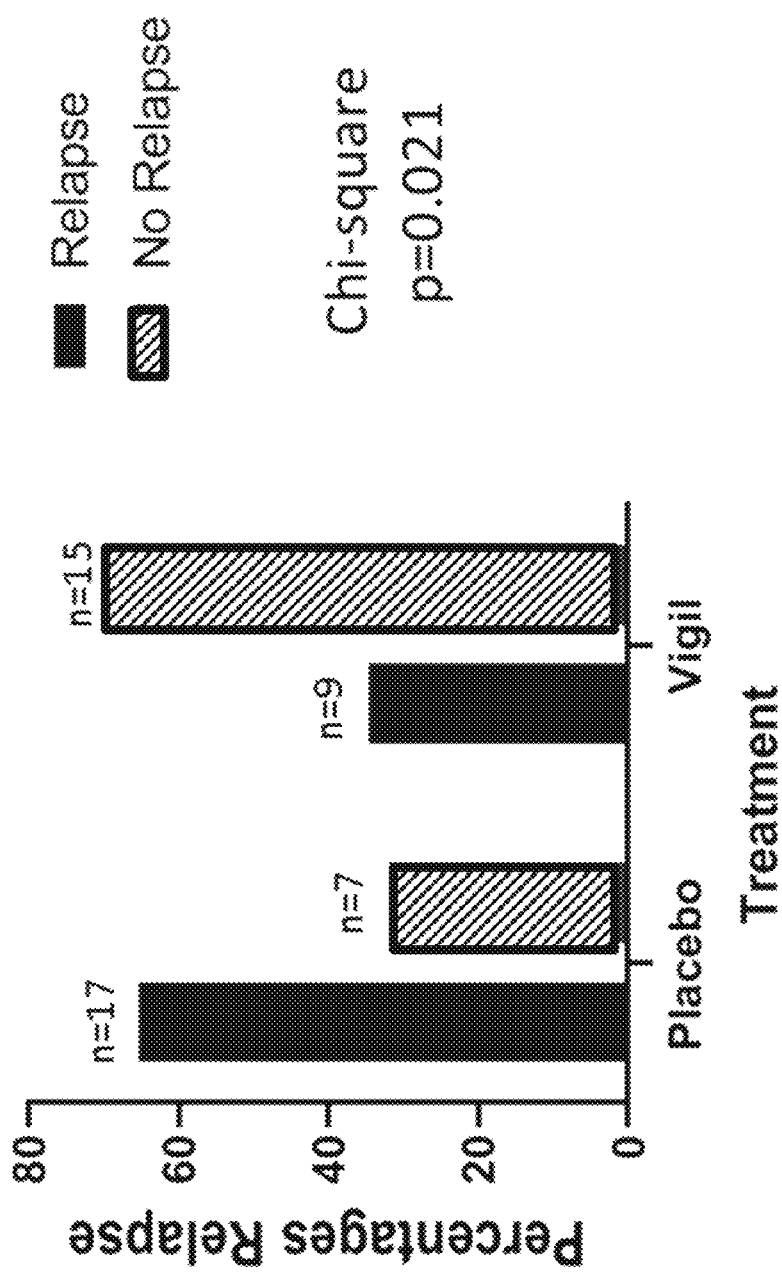
FIGS. 11A and 11B illustrate the fraction of all recurrent disease between Vigil® and placebo.
Figure 11B:
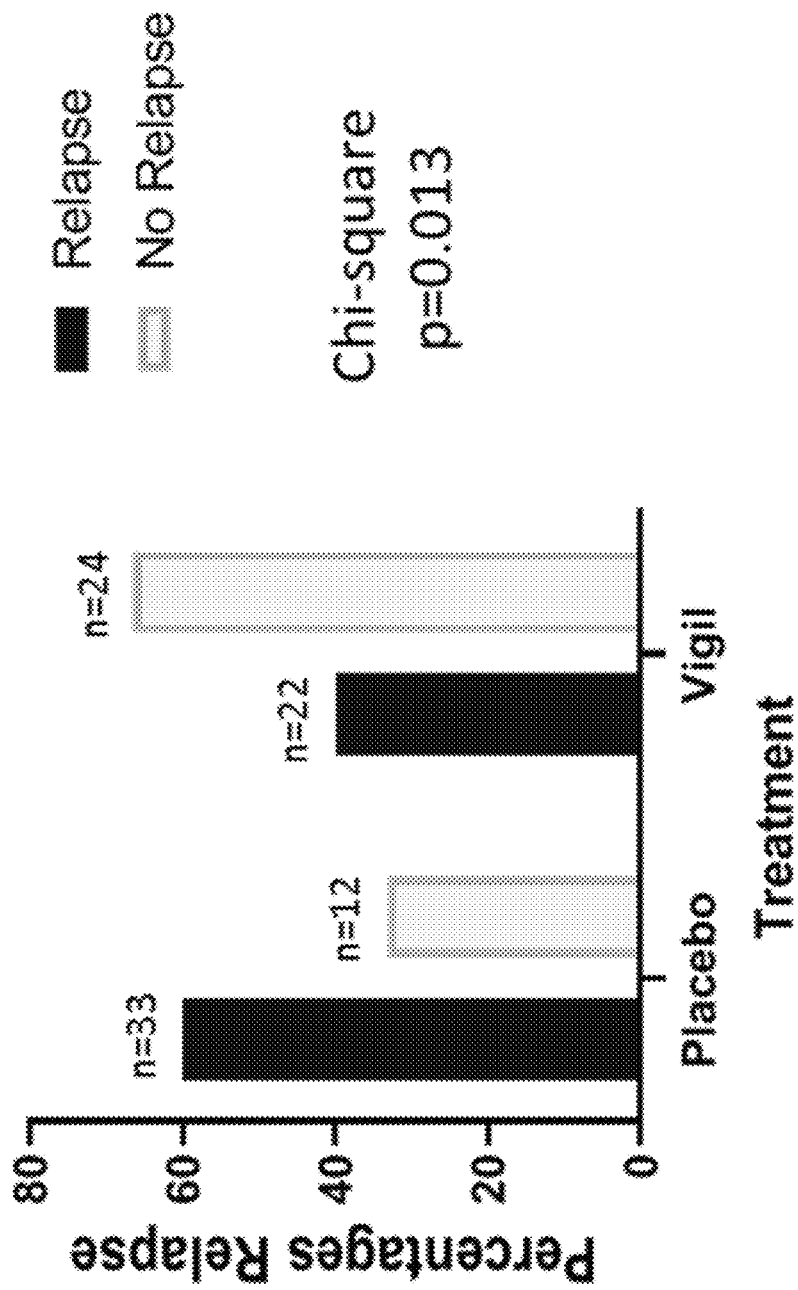
Figure 12:
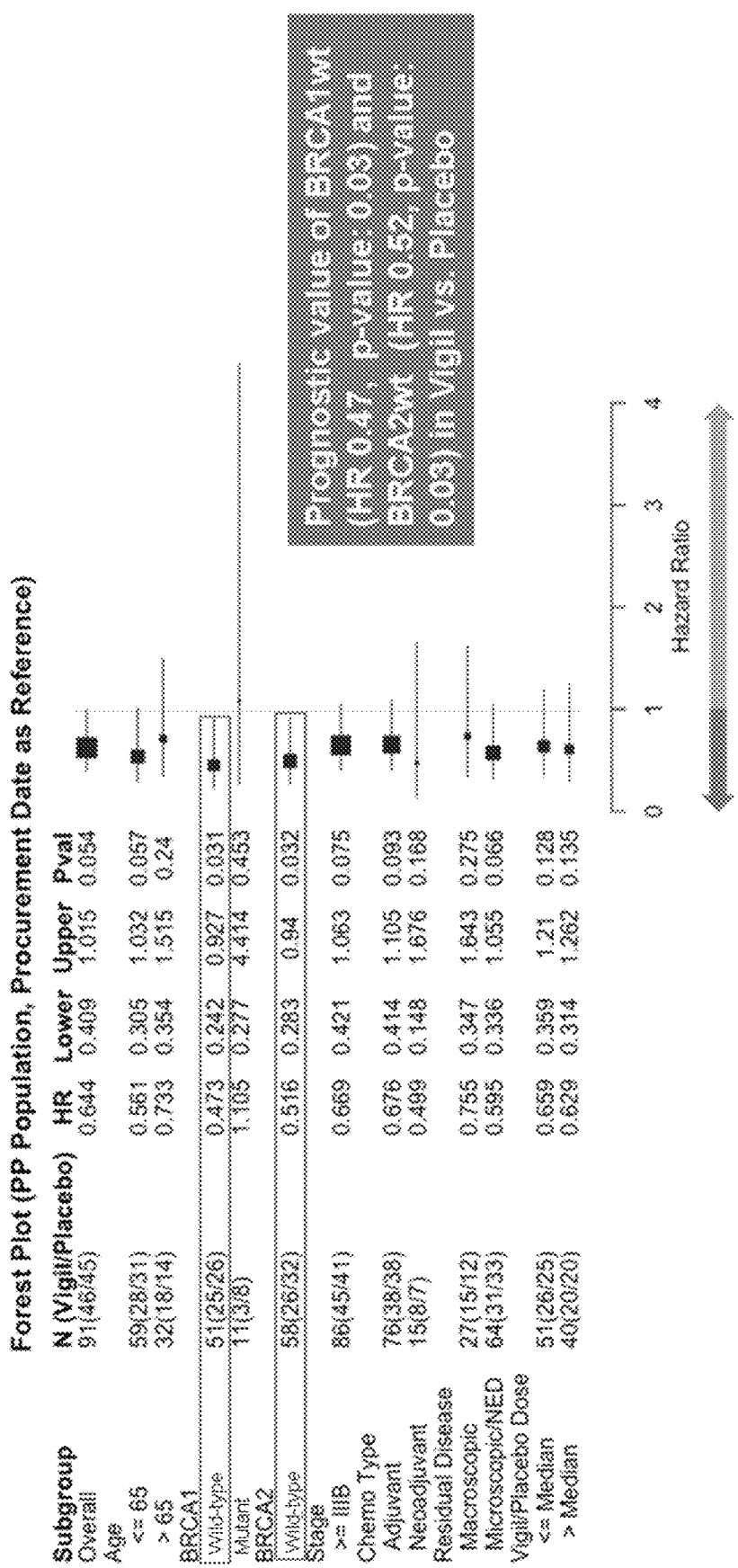
FIG. 12 illustrates forest plot key demographics between Vigil®/placebo patients.
Figure 14:
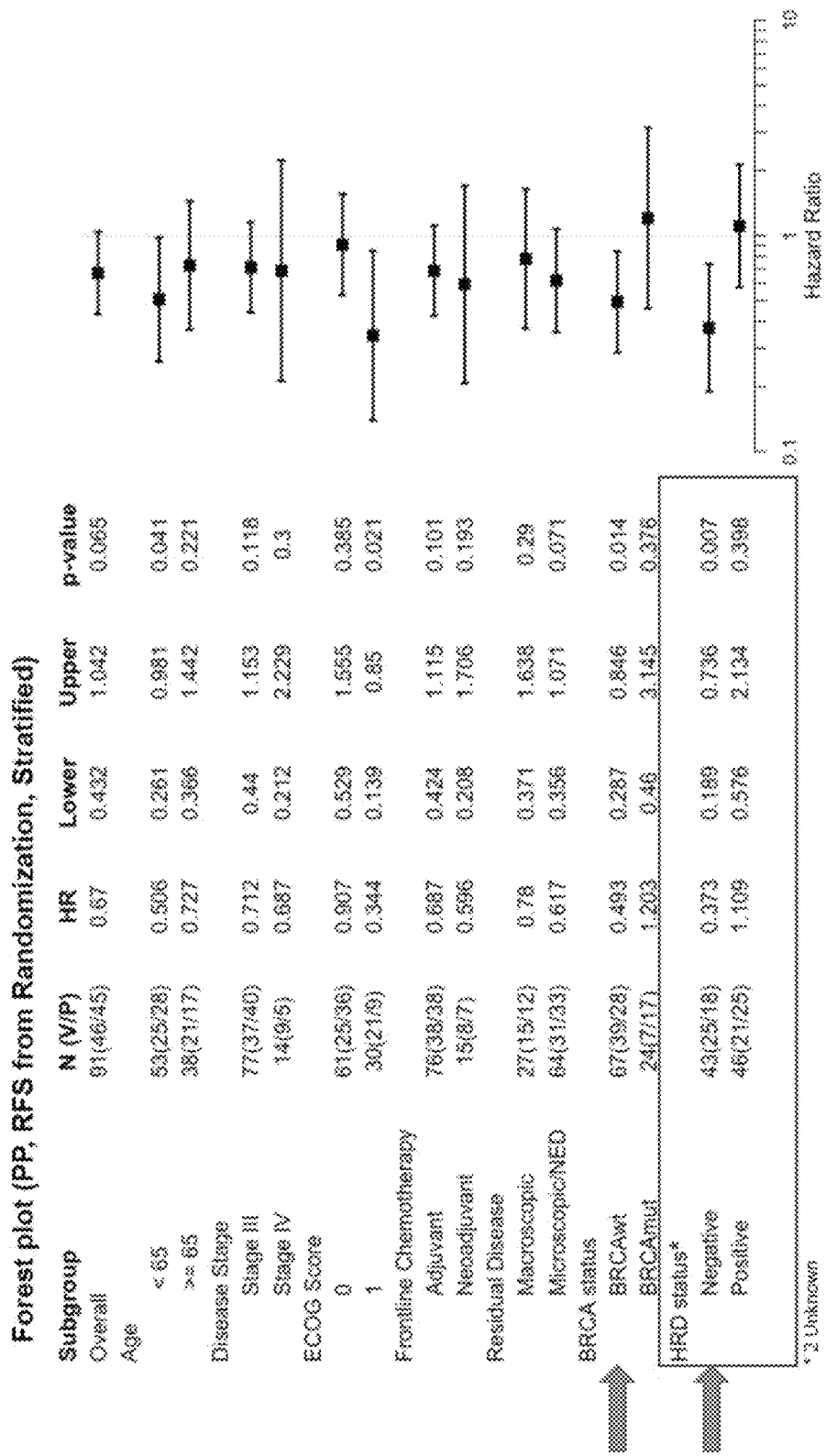
FIGS. 14 and 15 show forest plot key demographics between Vigil®/placebo patients.
Figure 15:
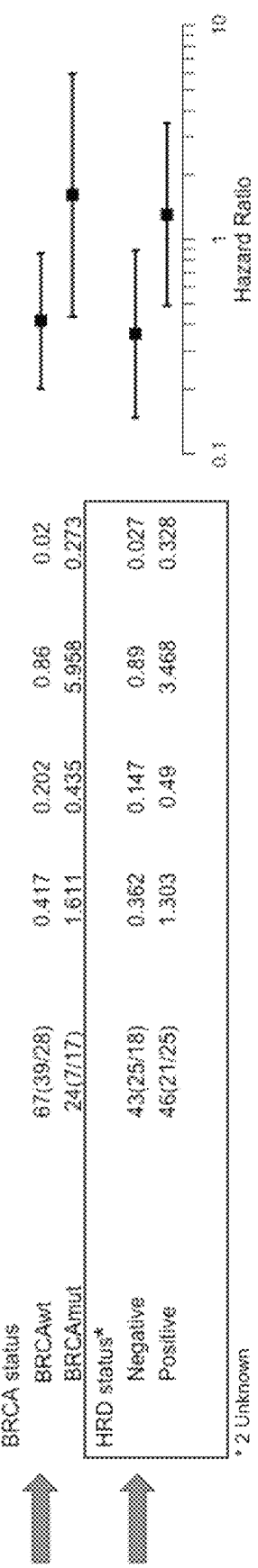
Figure 17:
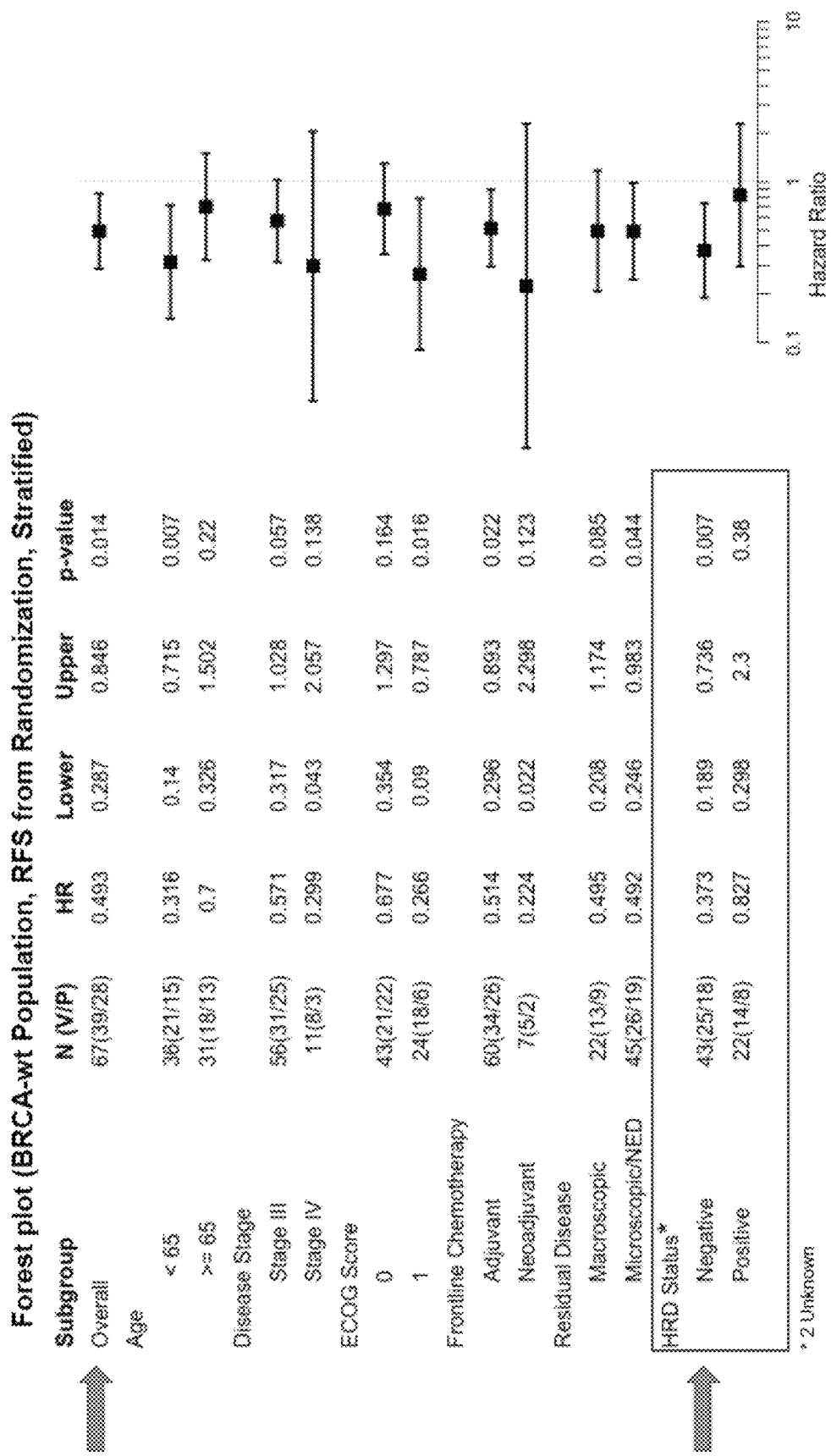
FIGS. 17-20 show forest plot key demographics between Vigil®/placebo patients.
Figure 18:
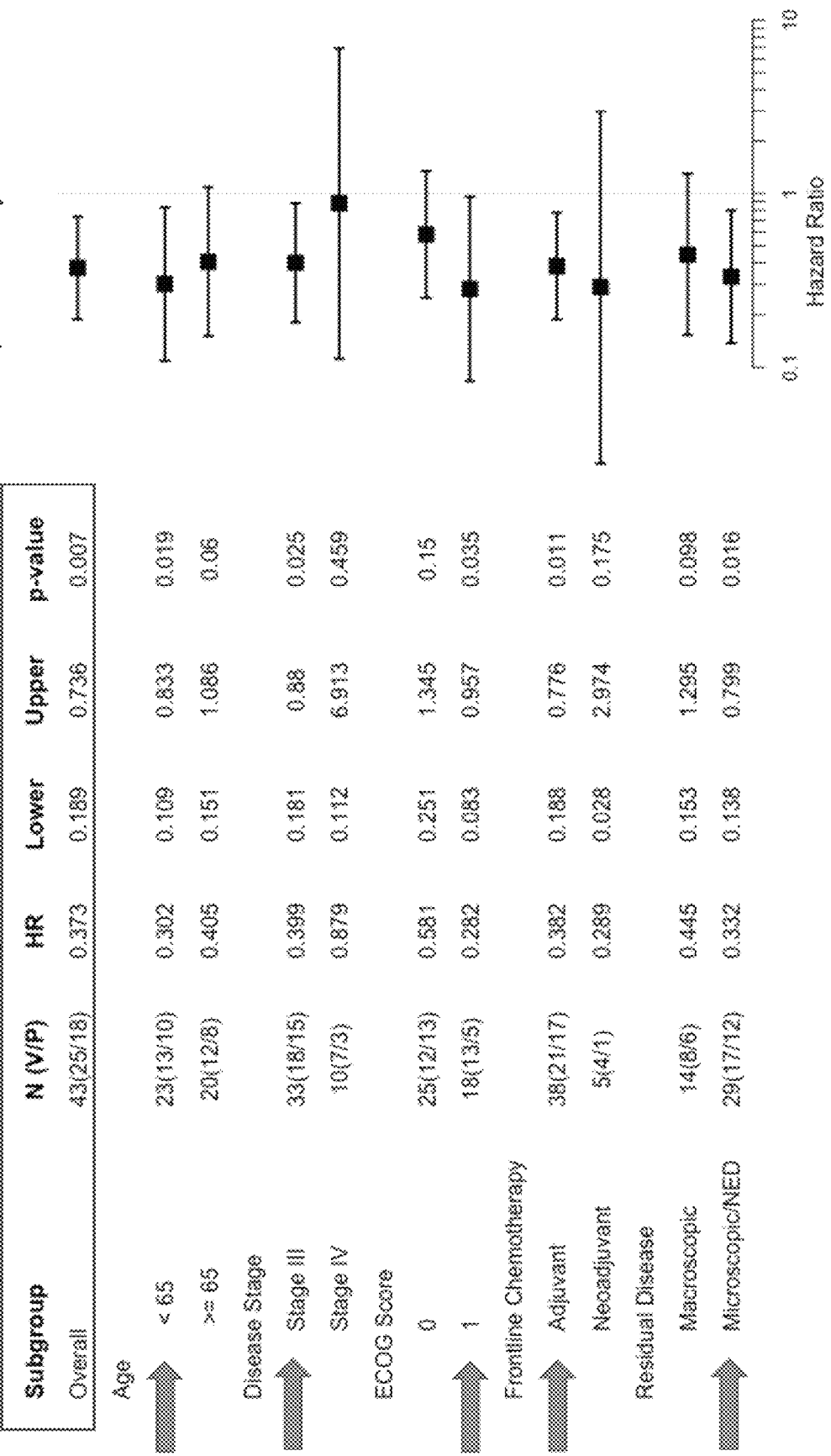
Figure 19:
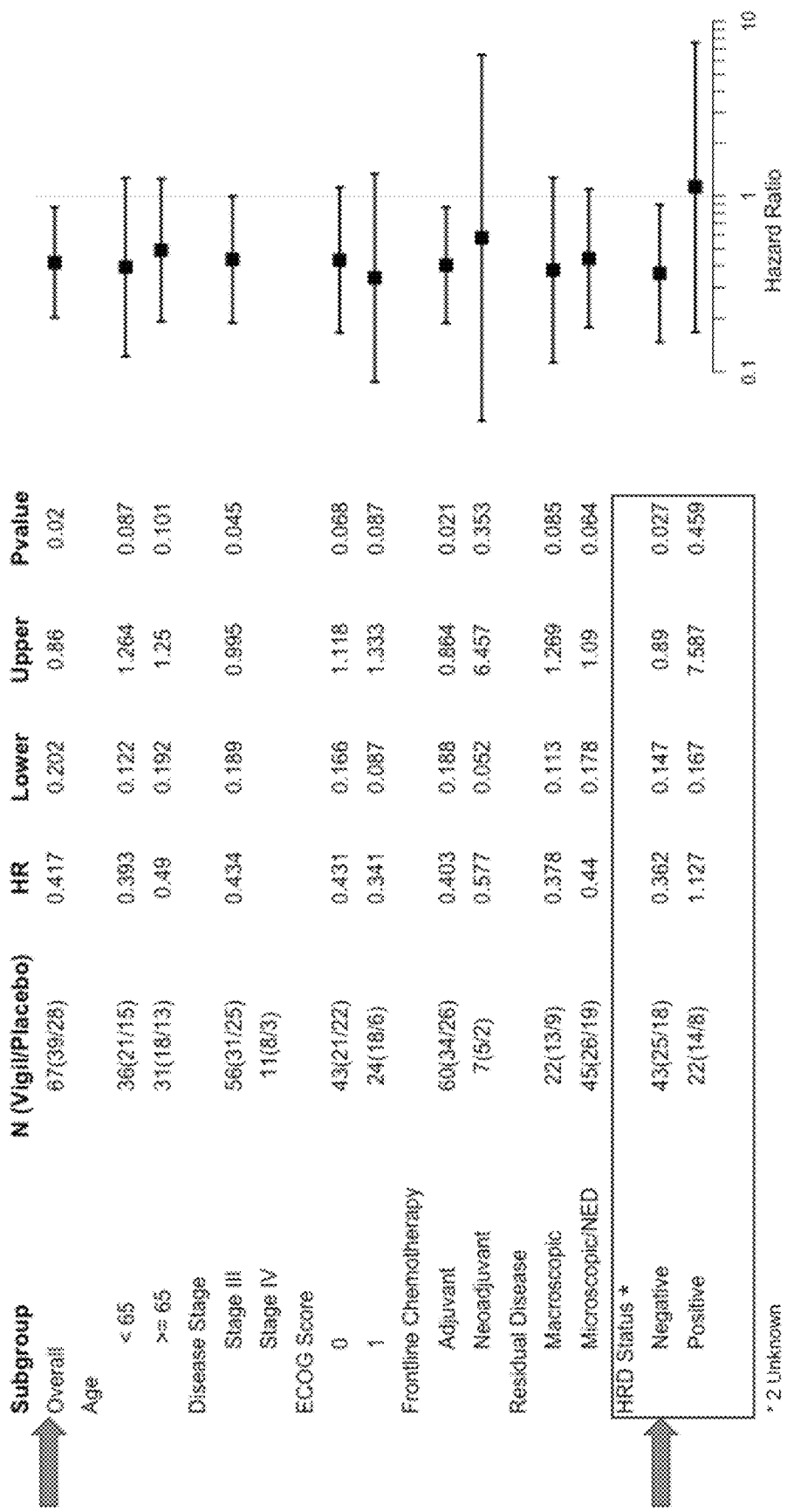
Figure 20:
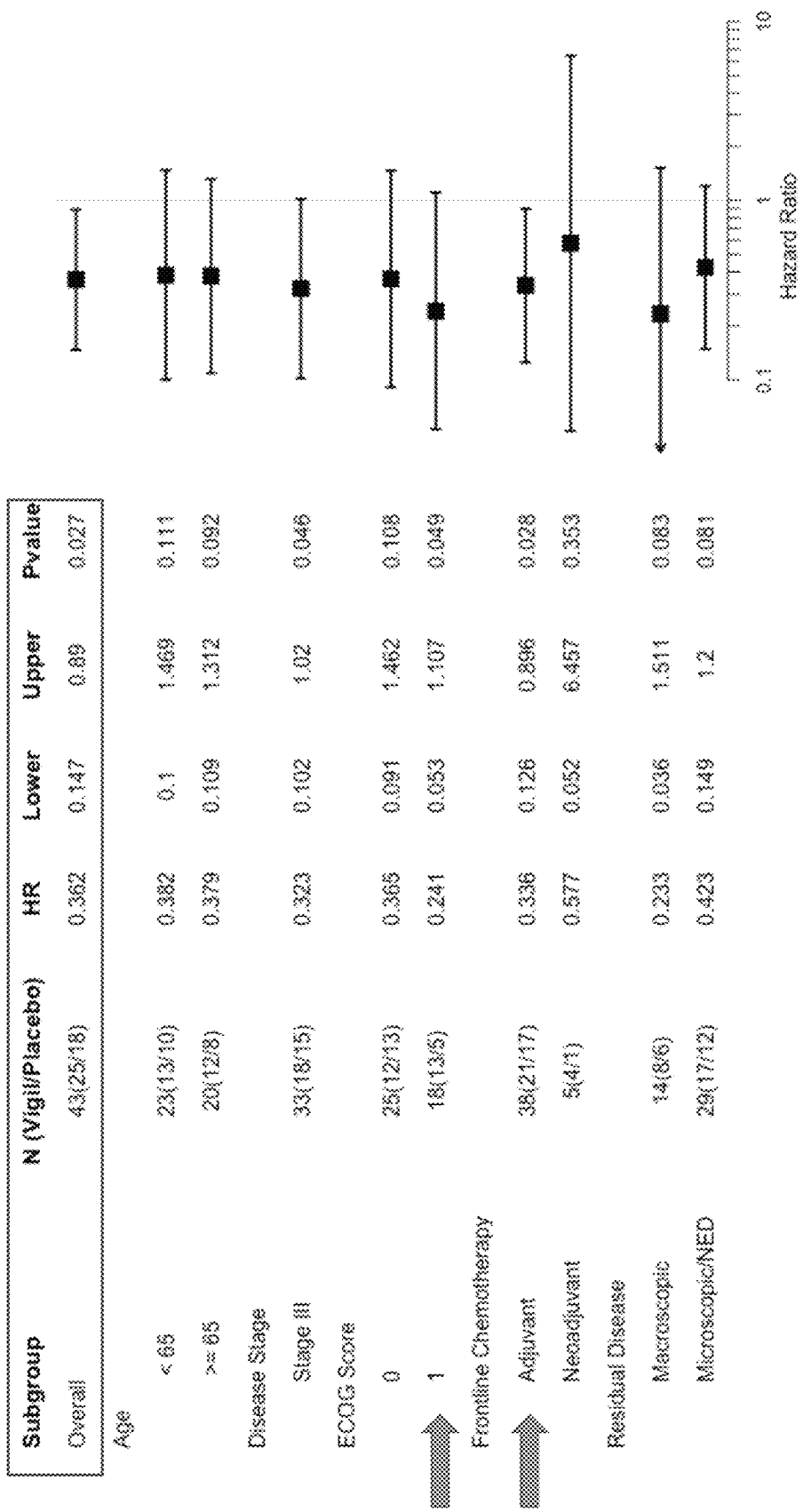
Figure 21:
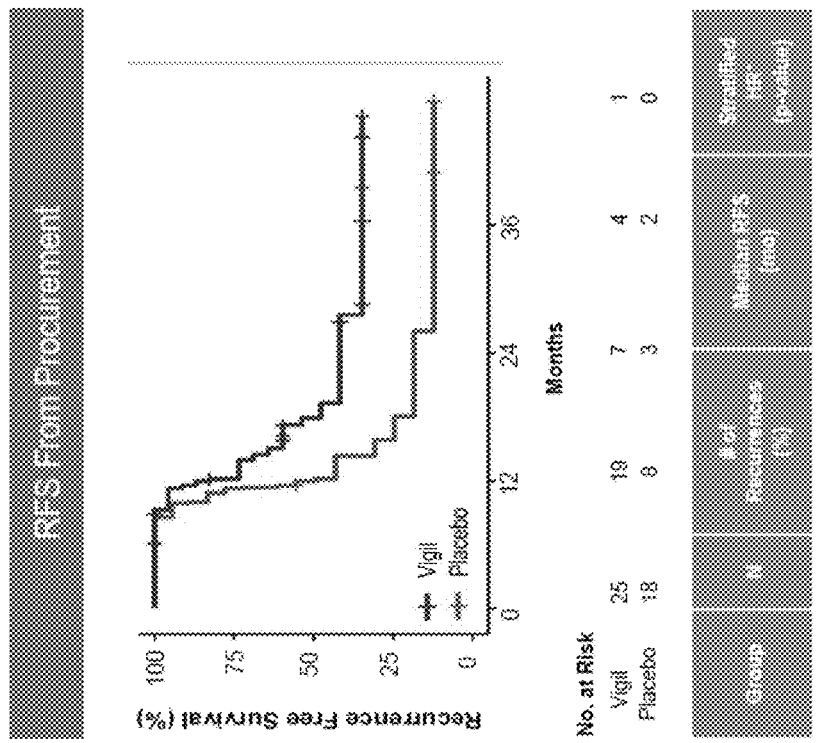
FIGS. 21 and 22 illustrate RFS of patient population from surgery/procurement (FIG. 13) and from randomization (FIG. 14).

RFS calculated from time of debulking surgery and from time of randomization regardless of BRCA1/2 status are shown in FIGS. 10C-10D. The median RFS calculated from time of randomization in the Vigil® cohort was 13.67 months (416 days) compared to 8.38 months (255 days) in the placebo cohort (HR=0.69, one-sided log rank p=−0.054). RFS calculated from time of debulking surgery was improved with a HR of 0.64 (one-sided p=0.054). Relapse was reported in 48% of Vigil® treated patients compared to 73% of placebo patients (chi-square p=0.013) (FIG. 11B). Other factors associated with trend advantage to Vigil® response was younger age ≤65 (p 0.057), late stage IIIb-IV (p 0.075), and microscopic residual disease (<10 mm)/no evidence of disease (p=0.066) (FIG. 12).

3. Discussion

BRCA1/2-wt patients demonstrated significant RFS (calculated from time of debulking surgery) advantage to Vigil® over placebo (not reached vs. 14.8 months; HR=0.49, one-sided p=0.038) and occurrence of lower relapse post treatment (38% vs. 71%, p=0.021). These results supported consideration of Vigil® as maintenance in BRCA1/2-wt ovarian cancer patients following complete debulking surgery and adjuvant or neoadjuvant chemotherapy. Safety analysis demonstrated no evidence of toxic effect to Vigil® over placebo.

Increasing evidence suggests that GMCSF is involved in the augmentation of tumor antigen presentation by dendritic cells (DCs). It has been shown to induce a subset of DCs that are superior for the phagocytosis of apoptotic tumor cells. It evokes higher levels of co-stimulatory molecules, which is characteristic of greater functional maturation and more efficient T cell stimulation, thereby broadening the arsenal of induced lymphocyte effector mechanisms. GMCSF also promotes the presentation of lipid antigens by dendritic cells which in turn leads to activation of Natural Killer T cells (NKT cells) a population of lymphocytes that may be pivotal in both endogenous and therapeutic responses to tumors. Dendritic cells prime antigen-specific immune responses and express diverse receptors that allow for the recognition and capture of antigens in peripheral tissues like the dermis. They process this material efficiently into the MHC Class I and II presentation pathways, upregulate costimulatory molecules upon maturation, and migrate to secondary lymphoid tissues where they present antigens to T cells. Vigil® GMCSF protein was upregulated at a robust mean/median of 1806/826 μg/10e6 cells. In 84 of the 91 (91%) patients manufactured, this was exclusively related to GMCSF plasmid transfer.

It had also previously been shown that ovarian malignant cell expression of TGFβ is much higher in malignant over non-malignant ovarian tissue. A gene expression meta-analysis conducted in over 1500 OvC patients identified high- and low-risk groups based on the expression of several genes and validated the results by IHC or qRT-PCR. Pathway analysis of the gene signature showed an enrichment of TGFβ signaling in poor-prognosis patients. TGFβ signal is mediated through binding to serine/threonine kinase receptors TGFβRI and II which leads to phosphorylation and activation of the intracellular effectors Smad2 and Smad3. Smad2/3 forms a transcriptional complex with Smad4, translocates to the nucleus, and regulates gene expression of TGFβ-regulated genes. TGFβ is involved in the progression from non-invasive serous ovarian tumors to invasive serous ovarian carcinoma. It can be activated by Smad-dependent and Smad-independent pathways and is thought to promote tumor metastasis in ovarian cancer. TGFβ overexpression and correlation with tumor cell proliferation and metastasis has also been described in prostate, colon and renal cell carcinoma.

Secreted TGFβ from ovarian cancer cells generate immunosuppressive Treg cell (CD4+CD25+) expansion in the tumor microenvironment. This has been shown to be associated with poor outcome in patients with high-grade serous ovarian carcinoma treated with frontline debulking surgery/ chemotherapy. TGFβ inhibits GMCSF induced maturation of bone marrow derived dendritic cells (DCs) as well as expression of MHC Class II and co-stimulatory molecules. TGFβ also inhibits activated macrophages including their antigen presenting function, as well as, ovarian cancer and tumor associated myeloid cell PD-L1 ligand expression, which has also been further linked to poor overall survival in ovarian cancer. Evidence reveals that modulation of related antitumor immunity can repair immune surveillance related to TGFβ.

TGFβ1 has also been shown to downregulate the miR181/BRCA1 axis thereby orchestrating DNA-repair deficiency and inducing "BRCAness" in breast cancers carrying wild-type BRCA genes. The term "BRCAness" has been used to identify sporadic tumors that have clinicopathological and molecular characteristics akin to those associated with BRCA1/2 germline mutations (DNA repair suppression). Additionally, it has been demonstrated that elevated TGFβ signaling in HRD-low tumors that can induce NF-kB activation and elicit antitumor immune responses in lymphocytes. Thus it appears that in addition to the BRCA molecular signal, the homologous recombination deficiency (HRD) scores may also be relevant to predict outcomes and responses to TGFβ modulating immunotherapies.

Results of improved RFS in the BRCA-wt population in this trial would further support a relationship of TGFβ suppression and immune responsiveness thereby supporting use of Vigil® in BRCA-wt patients as well as possibly other cancer subpopulations of other histologic types, such as prostate cancer, renal cell carcinoma, and colorectal cancer, with high TGFβ expression. High levels of furin mRNA and protein are also widely expressed in ovarian cancer and in many other human tumors where the gene is differentially expressed between malignant (high) and non-malignant (low) cell populations. The expression of furin which is a TGFβ1, TGFβ2 converting enzyme appears to be inversely correlated with survival and likely contributes significantly to the maintenance of tumor directed, TGFβ-mediated peripheral immune tolerance. Down regulation of furin using bi-shRNAi method, as verified in this trial, induced marked TGFβ1 expression reduction. Remarkably 73% of the Vigil® vaccines constructed had TGFβ1 knockdown of ≥90% compared to non-transfected same patient tumor cells.

BRCA-wt and HRD low ovarian cancers also demonstrate elevated tumor infiltrating lymphocyte (TIL) fraction in cancer microenvironment, high PD-L1 expression, high type 1 IFN gamma signal activity in mononuclear cells and high Perforin 1 expression, which generally would suggest improved immune responsiveness. However, several attempts to enhance both frontline and recurrent/refractory ovarian response to checkpoint inhibitor therapy have failed. This hypothetically could also be related to high TGFβ suppressive effect within local tumor microenvironment as previously described.

PARP inhibitors bind to and trap PARP proteins on DNA in addition to blocking their catalytic action. This leads to multiple double-strand DNA breaks and ultimately cell death. Lynparza® (olaparib) was one of the first PARP inhibitors approved for patients with high-grade serous ovarian cancer with germline BRCA mutations. Previous studies have shown increased progression-free survival in BRCA1/2-mu ovarian cancer (HR 0.3, p<0.0001). A recent long-term follow-up of olaparib (Study 19) in platinum-sensitive, recurrent ovarian cancer patients shows favorable OS results with HR 0.73 (p=0.0138) for all patients enrolled although activity appears to be limited to the BRCA-mu population HR 0.62 (p=0.02140) as opposed to the BRCA-wt population which did not show benefit HR 0.84 (p=0.34) in BRCA-wt (82). However, some BRCA-wt patients with recurrent or refractory disease who have high homologous recombination deficiency (HRD) may benefit from PARP inhibitors. Recent reports show that some HRD high tumors were associated with better response to niraparib. Moreover, recent studies showed that BRCA-wt and HRD-low tumors have elevated immunogenic signals including increased abundance of TILs demonstrating high IFN gamma 1 signaling. This is consistent with what was observed with Vigil® benefit in RFS most significantly demonstrated in the BRCA-wt population. Consideration of further clinical testing of Vigil® with PARP inhibition in BRCA-wt ovarian cancer is justified.

Bevacizumab is indicated maintenance therapy of frontline treated ovarian cancer although no evidence of recurrence free or overall survival advantage involving bevacizumab alone as maintenance has been observed. Vascular endothelial growth factor (VEGF) inhibitors (i.e. bevacizumab) target the pleiomorphic growth factor VEGF which is not only a key regulator of tumor angiogenesis but also suppresses the immune system. The hypoxic tumor microenvironment stimulates the secretion of the pro-angiogenic factor VEGF-A (known as VEGF) which binds to receptor tyrosine kinase VEGF receptors (VEGFRs)-1 (FLT1) and -2 (FLK1/KDR) and VEGFR co-receptors neuropilins (NRPs) 1 and 2. This pro-angiogenic switch in the tumor microenvironment not only favors tumor angiogenesis, tumor maturation, and metastatic dissemination, but also exerts immunosuppressive effects such as inhibition of dendritic cell (DC) maturation, promotion of regulatory T cell function and expands tumor-associated macrophage development, and accumulation of myeloid-derived suppressor cells. PD-1 expression on CD8+ T cells is also increased. In ovarian cancer, VEGF-A and its receptors VEGFR1, VEGFR2, and NRP1 are commonly upregulated.

Clinical effectiveness of bevacizumab in ovarian cancer however remains challenging not only as related to the limited clinical response and moderate toxicity profile but also from the relatively rapid activation of anticancer resistance following initiation of angiogenesis inhibition. However, a potential direction being explored in use of anti-angiogenesis inhibitors is intensification of the immunotherapeutic activity. There is evidence that combination of bevacizumab with therapeutic vaccines may induce infiltrating T lymphocyte response and will shift the immunosuppression balance from T regulatory suppression to CD8 T cells activation and will create a T cell inflamed tumor microenvironment ("hot tumor") that is more immunologically responsive to immunotherapy.

In conclusion, Vigil® demonstrated convincing RFS advantage and low toxic effect as single-agent maintenance therapy in frontline ovarian (Stage III/IV) cancer patients with BRCA1/2-wt molecular profile. Further studies as single agent and with combination angiogenesis inhibitors, PARP inhibitors and checkpoint inhibitors are also justified.

Example 4—Homologous Recombination Proficient (HRP) Ovarian Cancer: Gemogenovatucel-T (Vigil®), an Option in the Search for Efficient Maintenance Therapy A recent meta-analysis of ovarian cancer patients (Xu et al., *Oncoarget*, 8(1):285-302, 2017) confirms that consequent inefficient repair mechanisms in BRCA mutated (-m) tumors predict improved response rates to platinum chemotherapy as compared to BRCA wild-type (-wt) tumors.

Counterintuitively, genetic instability as a result of germline mutations in BRCA and other homologous recombination (HR) genes significantly increases the probability of developing ovarian cancer. However, patients with HR deficient (HRD) cancers (both BRCA-m and HR-m) also demonstrate an improved survival. Not only is this due to an impaired ability to repair chemotherapy-induced DNA damage but also, to the disrupted BRCA-regulated autophagy and subsequent effects on cancer stem cell maintenance and drug resistance. The therapeutic application of PARP inhibition (PARP-i), capitalizing on synthetic lethality predicted by network biomolecular analysis in HRD cancers, represents a significant positive shift in ovarian cancer therapy. Albeit a significant contribution to the treatment paradigm, PARP-i preferentially benefits patients with HRD cancer and is of lesser survival benefit in patients with HR proficient (HRP) ovarian cancer (González-Martin et al., New England Journal of Medicine, 381(25):2391-2402, 2019). Problematically, PARP inhibitors elicit moderate class toxicity that narrows the therapeutic index for long term maintenance therapy with some agents demonstrating Grade 3/4 adverse events in up to 65% of patients. Additionally, a 71% drug reduction rate and a 12% drug discontinuation rate is observed, thus allowing a less favorable therapeutic index of toxicity:benefit ratio for patients particularly those with HRP tumors (Gonzalez-Martin et al., N Engl J Med, 381(25): 2391-2402, 2019). Consequently, HRP tumors remain a subset of ovarian cancer with less effective primary treatment and maintenance vis-à-vis survival.

Bevacizumab also demonstrated a statistically improved progression-free survival (PFS) in ovarian cancer patients with recurrent disease and newly diagnosed patients with resectable Stage III/IV disease as consolidation and maintenance after debulking surgery, although long-term follow-up has failed to demonstrate OS benefit. Interestingly, with respect to limited relationship awareness of HRD and HRP to bevacizumab activity, in the GOG-0218 trial (NCT00262847). BRCA-wt/HRP ovarian cancer cohorts demonstrated a nearly 20-month lower survival compared to the BRCA-wt/HRD cohorts with and without bevacizumab in both consolidation and maintenance thereby also supporting limits in efficacy with bevacizumab involving BRCA-wt/HRP ovarian cancer (Tewari et al., J Clin Oncol, 37(26): 2317-2328, 2019).

We have previously described use of a novel autologous tumor cell vaccine as maintenance in newly diagnosed ovarian cancer, gemogenovatucel-T (Vigil®), constructed from harvested tissue during debulking surgery (Oh et al., Gynecol Oncol, 143(3):504-510, 2016). Vigil® incorporates a multigenic plasmid encoding the human immune-stimulatory GMCSF gene and a bifunctional short-hairpin RNA construct, which specifically knocks down the proprotein convertase furin and its downstream targets TGFβ1 and TGFβ2 (Maples et al., BioProcessing Journal, 8:4-14, 2010; Senzer et al., Mol Ther, 20(3):679-86, 2012; and Senzer et al., Journal of Vaccines & Vaccination, 4(8):209, 2013). Vigil® is designed to enhance cancer-associated neoantigen expression via upregulation of MHC-II and dendritic cell processing and thereby augment the afferent immune response creating a systemic antitumor immune response.

In a Phase 2 randomized double-blinded placebo controlled maintenance trial involving 25 sites, Vigil® further demonstrated a favorable therapeutic index with documented efficacy without any therapy related severe Grade 3/4 adverse events (Rocconi et al., Lancet Oncology, 2020). A non-statistically significant improvement in the primary endpoint, recurrence free survival (RFS), was determined for all patients receiving Vigil® compared to placebo; 11.5 vs. 8.4 months, respectively (n=91, HR=0.688, 90% CI 0.443 to 1.068; p=0.078). However, pre-planned determination of RFS in BRCA-wt patients, a prospective secondary endpoint, did reveal a hypothesis-engendering improvement in RFS of 12.7 vs. 8.0 months (n=67, HR=0.514; 90% CI 0.3 to 0.88; p=0.020). Additionally, in a planned subset analysis of BRCA-wt patients the median overall survival (OS) was not reached compared to 41.4 months for placebo (n=67, HR=0.493; CI 0.24 to 1.009; p=0.049). Furthermore, only 21 of 40 (52%) of BRCA-wt patients demonstrated relapsed disease following Vigil® at time of analysis compared to 20 of 27 (78%) placebo BRCA-wt patients (p=0.021, Fisher Exact). The 2 year RFS rate from randomization was observed with Vigil® (33%) vs. placebo (14%) (p=0.045, one-sided Z test) and 2 year OS advantage with Vigil® (90%) vs. placebo (67%) (p=0.020, one-sided Z test) was also demonstrated.

Given the relationship of enhanced immune response to Vigil® immunotherapy in the BRCA-wt population and limited advantage to standard of care in the HRP population, we determined homologous recombination status (HRD and HRP) of all patients entered and treated in the recently published Phase 2 trial (Rocconi et al., Lancet Oncology, 2020). This trial evaluated Vigil® vs. placebo as maintenance therapy in newly diagnosed ovarian cancer patients with resectable Stage III/IV disease who underwent debulking surgery and adjuvant treatment with platinum based chemotherapy in order to determine the effect of Vigil® on the HRP population.

Recently, Vigil® showed significant clinical benefit with improvement in progression free and overall survival in pre-planned subgroup analysis in stage III/IV newly diagnosed ovarian cancer patients with BRCA wild type molecular profile. Here we analyze homologous recombination status of patients enrolled in the Phase 2b VITAL study and determine clinical benefit of Vigil® in HRP patients.

1. Methods 1.1 Patient Population and Study Design

Vigil® plasmid construction, cGMP manufacturing, tissue processing and transfection were carried out as previously described (Maples et al., BioProcessing Journal, 8:4-14, 2010; Senzer et al., Mol Ther, 20(3):679-86, 2012; and Oh et al., Gynecologic Oncology, 143(3):504-510, 2016). The VITAL study was a randomized, Phase 2b, double blind, placebo controlled trial. Patient population and study design are previously published (Rocconi et al., Lancet Oncology, 2020). Briefly, patients were in complete response following surgical debulking and 5-8 cycles of chemotherapy with Stage III/IV high grade serious, endometroid or clear cell ovarian cancer. At time of study entry, patients were required to have an Eastern Cooperative Oncology Group (ECOG) performance status of 0 or 1 and adequate organ and marrow function. Patients received $1\times10^7$ cells/injection of Vigil® or placebo once per month for a minimum of 4 and maximum of 12 doses. Treatment continued until product exhaustion or disease progression. Adverse events were recorded following the first dose of treatment and continued for 30 days following last treatment. Disease recurrence was evaluated by blinded independent review and was defined as any measurable lesion or elevated CA-125 level greater than 35 U/mL in two consecutive measurements.

1.2 HRP Analysis

BRCA1/2 mutation status was determined as previously described (Rocconi et al., Lancet Oncology, 2020). Patients identified as BRCA12 wild type were sent for homologous recombination deficiency testing using MyChoice® CDx (Myriad, Inc, Salt Lake City, Utah). Per assay guidelines a score of ≥42 was used to identify patients who were HRD, and <42 were HRP.

1.3 Statistical Analysis

The primary endpoint of the VITAL study was relapse free survival from time of randomization. Post-hoc analysis of recurrence free and overall survival of Vigil® vs. placebo in HRP patients was performed via Kaplan-Meier analysis. Hazard ratio and confidence intervals were calculated using 90% CCI and p values were one sided. Stratification factors included residual disease and chemotherapy schedule. Restricted mean survival time difference (RMST) analysis was performed as a sensitivity analysis using a truncation point equal to the minimum of the longest follow-up time of each group and was performed without covariate adjustment.

2. Results 2.1 Baseline Characteristics and Demographics

In this assessment, 67 patients who had BRCA-wt tumors (60% of patients in Vigil® arm and 40% in Placebo arm) underwent HRD analysis. HR analysis of the tumor tissue revealed that 62.5% (n=25) in the Vigil® arm and 74.1% (n=20) of the placebo arm had assay-determined [threshold <42 (Myriad MyChoice®)] HRP tumors. Patient demographics are listed in Table 10. Demographics revealed higher number of poor performance status (ECOG 1) patients were randomized to receive Vigil®.

TABLE 10

| | BRCA-wt HRP | |
|---|---|---|
| Characteristic | Vigil ® | Placebo |
| No. of patients | 25 | 20 |
| Age, years | | |
| Median | 64 | 64.0 |
| Range | 51-84 | 46-79 |

TABLE 10-continued

| | BRCA-wt HRP | |
|---|---|---|
| Characteristic | Vigil ® | Placebo |
| <65 | 52.0% | 55.0% |
| ≥65 | 48.0% | 45.0% |
| FIGO stage | | |
| III | 72.0% | 85.0% |
| IV | 28.0% | 15.0% |
| *ECOG score | | |
| 0 | 48.0% | 75.0% |
| 1 | 52.0% | 25.0% |
| Frontline chemotherapy | | |
| Adjuvant | 83.0% | 84.1% |
| Neoadjuvant | 17.0% | 15.9% |
| Frontline surgery residual disease status | | |
| Macroscopic | 32.0% | 30.0% |
| Microscopic/NED | 68.0% | 70.0% |
| *BRCA mutational status | | |
| BRCA-wt | 25 | 20 |
| BRCA-m | N/A | N/A |
| HRP | 25 | 20 |
| HRD | N/A | N/A |

N/A = Not available 2.2 Safety

Adverse events for each treatment group are presented in Table 11. No patients in the Vigil® group reported Grade 3 or higher adverse events. There were also no treatment related deaths, no patients were removed from study due to adverse events and no dose modifications occurred. Patients received a mean of 7.12 Vigil® doses (range 1.00-12.00) compared to 6.90 (range 3.00-12.00) placebo doses.

TABLE 11

| | Adverse effects | | | | | | | | | | | |
|---|---|---|---|---|---|---|---|---|---|---|---|---|
| | Vigil ® (n = 25) | | | | | | Placebo (n = 20) | | | | | |
| | Grade 1 | | Grade 2 | | Grade 3 | | Grade 1 | | Grade 2 | | Grade 3 | |
| Organ Class-AE term | No. | % | No. | % | No. | % | No. | % | No. | % | No. | % |
| Gastrointestinal disorders | 4 | 16% | | 0% | | 0% | 2 | 8% | | 0% | | 0% |
| Abdominal pain | 1 | 4% | | 0% | | 0% | | 0% | | 0% | | 0% |
| Bloating | 1 | 4% | | 0% | | 0% | | 0% | | 0% | | 0% |
| Diarrhea | 1 | 4% | | 0% | | 0% | | 0% | | 0% | | 0% |
| Nausea | 1 | 4% | | 0% | | 0% | 2 | 8% | | 0% | | 0% |
| General disorders and administration site conditions | 16 | 64% | | 0% | | 0% | 5 | 20% | 2 | 8% | | 0% |
| Chills | 1 | 4% | | 0% | | 0% | | 0% | | 0% | | 0% |
| Edema extremities | 1 | 4% | | 0% | | 0% | | 0% | | 0% | | 0% |
| Fatigue | 2 | 8% | | 0% | | 0% | 1 | 4% | 2 | 8% | | 0% |
| Injection site reaction | 12 | 48% | | 0% | | 0% | 3 | 12% | | 0% | | 0% |
| Temperature intolerance | | 0% | | 0% | | 0% | 1 | 4% | | 0% | | 0% |
| Laboratory | | 0% | | 0% | | 0% | 2 | 8% | | 0% | | 0% |
| Platelets decreased | | 0% | | 0% | | 0% | 1 | 4% | | 0% | | 0% |
| WBC decreased | | 0% | | 0% | | 0% | 1 | 4% | | 0% | | 0% |
| Musculoskeletal and connective tissue disorders | 1 | 4% | 1 | 4% | | 0% | 3 | 12% | 1 | 4% | 2 | 8% |
| Arthralgia | | 0% | 1 | 4% | | 0% | 1 | 4% | | 0% | | 0% |
| Arthritis aggravated | | 0% | | 0% | | 0% | | 0% | 1 | 4% | | 0% |
| Back pain | | 0% | | 0% | | 0% | 1 | 4% | | 0% | | 0% |
| Bone pain | | 0% | | 0% | | 0% | | 0% | | 0% | 1 | 4% |
| Flank pain | | 0% | | 0% | | 0% | 1 | 4% | | 0% | | 0% |
| Generalized muscle weakness | | 0% | | 0% | | 0% | | 0% | | 0% | 1 | 4% |

TABLE 11-continued

Adverse effects

| | Vigil ® (n = 25) | | | | | | Placebo (n = 20) | | | | | |
|---|---|---|---|---|---|---|---|---|---|---|---|---|
| | Grade 1 | | Grade 2 | | Grade 3 | | Grade 1 | | Grade 2 | | Grade 3 | |
| Organ Class-AE term | No. | % | No. | % | No. | % | No. | % | No. | % | No. | % |
| Muscle pain | 1 | 4% | | 0% | | 0% | | 0% | | 0% | | 0% |
| Nervous system disorders | | 0% | 1 | 4% | | 0% | 1 | 4% | | 0% | 1 | 4% |
| Dizziness | | 0% | | 0% | | 0% | 1 | 4% | | 0% | | 0% |
| Headache | | 0% | 1 | 4% | | 0% | | 0% | | 0% | | 0% |
| Syncope | | 0% | | 0% | | 0% | | 0% | | 0% | 1 | 4% |
| Psychiatric disorders | | 0% | | 0% | | 0% | 1 | 4% | | 0% | | 0% |
| Psychiatric symptom NOS | | 0% | | 0% | | 0% | 1 | 4% | | 0% | | 0% |
| Renal and urinary disorders | 1 | 4% | | 0% | | 0% | | 0% | | 0% | | 0% |
| Urinary incontinence | 1 | 4% | | 0% | | 0% | | 0% | | 0% | | 0% |
| Reproductive system and breast disorders | | 0% | | 0% | | 0% | | 0% | 1 | 4% | | 0% |
| Pelvic pain | | 0% | | 0% | | 0% | | 0% | 1 | 4% | | 0% |
| Respiratory, thoracic and mediastinal disorders | | 0% | | 0% | | 0% | | 0% | | 0% | 1 | 4% |
| Dyspnea | | 0% | | 0% | | 0% | | 0% | | 0% | 1 | 4% |
| Skin and subcutaneous tissue disorders | 4 | 16% | 1 | 4% | | 0% | | 0% | | 0% | | 0% |
| Facial rash | 1 | 4% | | 0% | | 0% | | 0% | | 0% | | 0% |
| Pruritus | 1 | 4% | | 0% | | 0% | | 0% | | 0% | | 0% |
| Rash maculo-papular | | 0% | 1 | 4% | | 0% | | 0% | | 0% | | 0% |
| Skin hyperpigmentation | 1 | 4% | | 0% | | 0% | | 0% | | 0% | | 0% |
| Skin induration | 1 | 4% | | 0% | | 0% | | 0% | | 0% | | 0% |

2.3 Endpoint Analysis

Figure 22:
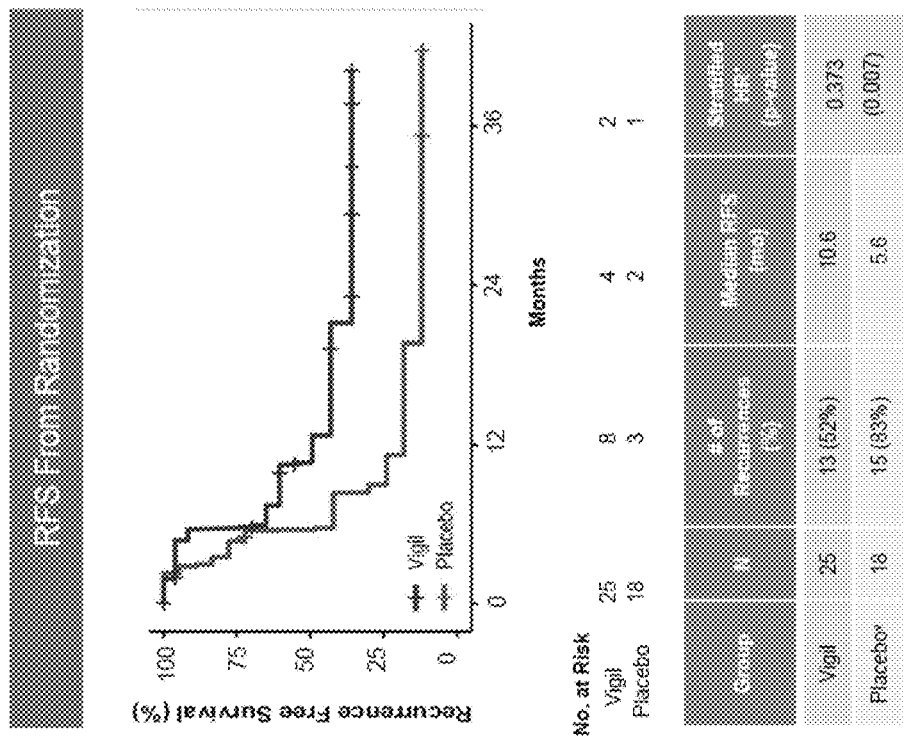
Figure 23:
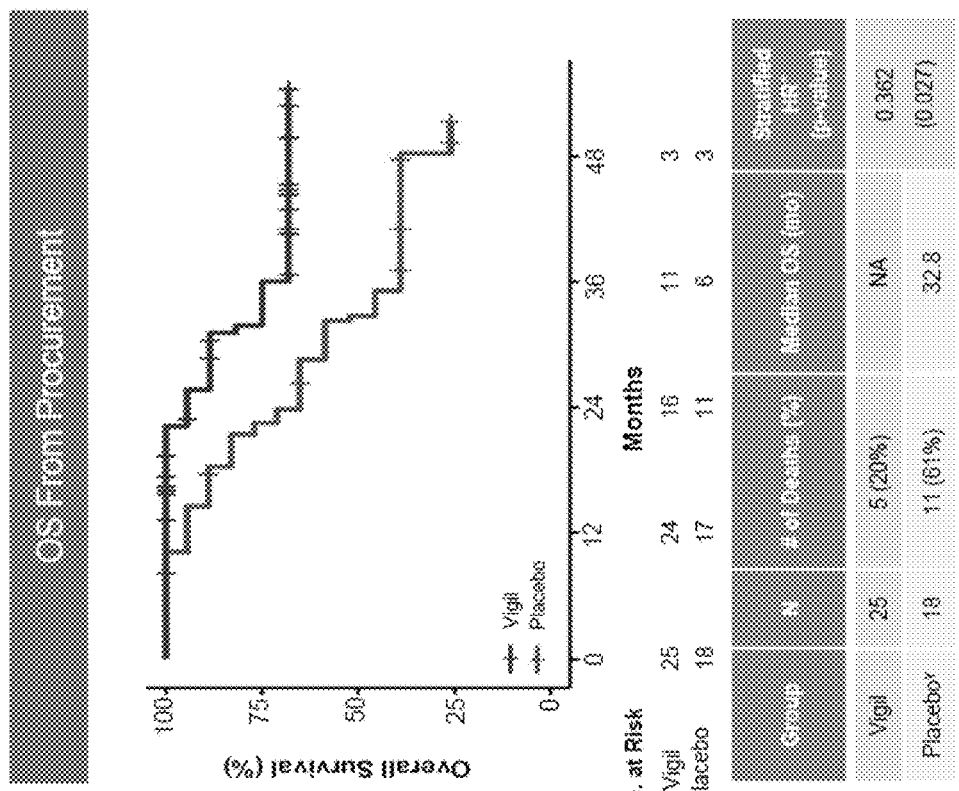
FIGS. 23 and 24 illustrate overall survival (OS) of patient population from surgery/procurement (FIG. 15) and from randomization (FIG. 16).
Figure 24:
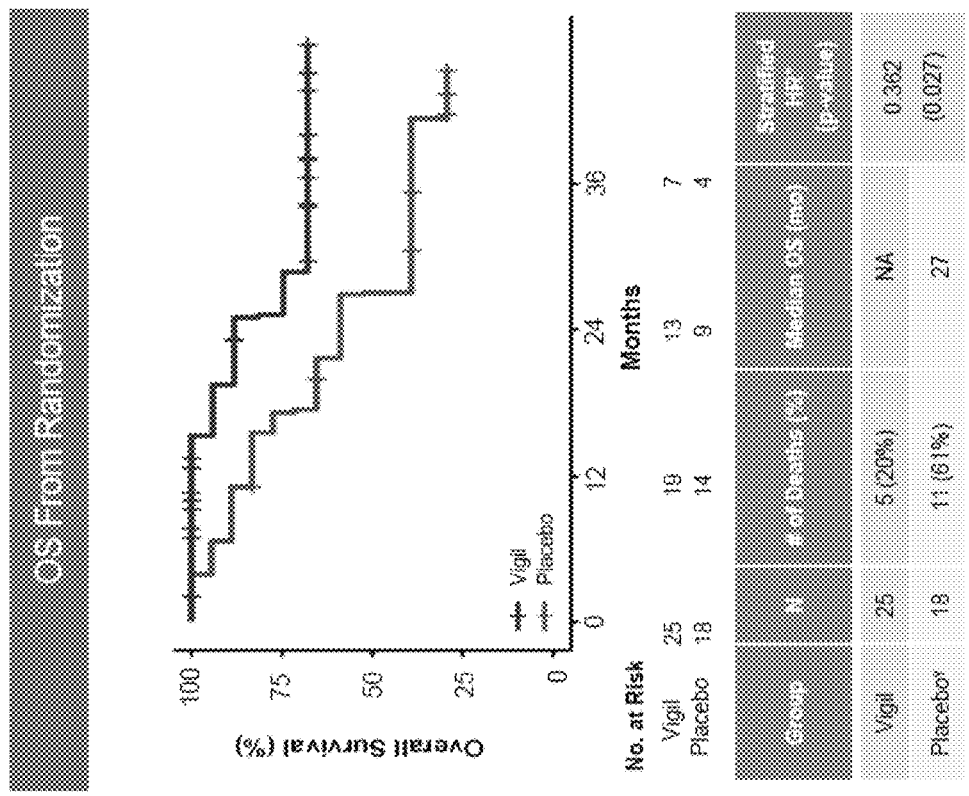
Figure 25:
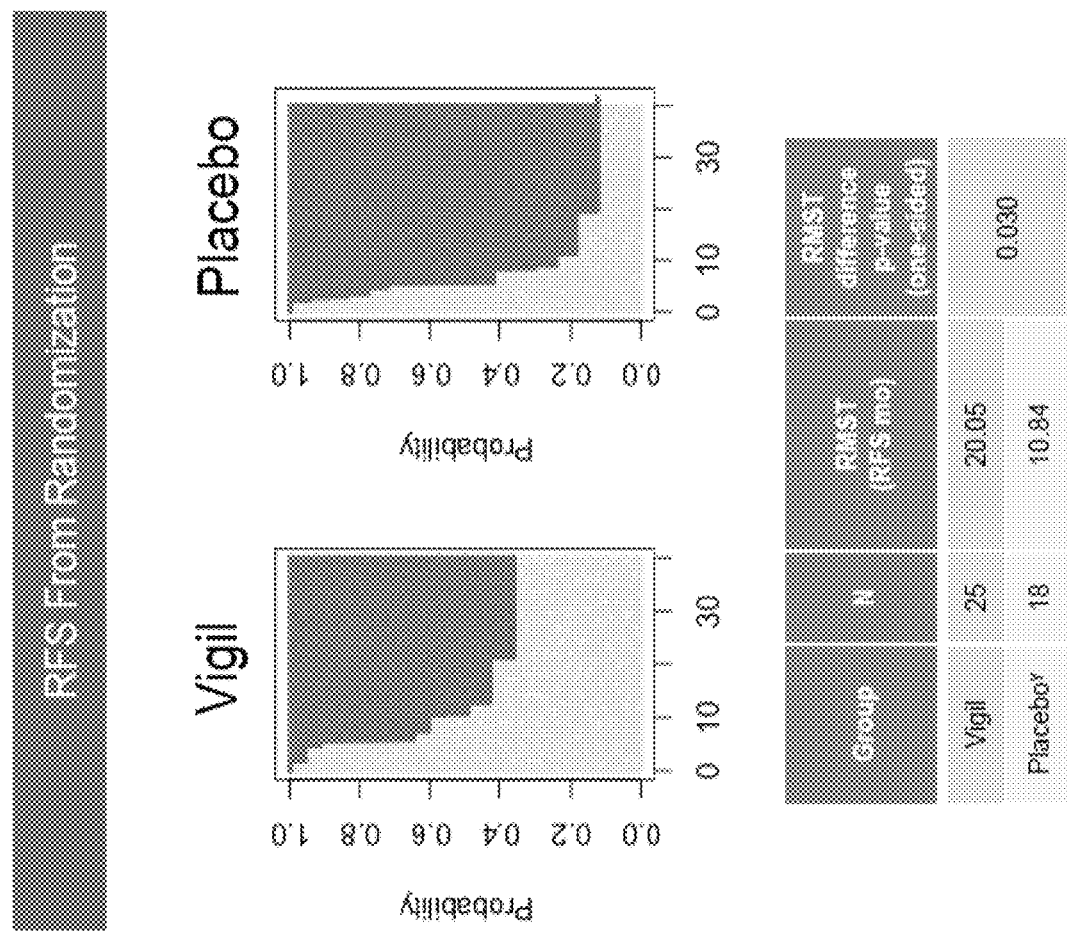
FIG. 25 shows the probability of RFS of patient population from randomization.
Figure 26:
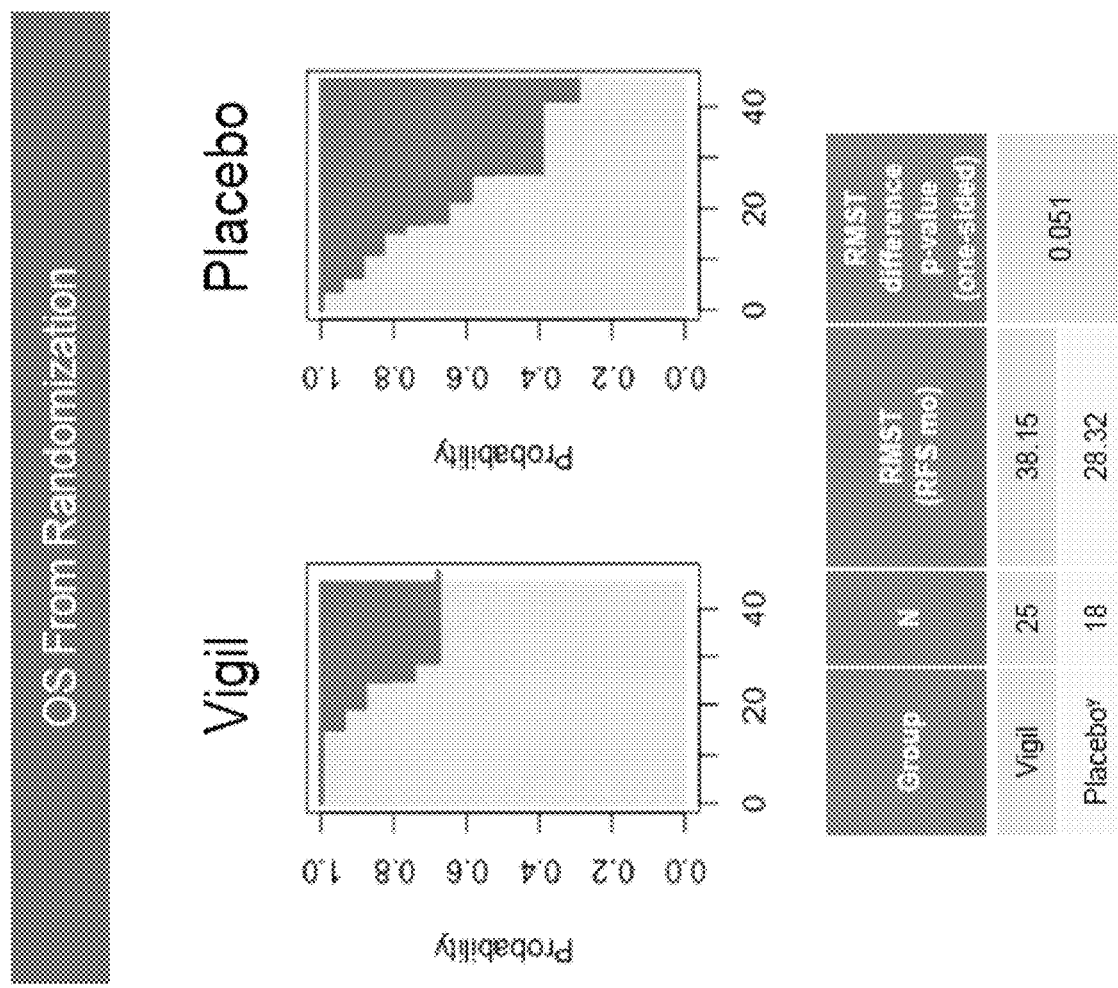
FIG. 26 shows the probability of OS of patient population from randomization.
Figure 28:
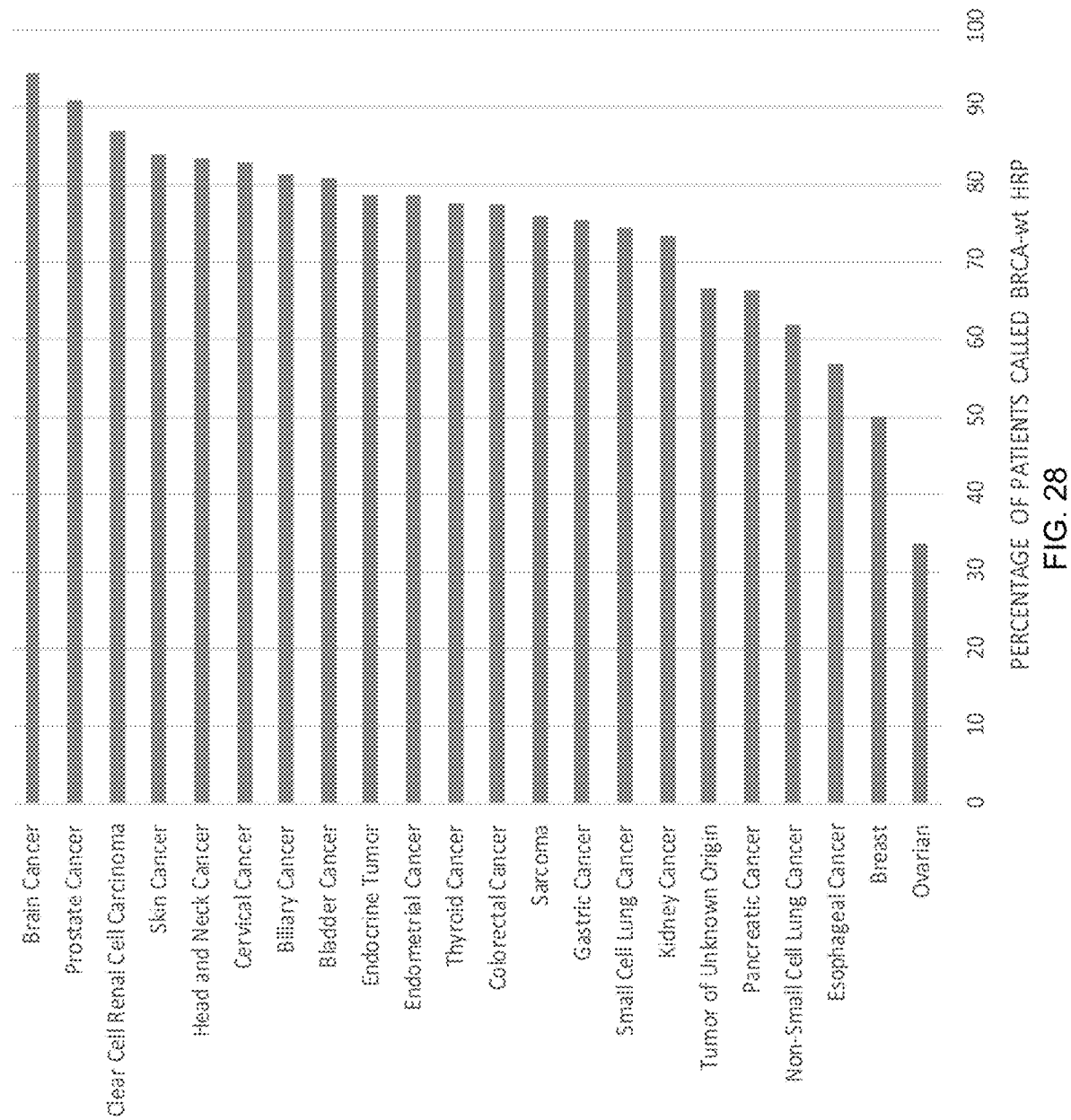
FIG. 28 shows the HR-DDR mutation frequency in various types of cancers.
Figure 30:
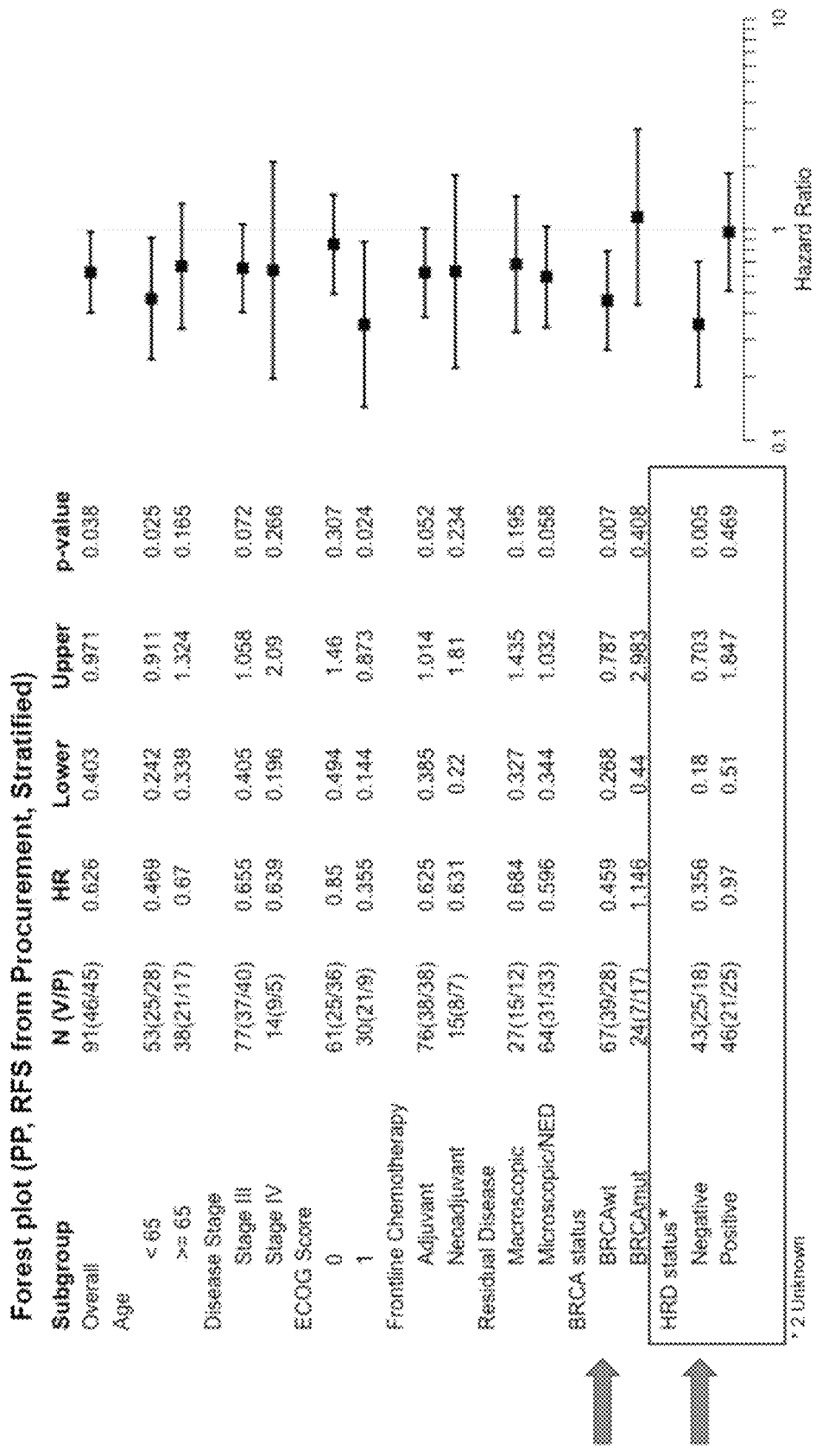
FIGS. 30 and 31 show forest plot key demographics between HRD negative and HRD positive patients.
Figure 31:
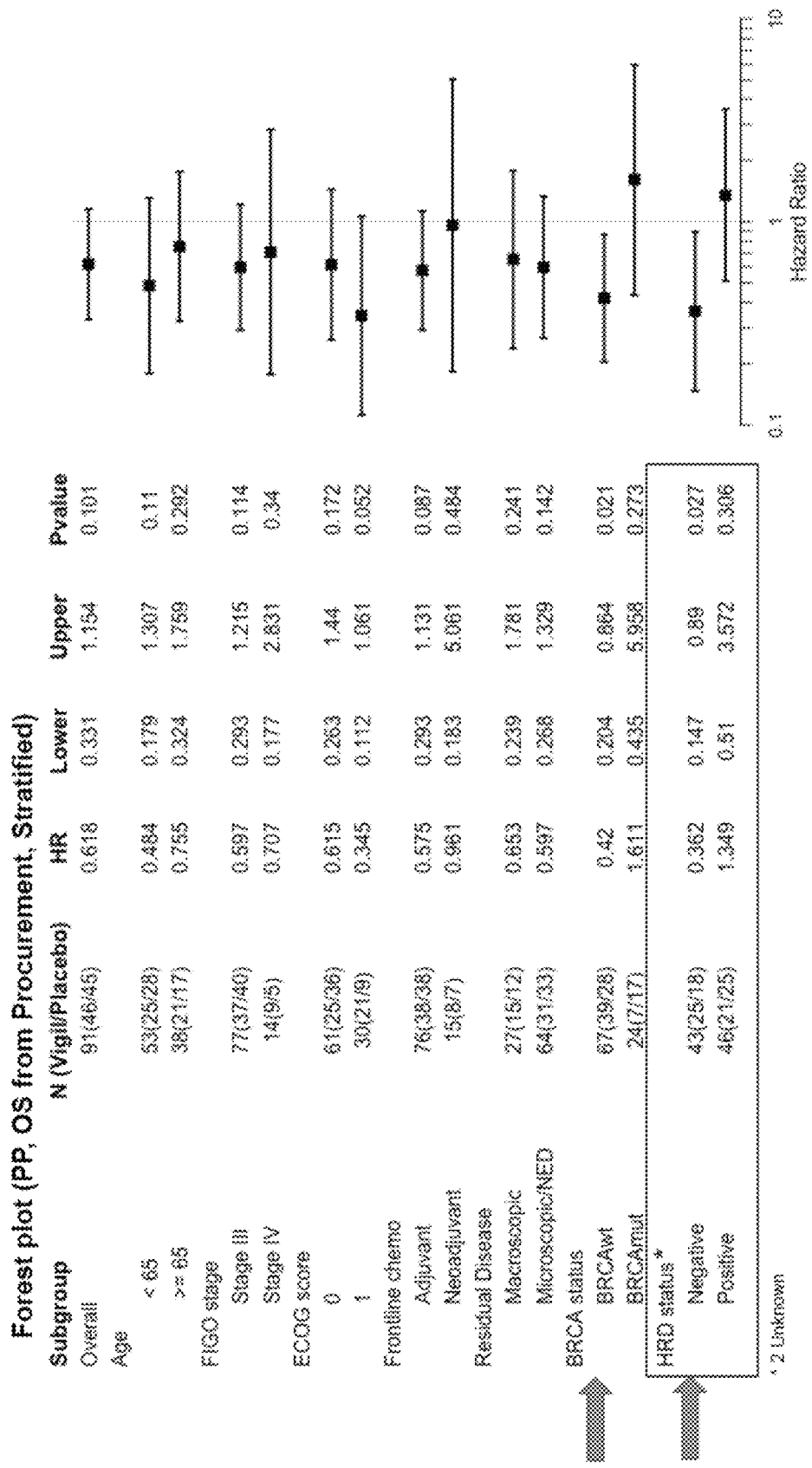
Figure 32:
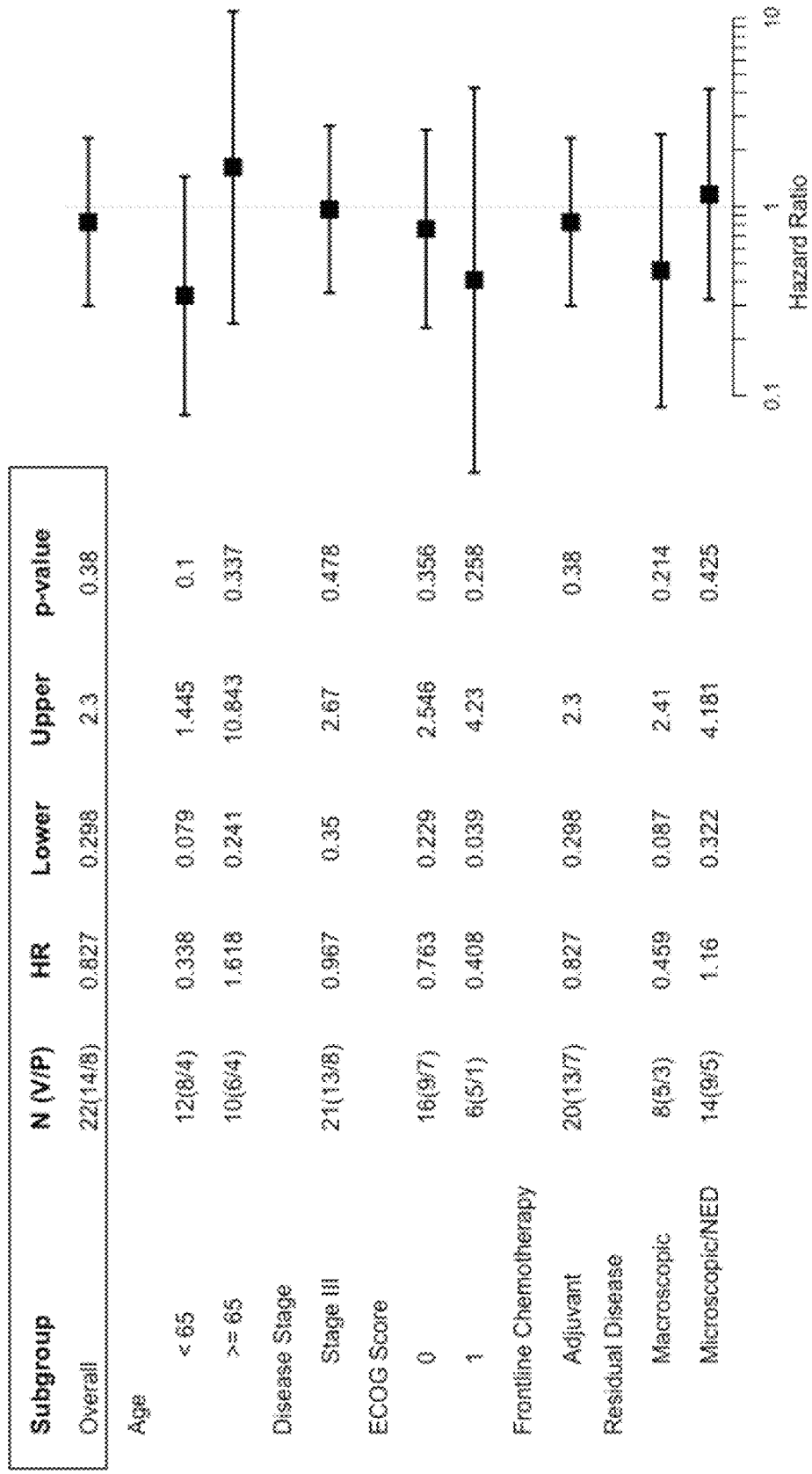
FIGS. 32 and 33 show forest plot key demographics of BRCA1/2-WT and HRD positive patients.
Figure 33:
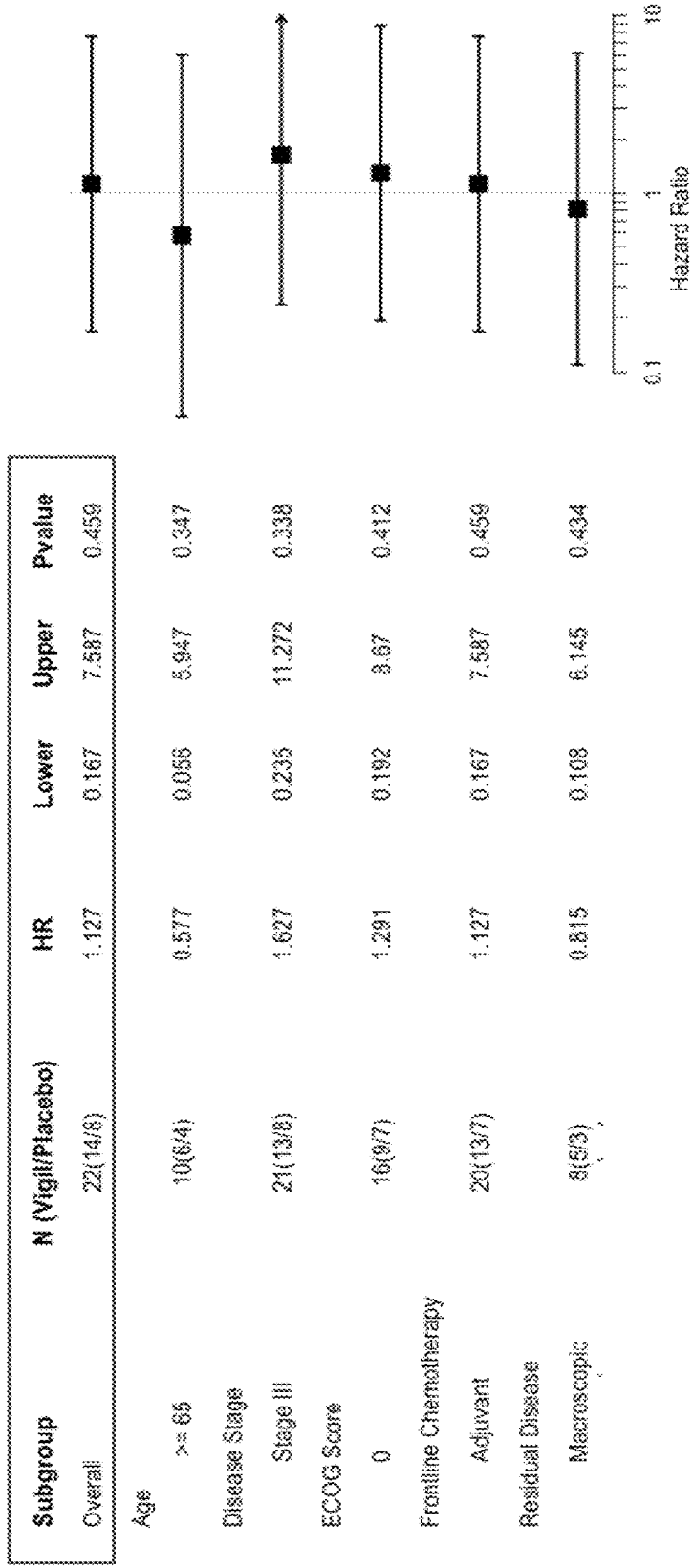

Kaplan Meier analysis demonstrated favorable improvement in both RFS HR=0.386 (90% CI 0.199-0.750), p=0.007 and OS HR=0.342 (90% CI 0.141-0.832), p=0.019 in the HRP Vigil®-treated subset from randomization (FIGS. 22 and 24). Further assessment of OS and RFS with RMST, which provides an alternative assessment comparing exposure over a specified time as opposed to hazard ratio which compares relative risks that vary with time and is based on number of events, also supported favorable advantage (FIGS. 25 and 26) of Vigil® over placebo in both RFS (p=0.017) and OS (p=0.008).

3. Results

Relationship of BRCA-wt expression in malignant tissue as opposed to BRCA-m (Morand et la., *JNCI Cancer Spectrum*, 2020) is associated with higher clonal neoantigen (McGranahan et al., *Science*, 351(6280):1463-9, 2016) expression and would potentially provide more appropriate neoantigen target identification of an induced immune effector response characterized as a "hot" tumor microenvironment in relationship to Vigil® induced immune activation (Kraya, A. A., et al. *Clin Cancer Res*, 25(14):4363-4374, 2019). Higher tumor mutation burden and higher median neoantigen burden is observed in HRD vs. HRP high-grade ovarian cancers, albeit at the lower end of the pan-tumor spectrum. However, the presence of a high subclonal mutation fraction (~40%) with greater intratumoral heterogeneity in HRD, presumably undercuts the immunogenic effect described in high clonal neoantigen tumors associated with a 'hot' inflamed tumor microenvironment and increased tumor infiltrating cells (McGranahan et al., *Science*, 351 (6280):1463-9, 2016) which is especially so in the setting of high neoantigen/high human leukocyte antigen (HLA) expressing HRP tumors. These HRP tumors are also enriched in effector memory T cells and enhanced IFNγ response while BRCA1 mutation tumors are associated with reduced Type I/II IFN response (McGranahan et al., *Science*, 351(6280):1463-9, 2016). Mechanistic assessment of Vigil® supports functional escalation of circulating mononuclear cell antitumor response induction following Vigil® treatment in correlation with clinical benefit as assessed by ELISPOT assay (Oh et al., *Gynecol Oncol*, 143(3):504-510, 2016). Moreover, circulating CD3+/CD8+ mononuclear cells specifically were shown to be systemically upregulated following Vigil® treatment in a small group of treated patients (Herron et al., Cancer Science and Research, 2020). Additionally, higher subclonal neoantigen expression in BRCA-m expressive cancer may provide higher proportion of subpopulations of malignant cell "nests" thereby diluting clonal neoantigen visibility (likely enhanced in the BRCA-wt population) and efficiency of immune response to targeting of clonal neoantigens (McGranahan et al., *Science*, 351(6280):1463-9, 2016). Persistent expression of elevated ELISPOT activity following Vigil® has also been observed with durability of induced antitumor activity months beyond discontinuation of Vigil® (Senzer et al., *Journal of Vaccines & Vaccination*, 4(8):209, 2013). These results are suggestive of memory T-cell induction (Craig et al., *Vaccines (Basel)*, 8(4), 2020).

As previously described, the addition of PARP-i to our treatment opportunity in ovarian cancer has made an impact. However, the molecular profile of individual ovarian cancers is diverse and relationship of RFS, PFS and OS to molecular profile is under close evaluation throughout the cancer spectrum, including ovarian cancer. Based on this and other PARP-i reports involving newly diagnosed and second-line ovarian cancer treatment course therapy several treatment indications have been granted, however the majority of the benefit is seen in ovarian cancer patients with BRCA-m or BRCA-wt HRD tumors.

Given the clinical difficulty with both anti-angiogenic agents and PARP-i arising from their moderate toxicity profiles and limited efficacy in the BRCA-wt/HRP population in comparison to the BRCA-m and BRCA-wt/HRD population, Vigil® consideration in the HRP ovarian cancer population is warranted. PARP-i's are associated with a significant proportion of Grade 3/4 drug related toxic effects, which can result with as many as 75% of patients undergoing dose interruption (Gonzalez-Martin et al., *N Engl J Med*, 381(25):2391-2402, 2019). Although the toxicity profile is lower with anti-angiogenic agents, toxicity can be serious if not lethal with risks of bleeding, hypertension, bowel perforations, as well as venous and arterial thrombosis. Considering recent niraparib approval as maintenance for "all comers" (Gonzalez-Martin et al., *N Engl J Med*, 381(25): 2391-2402, 2019), which includes patients with HRP tumors and given both the quantitative and qualitative toxic limitations weighted against the limited benefit in the HRP population, further development of Vigil® and other potentially effective wider therapeutic index approaches as well as other sensitive molecular subset populations are justified.

Vigil® immunotherapy represents the first randomized proof of principle study of the effectiveness of immunotherapy in HRP epithelial ovarian cancer (Rocconi et al., *Lancet Oncology*, 2020). Achievement of both prolonged delay of recurrent disease and overall survival advantage with a wide therapeutic index in conjunction with the convenience of monthly intradermal injections are key components of optimal maintenance therapy in clinically disease-free patients. The study of Vigil® vaccine maintenance therapy in primary HRP ovarian cancer responds to the area of encouragement from NRG Oncology to develop and apply therapies that target this subset of ovarian cancers. Phase 3 investigation of Vigil® is thus justified, particularly in the HRP ovarian cancer population and possibly in other solid tumor populations with HRP profile.

Example 5. Gemogenovatucel-T (Vigil®) Immunotherapy as Maintenance in Frontline Stage III/IV Ovarian Cancer (VITAL): A Randomised, Double-Blind, Placebo-Controlled, Phase 2b Trial Evidence Before this Study We searched PubMed from Jan. 1, 1999, to Mar. 1, 2020, for clinical trials, studies, and research articles published in English with the search terms "current standard of care", "ovarian cancer maintenance", "PARP inhibitors", "BRCA mutation status ovarian cancer", and "homologous recombination deficient". Our search yielded 21 159 papers. Literature review revealed several studies involving poly (ADP-ribose) polymerase (PARP) inhibitors showing improved progression-free survival, but no advantage in recurrence-free survival or overall survival in front-line ovarian cancer involving systemic maintenance therapy. There are few options for advanced front-line ovarian cancer management. Delayed but persistent relapse occurs at a rate of almost 75% within the first 2 years after primary standard of care management of either primary debulking surgery followed by adjuvant chemotherapy or neoadjuvant chemotherapy with interval debulking surgery. Consolidation or maintenance treatment has not shown improvement in recurrence-free survival or overall survival when compared with standard management. Despite some studies showing progression-free survival benefit in patients who are homologous recombination proficient, the survival benefit for ARP inhibitors preferentially involves patients with germline and somatic BRCA mutations or a homologous recombination deficient molecular profile. ARP inhibition also shows little efficacy for overall survival, with most benefit observed in patients with BRCA mutations or homologous recombination deficiency and less benefit in patient with homologous recombination proficiency. Moreover, toxic effects related to marrow suppression and, rarely, treatment-related leukaemia limit dose administration, 5-year survival for patients with ovarian cancer remains poor, indicating an unmet medical need. Thus, supported by robust phase 1 safety and immune response mechanism results, and significant evidence of benefit in a phase 2a clinical trial, we initiated the VITAL trial to evaluate the safety and efficacy of gemogenovatucel-T in newly diagnosed patients with stage III/IV ovarian cancer who were candidates for primary debulking surgery.

Added Value of this Study

To our knowledge, the VITAL study is the first to investigate the effect of a triple mechanism immune modulatory autologous tumour vaccine as a front-line maintenance treatment of ovarian cancer, and shows the first evidence of an immunotherapy benefit in this population. The results of this study indicate that gemogenovatucel-T is non-toxic and treatment led to improved recurrence-free and overall survival in patients with advanced ovarian cancer who are wild type for BRCA1 and BRCA2 (BRCA). Most patients newly diagnosed with ovarian cancer are BRCA.

Implications of all the Available Evidence

Gemogenovatucel-T is a first-in-class immune therapy platform technology with single agent activity. Future studies of gemogenovatucel-T are justified in combination with checkpoint inhibitors, PARP inhibitors, and angiogenesis inhibitors.

Background

Gemogenovatucel-T is an autologous tumour cell vaccine manufactured from harvested tumour tissue, which specifically reduces expression of furin and downstream TGF-I31 and TGF-I32. The aim of this study was to determine the safety and efficacy of gemogenovatucel-T in front-line ovarian cancer maintenance.

Methods

This randomised, double-blind, placebo-controlled, phase 2b trial involved 25 hospitals in the USA. Women aged 18 years and older with stage III/IV high-grade serous, endometrioid, or clear cell ovarian cancer in clinical complete response after a combination of surgery and five to eight cycles of chemotherapy involving carboplatin and paclitaxel, and an Eastern Cooperative Oncology Group status of 0 or 1 were eligible for inclusion in the study. Patients were randomly assigned (1:1) to gemogenovatucel-T or placebo by an independent third party interactive response system after successful screening using randomly permuted block sizes of two and four and stratified by extent of surgical cytoreduction and neoadjuvant versus adjuvant chemotherapy. Gemogenovatucel-T ($1 \times 10e7$ cells per injection) or placebo was administered intradermally (one per month) for a minimum of four and up to 12 doses. Patients, investigators, and clinical staff were masked to patient allocation until after statistical analysis. The primary endpoint was recurrence-free survival, analysed in the per-protocol population. All patients who received at least one dose of gemogenovatucel-T were included in the safety analysis. The study is registered with ClinicalTrials., NCT02346747.

Findings

Between Feb. 11, 2015, and Mar. 2, 2017, 310 patients consented to the study at 22 sites. 217 were excluded. 91 patients received gemogenovatucel-T (n=47) or placebo (n=44) and were analysed for safety and efficacy. The median follow-up from first dose of gemogenovatucel-T was 40-0 months (IQR 35.0-44.8) and from first dose of placebo was 39.8 months (35.5-44.6). Recurrence-free survival was 11-5 months (95% CI 7.5—not reached) for patients assigned to gemogenovatucel-T versus 8.4 months (7.9-15.5) for patients assigned to placebo (HR 0.69, 90% CI 0.44-1.07; one-sided p=0.078). Gemogenovatucel-T resulted in no grade 3 or 4 toxic effects. Two patients in the placebo group had five grade 3 toxic events, including arthralgia, bone pain, generalised muscle weakness, syncope, and dyspnea. Seven patients (four in the placebo group and three in the gemogenovatucel-T group) had 11 serious adverse events. No treatment-related deaths were reported in either of the groups.

Interpretation Front-line use of gemogenovatucel-T immunotherapy as maintenance was well tolerated but the primary endpoint was not met. Further investigation of gemogenovatucel-T in patients stratified by BRCA mutation status is warranted.

Most women diagnosed with ovarian cancer present at an advanced stage. The optimal standard of care can achieve 5-year survival rates that vary by stage, from 41% (stage IIIa) to 20% (stage IV). The standard of care for newly diagnosed ovarian cancer (stage III or IV) involves primary debulking surgery followed by adjuvant chemo-therapy with paclitaxel and carboplatin or neoadjuvant chemotherapy with interval debulking surgery. Although most patients achieve complete remission with either approach, around 75% will relapse within 2 years.

Several studies involving bevacizumab and poly (ADP-ribose) polymerase (PARP) inhibitors have attempted to improve outcomes in front-line treated ovarian cancer by administering maintenance therapy after patients achieve complete response, but despite a benefit in progression-free survival, to our knowledge, no study has shown significant benefits for recurrence-free survival or overall survival. Additionally, moderate drug-related toxic effects of both bevacizumab and some PARP inhibitors limit dosing. PARP inhibitors have offered clinicians a novel platform for front-line maintenance for ovarian cancer but activity is predominantly seen in patients with BRCA germline and somatic mutations. PARP inhibitors are also approved in recurrent platinum-sensitive maintenance regardless of BRCA status; however, the magnitude of benefit is greatest in patients with BRCA mutated (BRCAmut) tumours or those with evidence of homologous recombination deficiency.

Gemogenovatucel-T is an autologous tumour cell vaccine manufactured from harvested tumour tissue and transfected ex vivo with a multigenic plasmid encoding the human granulocyte macrophage colony stimulating factor (GMCSF) gene, an immune-stimulatory cytokine, and a bifunctional short-hairpin RNA (bi-shRNA) construct, which specifically reduces expression of furin and downstream TGF-β1 and TGF-β2.4 Activation of TGF-β1 and TGF-β2 is not the only function of furin. Furin cleavage activates several other proteins, including growth factors, cytokines, hormones, and receptors. However, TGF-β protein is more highly expressed in malignant ovarian tissue compared with non-malignant ovarian tissue.5 Pathway analysis of gene signatures showed an enrichment of TGF-β signalling in patients with ovarian cancer with a poor prognosis (6). TGF-β is involved in the progression from non-invasive serous ovarian tumours to invasive serous ovarian carcinoma.

Moreover, TGF-β overexpression is associated with BRCA germline and somatic mutations. PARP inhibitors tumour cell proliferation and metastasis and is increased are also approved in recurrent platinum-sensitive main-in patients with sub optimally debulked ovarian cancer.

Early clinical testing of TGF-β, GMCSF DNA products, magnitude of benefit is greatest in patients with BRCA including phase 1 testing of gemogenovatucel-T in mutated (BRCAmut) tumours or those with evidence of recurrent or refractory solid tumours, showed safe intradermal administration at $1\times10^7$ cells per dose per month and upregulation of the autologous peripheral blood mononuclear cell γ interferon response to self tumour cell antigens via enzyme-linked immunospot assay. (9-11). A recurrence-free survival benefit and correlative treatment-related immune response was shown in a phase 2a study with gemogenovatucel-T as front-line maintenance therapy in patients with stage III or IV resectable ovarian cancer. Given the limitations of front-line treatment for advanced ovarian cancer, particularly in patients with BRCA wild type (BRCA) disease, we initiated the VITAL study. The aim of this study was to determine the safety and efficacy of gemogenovatucel-in front-line ovarian cancer maintenance.

Methods

Study Design and Participants

This randomised, phase 2b, double-blind, placebo-controlled trial involved 25 hospitals in the USA, of which 22 enrolled patients; the other three sites did not enroll patients after institutional review board approval). Women aged 18 years and older with stage III or IV high-grade serous, endometrioid, or clear cell ovarian cancer in clinical complete response after a combination of surgery and five to eight cycles of chemotherapy involving carboplatin and paclitaxel were eligible for inclusion in the study. Patients had to have an Eastern Cooperative Oncology Group (ECOG) performance status of 0-1 with normal organ and mar-row function. Concurrent PARP inhibitors or bevacizumab maintenance therapy was not allowed per study protocol. Patients were ineligible for study enrolment if they required chronic steroid or immune suppressive regimens, had congestive heart failure, unstable angina, ventricular or haemodynamically significant atrial arrhythmia, cardiovascular disease, mycardial infarction, brain metastasis, HIV, chronic hepatitis B or C infection, previous solid organ or bone marrow transplantation, or history of or active autoimmune disease. Patients with histologically confirmed papillary serous adenocarcinoma of the uterus or any disease involving the myometrium or endothelium, or brain metastasis were also excluded.

Tumour harvest for vaccine production occurred during laparoscopic debulking before neoadjuvant therapy or at the debulking surgery in patients not receiving neoadjuvant therapy. All tumour harvest procedures were done before any chemotherapy.

A washout period of 3 weeks after chemotherapy, 4 weeks after surgery involving general anesthesia, radiotherapy, immunotherapy or investigational drugs, and 14 days after immunosuppressive therapy was required. All patients provided written informed consent before tissue procurement. A drug safety monitoring board (BSMB) was put in place before study initiation to maintain the safety of all study patients. No toxic effects greater than or equal to grade 3 or 4 were observed. The DSMB recommendation was that study continue as planned. Written documentation of institutional review board and ethics approval of the protocol and written informed consent at each individual site was required before a patient could be registered.

Randomisation and Masking

Eligible study participants were randomly assigned (1:1) to receive gemogenovatucel-T or placebo. Patients were randomly assigned across the study by Clinipace (Morrisville, N.C., USA) through an interactive response system (Tempo system; Clinipace; Morrisville. N.C., USA) using randomly permuted block sizes of two and four, which occurred 3-8 weeks after completion of chemo-therapy. Randomisation was stratified by extent of surgical cytoreduction (microscopic vs macroscopic) and neoadjuvant versus adjuvant chemotherapy. To ensure masking was maintained, pharmacists on site were required to wrap blinding tape around the barrel of the syringe used for treatment administration to prevent the ability to distinguish drug from placebo. All trial staff, clinical investigators, and patients remained masked to study assignment. The sponsor study team, except for the quality assurance staff, were masked to patient treatment allocation.

Procedures

Gradalis (Carrollton, Tex., USA) manufactured gemogenovatucel-T from harvested tumour tissue. Tumour harvest for vaccine production occurred before any chemotherapy. Equal doses of placebo based on the number of vials of gemogenovatucel-T were manufactured. 10-30 g of tumour tissue was required for vaccine manufacture. Lesions that extended into the bowel lumen were excluded because of the risk of bacterial contamination. Placebo consisted of freeze media aseptically aliquoted into sterile 2.0 mL borosilicate glass vials to a final fill volume of 1.2 mL. After slow freezing the media to −80° C., the vials were stored in the vapour phase of liquid nitrogen pending sterility and endotoxin release testing. Placebo vial production was matched to the available product doses manufactured for the patients. Protocol enrollment exceptions were granted on the basis of partial plasmid elevated GMCSF expression or reduced (knockdown) TGF-β1 expression, which adequately represents evidence of plasmid transfer. Further details are provided in Table 12, below.

TABLE 12

Summary of Product Release

| | Viability | GMCSF Production | TGF-β1 Knockdown | Gel-clot Endotoxin (Vaccine |
|---|---|---|---|---|
| Count | 91 | 84 | 84 | 91 |
| Average | 86% | 2334 | 96% | 0.4 |
| StDev | 5% | 4541 | 8% | 0.4 |
| Median | 87% | 863 | 100% | 0.4 |
| Min | 72% | 36 | 66% | 0.2 |
| Max | 98% | 37669 | 100% | 3.2 |
| Range | 26% | 37633 | 34% | 3.0 |

Cell dose $1 \times 10^7$ for all patients; USP<71> sterility negative all patients; mycoplasma DNA negative all patients Patients received either $1 \times 10^7$ cells per intradermal injection of gemogenovatucel-T or placebo once a month (within 8 weeks after last chemotherapy) for a minimum of four and up to 12 doses. Protocol-defined treatment was stopped after the following events: patient had unacceptable (grade 3 or worse) toxic effects thought to be treatment-related by the patient's clinician, grade 3 or 4 toxic effects unrelated to treatment that did not resolve within 4 weeks, grade 3 or worse allergic reaction to study reagent, grade 2 autoimmune reaction unless evidence of clinical benefit, grade 3 or worse auto-immune reactions, any illness that could affect assessment of study endpoints, non-protocol therapy including chemotherapy, patient non-compliance, or withdrawal of consent. Criteria for dose modification included grade or worse toxic effects according to National Cancer Institute Common Toxicity Criteria—excluding injection site reactions (grade 2 or 3) related to study treatment—at which point the dose would be reduced by 50%.

Treatment delays of up to 4 weeks were acceptable to allow for recovery. In the event of treatment delay due to other factors unrelated to a toxic event, injection was administered within 3 days. If delay was due to infection or disease symptoms, a 2-week delay was allowed.

Baseline laboratory tests consisting of complete blood count with differential, C-125, and serum chemistry were done, along with CT of the chest, abdomen, and pelvis. Germline or somatic BRCA1 and BRCA2 molecular profiling data for all tissue and blood samples were collected and analysed centrally using next-generation sequencing (Ocean Ridge Biosciences; Deerfield Beach, Fla., USA).

Patients were monitored for disease progression by CT of the chest, abdomen, and pelvis every 3 months for the first 3 years on study and at the end of treatment or recurrence. During follow-up, CT scans were done every 6 months and planned for up to 5 years. Patients remained on study treatment until disease progression as defined by masked independent central review (World Care Clinical; Boston, Mass., USA; using Response Evaluation Criteria in Solid Tumors version 1.1) or until supply of gemogenovatucel-T or placebo was exhausted (minimum of four doses on the basis of previous clinical immune response).12 All laboratory assessments (complete blood count with differential, C-125, and serum chemistry) were done once per month during study enrolment. Upon disease recurrence or end of treatment, laboratory assessments were repeated and then continued every 6 months during follow-up.

Adverse events were recorded after the first dose of gemogenovatucel-T and continued until 30 days after the last study treatment. Adverse events were graded and reported using Common Toxicity Criteria for Adverse Events version 4.03. All adverse events, regardless of causal relationship to study treatment, were recorded.

Outcomes

The primary endpoint was recurrence-free survival from time of randomisation. Secondary endpoints, in order of priority, were recurrence-free survival of patients with BRCA disease from time of tumour tissue procurement, recurrence of BRCA disease from the time of randomisation, recurrence-free survival of all patients from the time of tumour tissue procurement, overall survival of all patients from time from randomisation, and overall survival of all patients from time of tumour tissue procurement. Time of procurement was the time since surgery when the autologous tumour cells were harvested. Recurrence-free survival from randomisation or tumour tissue procurement was defined as the time from random assignment or procurement date to either the date the patient was first recorded as having disease recurrence (even if the patients stopped treatment because of toxic effects), or the date of death if the subject died from any cause before disease recurrence. Disease recurrence was defined as the appearance of any measurable or evaluable lesion or as asymptomatic CA-125 concentration greater than 35 U/mL at two consecutive measurements, at least 1 month apart. Overall survival was defined as the duration from the date of random assignment or tumour tissue procurement until the date of death.

Statistical Analysis

Based on sample size calculations, 54 recurrence-free survival events were needed for 90% power, an assumed true hazard ratio (HR) of 0.45, and a one-sided α level of 0.05. After analysis of the primary endpoint, the secondary endpoints would be tested using the hierarchical testing method according to the order listed in the statistical analysis plan. This method was used for multiplicity adjustment. The primary efficacy analyse were based on the per-protocol population, which included patients who were randomly assigned and received one or more doses of their assigned study treatment, attended at least 80% of their study visits, and had no major protocol deviations. All patients who received at least one dose of gemogenovatucel-T or placebo were included in the safety analyses. As a sensitivity analysis, recurrence-free survival and overall survival from randomisation were also analysed in the intention-to-treat population (all 92 patients who were randomly assigned). The distributions of recurrence-free survival and overall survival were estimated using the Kaplan-Meier method and compared using the stratified log-rank test. A one-sided p value of 0.05 or less (stratified log-rank test as stratified by the randomisation stratification factors of residual disease and chemotherapy schedule) was considered to indicate significance. The 90% CI is presented for treatment effect comparison and 95% CI for individual statistics. HRs were estimated via a Cox proportional hazards model stratified by the random-isation stratification factors. Grambsch and Therneau's test was done at the two-sided 0.05 significance level to check the proportional hazards assumption for the Cox model with stratification.

The additional exploratory post-hoc analysis of 1-year and 2-year recurrence-free and overall survival were estimated with the Kaplan-Meier method and compared using the asymptotic Z-test, with the variance of rate difference estimated using the Greenwood method. Restricted mean survival time difference was calculated as a sensitivity analysis, with the truncation point being equal to the minimum of the longest follow-up time of either study group. Restricted mean survival time difference was calculated without covariate adjustment. Recurrence-free survival and overall survival of patients with germline and somatic BRCA1 or BRCA2 mutation and BRCA (non-mutation groups) from the time of randomisation or tumour tissue procurement was a preplanned subgroup analysis. The reason for including both survival endpoints was to more accurately reflect previous maintenance therapy trials that incorporated groups including both concomitant therapy with or without maintenance therapy. Percentages of patients with disease relapse were analysed by Fisher's exact t test. Forest plots were constructed for planned subgroup analyses (by age, disease stage, ECOG performance status, chemotherapy timing, residual disease status, BRCA mutation status, TGF-β1 (% knockdown), granulocyte macrophage colony stimulating factor expression, viability, and number of vaccines manufactured) for all patients and patients with BRCA disease. Pinteraction was calculated to assess the effect of modification between BRCA subgroups. Post-hoc analysis of the p value of the interaction term between BRCA status and treatment to assess effect modification between the BRCA subgroups for recurrence-free survival were done by including an interaction term in the Cox proportional hazards model.

All statistical analyses planned before unmasking were done independently (StatBeyond Consulting; Irvine, Calif., USA). All statistical analyses were done with R version 4.0.0. The study is registered with ClinicalTrials.gov, NCT02346747.

Results

Figure 34:
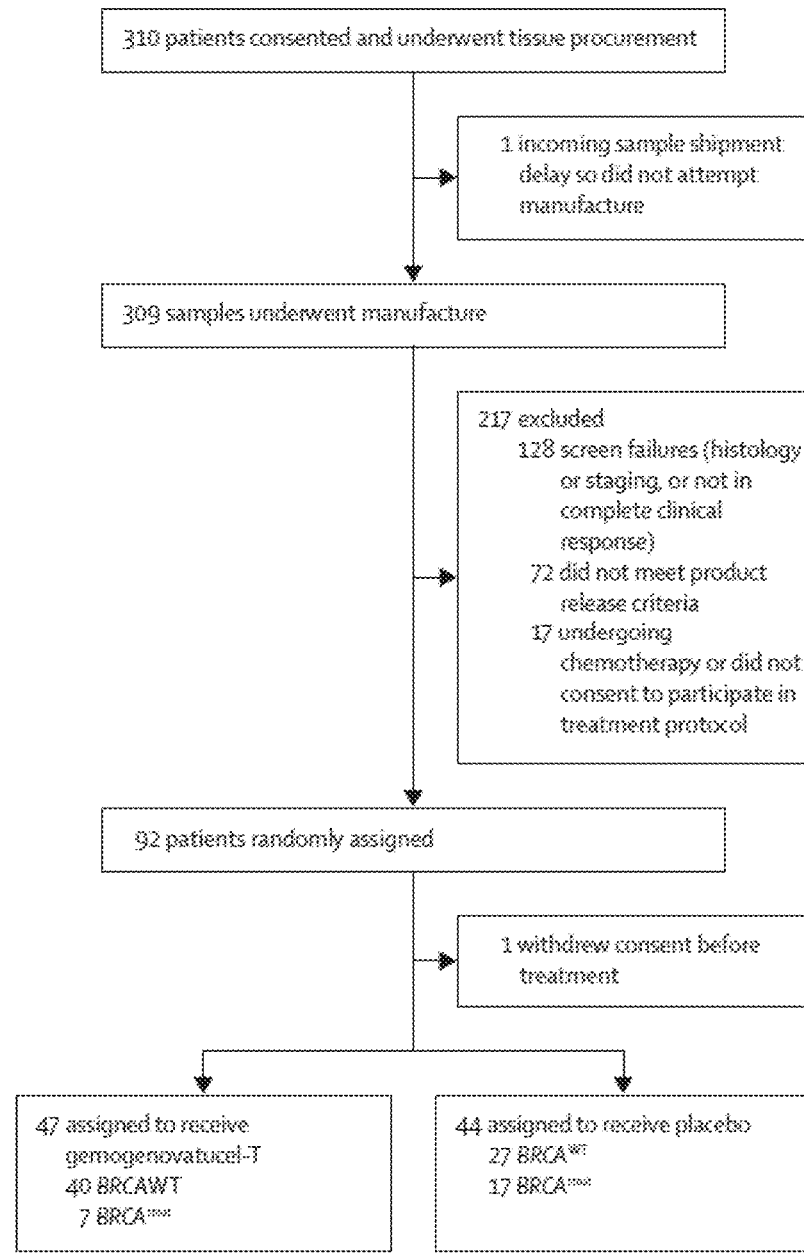
FIG. 34 shows the trial patient profile. $BRCA^{WT}$=BRCA wild type.
$BRCA^{mut}$=BRCA mutant.

Between Feb. 11, 2015, and Mar. 2, 2017, 310 patients consented to the study at 22 sites; from these 309 samples underwent manufacturing. 217 patients were excluded (FIG. 34). 91 patients received gemogenovatucel-T (n=47) or placebo (n=44) and were analysed for safety and efficacy. 67 patients were BRCA and 24 were BRCAmut (appendix p 16). Patient baseline characteristics are shown in Table 13.

TABLE 13

| Baseline characteristics | | |
|---|---|---|
| | Gemogenovatucel-T (n = 47) | Placebo (n = 44) |
| Age, years | | |
| Median (IQR) | 63 (56-71) | 63 (53-67) |
| Range | 42-84 | 38-79 |
| <65 | 25 (53%) | 28 (64%) |
| ≥65 | 22 (47%) | 16 (36%) |
| Race | | |
| Asian | 0 | 2 (5%) |
| Black or African American | 1 (2%) | 4 (9%) |
| White | 46 (98%) | 37 (84%) |
| Not reported | 0 | 1 (2%) |
| Ethnicity | | |
| Hispanic or Latino | 1 (2%) | 0 |
| Non-Hispanic or non-Latino | 46 (98%) | 43 (98%) |
| Not reported | 0 | 1 (2%) |
| Eastern Cooperative Oncology Group performance status | | |
| 0 | 26 (55%) | 35 (80%) |
| 1 | 21 (45%) | 9 (20%) |
| International Federation of Gynecology and Obstetrics stage | | |
| III | 38 (81%) | 39 (89%) |
| IV | 9 (19%) | 5 (11%) |
| Frontline chemotherapy | | |
| Neoadjuvant | 8 (17%) | 7 (16%) |
| Adjuvant | 39 (83%) | 37 (84%) |
| Number of chemotherapy cycles | | |
| Mean (SD) | 6·00 (0·30) | 6·00 (0·43) |
| Median (IQR) | 6 (6-6) | 6 (6-6) |
| Range | 5-7 | 5-8 |

TABLE 13-continued

Baseline characteristics

| | Gemogenovatucel-T (n = 47) | Placebo (n = 44) |
|---|---|---|
| Frontline surgery residual disease status | | |
| Macroscopic | 16 (34%) | 11 (25%) |
| Microscopic or non-evaluable disease | 31 (66%) | 33 (75%) |
| Histology | | |
| Endometrioid carcinoma | 1 (2%) | 0 |
| Mixed serous or clear cell carcinoma | 0 | 1 (2%) |
| High-grade serous carcinoma | 46 (98%) | 43 (98%) |
| BRCA mutational status | | |
| BRCA wild type | 40 (85%) | 27 (61%) |
| BRCA mutated | 7 (15%) | 17 (39%) |
| Times between last chemotherapy given and first dose of gemogenovatucel-T or placebo, days | | |
| Mean (SD) | 49 (16) | 47 (18) |
| Median (IQR) | 49 (41-55) | 47 (35-56) |
| Range | 22-121 | 16-110 |
| Solid tumour weight, g | | |
| Mean (SD) | 54 (28) | 55 (31) |
| Median (IQR) | 51 (29-75) | 50 (33-72) |
| Range | 10-137 | 8-138 |
| Cells harvested per g of tumour tissue (x $10^6$) | | |
| Mean (SD) | 6 (4) | 7 (7) |
| Median (IQR) | 5 (3-6) | 5 (3-7) |
| Range | 1-17 | 2-34 |
| Times from surgery to randomisation, days | | |
| Mean (SD) | 215 (45) | 200 (30) |
| Median (IQR) | 209 (195-223) | 199 (178-212) |
| Range | 161-471 | 156-315 |

Data are n (%), unless otherwise indicated. Some percentages sum to more than 100% because of rounding.

84 (92%) of 91 patients met all product release criteria. The median tumour mass harvested was 50 g (IQR 31-75). The median viability of product release was 88% (IQR 83-90; assessed in 91 patients). Seven (8%) of 91 patients (five patients assigned t gemogenovatucel-T, and two patients assigned to placebo) did not show an increase to above 30 pg/mL per $10^7$ cells in GMCSF expression after plasmid transfer. However, six (86%) of these seven patients had adequate TGF-01 knockdown of at least 30%. Evaluable median GMCSF production was 860 pg/mL per $10^7$ cells (IQR 254-2506, 84 patients: seven patients were below the threshold) and evaluable median TGF-$\beta$1 knockdown was 100% (100-100, 84 patients; Table 12). TGF-$\beta$1 knockdown results were undetermined in seven patients (six with adequate GMCSF expression release; four patients assigned to gemogenovatucel-T and three assigned to placebo). 78 (86%) of 91 patients had at least 80% TGF-$\beta$1 knockdown. Given that TGF-$\beta$1 signalling is downstream of furin expression, these results support robust activity related to furin bi-shRNA knockdown. Baseline TGF-$\beta$1 production before plasmid transfection showed median TGF-$\beta$1 expression of 164 μg per $10^6$ cells (IQR 119-336; mean 241 [SD 162]). TGF-$\beta$1 expression in patients who were BRCA1 and BRCA2 wild type (BRCA) showed a median of 181 μg per $10^6$ cells (IQR 125-350; mean 249 [154]). TGF-$\beta$1 expression in patients who were BRCA1 or BRCA2 mutant (BRCAmut) showed a median of 146 pg per $10^6$ cells (IQR 115-267; mean 219 [183]).

The median follow-up from first dose of gemgenovatucel-T was 40.0 months (IQR 35.0-44.8) and from first dose of placebo was 39.8 months (35.5-44.6). The median time from surgery to random assignment was 7-0 months (IQR 6.5-7.4) for patients in the gemogenovatucel-T group and 6.7 months (5.9-7.1) for patients in the placebo group. The median duration from the end of previous chemotherapy treatment to the start of treatment was 1.6 months (IQR 1.4-1.8) for patients in the gemogenovatucel-T group and 1.5 months (1.2-1.9) for patients in the placebo group. By Jan. 21, 2020, 59 recurrence events were observed in the trial by independent third-party radiological evaluation. Recurrence-free survival calculated from the time of randomisation for patients assigned to gemogenovatucel-T compared with patients assigned to placebo was 11.5 months (95% CI 7.5—not reached) versus 8.4 months (7.9-15.5; HR 0.69, 90% CI 0.44-1.07; one-sided p=0.078; FIG. 2A). 26 patients in the gemogenovatucel-T group versus 33 patients in the placebo group had a recurrence event.

The proportional hazards assumption was met based on the Grambsch and Thernau test. At the time of efficacy assessment, 33 (75%) of 44 patients had relapsed disease in the placebo group compared with 26 (55%) of 47 patients in the gemogenovatucel-T group. In a post-hoc analysis, the 1-year recurrence-free survival rate was 49% (95% CI 36-68) for patients in the gemogenovatucel-T group versus 39% (27-58) for patients in the placebo group (p=0-18) from the time of random assignment. In a post-hoc analysis, the 2-year recurrence-free survival rate was 32% (95% CI 19-53) for patients in the gemogenovatucel-T group versus 25% (15-44) for patients in the placebo group (p=0.26) from the time of random assignment.

The recurrence-free survival from the time of tissue procurement in all patients was longer in those who received gemogenovatucel-T than in those who received placebo (FIG. 35B)

The secondary endpoint of recurrence-free survival calculated from the time of tissue procurement of patients with BRCA disease was significantly longer in those who received gemogenovatucel-T than in those who received placebo (FIG. 35D). At the time of efficacy assessment, 21 (52%) of 40 patients with BRCA disease in the gemogenovatucel-T group showed relapsed disease compared with 21 (78%) of 27 patients with BRCA disease in the placebo group. In a post-hoc analysis, the 1-year recurrence-free survival rate was 81% (95% CI 69-95) for patients in the gemogenovatucel-T group with BRCA disease compared with 63% (47-84) for patients in the placebo group with BRCA disease from the time of surgery or tissue procurement (p=0.056). The 2-year recurrence-free survival rate for patients with BRCA disease was 42% (95% CI 28-64) for patients in the gemogenovatucel-T group versus 24% (11-49) for patients in the placebo group (p=0-073) from time of surgery or tissue procurement. The recurrence-free survival of patients with BRCA disease from randomisation was significantly longer in those who received gemogenovatucel-T than in those who received placebo (21 [52%] of 40 patients in the gemogenovatucel-T group vs to 21 [78%] of 27 patients in the placebo group has a recurrence-free survival event; FIG. 35C), or patients with BRCA disease, in a post-hoc analysis the 1-year recurrence-free survival rate was 51% (95% CI 36-71) for those in the gemogenovatucel-T group versus 28% (15-53) for those in the placebo group (p=0.036) from the time of randomisation. In a post-hoc analysis, the 2-year recurrence-free survival rate for patients with BRCA disease was 33% (95% CI 20-57) for those in the gemogenovatucel-T group versus 14% (5-39) for those in the placebo group (p=0.048) from the time of randomisation.

In a post-hoc analysis, recurrence-free survival from the time of random assignment and time of surgery or tissue procurement in patients with BRCA1 or BRCA2 mutant disease is shown in FIG. 41A and FIG. 41B. Preplanned intention-to-treat analysis of recurrence-free survival calculated from the time of random assignment and the time of surgery or tis sue procurement showed similar results to the per protocol analysis (FIGS. 37A-37D).

Overall survival from time of randomisation or time of procurement was not significantly longer in the gemogenovatucel-T than in the placebo group (FIG. 35E, FIG. 35F). 13 (28%) of 47 patients died in the gemogenovatucel-T group versus 17 (39%) of 44 patients in the placebo group. Intention-to-treat analysis of overall survival calculated from time of random assignment and time of surgery or tissue procurement showed similar results to the per-protocol analysis. The proportional hazards assumptions in secondary endpoints analyses were all met based on the Grambsch and Thernau test.

Figure 36A:
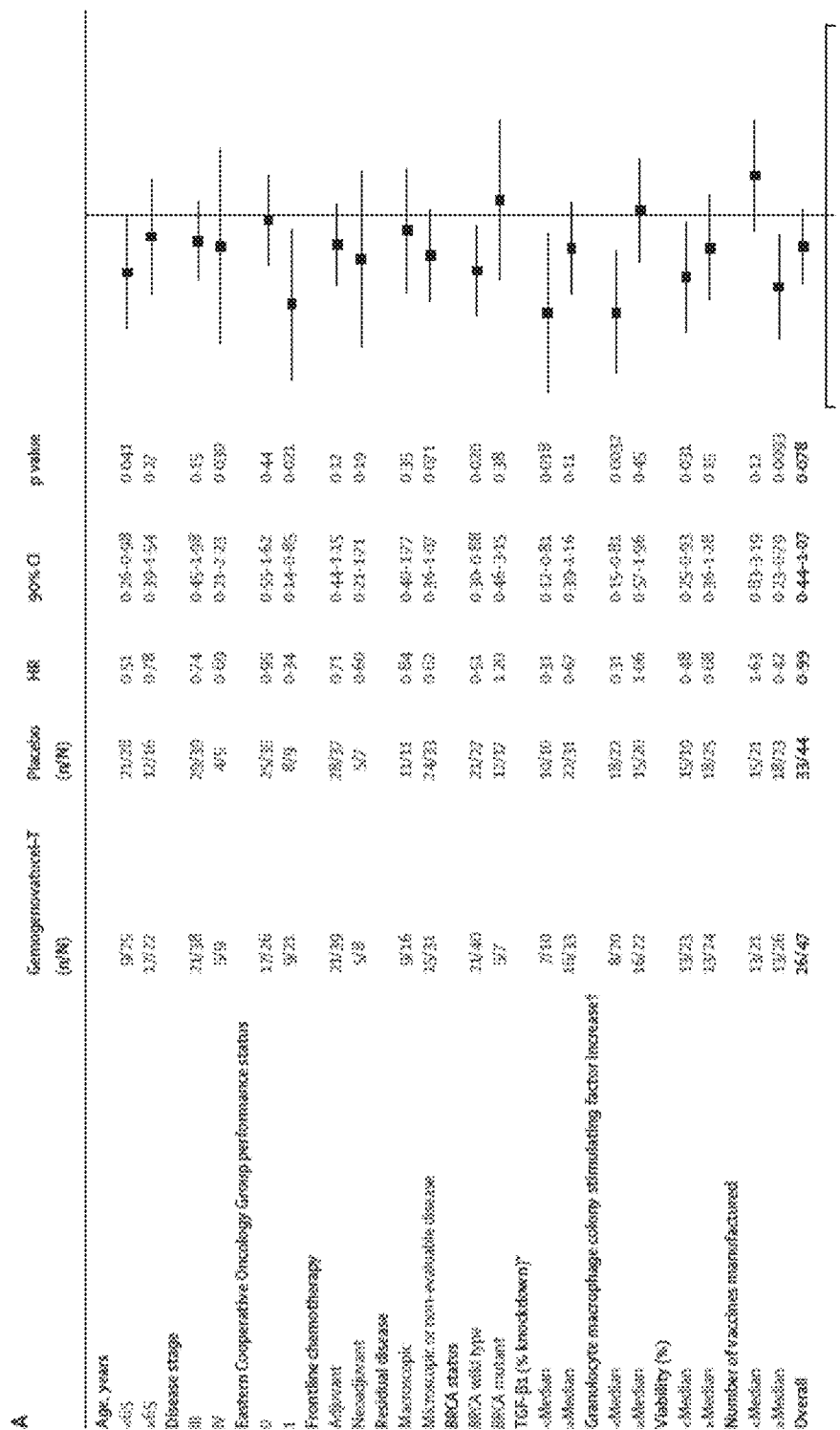
FIGS. 36A and 36B show recurrence-free survival for key subgroups of the per-protocol population (36A) and BRCA wild type population (36B) calculated from time of randomisation until the first date of documented recurrence or death. Data are number of events/number of patients, unless otherwise indicated. HR=hazard ratio. *Above 30% knockdown. †Above 30 pg per $10^6$ cells release threshold.
Figure 36B:
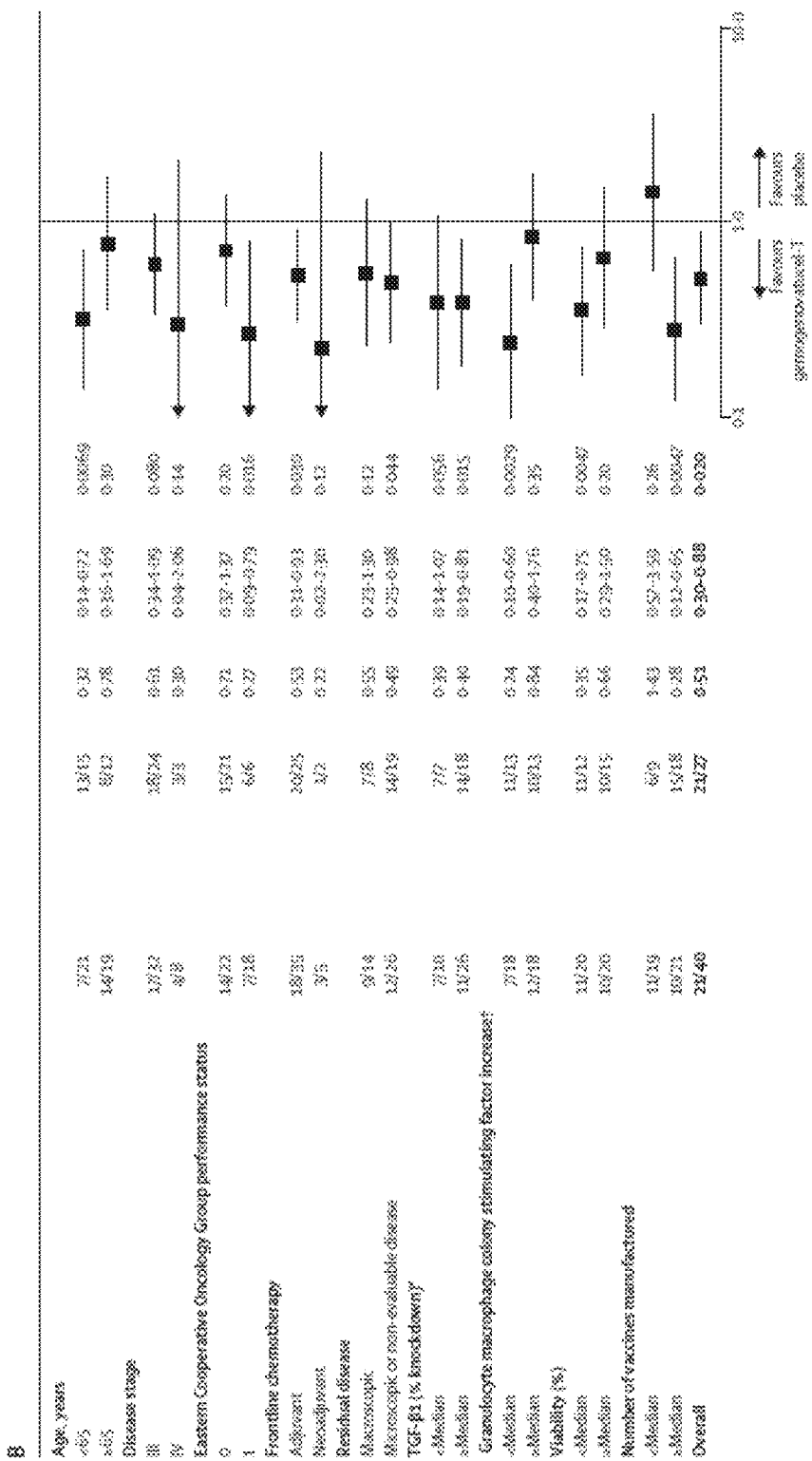
Figures 37A, 37B:
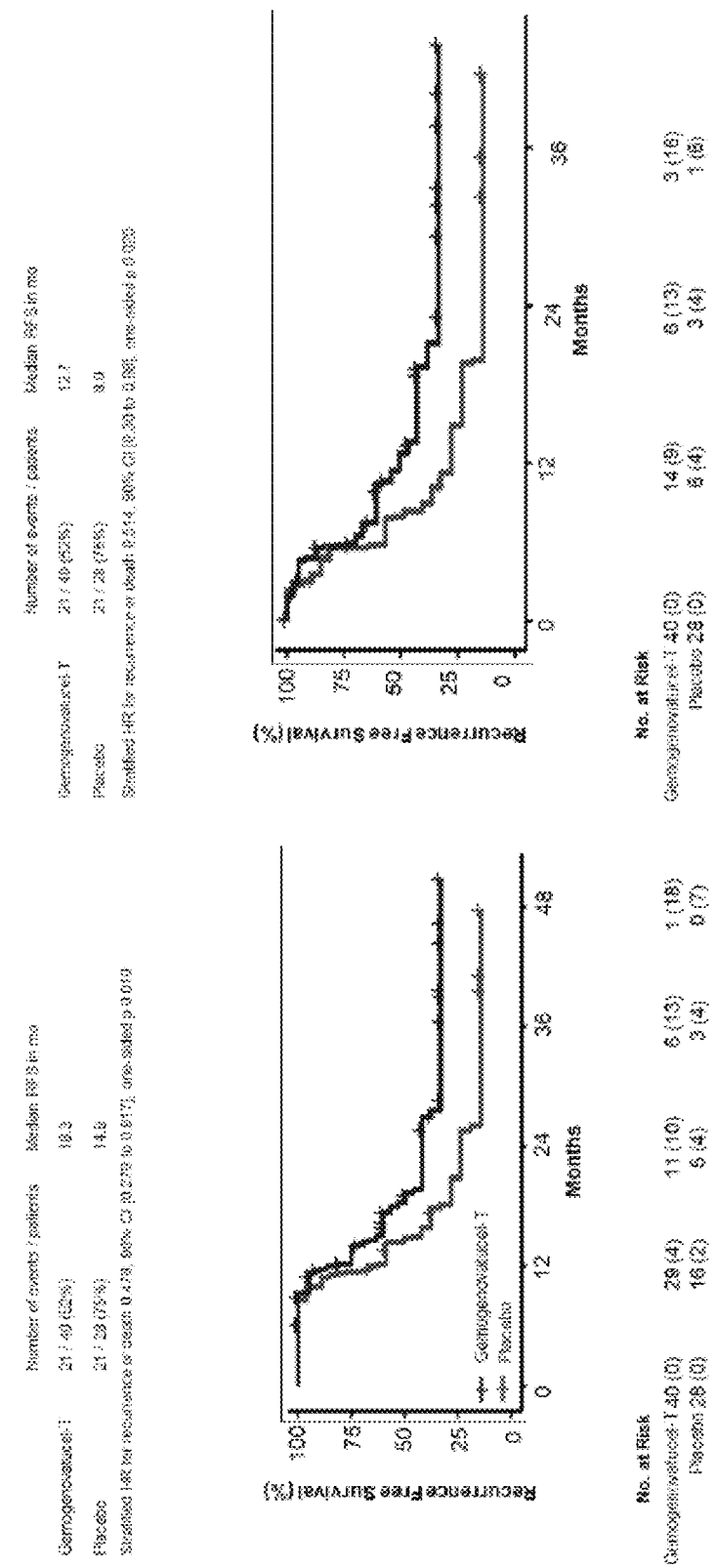
FIG. 37A-37D show Kaplan Meier Analysis of ITT population. Recurrence-free survival of BRCA wild type intent to treat patients from tissue procurement (A) and randomization (B). Recurrence-free survival of all intent to treat patients from tissue procurement (C) and randomization (D).
Figures 37C, 37D:
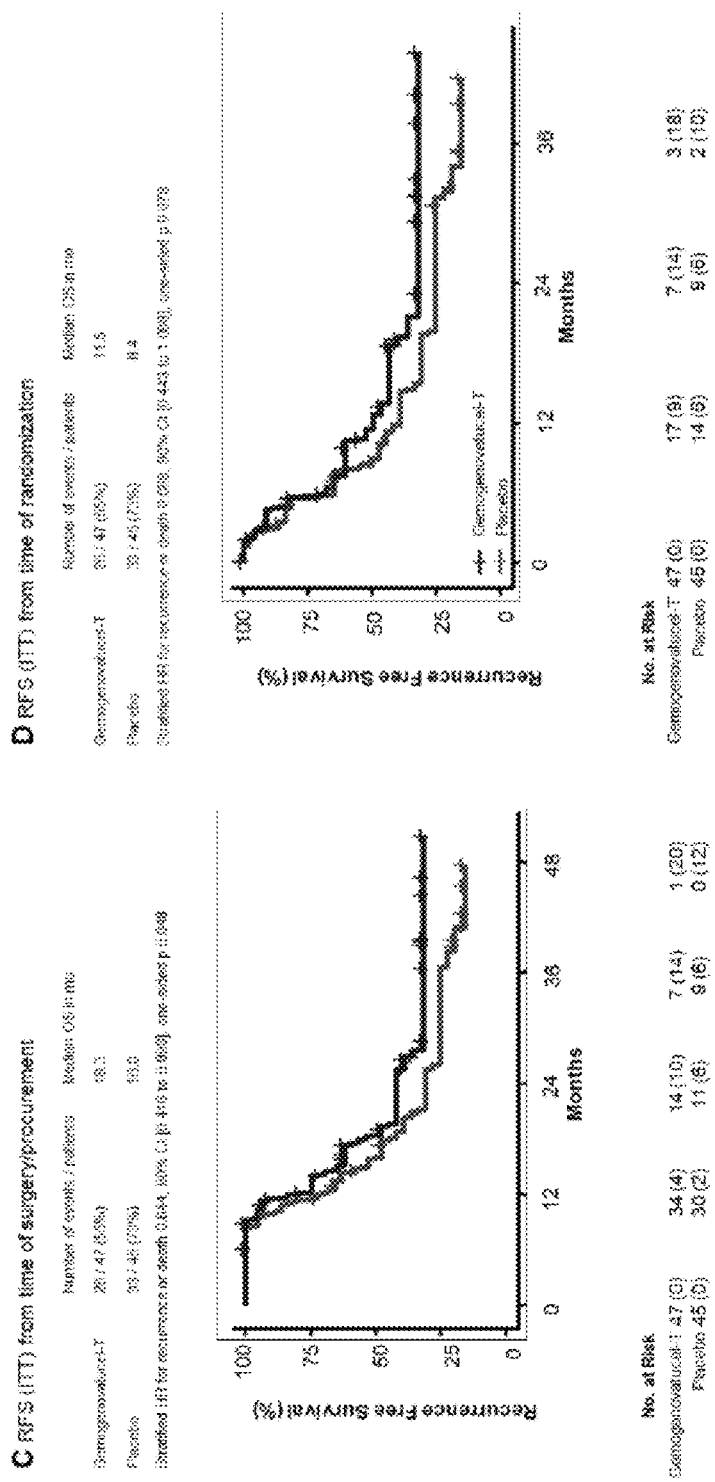
Figure 38:
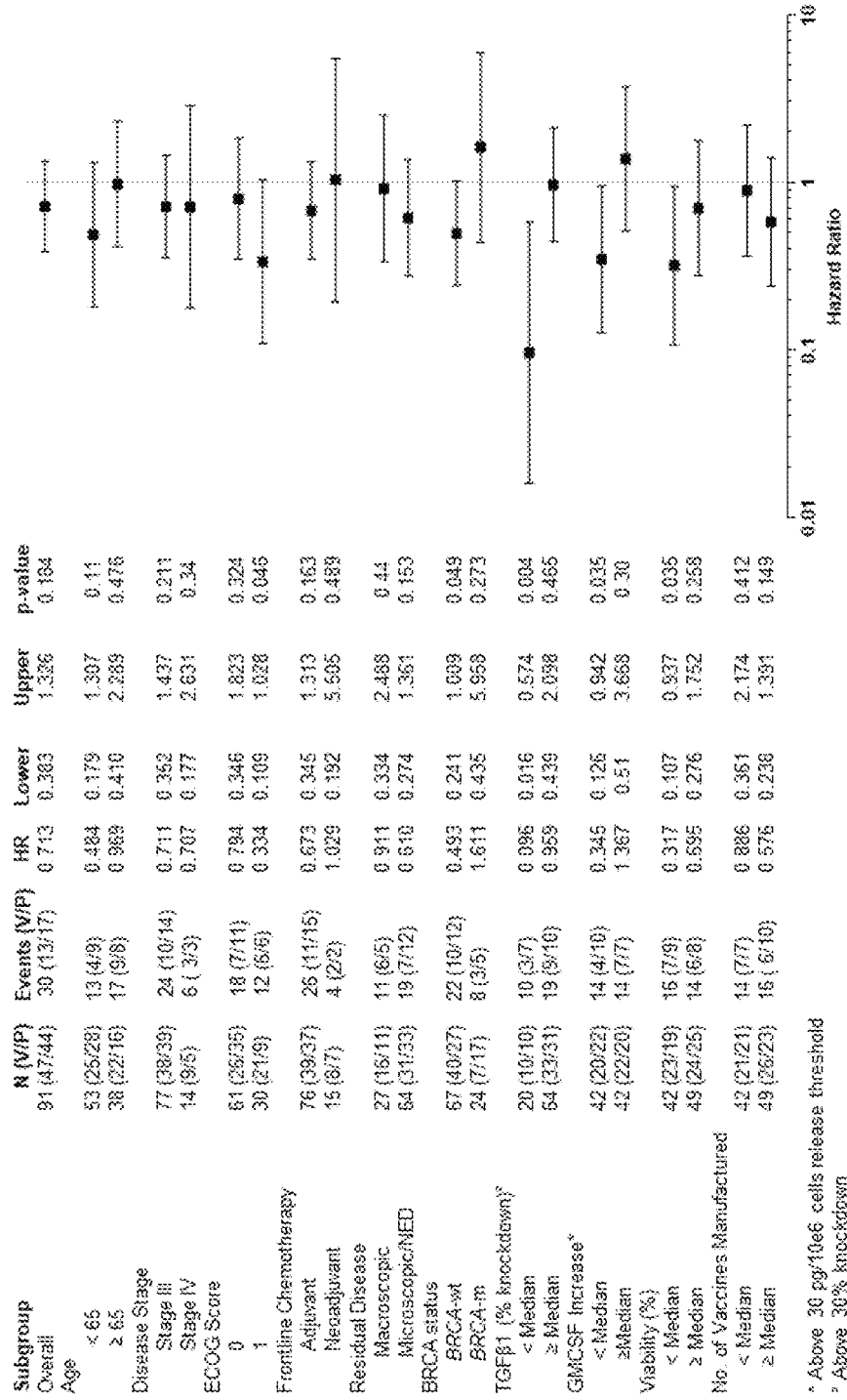
FIG. 38 shows forest plot of overall survival from time of randomization of patient population.
Figure 39:
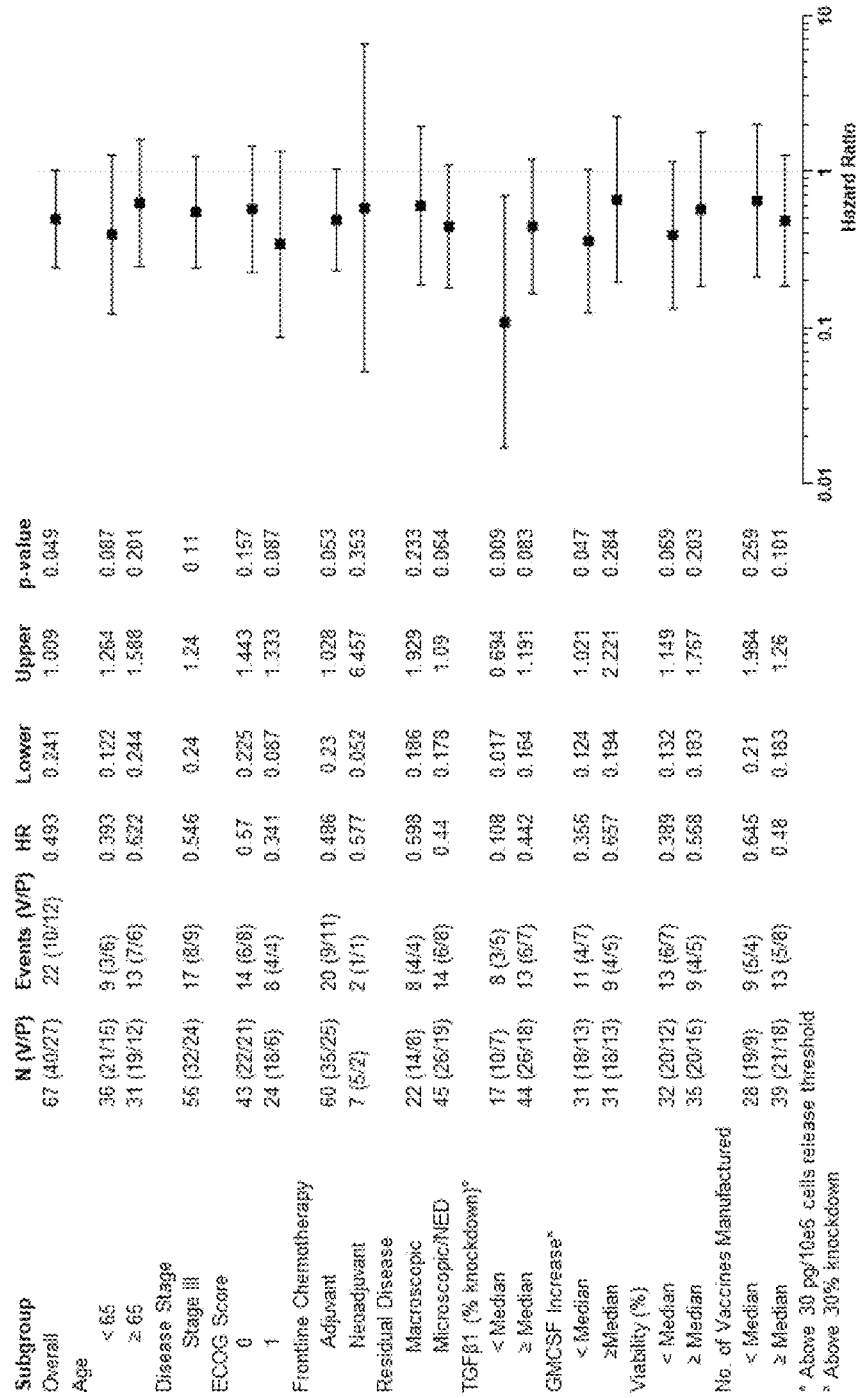
FIG. 39 shows overall survival forest plot of per protocol population and BRCA wild type population.
Figures 40A, 40B:
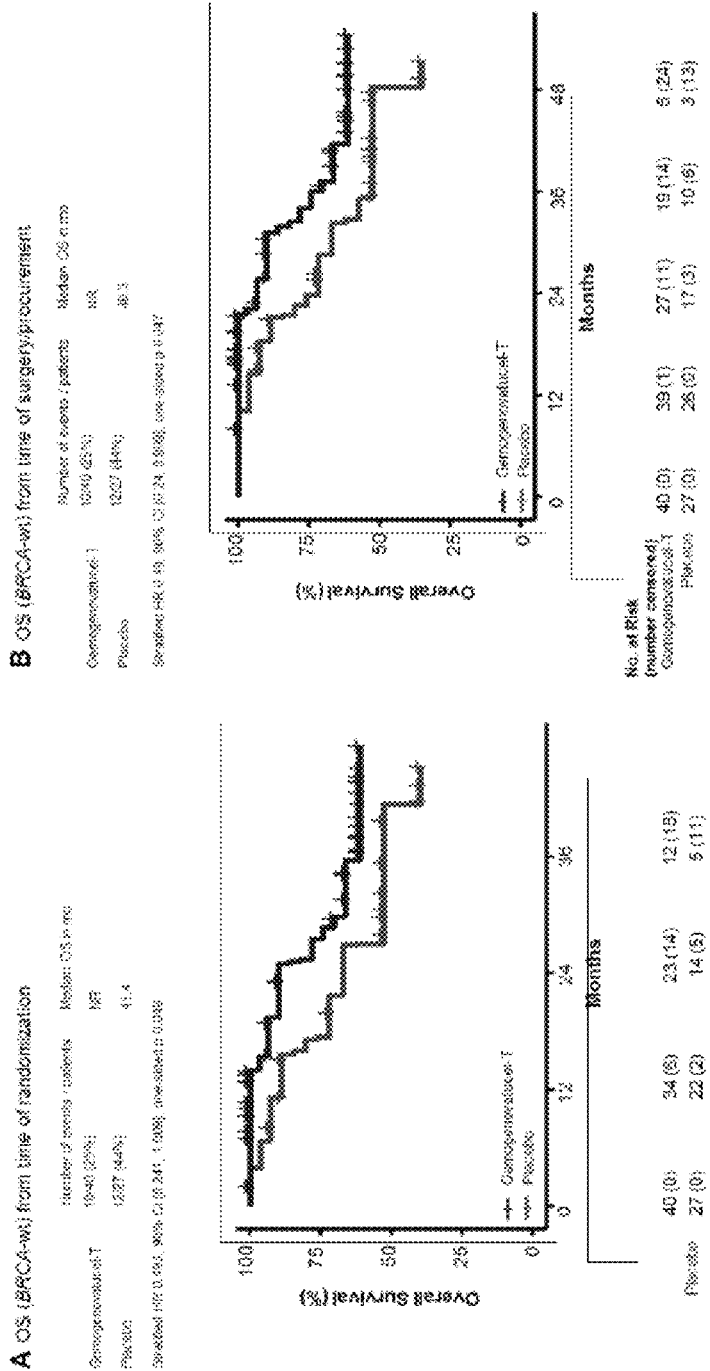
FIGS. 40A-40D show overall survival of BRCA wild type patients from time of randomization (FIG. 40A) and tissue procurement (FIG. 40B). Overall survival of BRCA mutant patients from time of randomisation (FIG. 40C) and tissue procurement (FIG. 40D).
Figure 40C:
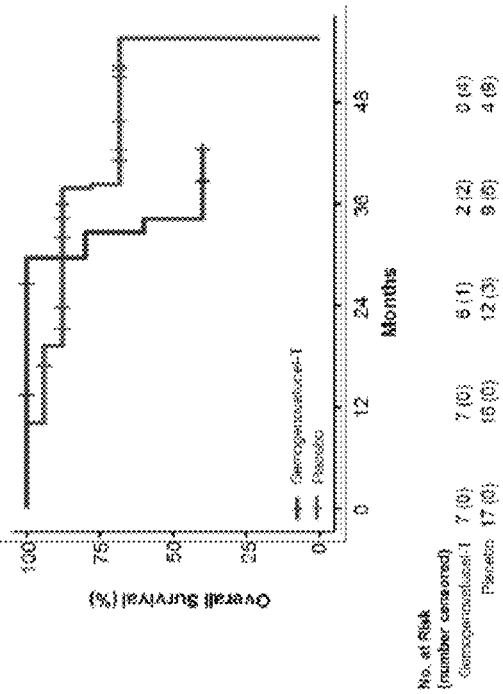
Figure 40D:
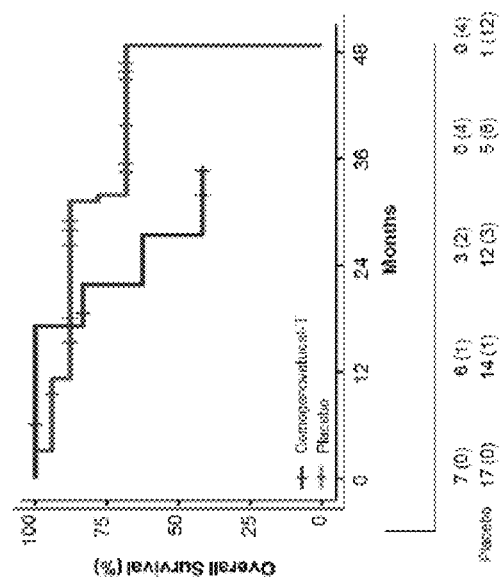

We observed an overall survival advantage in the vaccine group in a planned sub-analysis of patients with BRCA disease assigned to gemogenovatucel-T from randomisation (median overall survival not reached, 95% CI 356—not reached vs 41.4 months, 26.9—not reached; HR 0.49, 90% CI 0.24-1.01; p=0.049) and time of tissue procurement (median overall survival not reached, 95% CI 41.6—not reached vs 48.3 months, 32.3—not reached; 0.49, 0.24-1.00; p=0.047). From the time of randomisation, in a post-hoc analysis, the 1-year overall survival rate was 100% (95% CI 100-100) for patients with BRCA disease in the gemogenovatucel-T group versus 89% (78-100) for patients with BRCA disease in the placebo group (p=0.033). In a post-hoc analysis, the 2-year overall survival rate from the time of random assignment was 90% (95% CI 79-100) for patients with BRCA disease in the gemogenovatucel-T group versus 67% (51-89) for patients with BRCA disease in the placebo group (p=0.021). We observed no overall survival difference between patients in the gemogenovatucel-T group and patients in placebo group in those with BRCAmut disease (FIGS. 40A-40D). The $p_{interaction}$ value between patient BRCA status and treatment to assess effect modification between the BRCA subgroups for recurrence-free survival from the time of randomisation was 0.173, for overall survival from the time of randomisation was 0.072, and for overall survival from the time of tissue procurement was 0.090. Baseline demographics related to disease effect (planned sub-analysis) including preidentified stratification factors and product release criteria are shown for patients with BRCA disease and all patients for recurrence-free survival from time of randomisation (FIG. 36A-36B) and for overall survival from the time of randomisation in FIG. 38 and FIG. 39.

The restricted mean survival time difference between patients with BRCA$^{WT}$ disease in the gemogeno vatucel-T group and in the placebo group was 7.2 months (90% CI 0.8-13.5; p=0.032) for recurrence-free survival from the time of random assignment and 5.6 months (0.2-11.5; p=0.057) for overall survival from the time of random assignment. A truncation point equal to the minimum of the longest follow-up time of either study group was used in the restricted mean survival time analysis.

A median of six (range 1-12, IQR 5-10) gemogenovatucel-T injections or six (3-12, 6-9) placebo injections were administered per patient. A treatment delay in a patient in the placebo group due to a pelvic infection was recorded as possibly related to study drug. During the study, two deaths due to disease occurred in the gemogenovatucel-T group compared with eight deaths in the placebo group, and no treatment-related deaths occurred in either group. No patients were excluded from study because of adverse events and no dose modifications were reported. No major protocol deviations that affected patient safety were reported.

The numbers of adverse events by grade in each treatment group are reported in Table 14. Two patients in the placebo group had grade 3 treatment-related toxicity (one patient with arthralgia, one patient with bone pain, generalized muscle weakness, syncope, and dyspnoea [these were serious adverse events]). No gemogenovatucel-T grade 3 treatment-related adverse events were reported. Seven patients (four in the placebo group and three in the gemogenovatucel-T group) had 11 serious adverse events. All but one of these events were reported as unlikely to be related or not related to study treatment.

Table 14

| | Gemogenovatucel-T (n = 47) | | | Placebo (n = 44) | | |
|---|---|---|---|---|---|---|
| | Grade 1 and 2 | Grade 3 | Grade 4 | Grade 1 and 2 | Grade 3 | Grade 4 |
| Blood and lymphatic system | 1 (2%) | 0 | 0 | 0 | 0 | 0 |
|   Anaemia | 1 (2%) | 0 | 0 | 0 | 0 | 0 |
| Gastrointestinal disorders | 4 (9%) | 0 | 0 | 3 (7%) | 0 | 0 |
|   Abdominalpain | 1 (2%) | 0 | 0 | 0 | 0 | 0 |
|   Bloating | 1 (2%) | 0 | 0 | 0 | 0 | 0 |
|   Diarrhoea | 1 (2%) | 0 | 0 | 0 | 0 | 0 |
|   Nausea | 1 (2%) | 0 | 0 | 3 (7%) | 0 | 0 |
| General disorders and administration site conditions | 22 (47%) | 0 | 0 | 15 (34%) | 0 | 0 |
|   Chills | 1 (2%) | 0 | 0 | 1 (2%) | 0 | 0 |
|   Oedema in extremities | 1 (2%) | 0 | 0 | 0 | 0 | 0 |
|   Fatigue | 3 (6%) | 0 | 0 | 4 (9%) | 0 | 0 |
|   Fever | 0 | 0 | 0 | 1 (2%) | 0 | 0 |
|   Injection site reaction | 16 (34%) | 0 | 0 | 7 (16%) | 0 | 0 |
|   Pain | 1 (1%) | 0 | 0 | 1 (1%) | 0 | 0 |
|   Temperature intolerance | 0 | 0 | 0 | 1 (2%) | 0 | 0 |
| Infections and infestations | 1 (2%) | 0 | 0 | 1 (2%) | 0 | 0 |
|   Gastrointestinal viral infection | 1 (2%) | 0 | 0 | 0 | 0 | 0 |
|   Psoas abscess | 0 | 0 | 0 | 1 (2%) | 0 | 0 |
| Investigations | 3 (6%) | 0 | 0 | 2 (5%) | 0 | 0 |
|   Increased alanine aminotransferase | 1 (2%) | 0 | 0 | 0 | 0 | 0 |
|   Increased creatinine | 2 (4%) | 0 | 0 | 0 | 0 | 0 |
|   Decreased platelets | 0 | 0 | 0 | 1 (2%) | 0 | 0 |
|   Decreased white blood cells | 0 | 0 | 0 | 1 (2%) | 0 | 0 |
| Metabolism and nutrition disorders | 1 (2%) | 0 | 0 | 1 (2%) | 0 | 0 |
|   Fluid retention | 0 | 0 | 0 | 1 (2%) | 0 | 0 |
|   Hyperglycaemia | 1 (2%) | 0 | 0 | 0 | 0 | 0 |
| Musculoskeletal and connective tissue disorders | 6 (13%) | 0 | 0 | 15 (34%) | 3 (7%) | 0 |
|   Arthralgia | 5 (11%) | 0 | 0 | 6 (14%) | 1 (2%) | 0 |
|   Arthritis aggravated | 0 | 0 | 0 | 1 (2%) | 0 | 0 |
|   Back pain | 0 | 0 | 0 | 3 (7%) | 0 | 0 |
|   Bone pain | 0 | 0 | 0 | 3 (7%) | 1 (2%) | 0 |
|   Flank pain | 0 | 0 | 0 | 1 (2%) | 0 | 0 |
|   Generalised muscle weakness | 0 | 0 | 0 | 0 | 1 (2%) | 0 |
|   Muscle pain | 1 (2%) | 0 | 0 | 0 | 0 | 0 |
|   Pain in extremity | 0 | 0 | 0 | 1 (2%) | 0 | 0 |
| Nervous system disorders | 3 (6%) | 0 | 0 | 6 (14%) | 1 (2%) | 0 |
|   Dizziness | 0 | 0 | 0 | 1 (2%) | 0 | 0 |
|   Headache | 2 (4%) | 0 | 0 | 1 (2%) | 0 | 0 |
|   Intermittent headache | 1 (2%) | 0 | 0 | 0 | 0 | 0 |
|   Neuralgia | 0 | 0 | 0 | 1 (2%) | 0 | 0 |
|   Numbness in hand | 0 | 0 | 0 | 1 (2%) | 0 | 0 |
|   Peripheral sensory neuropathy | 0 | 0 | 0 | 2 (5%) | 0 | 0 |
|   Syncope | 0 | 0 | 0 | 0 | 1 (2%) | 0 |
| Psychiatric disorders | 0 | 0 | 0 | 1 (2%) | 0 | 0 |
|   Psychiatric symptom not otherwise specified | 0 | 0 | 0 | 1 (2%) | 0 | 0 |
| Renal and urinary disorders | 1 (2%) | 0 | 0 | 0 | 0 | 0 |
|   Urinary incontinence | 1 (2%) | 0 | 0 | 0 | 0 | 0 |
| Reproductive system and breast | 0 | 0 | 0 | 1 (2%) | 0 | 0 |

Table 14-continued

| | Adverse events | | | | | |
|---|---|---|---|---|---|---|
| | Gemogenovatucel-T (n = 47) | | | Placebo (n = 44) | | |
| | Grade 1 and 2 | Grade 3 | Grade 4 | Grade 1 and 2 | Grade 3 | Grade 4 |
| Pelvic pain | 0 | 0 | 0 | 1 (2%) | 0 | 0 |
| Respiratory, thoracic, and mediastinal disorders | 0 | 0 | 0 | 0 | 1 (2%) | 0 |
| Dyspnoea | 0 | 0 | 0 | 0 | 1 (2%) | 0 |
| Skin and subcutaneous tissue disorders | 8 (17%) | 0 | 0 | 0 | 0 | 0 |
| Alopecia | 1 (2%) | 0 | 0 | 0 | 0 | 0 |
| Bullous dermatitis | 1 (2%) | 0 | 0 | 0 | 0 | 0 |
| Facial rash | 1 (2%) | 0 | 0 | 0 | 0 | 0 |
| Pruritus | 2 (4%) | 0 | 0 | 0 | 0 | 0 |
| Maculopapular rash | 1 (2%) | 0 | 0 | 0 | 0 | 0 |
| Skin hyperpigmentation | 1 (2%) | 0 | 0 | 0 | 0 | 0 |
| Skin induration | 1 (2%) | 0 | 0 | 0 | 0 | 0 |
| Vascular disorders | 1 (2%) | 0 | 0 | 1 (2%) | 0 | 0 |
| Hot flashes | 1 (2%) | 0 | 0 | 1 (2%) | 0 | 0 |

Data are n (%).
No deaths due to adverse events were recorded.

Discussion

Gemogenovatucel-T did not show an improvement in the primary endpoint of recurrence-free survival. However, several secondary endpoints, considered hypothesis generating, showed significant improvements for gemogenovatucel-T compared with placebo in recurrence-free survival and overall survival, specifically in patients with BRCA tumours. These results suggest that patients with BRCA ovarian cancer might be more sensitive than patients with BRCA mutant ovarian cancer to gemogenovatucel-T.

The current landscape for front-line treatment of advanced stage ovarian cancer has not changed substantially over the past 25 years. Despite many efforts, addition of alternative approaches, either as combination therapy or maintenance therapy, has largely not resulted in a global change in the standard of care for all patients with ovarian cancer. However, one exception has been the development of PARP inhibitors. For example, niraparib as maintenance therapy in patients with stage III or IV ovarian cancer showed improvement in progression-free survival (HR 0.62, 95% CI 0.50-0.76; p<0.001) and in 2-year overall survival compared with placebo (HR 0.70, 95% 0.44-1.11). However, high proportions of grade 3 or 4 drug-related toxic effects and dose interruptions related to toxicity were concerning.

GMCSF is involved in the augmentation of tumour antigen presentation by dendritic cells and promotes higher concentrations of co-stimulatory molecules, which induce more efficient-cell stimulation. GMCSF also promotes the presentation of lipid antigens by dendritic cells, which in turn leads to activation of natural killer T cells.

Secreted TGF-β from ovarian cancer cells generates immunosuppressive regulatory T-cell (CD4+, CD25+) expansion in the tumour microenvironment. (26) This response has been associated with poor outcomes in front-line treated patients with high-grade serous ovarian carcinoma. TGF-β inhibits GMCSF-induced maturation of bone marrow derived dendritic cells and expression of MHC-II and co-stimulatory molecules. TGF-β also inhibits activated macrophages, including their antigen-presenting function, and ovarian cancer and tumour-associated myeloid cell PD-L1 expression, which has been linked to poor overall survival in patients with ovarian cancer. Knockdown of TGF-β1, as shown in this trial, might contribute to suppression of the effect of TGFβ, which could be more relevant in patients with BRCA disease.

Studies investigating immunotherapy in ovarian cancer are few. Most recently, despite case reports and phase 1/2 trial evidence of responses in ovarian cancer with checkpoint inhibitors, no benefit was shown in several trials involving avelumab combination in front-line and recurrent ovarian cancer, although 11 of 38 women with relapsed ovarian cancer achieved an objective response with combination nivolumab plus bevacizumab in another study. Further studies are ongoing involving checkpoint inhibitor therapy in patients with ovarian cancer.

Gemogenovatucel-T is well tolerated, easily administered, and shows promising efficacy, potentially making it an ideal maintenance therapy for patients with ovarian cancer. A strength of our study results is the safety and clinical observation of recurrence-free survival and overall survival advantage in patients with BRCA disease. However, the BRCA subset was a secondary endpoint and use of autologous tumour harvest as a component of product manufacturing provides timing and manufacturing success rate limits to product application. Insufficient tumour tissue was related to manufacturing failure, but there is no evidence to suggest that the number of vaccines manufactured correlated with the number of vaccines administered to the patient or health status. Insufficient cell failure rates did increase with lower weight of resected tumour tissue.

As only a small population of patients with BRCAmut disease received gemogenovatucel-T, our conclusion of a negative effect in such patients requires further study. Further evaluation of gemogenovatucel-T with bevacizumab or other PARP inhibitors is planned. Moreover, combination with checkpoint inhibitor therapy could be considered to further augment the gemogenovatucel-T immune response.

In conclusion, gemogenovatucel-T showed benefit as a front-line maintenance therapy in patients with ovarian cancer with a BRCA tumour molecular profile. This discovery warrants further study.

Example 6. Supplementary Information

Study Design and Participants

Normal organ and marrow function were required and defined per protocol (Absolute granulocyte count—≥1,500/mm3; Absolute lymphocyte count—≥500/mm3; Platelets—≥75,000/mm3; Total bilirubin—≤2 mg/dL; AST (SGOT)/ALT(SGPT)—≤2× institutional upper limit of normal; Creatinine—<1.5 mg/dL). All patients were required to have the ability to understand and the willingness to sign a written informed protocol specific consent.

Procedures

Surgically excised tumor tissue was procured and cut into 1/4-1/2 inch sections before being placed in specimen containers supplemented with gentamicin (Fresenius Kabi) and packaged in wet ice for overnight transport. On Day 1, transport medium and tumor specimen were tested for sterility (BacT/Alert 3D Microbial Identification System, BioMerieux). On Day 1, the tumor tissue was trimmed and dissociated by scalpel followed by enzymatic dissociation (Type I collagenase solution) and incubated at 37° C. to form a single cell suspension. The cell suspension was filtered across a sterile 100 um strainer (Corning) to separate the cells from the debris, and the liberated cells were washed with PlasmaLyte (Baxter) supplemented with 1% Human Serum Albumin (Octapharma) and manually counted via hemocytometer (InCyto). Quality control (QC) samples were removed for retain, immune monitoring, and a pre-transfection culture initiated to obtain baseline cytokine levels by ELISA for GMCSF (R&D Systems), TGFβ1 (R&D Systems) and TGFβ2 (R&D Systems). The suspension was adjusted to a concentration of 40 million cells/mL and electroporated using a Gene Pulser XL (BioRad) to facilitate plasmid insertion. The transfected cells were plated into sterile T-225cm2 flasks (Corning) at 1×10e6 cells/mL in X-VIVO 10 media (Lonza) supplemented with gentamicin (Fresenius Kabi) and incubated overnight (14 to 22 hrs) at 37° C. with 5% CO2 overlay (Sanyo) to allow for incorporation of bi-shRNA furin and GMCSF mRNA into the tumor cells.

On Day 2, the overnight culture was harvested and resuspended in fresh X-VIVO media. QC samples and a minimum of 4 doses per patient were required before proceeding.

Two 1-mL mycoplasma samples containing cells were taken and frozen at −80° C. The cells were irradiated 4×25Gy cycles using gamma-ray irradiator to arrest replication/growth. The cells were washed with PlasmaLyte (Baxter) supplemented with 1% Human Serum Albumin (HSA) (Octapharma) and QC samples were removed. The cells were placed into freeze media consisting of 10% DMSO (dimethyl sulfoxide; Cryoserv USP; Mylan), 1% HSA (Octapharma) in Plasma-Lyte A at pH 7.4 (Baxter) and aseptically aliquoted at 1×10e7 cells/mL into sterile 2.0 mL borosilicate glass vials (Algroup Wheaton Pharmaceutical and Cosmetics Packaging); closed with a butyl rubber stopper coated with Flurotec® barrier file (West Pharmaceutical Services) with a final fill volume of 1.2 mL. The final product vials were frozen at a controlled rate using CoolCell® freezing containers (Biocision) placed into −80° C. freezers (Sanyo). Product release testing specifications are described in appendix Table 3. After freezing, the cells were stored in the vapor phase of liquid nitrogen tanks pending release testing. Frozen product vials were used for sterility (USP <71>) and endotoxin testing by gel-clot (Limulus Amoebocyte Lysate, Lonza). Product release testing specifications for individual patients are summarized in Table 12, above. Assay validation for (GMCSF, TGFβ1. TGFβ2) was completed after the study and data shown are calculated with appropriate validated parameters. As a result, TGFβ2 knockdown is no longer used as a product release criteria.

Placebo was made up of freeze media consisting of 10% DMSO (Cryoserv USP; Mylan), 1% HSA (Octapharma) in Plasma-Lyte A at pH 7.4 (Baxter). After slow freezing the media to −80° C. the vials were stored in the vapor phase of liquid nitrogen pending sterility and endotoxin release testing. Placebo vial production was matched to the available product doses manufactured for the subject.

Sample Processing for NGS Sequencing

High molecular weight (HMW) DNA was isolated from the cryopreserved samples using the Qiagen MagAttract HMW DNA Kit. Fragmentation of HMW DNA was performed using dsDNA Fragmentase targeting a nucleic acid range of 200-300 nt. Fragmented HMW DNA were used to generate DNA libraries using the SMARTer ThruPLEX DNA-Seq Kit with an input of 5 ng. The libraries were combined into 5-6 plex pools that were hybridized and selected for certain gene sequences using the SeqCap EZ Human Oncology Panel (981 genes, 2.75 Mb of exonic regions) in combination with the HyperCap Target Enrichment Kit. The gene selected libraries were pooled and sequenced using the NextSeq 500 Mid Output v2.5 (300 cycles) kit.

Samples were run on the NextSeq 500. Variant calls were made using GATK HaplotypeCaller v 4.1.2.0. The .vcf files were split into SNP and Indel parts using GATK SelectVariants v 4.1.2.0 and each file was counted using GATK CountVariants v 4.1.2.0. After exporting variant lists from IVA software, variants were further filtered to retain polymorphisms of specific classes based on American College of Medical Genetics and Genomics (ACMGG) classification guidelines as implemented in IVA (33) and supplemented by ClinVar1. The ACMGG classification guidelines group predicted deleterious variants into 5 possible categories: pathogenic, likely pathogenic, uncertain significance, likely benign, and benign. The classifications are based on missense prediction, splice site prediction, nucleotide conservation prediction, well-established functional studies, and many other factors. The Predicted Deleterious column of Table IV contains the total number of BRCA and Non-BRCA HRD mutations that were identified in each of the 17 samples belonging to all 5 IVA pathogenicity classifications mentioned above. The final classification assigned by ORB was based on selecting the most severe classification from either IVA or ClinVar for variants originally assigned by IVA as pathogenic, likely pathogenic, or uncertain significance. Variants called as likely benign or benign by IVA were maintained as such in the ORB classification. Variants found within more than 20% of the samples (both PBMC and tumor samples) were filtered out along with those that appeared in >5% of the general population within Allele Frequency Community (AFC), 1000 genomes, EXac, or GnomAD databases. Variants were classified as either germline or somatic by comparing the allele fraction of each variant in the tumor sample to the PBMC sample. If the variant had a tumor sample allele fraction of 0, the variant was classified as germline. If the variant had a tumor sample allele fraction greater than zero and the PBMC sample allele fraction was zero, the variant was classified as somatic. If both allele fractions were greater than zero, the variant was classified as germline unless the allele fraction of the tumor sample was more than 10 times higher in which case the variant was classified as somatic.

TABLE 15

Baseline characteristics for BRCA wild type population

| Characteristic | BRCA1/2-wt | |
|---|---|---|
| | Gemogenovatucel- | Placebo |
| No. of patients | 40 | 27 |
| Age, years | | |
|   Median (IQR) | 63.5 (56.0-69.2) | 64.0 (52.0-69.0) |
|   Range | 42-84 | 38-79 |
|   <65 | 21 (52.5%) | 15 (55.6%) |
|   >=65 | 19 (47.5%) | 12 (44.4%) |
| Race | | |
|   Asian | 0 (0%) | 1 (3.7%) |
|   Black or African American | 0 (0%) | 2 (7.4%) |
|   White | 40 (100%) | 23 (85.2%) |
|   Not Reported | 0 (0%) | 1 (3.7%) |
| Ethnicity | | |
|   Hispanic or Latino | 1 (2.5%) | 0 (0%) |
|   Non Hispanic or Latino | 39 (97.5%) | 26 (96.3%) |
|   Not Reported | 0 (0%) | 1 (3.7%) |
| ECOG | | |
|   0 | 22 (55.0%) | 21 (77.8%) |
|   1 | 18 (45.0%) | 6 (22.2%) |
| FIGO Stage | | |
|   III | 32 (80.0%) | 24 (88.9%) |
|   IV | 8 (20.0%) | 3 (11.1%) |
| Frontline Chemotherapy | | |
|   Neoadjuvant | 5 (12.5%) | 2 (7.4%) |
|   Adjuvant | 35 (87.5%) | 25 (92.6%) |
| No. of Chemotherapy cycles | | |
|   Mean (SD) | 6 (0.28) | 6 (0.28) |
|   Median (IQR) | 6 (6-6) | 6 (6-6) |
|   Range | 5-7 | 5-7 |
| Frontline surgery residual disease | | |
|   Macroscopic | 14 (35.0%) | 8 (29.6%) |
|   Microscopic/NED | 26 (65.0%) | 19 (70.4%) |
| Histology | | |
|   Endometrioid carcinoma | 1 (2.5%) | 0 (0%) |
|   Mixed serous/clear cell | 0 (0%) | 1 (3.7%) |
|   High grade serous carcinoma | 39 (97.5%) | 26 (96.3%) |
| BRCA mutational status | | |
|   BRCA-wt | 40 (100%) | 27 (100%) |
|   BRCA-m | 0 (0%) | 0 (0%) |
| Days from last chemo given to | | |
|   Mean (SD) | 49.5 (16.0) | 48.0 (19.0) |
|   Median (IQR) | 49 (40.8-54.2) | 47 (35.5-49) |
|   Range | 22-121 / 0.7-4.0 | 23-110 / 0.8-3.6 |
| Solid Tumor Weight (g) | | |
|   Mean (SD) | 55 (27) | 58 (28) |
|   Median (IQR) | 53 (32-75) | 48 (39-74) |
|   Range | 10-136 | 11-114 |
| Cells harvested per gram of tumor | | |
|   Mean (SD) | 5 (3) | 6 (5) |
|   Median (IQR) | 5 (3.3-6.1) | 5 (3.6-6.3) |
|   Range | 1-13 | 2-29 |
| Days from surgery to randomization | | |
|   Mean (SD) | 206.4 (23.7) | 200.7 (33.1) |
|   Median (IQR) | 204 (193.5-218.5) | 197 (179.0-211.5) |
|   Range | 161-286 | 156-315 |

1. Markman M, Liu P Y, Wilczynski S, et al. Phase III randomized trial of 12 versus 3 months of maintenance paclitaxel in patients with advanced ovarian cancer after complete response to platinum and paclitaxel-based chemotherapy: a Southwest Oncology Group and Gynecologic Oncology Group trial. J Clin Oncol 2003; 21: 2460-65.

2. LaFargue C J, Dal Molin G Z, Sood A K, Coleman R L. Exploring and comparing adverse events between PARP inhibitors. Lancet Oncol 2019; 20:e15-28.

3. Coleman R L, Oza A M, Lorusso D, et al. Rucaparib maintenance treatment for recurrent ovarian carcinoma after response to platinum therapy (ARIEL3): a randomised, double-blind, placebo-controlled, phase 3 trial. Lancet 2017; 390: 1949-61.

4. Maples P, Kumar P, Oxendine I, et al. TAG vaccine: autologous tumor vaccine genetically modified to express GM-CSF and block production of TGFB2. BioProcess J 2009; 8:38-44.

5. Bristow R E, Baldwin R L, Yamada S D, Korc M, Karlan B Y. Altered expression of transforming growth factor-beta ligands and receptors in primary and recurrent ovarian carcinoma. Cancer 1999; 85: 658-68.

6. Riester M, Wei W, Waldron L, et al. Risk prediction for late-stage ovarian cancer by meta-analysis of 1525 patient samples. J Natl Cancer Inst 2014; 106: dju048.

7. Kang Y, Massagui J. Epithelial-mesenchymal transitions: twist in development and metastasis. Cell 2004; 118: 277-79.
8. Roane B M, Arend R C, Birrer M J. Review: targeting the transforming growth factor-beta pathway in ovarian cancer. Cancers (Basel) 2019; 11: e668.
9. Senzer N, Barve M. Nemunaitis J, et al. Long term follow up: phase 1 trial of "bi-shRNA furin/GMCSF DNA/autologous tumor cell" immunotherapy (FANGTM) in advanced cancer. J Vaccines Vaccin 2013; 4: 209.
10. Olivares J, Kumar P, Yu Y, et al. Phase 1 trial of TGF-beta 2 antisense GM-CSF gene-modified autologous tumor cell (TAG) vaccine. Clin Cancer Res 2011; 17: 183-92.
11. Nemunaitis J, Dillman R O, Schwarzenberger P O, et al. Phase 2 study of belagenpumatucel-L, a transforming growth factor beta-2 antisense gene-modified allogeneic tumor cell vaccine in non-small-cell lung cancer. J Clin Oncol 2006; 24: 4721-30.
12. Oh J, Barve M, Matthews C M, et al. Phase 2 study of Vigil® DNA engineered immunotherapy as maintenance in advanced stage ovarian cancer. Gynecol Oncol 2016; 143: 504-10.
13. Gonzalez-Martin A, Pothuri B, Vergote I, et al. Niraparib in patients with newly diagnosed advanced ovarian cancer. N Engl J Med 2019; 381: 2391-402.
14. Ison G, Howie L J, Amiri-Kordestani L, et al. FDA approval summary: niraparib for the maintenance treatment of patients with recurrent ovarian cancer in response to platinum-based chemotherapy. Clin Cancer Res 2018; 24: 4066-71.
15. Kim G, Ison G, McKee A E, et al. FDA approval summary: olaparib monotherapy in patients with deleterious germline BRCA-mutated advanced ovarian cancer treated with three or more lines of chemotherapy. Clin Cancer Res 2015; 21: 4257-61.
16. Konstantinopoulos P A, Caccaldi R, Shapiro G I, D'Andrea A D. Homologous recombnination deficiency: exploiting the fundamental vulnerability of ovarian cancer. Cancer Discov 2015; 5: 1137-54.
17. Thiese M S, Ronna B, Ott U. P value interpretations and considerations. J Thorac Dis 2016; 8: e928-31.
18. Goodman S N. Multiple comparisons, explained. Am J Epidemiol 1998; 147: 807-12.
19. Drachman D. Adjusting for multiple comparisons. J Clin Res Best Pract 2012; 8: 1-3.
20. McGranahan N, Furness A J, Rosenthal R, et al. Clonal neoantigens elicit T cell immunoreactivity and sensitivity to immune checkpoint blockade. Science 2016; 351: 1463-69.
21. Kraya A A, Maxwell K N, Wubbenhorst B, et al. Genomic signatures predict the immunogenicity of BRCA-deficient breast cancer. Clin Cancer Res 2019; 25: 4363-74.
22. Esteve J M, Armengod M E, Knecht E. BRCA1 negatively regulates formation of autophagic vacuoles in MCF-7 breast cancer cells. Exp Cell Res 2010; 316: 2618-29.
23. Folkerts H, Hilgendorf S, Vellenga E, Bremer E, Wiersma V R. The multifaceted role of autophagy in cancer and the microenvironment. Med Res Rev 2019; 39: 517-60.
24. Dranoff G, Jaffee E, Lazenby A, et al. Vaccination with irradiated tumor cells engineered to secrete murine granulocyte-macrophage colony-stimulating factor stimulates potent, specific, and long-lasting anti-tumor immunity. Proc Natl Acad Sci USA 1993; 90: 3539-43.
25. Smyth M J, Crowe N Y. Hayakawa Y, Takeda K, Yagita H, Godfrey D I. NKT cells—conductors of tumor immunity? Curr Opin Immunol 2002; 14: 165-71.
26. Li X, Ye F, Chen H, Lu W, Wan X, Xie X. Human ovarian carcinoma cells generate CD4(+)CD25(+) regulatory T cells from peripheral CD4(+)CD25(−) T cells through secreting TGF-beta. Cancer Lett 2007; 253: 144-53.
27. Pölcher M, Braun M, Friedrichs N, et al. Foxp3(+) cell infiltration and granzyme B(+)/Foxp3(+) cell ratio are associated with outcome in neoadjuvant chemotherapy-treated ovarian carcinoma. Cancer Immunol Immunother 2010; 59: 909-19.
28. Geissmann F, Revy P, Regnault A, et al. TGF-beta 1 prevents the noncognate maturation of human dendritic Langerhans cells. J Immunol 1999; 162: 4567-75.
29. Curiel T J. Wei S, Dong H, et al. Blockade of B7-H1 improves myeloid dendritic cell-mediated antitumor immunity. Nat Med 2003; 9: 562-67.
30. Hamanishi J, Mandai M, Iwasaki M, et al. Programmed cell death 1 ligand 1 and tumor-infiltrating CD8+T lymphocytes are prognostic factors of human ovarian cancer. Proc Natl Acad Sci USA 2007: 104: 3360-65.
31. Pujade-Lauraine E, Fujiwara K. Ledermann J A, et al. Avelumab alone or in combination with pegylated liposomal doxorubicin versus pegylated liposomal doxorubicin alone in platinum-resistant or refractory epithelial ovarian cancer: primary and biomarker analysis of the phase 3 JAVELIN Ovarian 200 trial. Gynecol Oncol 2019; 154: 21-22.
32. Liu J F, Herold C, Gray K P, et al. Assessment of combined nivolumab and bevacizumab in relapsed ovarian cancer: a phase 2 clinical trial. JAMA Oncol 2019; 5: 1731-38.
33. Richards, S., et al., Standards and guidelines for the interpretation of sequence variants: a joint consensus recommendation of the American College of Medical Genetics and Genomics and the Association for Molecular Pathology. Genet Med, 2015. 17(5): p. 405-24

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method of treating a cancer in an individual in need thereof, the method comprising administering to the individual an expression vector comprising:
   (a) a first insert comprising a nucleic acid sequence encoding a Granulocyte Macrophage Colony Stimulating Factor (GM-CSF) sequence; and
   (b) a second insert comprising a sequence of SEQ ID NO:4,
   wherein the individual is homologous recombination deficiency (HRD)-negative, and/or wherein the individual has a wild-type BRCA1 gene, a wild-type BRCA2 gene, or a combination thereof.

2. The method of claim 1, wherein the cancer is selected from the group consisting of a solid tumor cancer, ovarian cancer, adrenocortical carcinoma, bladder cancer, breast cancer, cervical cancer, cholangiocarcinoma, colorectal cancers, esophageal cancer, glioblastoma, glioma, hepatocellular carcinoma, head and neck cancer, kidney cancer, leukemia, lymphoma, lung cancer, melanoma, mesothelioma, multiple myeloma, pancreatic cancer, pheochromocytoma, plasmacytoma, neuroblastoma, prostate cancer, sarcoma, stomach cancer, uterine cancer, thyroid cancer, and a hematological cancer.

3. The method of claim 2, wherein the cancer is ovarian cancer, breast cancer, melanoma, or lung cancer.

4. The method of claim 3, wherein the individual has been eradicated of ovarian cancer.

5. The method of claim 1, wherein the expression vector is administered within an autologous cancer cell.

6. The method of claim 1, wherein the expression vector further comprises a promoter, a CMV enhancer sequence, and/or a CMV intron sequence.

7. The method of claim 1, wherein the expression vector further comprises a nucleic acid sequence encoding a picornaviral 2A ribosomal skip peptide between the first and the second nucleic acid inserts.

8. A method of treating BRCA1/2 wild type ovarian cancer in an individual in need thereof, the method comprising administering to the individual an autologous tumor cell transfected with an expression vector comprising:
   (a) a first insert comprising a nucleic acid sequence encoding a Granulocyte Macrophage Colony Stimulating Factor (GM-CSF) sequence; and
   (b) a second insert comprising a sequence of SEQ ID NO:4.

9. The method of claim 8, wherein the method comprises administering to the individual one or more doses of an autologous tumor cell vaccine comprising the autologous tumor cell.

10. The method of claim 9, wherein the method further comprises administering to the individual at least one dose of an additional therapeutic agent.

11. A method of treating ovarian cancer in an individual in need thereof, wherein the individual has been eradicated of ovarian cancer and the method prevents or delays relapse of the eradicated ovarian cancer, the method comprising administering to the individual an expression vector comprising:
(a) a first insert comprising a nucleic acid sequence encoding a Granulocyte Macrophage Colony Stimulating Factor (GM-CSF) sequence; and
(b) a second insert comprising a sequence of SEQ ID NO:4, wherein the individual is homologous recombination deficiency (HRD)-negative, and/or wherein the individual has a wild-type BRCA1 gene, a wild-type BRCA2 gene, or a combination thereof.

12. The method of claim 11, wherein the expression vector is administered within an autologous cancer cell.

13. The method of claim 11, wherein the expression vector further comprises a promoter, a CMV enhancer sequence, and/or a CMV intron sequence.

14. The method of claim 11, wherein the individual is homologous recombination deficiency (HRD)-negative, and wherein the individual has a wild-type BRCA2 gene.

15. The method of claim 11, wherein the individual is homologous recombination deficiency (HRD)-negative, and wherein the individual has a wild-type BRCA1 gene.

16. The method of claim 11, wherein the individual is homologous recombination deficiency (HRD)-negative, and wherein the individual has a combination of a wild-type BRCA1 gene and a wild-type BRCA2 gene.

17. The method of claim 11, wherein the individual is administered an autologous tumor cell transfected with the expression vector.

18. The method of claim 17, wherein the autologous tumor cell is a vaccine.

\* \* \* \* \*